(12) United States Patent
Sleeman et al.

(10) Patent No.: US 12,269,897 B2
(45) Date of Patent: *Apr. 8, 2025

(54) ANTI-PCSK9 ANTIBODIES

(71) Applicant: REGENERON PHARMACEUTICALS, INC., Tarrytown, NY (US)

(72) Inventors: Mark W. Sleeman, Victoria (AU); Joel H. Martin, Putnam Valley, NY (US); Tammy T. Huang, Cross River, NY (US); Douglas MacDonald, New York, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/296,265

(22) Filed: Apr. 5, 2023

(65) Prior Publication Data

US 2023/0340153 A1    Oct. 26, 2023

Related U.S. Application Data

(60) Continuation of application No. 17/160,634, filed on Jan. 28, 2021, now abandoned, which is a continuation of application No. 15/996,773, filed on Jun. 4, 2018, now Pat. No. 10,941,210, which is a continuation of application No. 15/377,364, filed on Dec. 13, 2016, now Pat. No. 10,023,654, which is a continuation of application No. 14/737,488, filed on Jun. 12, 2015, now Pat. No. 9,550,837, which is a continuation of application No. 13/690,585, filed on Nov. 30, 2012, now abandoned, which is a continuation of application No. 12/949,846, filed on Nov. 19, 2010, now Pat. No. 8,501,184, which is a division of application No. 12/637,942, filed on Dec. 15, 2009, now Pat. No. 8,062,640.

(60) Provisional application No. 61/261,776, filed on Nov. 17, 2009, provisional application No. 61/249,135, filed on Oct. 6, 2009, provisional application No. 61/218,136, filed on Jun. 18, 2009, provisional application No. 61/168,753, filed on Apr. 13, 2009, provisional application No. 61/210,566, filed on Mar. 18, 2009, provisional application No. 61/122,482, filed on Dec. 15, 2008.

(51) Int. Cl.
| | |
|---|---|
| C12P 21/06 | (2006.01) |
| A61K 39/08 | (2006.01) |
| C07H 21/04 | (2006.01) |
| C07K 16/12 | (2006.01) |
| C07K 16/40 | (2006.01) |
| C12N 1/20 | (2006.01) |
| C12N 15/00 | (2006.01) |
| C12N 15/09 | (2006.01) |
| C12N 15/87 | (2006.01) |
| G01N 33/569 | (2006.01) |
| A61K 39/00 | (2006.01) |

(52) U.S. Cl.
CPC ............. *C07K 16/40* (2013.01); *A61K 39/08* (2013.01); *C07K 16/1282* (2013.01); *C12N 15/09* (2013.01); *C12Y 304/21061* (2013.01); *G01N 33/56911* (2013.01); *A61K 2039/505* (2013.01); *A61K 2039/507* (2013.01); *C07K 2317/21* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/92* (2013.01); *G01N 2333/33* (2013.01); *Y10S 424/809* (2013.01)

(58) Field of Classification Search
None
See application file for complete search history.

(56) References Cited

U.S. PATENT DOCUMENTS

| | | | |
|---|---|---|---|
| 4,997,423 | A | 3/1991 | Okuda et al. |
| 5,016,784 | A | 5/1991 | Batson |
| 5,260,440 | A | 11/1993 | Hirai et al. |
| 5,273,995 | A | 12/1993 | Roth et al. |
| 5,399,670 | A | 3/1995 | Bhattacharya et al. |
| 5,480,796 | A | 1/1996 | Kishimoto |
| 5,670,373 | A | 9/1997 | Kishimoto |
| 5,723,120 | A | 3/1998 | Brackenhoff et al. |

(Continued)

FOREIGN PATENT DOCUMENTS

| | | |
|---|---|---|
| AU | 2012210480 B2 | 5/2017 |
| CA | 2825838 A1 | 8/2012 |

(Continued)

OTHER PUBLICATIONS

Extended European Search Report received for European Application No. 23154403.2, dated Jul. 21, 2023.

(Continued)

*Primary Examiner* — Maher M Haddad
(74) *Attorney, Agent, or Firm* — LATHROP GPM LLP; James V. DeGiulio, Esq.; James H. Velema, Esq.

(57) ABSTRACT

An human antibody or antigen-binding fragment of a human antibody that specifically binds and inhibits human proprotein convertase subtilisin/kexin type 9 (hPCSK9) characterized by the ability to reduce serum LDL cholesterol by 40-80% over a 24, 60 or 90 day period relative to predose levels, with little or no reduction in serum HDL cholesterol and/or with little or no measurable effect on liver function, as determined by ALT and AST measurements.

12 Claims, 14 Drawing Sheets

Specification includes a Sequence Listing.

(56) References Cited

U.S. PATENT DOCUMENTS

| | | | |
|---|---|---|---|
| 5,795,965 A | 8/1998 | Tsuchiya | |
| 5,817,790 A | 10/1998 | Tsuchiya | |
| 5,851,999 A | 12/1998 | Ulrich et al. | |
| 5,888,510 A | 3/1999 | Kishimoto | |
| 5,888,511 A | 3/1999 | Skurkovich et al. | |
| 5,908,686 A | 6/1999 | Sudo et al. | |
| 5,939,598 A | 8/1999 | Kucherlapati et al. | |
| 6,011,003 A | 1/2000 | Charmock-Jones et al. | |
| 6,086,874 A | 7/2000 | Yoshida et al. | |
| 6,171,586 B1 | 1/2001 | Lam et al. | |
| 6,261,560 B1 | 7/2001 | Tsujinaka et al. | |
| 6,267,958 B1 | 7/2001 | Andya et al. | |
| 6,270,993 B1 | 8/2001 | Shibuya et al. | |
| 6,286,699 B1 | 9/2001 | Sudo | |
| 6,410,691 B1 | 6/2002 | Kishimoto | |
| 6,596,541 B2 | 7/2003 | Murphy et al. | |
| 6,629,949 B1 | 10/2003 | Douglas | |
| 6,632,927 B2 | 10/2003 | Adair | |
| 6,645,635 B2 | 11/2003 | Muraki | |
| 6,659,982 B2 | 12/2003 | Douglas et al. | |
| 6,670,373 B1 | 12/2003 | Bonjouklian et al. | |
| 6,692,742 B1 | 2/2004 | Nakamura et al. | |
| 6,723,319 B1 | 4/2004 | Ito | |
| 6,875,432 B2 | 4/2005 | Liu et al. | |
| 6,946,548 B2 | 9/2005 | Sarkar et al. | |
| 7,001,892 B1 | 2/2006 | Chmielweski et al. | |
| 7,029,895 B2 | 4/2006 | Glucksmann et al. | |
| 7,060,268 B2 | 6/2006 | Andya et al. | |
| 7,129,338 B1 | 10/2006 | Ota et al. | |
| 7,226,554 B2 | 6/2007 | Sudo et al. | |
| 7,300,754 B2 | 11/2007 | Fadel et al. | |
| 7,320,792 B2 | 1/2008 | Ito et al. | |
| 7,479,543 B2 | 1/2009 | Tsuchiya et al. | |
| 7,482,147 B2 | 1/2009 | Glucksmann et al. | |
| 7,572,618 B2 | 8/2009 | Mintier et al. | |
| 7,608,693 B2 | 10/2009 | Martin et al. | |
| 7,754,208 B2 | 7/2010 | Ledbetter et al. | |
| 8,030,457 B2 | 10/2011 | Jackson et al. | |
| 8,062,640 B2 | 11/2011 | Sleeman et al. | |
| 8,080,243 B2 | 12/2011 | Liang et al. | |
| 8,092,803 B2 | 1/2012 | Furfine et al. | |
| 8,168,762 B2 | 5/2012 | Jackson et al. | |
| 8,188,233 B2 | 5/2012 | Condra et al. | |
| 8,188,234 B2 | 5/2012 | Condra et al. | |
| 8,192,741 B2 | 6/2012 | Radin et al. | |
| 8,357,371 B2 * | 1/2013 | Sleeman | A61K 39/3955 530/387.9 |
| 8,440,890 B1 | 5/2013 | Carlone, Jr. | |
| 8,501,184 B2 * | 8/2013 | Sleeman | A61K 39/08 530/387.9 |
| 8,748,115 B2 | 6/2014 | Ni et al. | |
| 8,795,669 B2 | 8/2014 | Walsh et al. | |
| 8,829,165 B2 | 9/2014 | Jackson et al. | |
| 8,869,904 B2 | 10/2014 | Jani | |
| 8,883,157 B1 | 11/2014 | Clube | |
| 8,945,560 B1 | 2/2015 | Clube | |
| 9,034,332 B1 | 5/2015 | Clube | |
| 9,120,851 B2 | 9/2015 | Sleeman et al. | |
| 9,127,068 B2 | 9/2015 | Okamoto et al. | |
| 9,173,880 B2 | 11/2015 | Dix et al. | |
| 9,193,801 B2 | 11/2015 | Walsh et al. | |
| 9,358,287 B2 | 6/2016 | Harp et al. | |
| 9,540,449 B2 | 1/2017 | Yancopoulos et al. | |
| 9,550,837 B2 * | 1/2017 | Sleeman | C12N 15/09 |
| 9,561,155 B2 | 2/2017 | Hanotin et al. | |
| 9,682,013 B2 | 6/2017 | Hanotin et al. | |
| 9,724,411 B2 * | 8/2017 | Sleeman | A61P 3/00 |
| 9,884,916 B2 | 2/2018 | Stevens et al. | |
| 10,023,654 B2 | 7/2018 | Sleeman et al. | |
| 10,023,657 B2 | 7/2018 | Leuscher et al. | |
| 10,072,086 B2 | 9/2018 | Dix et al. | |
| 10,076,571 B2 | 9/2018 | Swergold et al. | |
| 10,111,953 B2 | 10/2018 | Swergold et al. | |
| 10,428,157 B2 | 10/2019 | Baccara-Dinet et al. | |
| 10,472,425 B2 | 11/2019 | Walsh et al. | |
| 10,494,442 B2 | 12/2019 | Sasiela et al. | |
| 10,544,232 B2 | 1/2020 | Baccara-Dinet et al. | |
| 10,752,701 B2 | 8/2020 | Walsh et al. | |
| 10,772,956 B2 | 9/2020 | Pordy et al. | |
| 10,927,435 B2 | 2/2021 | Huang et al. | |
| 10,941,210 B2 | 3/2021 | Sleeman et al. | |
| 10,995,150 B2 | 5/2021 | Sasiela et al. | |
| 11,116,839 B2 | 9/2021 | Swergold et al. | |
| 11,246,925 B2 | 2/2022 | Hanotin et al. | |
| 11,306,155 B2 | 4/2022 | Baccara-Dinet et al. | |
| 11,904,017 B2 | 2/2024 | Pordy et al. | |
| 2002/0187150 A1 | 12/2002 | Mihara et al. | |
| 2003/0092606 A1 | 5/2003 | L'Italien et al. | |
| 2003/0113316 A1 | 6/2003 | Kaisheva et al. | |
| 2003/0118592 A1 | 6/2003 | Ledbetter et al. | |
| 2003/0133939 A1 | 7/2003 | Ledbetter et al. | |
| 2004/0071706 A1 | 4/2004 | Ito et al. | |
| 2004/0101920 A1 | 5/2004 | Radziejewski et al. | |
| 2004/0115197 A1 | 6/2004 | Yoshizaki et al. | |
| 2004/0197324 A1 | 10/2004 | Liu et al. | |
| 2004/0219156 A1 | 11/2004 | Goldenberg et al. | |
| 2005/0142635 A1 | 6/2005 | Tsuchiya et al. | |
| 2005/0238644 A1 | 10/2005 | Mihara et al. | |
| 2005/0281831 A1 | 12/2005 | Davis-Smyth et al. | |
| 2006/0078531 A1 | 4/2006 | Sota | |
| 2006/0078532 A1 | 4/2006 | Omoigui | |
| 2006/0078533 A1 | 4/2006 | Omoigui | |
| 2006/0147945 A1 | 7/2006 | Edmonds et al. | |
| 2006/0177436 A1 | 8/2006 | Ghilardi et al. | |
| 2006/0251653 A1 | 11/2006 | Okuda et al. | |
| 2006/0275294 A1 | 12/2006 | Omoigui | |
| 2006/0292147 A1 | 12/2006 | Yoshizaki et al. | |
| 2007/0036785 A1 | 2/2007 | Kishimoto et al. | |
| 2007/0036788 A1 | 2/2007 | Sheriff et al. | |
| 2007/0082345 A1 | 4/2007 | Ota et al. | |
| 2007/0098714 A1 | 5/2007 | Nishimoto et al. | |
| 2007/0148169 A1 | 6/2007 | Yoshizaki et al. | |
| 2007/0224663 A1 | 9/2007 | Rosen et al. | |
| 2008/0008697 A1 | 1/2008 | Mintier et al. | |
| 2008/0124325 A1 | 5/2008 | Ito et al. | |
| 2008/0131374 A1 | 6/2008 | Medich et al. | |
| 2008/0145367 A1 | 6/2008 | Bove et al. | |
| 2009/0142352 A1 | 6/2009 | Jackson et al. | |
| 2009/0232795 A1 | 9/2009 | Condra et al. | |
| 2009/0246192 A1 | 10/2009 | Condra et al. | |
| 2009/0269350 A1 | 10/2009 | Glucksmann et al. | |
| 2009/0318536 A1 | 12/2009 | Freier et al. | |
| 2009/0326202 A1 | 12/2009 | Jackson et al. | |
| 2010/0040610 A1 | 2/2010 | Sitlani et al. | |
| 2010/0040611 A1 | 2/2010 | Sparrow et al. | |
| 2010/0041102 A1 | 2/2010 | Sitlani et al. | |
| 2010/0068199 A1 | 3/2010 | Liang et al. | |
| 2010/0136028 A1 | 6/2010 | Sparrow et al. | |
| 2010/0150937 A1 | 6/2010 | Sparrow et al. | |
| 2010/0166468 A1 | 7/2010 | Tamaki | |
| 2010/0166768 A1 | 7/2010 | Sleeman et al. | |
| 2010/0216667 A1 | 8/2010 | Meyer et al. | |
| 2010/0233177 A1 | 9/2010 | Yowe et al. | |
| 2011/0009628 A1 | 1/2011 | Liu et al. | |
| 2011/0015252 A1 | 1/2011 | Fitzgerald et al. | |
| 2011/0027287 A1 | 2/2011 | Jackson et al. | |
| 2011/0033465 A1 | 2/2011 | Hedrick et al. | |
| 2011/0065902 A1 | 3/2011 | Sleeman et al. | |
| 2011/0098450 A1 | 4/2011 | Igawa et al. | |
| 2011/0111406 A1 | 5/2011 | Igawa et al. | |
| 2011/0142849 A1 | 6/2011 | Rue et al. | |
| 2011/0171241 A1 | 7/2011 | Dix et al. | |
| 2011/0229489 A1 | 9/2011 | Pons et al. | |
| 2011/0230542 A1 | 9/2011 | Tan et al. | |
| 2011/0245473 A1 | 10/2011 | Igawa et al. | |
| 2011/0256148 A1 | 10/2011 | Sleeman et al. | |
| 2011/0313024 A1 | 12/2011 | Beigelman et al. | |
| 2012/0014951 A1 | 1/2012 | Liang et al. | |
| 2012/0015435 A1 | 1/2012 | Liang et al. | |
| 2012/0020975 A1 | 1/2012 | Jackson et al. | |
| 2012/0027765 A1 | 2/2012 | Jackson et al. | |
| 2012/0076799 A1 | 3/2012 | Sparrow et al. | |
| 2012/0077964 A1 | 3/2012 | Sparrow et al. | |
| 2012/0082679 A1 | 4/2012 | Sparrow et al. | |

(56) References Cited

U.S. PATENT DOCUMENTS

| | | |
|---|---|---|
| 2012/0082680 A1 | 4/2012 | Sitlani et al. |
| 2012/0093818 A1 | 4/2012 | Jackson et al. |
| 2012/0097565 A1 | 4/2012 | Dix et al. |
| 2012/0122954 A1 | 5/2012 | Staarup et al. |
| 2012/0195910 A1 | 8/2012 | Wu et al. |
| 2012/0213794 A1 | 8/2012 | Luo et al. |
| 2012/0213797 A1 | 8/2012 | Jackson et al. |
| 2012/0219558 A1 | 8/2012 | Ni et al. |
| 2012/0231005 A1 | 9/2012 | Luo et al. |
| 2012/0251544 A1 | 10/2012 | Jackson et al. |
| 2013/0011866 A1 | 1/2013 | Igawa et al. |
| 2013/0014958 A1 | 1/2013 | Jani |
| 2013/0064825 A1 | 3/2013 | Chan et al. |
| 2013/0064834 A1 | 3/2013 | Sleeman et al. |
| 2013/0071405 A1 | 3/2013 | Davies et al. |
| 2013/0085266 A1 | 4/2013 | Sleeman et al. |
| 2013/0115223 A1 | 5/2013 | Sparrow et al. |
| 2013/0189277 A1 | 7/2013 | Walsh et al. |
| 2013/0243784 A1 | 9/2013 | Swergold |
| 2013/0245235 A1 | 9/2013 | Jackson et al. |
| 2014/0004122 A1 | 1/2014 | Chan et al. |
| 2014/0030270 A1 | 1/2014 | Clogston et al. |
| 2014/0044730 A1 | 2/2014 | Yancopoulos et al. |
| 2014/0065649 A1 | 3/2014 | Schafer et al. |
| 2014/0099312 A1 | 4/2014 | Sleeman et al. |
| 2014/0154262 A1 | 6/2014 | Hanotin et al. |
| 2014/0161821 A1 | 6/2014 | Udata |
| 2014/0178402 A1 | 6/2014 | Hanotin et al. |
| 2014/0341928 A1 | 11/2014 | Walsh et al. |
| 2014/0356370 A1 | 12/2014 | Swergold et al. |
| 2014/0356371 A1 | 12/2014 | Swergold et al. |
| 2015/0140002 A1 | 5/2015 | Baccara-Dinet et al. |
| 2015/0152191 A1 | 6/2015 | Baccara-Dinet et al. |
| 2015/0231236 A1 | 8/2015 | Pordy et al. |
| 2015/0283236 A1 | 10/2015 | Baccara-Dinet et al. |
| 2015/0284473 A1 | 10/2015 | Bessac et al. |
| 2015/0284474 A1 | 10/2015 | Sleeman et al. |
| 2016/0032015 A1 | 2/2016 | Walsh et al. |
| 2016/0115246 A1 | 4/2016 | Sasiela et al. |
| 2016/0137745 A1 | 5/2016 | Baccara-Dinet et al. |
| 2016/0137746 A1 | 5/2016 | Hanotin et al. |
| 2016/0152734 A1 | 6/2016 | Udata |
| 2017/0049886 A1 | 2/2017 | Pordy et al. |
| 2017/0096496 A1 | 4/2017 | Sleeman et al. |
| 2017/0266279 A1 | 9/2017 | Hanotin et al. |
| 2017/0296657 A1 | 10/2017 | Sleeman et al. |
| 2017/0340515 A1 | 11/2017 | Hanotin et al. |
| 2018/0044436 A1 | 2/2018 | Walsh et al. |
| 2018/0244801 A1 | 8/2018 | Sasiela et al. |
| 2018/0296670 A1 | 10/2018 | Jasson et al. |
| 2018/0296672 A1 | 10/2018 | Pordy et al. |
| 2018/0296675 A1 | 10/2018 | Coleman et al. |
| 2018/0333490 A1 | 11/2018 | Swergold |
| 2019/0031774 A1 | 1/2019 | Bujas-Bobanovic |
| 2019/0135941 A1 | 5/2019 | Sleeman et al. |
| 2019/0284301 A1 | 9/2019 | Walsh et al. |
| 2019/0292273 A1 | 9/2019 | Hanotin et al. |
| 2019/0330371 A1 | 10/2019 | Swergold et al. |
| 2019/0343719 A1 | 11/2019 | Hanotin et al. |
| 2020/0024364 A1 | 1/2020 | Baccara-Dinet et al. |
| 2020/0071422 A1 | 3/2020 | Sasiela et al. |
| 2020/0216565 A1 | 7/2020 | Baccara-Dinet et al. |
| 2020/0255544 A1 | 8/2020 | Hanotin et al. |
| 2021/0054100 A1 | 2/2021 | Walsh et al. |
| 2021/0100900 A1 | 4/2021 | Pordy et al. |
| 2021/0230719 A1 | 7/2021 | Huang et al. |
| 2021/0253735 A1 | 8/2021 | Sleeman et al. |
| 2022/0144969 A1 | 5/2022 | Bessac et al. |
| 2022/0218823 A1 | 7/2022 | Hanotin et al. |
| 2022/0315669 A1 | 10/2022 | Baccara-Dinet et al. |
| 2023/0340153 A1 | 10/2023 | Sleeman et al. |
| 2023/0406957 A1 | 12/2023 | Baccara-Dinet et al. |
| 2023/0406959 A1 | 12/2023 | Walsh et al. |
| 2024/0261400 A1 | 8/2024 | Pordy et al. |

FOREIGN PATENT DOCUMENTS

| | | |
|---|---|---|
| CL | 2013002162 A1 | 2/2014 |
| CL | 590-2014 A | 10/2014 |
| CN | 101489565 A | 7/2009 |
| CN | 101589143 A | 11/2009 |
| CN | 101932607 A | 12/2010 |
| CN | 102245641 A | 11/2011 |
| CN | 103476796 A | 12/2013 |
| CN | 103476797 A | 12/2013 |
| CN | 106794244 A | 5/2017 |
| CO | 11-37695 A | 12/2011 |
| EP | 0521471 A1 | 10/2000 |
| EP | 1067182 A2 | 1/2001 |
| EP | 0409281 A1 | 10/2001 |
| EP | 1514933 A1 | 3/2005 |
| EP | 1317537 B1 | 12/2006 |
| EP | 1618212 B1 | 11/2007 |
| EP | 2358756 A1 | 8/2011 |
| EP | 2387989 A2 | 11/2011 |
| EP | 1528933 B1 | 5/2012 |
| EP | 1802344 B1 | 8/2012 |
| EP | 2238985 B9 | 12/2012 |
| EP | 2275119 B1 | 9/2013 |
| EP | 2668211 A1 | 12/2013 |
| EP | 2668212 A2 | 12/2013 |
| EP | 2702413 A1 | 3/2014 |
| EP | 2703008 A1 | 3/2014 |
| EP | 2703009 A1 | 3/2014 |
| EP | 2706070 A1 | 3/2014 |
| EP | 2328559 B1 | 1/2015 |
| EP | 2822587 B1 | 2/2016 |
| EP | 3004171 A1 | 4/2016 |
| EP | 3055333 A2 | 8/2016 |
| EP | 3068803 A1 | 9/2016 |
| EP | 2648750 B1 | 1/2017 |
| EP | 3119810 A1 | 1/2017 |
| EP | 3156422 A2 | 4/2017 |
| EP | 3169353 A1 | 5/2017 |
| EP | 3169362 A1 | 5/2017 |
| EP | 2704742 B1 | 7/2017 |
| EP | 3326648 A1 | 5/2018 |
| EP | 3337828 A1 | 6/2018 |
| EP | 3395836 A1 | 10/2018 |
| EP | 3634469 A1 | 4/2020 |
| EP | 3677277 A1 | 7/2020 |
| EP | 3689913 A1 | 8/2020 |
| EP | 3753575 A1 | 12/2020 |
| EP | 3882273 A1 | 9/2021 |
| EP | 3943510 A2 | 1/2022 |
| JP | 2000-509018 A | 7/2000 |
| JP | 2002-501886 A | 1/2002 |
| JP | 2010-523135 A | 7/2010 |
| JP | 2010-536384 A | 12/2010 |
| JP | 2011-501952 A | 1/2011 |
| JP | 2011-511637 A | 4/2011 |
| JP | 2011-512129 A | 4/2011 |
| JP | 2012-511913 A | 5/2012 |
| JP | 2014-508142 A | 4/2014 |
| JP | 2014-511361 A | 5/2014 |
| JP | 2014-527967 A | 10/2014 |
| JP | 2016-538248 A | 12/2016 |
| JP | 2017-137338 A | 8/2017 |
| JP | 2017-522316 A | 8/2017 |
| KR | 10-2016-0132459 A | 11/2016 |
| MA | 34923 B1 | 2/2014 |
| NZ | 613867 A | 9/2015 |
| RU | 2011129316 A | 1/2013 |
| RU | 2013139727 A | 3/2015 |
| RU | 2538801 C2 | 10/2015 |
| RU | 2576034 C2 | 2/2016 |
| RU | 2604139 C2 | 12/2016 |
| SG | 192117 A1 | 8/2013 |
| TW | 201036633 A | 10/2010 |
| WO | WO 1993/000807 A1 | 1/1993 |
| WO | WO 1997/035620 A1 | 10/1997 |
| WO | WO 1998/022136 A2 | 5/1998 |
| WO | WO 1999/038495 A2 | 8/1999 |
| WO | WO 2001/057081 A2 | 8/2001 |

(56) References Cited

FOREIGN PATENT DOCUMENTS

| | | |
|---|---|---|
| WO | WO 2002/020767 A2 | 3/2002 |
| WO | WO 2004/055164 A2 | 7/2004 |
| WO | WO 2004/097047 A1 | 11/2004 |
| WO | WO 2005/058365 A1 | 6/2005 |
| WO | WO 2005/103081 A2 | 11/2005 |
| WO | WO 2005/016280 A2 | 2/2006 |
| WO | WO 2006/033702 A2 | 3/2006 |
| WO | WO 2007/062040 A1 | 5/2007 |
| WO | WO 2007/143315 A2 | 12/2007 |
| WO | WO 2007/146511 A2 | 12/2007 |
| WO | WO 2007/149334 A2 | 12/2007 |
| WO | WO 2008/057457 A2 | 5/2008 |
| WO | WO 2008/057458 A2 | 5/2008 |
| WO | WO 2008/057459 A2 | 5/2008 |
| WO | WO 2008/063382 A2 | 5/2008 |
| WO | WO 2008/066776 A2 | 6/2008 |
| WO | WO 2008/125623 A2 | 10/2008 |
| WO | WO 2008/133647 A2 | 11/2008 |
| WO | WO 2008/138536 A2 | 11/2008 |
| WO | WO 2009/026558 A1 | 2/2009 |
| WO | WO 2009/042765 A1 | 4/2009 |
| WO | WO 2009/055783 A1 | 4/2009 |
| WO | WO 2009/100297 A1 | 8/2009 |
| WO | WO 2009/100318 A1 | 8/2009 |
| WO | WO 2009/125825 A1 | 10/2009 |
| WO | WO 2010/029513 A2 | 3/2010 |
| WO | WO 2010/032220 A1 | 3/2010 |
| WO | WO 2010/077854 A1 | 7/2010 |
| WO | WO 2010/102241 A1 | 9/2010 |
| WO | WO 2010/148337 A1 | 12/2010 |
| WO | WO 2011/028938 A1 | 3/2011 |
| WO | WO 2011/039578 A1 | 4/2011 |
| WO | WO 2011/053759 A1 | 5/2011 |
| WO | WO 2011/061712 A1 | 5/2011 |
| WO | WO 2011/072263 A1 | 6/2011 |
| WO | WO 2011/111007 A2 | 9/2011 |
| WO | WO 2011/117401 A1 | 9/2011 |
| WO | WO 2012/010125 A2 | 1/2012 |
| WO | WO 2012/054438 A1 | 4/2012 |
| WO | WO 2012/064792 A2 | 5/2012 |
| WO | WO 2012/101251 A1 | 8/2012 |
| WO | WO 2012/101252 A2 | 8/2012 |
| WO | WO 2012/101253 A1 | 8/2012 |
| WO | WO 2012/109530 A1 | 8/2012 |
| WO | WO 2012/145685 A1 | 10/2012 |
| WO | WO 2012/146776 A1 | 11/2012 |
| WO | WO 2012/154999 A1 | 11/2012 |
| WO | WO 2012/168491 A1 | 12/2012 |
| WO | WO 2013/039958 A1 | 3/2013 |
| WO | WO 2013/039969 A1 | 3/2013 |
| WO | WO 2013/158984 A1 | 10/2013 |
| WO | WO 2013/166448 A1 | 11/2013 |
| WO | WO 2013/169886 A1 | 11/2013 |
| WO | WO 2013/177536 A2 | 11/2013 |
| WO | WO 2014/194111 A1 | 12/2014 |
| WO | WO 2014/197752 A1 | 12/2014 |
| WO | WO 2015/054619 A2 | 4/2015 |
| WO | WO 2015/073494 A1 | 5/2015 |
| WO | WO 2015/123423 A2 | 8/2015 |
| WO | WO 2015/140079 A1 | 9/2015 |
| WO | WO 2015/142668 A1 | 9/2015 |
| WO | WO 2016/011256 A1 | 1/2016 |
| WO | WO 2016/011260 A1 | 1/2016 |
| WO | WO 2018/225041 A1 | 12/2018 |
| WO | WO 2019/173530 A1 | 9/2019 |

OTHER PUBLICATIONS

Robinson, Odyssey Long Term, Long-Term LDL-C improvement with alirocumab combination, NJEM, Apr. 15, 2015, Retrieved from url: https://www.carenet.com/news/journal/carenet/39780.
Sonne et al., "Standards of Medical Care in Diabetes", Diabetes Care, Jan. 2017, vol. 40(Suppl. 1): S1-S135.
U.S. Appl. No. 14/539,199 2015/0152191 U.S. Pat. No. 10,428,157, filed Nov. 12, 2014 Jun. 4, 2015 Oct. 1, 2019, Marie Baccara-Dinet, Dosing Regimens for Use with PCSK9 Inhibitors.
U.S. Appl. No. 18/301,638, filed Apr. 17, 2023, Marie Baccara-Dinet, Dosing Regimens for Use with PCSK9 Inhibitors.
U.S. Appl. No. 14/801,384 2016/0137745 U.S. Pat. No. 10,544,232, filed Jul. 16, 2015 May 19, 2016 Jan. 28, 2020, Marie Baccara-Dinet, Methods for Treating Patients With Heterozygous Familial Hypercholesterolemia (heFH) With and Anti-PCSK9 Antibody.
U.S. Appl. No. 17/693,837 2022/0315669, filed Mar. 14, 2022 Oct. 6, 2022, Marie Baccara-Dinet, Methods for Treating Patients With Heterozygous Familial Hypercholesterolemia (heFH) With an Anti-PCSK9 Antibody.
U.S. Appl. No. 14/657,192 2015/0284473, filed Mar. 13, 2015 Oct. 8, 2015, Laurence Bessac, Methods for Reducing Caridovascular Risk.
U.S. Appl. No. 17/504,921 2022/0144969, filed Oct. 19, 2021 May 12, 2022, Laurence Bessac, Methods for Reducing Cariovascular Risk.
U.S. Appl. No. 12/949,846 2011/0065902 U.S. Pat. No. 8,501,184, filed Nov. 19, 2010 Mar. 17, 2011 Aug. 6, 2013, Mark W. Sleeman, High Affinity Human Antibodies to PCSK9.
U.S. Appl. No. 14/737,488 2015/0284474 U.S. Pat. No. 9,550,837, filed Jun. 12, 2015 Oct. 8, 2015 Jan. 24, 2017, Mark W. Sleeman, Therapeutic Uses of Anti-PCSK9 Antibodies.
U.S. Appl. No. 15/377,364 2017/0096496 U.S. Pat. No. 10,023,654, filed Dec. 13, 2016 Apr. 6, 2017 Jul. 17, 2017, Mark W. Sleeman, Anti-PCSK9, Antibodies.
U.S. Appl. No. 14/319,730 2014/0341928 U.S. Pat. No. 9,193,801, filed Jun. 30, 2014 Nov. 20, 2014 Nov. 24, 2015, Scott M. Walsh, Stabilized Formulations Containing Anti-PSCK9 Antibodies.
U.S. Appl. No. 15/603,732 2018/0044436 U.S. Pat. No. 10,472,425, filed May 24, 2017 Feb. 15, 2018 Nov. 12, 2019, Scott M. Walsh, Stabilized Formulations Containing Anti-PCSK9 Antibodies.
U.S. Appl. No. 18/308,769, filed Apr. 28, 2023, Scott M. Walsh, Stabilized Formulations Containing Anti-PCSK9 Antibodies.
U.S. Appl. No. 13/611,405 2013/0243784 U.S. Pat. No. 10,076,571, filed Sep. 12, 2012 Sep. 19, 2013 Sep. 18, 2018, Gary Swergold, Method for Reducing Lipoprotein(a) Levels by Administering and Inhibitor of Proprotein Convertase Subtilisin Kexin-9 (PCSK9).
U.S. Appl. No. 14/290,544 2014/0356371 U.S. Pat. No. 10,111,953, filed May 29, 2014, Gary Swergold, Methods for Reducing Remnant Cholesterol and Other Lipoprotein Fractions by Administering an Inhibitor of Proprotein Convertase Subtilisin Kexin-9 (PCSK9).
U.S. Appl. No. 15/238,890 2017/0049886 U.S. Pat. No. 10,772,956, filed Aug. 17, 2016 Feb. 23, 2017 Sep. 15, 2020, Robert C. Pordy, Methods for Reducing or Eliminating The Need for Lipoprotein Apheresis In Patients With Hyperlipidemia by Administering Alirocumab.
U.S. Appl. No. 16/991,269 2021/0100900, filed Aug. 12, 2020 Apr. 8, 2021, Robert C. Pordy, Methods for Reducing or Eliminating The Need for Lipoprotein Apheresis In Patients With Hyperlipidemia by Administering Alirocumab.
Dec. 13, 2016) "Odyssey Long Term", Wiki journal club.
Jul. 2005) "Guidance for Industry Estimating the Maximum Safe Starting Dose in Initial Clinical Trials for Therapeutics in Adult Healthy Volunteers", U.S. Department of Health and Human Services Food and Drug Administration Center for Drug Evaluation and Research (CDER), FDA Journal, XP055152598, 30 pages.
Sep. 1, 1975) "A Classification and Outline of Cerebrovascular Diseases II", Advisory Council for the National Institute of Neurological and Communicative Disorders and Stroke, vol. 6, No. 5, pp. 564-616.
AACE Guidelines, "American Association of Clinical Endocrinologists' Guidelines for Management of Dyslipidemia and Prevention of Atherosclerosis", Endocrine Practice, Mar./Apr. 2012, 18(Suppl 1): 1-78.
Abdallah et al. (Jun. 2016) "Ipilimumab-Induced Necrotic Myelopathy in a Patient with Metastatic Melanoma: A Case Report and Review of Literature", Journal of Oncology Pharmacy Practice, vol. 22, No. 3, pp. 537-542.
Abifadel et al. (2003) "Mutations in PCSK9 cause autosomal dominant hypercholesterolemia," Nature Genetics 34(2):154-156.

(56) References Cited

OTHER PUBLICATIONS

Abifadel et al. (2009) "Mutations and polymorphisms in the proprotein convertase subtilisin kexin 9 (PCSK9) gene in cholesterol metabolism and disease," Human Mutation 30(4):520-529.

Abifadel et al. (May 17, 2012) "Identification and characterization of new gain-of-function mutations in the PCSK9 gene responsible for autosomal dominant hypercholesterolemia" Atherosclerosis 223(2):394-400.

Alborn et al. (2007) "Serum proprotein convertase subtilisin Kexin type 9 is correlated directly with serum LDL cholesterol," Clinical Chemistry 53(10):1814-1819.

Almagro et al. (2008) "Humanization of antibodies," Frontiers in Bioscience. 13:1619-1633.

Al-Mashhadi et al., "Familial hypercholesterolemia and atherosclerosis in cloned minipigs created by DNA transposition of a human PCSK9 gain-of-function mutant", Sci Transl Med, 2013; 5(166-170): 44-53.

American College of Cardiology Press Release available at: http://www.acc.org/about-acc/pressreleases/2018/03/09/16/08/sat-9am-et-alirocumab-reducescardiovascular-events-after-acute-coronary-syndrome, Mar. 10, 2018.

American Diabetes Association (Jan. 2012) Standards of Medical Care in Diabetes—2012, Diabetes Care, vol. 35, Supplement 1, pp. S11-S63.

American Medical Association (Sep. 21, 2015) "Proprotein Convertase Subtilisin Kexin 9 (PCSK9) Inhibitors", Policy No. DRUG.00078, Retrieved from: <<https://www.anthem.com/ca/medicalpolicies/policies/mp_pw_c182635.htm>>.

Amgen Inc. (May 27, 2010) "Ascending Multiple Dose Study to Evaluate the Safety, Tolerability, Pharmacokinetics and Pharmacodynamics of AMG 145 in Subjects With Hyperlipidemia on Stable Doses of a Statin," Accessible on the Internet at URL: URL:http://clinicaltrials.gov/ct2/show/nct01133522?term=amg+145&rank=2. [Last Accessed Aug. 6, 2014].

Amit et al., "Three-Dimensional Structure of an Antigen-Antibody Complex at 2.8 a Resolution" Science (Aug. 1986) 233:747-753.

Angal et al. (1993) "A single amino acid substitution abolishes the heterogeneity of chimeric mouse/human (IgG4) antibody," Molecular Immunology. 30(1):105-108.

Anthem (Sep. 21, 2015) "Proprotein Convertase Subtilisin Kexin 9 (PCSK9) Inhibitors," Policy No. DRUG.00078. American Medical Association. Accessible on the Internet at URL: https://www.anthem.com/ca/medicalpolicies/policies/mp_pw_c182635.htm. [Last Accessed Apr. 27, 2016].

Antonopoulos, et al. (Apr. 2012) "Statins as Anti-Inflammatory Agents in Atherogenesis: Molecular Mechanisms and Lessons from the Recent Clinical Trials", Current Pharmaceutical Drugs, vol. 18, No. 11, pp. 1519-1530.

Arai, Hidenori, "Dyslipidemia of diabetic patients" from new "Guidelines for prevention of arteriosclerosis diseases 2012 edition", Seasonal Post, (Diabetes network editorial department (Sousinsya)), Sep. 1, 2012, vol. 4, No. 3, pp. 1-3. (with English Abstract translation).

Ason, et al., "Improved Efficacy for Ezetimibe and Rosuvastatin by Attenuating the Induction of PCSK9", Journal of Lipid Research, vol. 52, No. 4, pp. 679-687, 2011.

Attarwala (Jul. 1, 2010) "TGN1412: From Discovery to Disaster", Journal of young pharmacists, vol. 2, No. 3, XP055407473, pp. 332-336.

Attie et al. (2005) "Dual regulation of the LDL receptor—Some clarity and new questions," Cell Metabolism 5:290-292.

Australian Public Assessment Report for Alirocumab (rch) (2016) Australian Government Department of Health, Therapeutic Goods Administration. Sponsor: Sanofi-Aventis Australia Pty Ltd, 93 pages.

Bambauer et al. (2003) "Low-density Lipoprotein Apheresis: An Overview," Therapeutic Apheresis and Dialysis. 7(4):382-390.

Bambauer et al., (2012) "LDL-Apheresis: Technical and Clinical Aspects", The Scientific World Journal, vol. 2012, Article ID 314283, 19 pages.

Barbie et al. (1998) "The Human Immunoglobulin Kappa Variable (IGKV) Genes and Joining (IGKJ) Segments," Exp. Clin. Immunogenet. 15:171-183.

Bartelds, et al. (2010) "Surprising Negative Association Between IgG1 Allotype Disparity and Anti-Adalimumab Formation: A Cohort Study", Arthritis Research & Therapy, vol. 12, No. 6: R221, pp. 1-7.

Barter, et al. (Nov. 2007,) "Effects of Torcetrapib in Patients at High Risk for Coronary Events", The New England Journal of Medicine, vol. 357, No. 21, pp. 2109-2122.

Bays et al. (2014) "PCSK9 Inhibitor Alirocumab as Add-on to Atorvastatin versus Other Lipid Treatment Strategies in Patients at High CVD Risk: Odyssey Options I," Circulation. 130:A16194.

Bays et al. (Dec. 2, 2014) "Efficacy and safety of combining alirocumab with atorvastatin or rosuvastatin versus statin intensification or adding ezetimibe in high cardiovascular risk patients: Odyssey Options I and II," Circulation. 130:2118-2119.

Bays et al. (May 2015) "Alirocumab treatment effect on non-HDL-C: pooled analyses of ten Phase 3 trials in the Odyssey program," J Clin Lipidol. 9(3):471-472. Abstract 183.

Bee et al. (2009) "Precipitation of a monoclonal antibody by soluble tungsten," Journal of Pharmaceutical Sciences. 98(9):3290-3301.

Beliard et al. (Mar. 3, 2014) "Improvement in LDL-cholesterol levels of patients with familial hypercholesterolemia: can we do better? Analysis of results obtained during the past two decades in 1669 French subjects," Atherosclerosis. 234:136-141.

Bendig, "Humanization of Rodent Monoclonal Antibodies by CDR Grafting", Methods: A Companion to Methods in Enzymology, vol. 8, pp. 83-93, 1995.

Benjannet et al. (2006) "The Proprotein Convertase (PC) PCSK9 Is Inactivated by Furin and/or PC5/6A," J. Biological Chemistry 281(41):30561-30572.

Benjannet, et al., "NARC-1/PCSK9 and its Natural Mutants: Zymogen Cleavage and Effects on the Low Density Lipoprotein (LDL) Receptor and LDL Cholesterol", Journal of Biological Chemistry, vol. 279, No. 47, pp. 48865-48875, Sep. 9, 2004.

Berthold et al. (Jan. 2013) "Hyperlipoproteinemia(a): Clinical significance and treatment options," Atherosclerosis Supplements 14:1-5.

Bhatt et al. (May 2009) "The Use of Vectors Based on Gene Amplification for The Expression of Cloned Genes Mammalian Cells", European Heart Journal, vol. 30, Issue 10, pp. 1195-1202.

Bird et al. (1988) "Single-chain antigen-binding proteins," Science. 242(4877):423-426.

Blom et al. (May 8, 2014) "A 52-Week Placebo-Controlled Trial of Evolocumab in Hyperlipidemia," The New England Journal of Medicine. 370(19):1809-1819.

Boersma et al. (2011) "DARPins and other repeat protein scaffolds: advances in engineering and applications," Current Opinion in Biotechnology, 22:849-857.

Boerwinkle et al. (1992) "Apolipoprotein(a) Gene Accounts for Greater Than 90% of the Variation in Plasma Lipoprotein(a) Concentrations," J. Clin. Invest. 90:52-60.

Boes, et al., "Accelerated Development of IgG Autoantibodies and Autoimmune Disease in the Absence of Secreted IgM", Proceedings of the National Academy of Sciences, vol. 97, No. 3, pp. 1184-1189, 2000.

Borberg (Apr. 2013) "The lower the better: Target values after LDL-Apheresis and semi-selective LDL-elimination therapies," Transfusion and Apheresis Science. 48:203-206.

Breen et al. (2001) "Effect of moisture on the stability of a lyophilized humanized monoclonal antibody formulation," Pharmaceutical Research. 18(9):1345-1353.

Brouwers, et al. (Nov. 2013) "Plasma Proprotein Convertase Subtilisin Kexin Type 9 Levels are Related to Markers of Cholesterol Synthesis in Familial Combined Hyperlipidemia", Nutrition, Metabolism and Cardiovascular Diseases, vol. 23, Issue 11, pp. 1115-1121.

Cannon et al. (Aug. 31, 2014) "Efficacy and safety of alirocumab in high cardiovascular risk patients with inadequately controlled hypercholesterolaemia on maximally tolerated daily statin: results from the Odyssey Combo II study," presentation presented at the ESC Congress 2014.

Cannon et al. (Feb. 16, 2015) "Efficacy and safety of alirocumab in high cardiovascular risk patients with inadequately controlled

(56) References Cited

OTHER PUBLICATIONS hypercholesterolaemia on maximally tolerated doses of statins: the Odyssey Combo II randomized controlled trial," Eur Heart J. 36(19):1186-1194.
Cariou et al. (May 23-26, 2015) "Patient and physician perspectives on administration of the PCSK9 monoclonal antibody alirocumab, an injectable medication to lower LDL-C levels," International Symposium on Atherosclerosis. Abstract No. 1039.
Carpenter (1997) "Rational Design of Stable Lyophilized Protein Formulations: Some Practical Advice," Pharm. Res. 14(8):969-975.
Catapano et al. (Feb. 8, 2013) "The safety of therapeutic monoclonal antibodies: implications for cardiovascular disease and targeting the PCSK9 pathway," Atherosclerosis. 228(1):18-28.
Chan et al. (2009) "A proprotein convertase subtilisin/kexin type 9 neutralizing antibody reduces serum cholesterol in mice and non-human primates," Proc. Natl. Acad. Sci. USA. 106(24):9820-9825.
Chaparro-Riggers et al. (Jan. 31, 2012) "Increasing serum half-life and extending cholesterol lowering in vivo by engineering antibody with pH-sensitive binding to PCSK9," J. Biological Chemistry 287(14):11090-11097.
Chaudhary, et al., "PCSK9 Inhibitors: A New Era of Lipid Lowering Therapy", World Journal of Cardiology, vol. 9, Issue 2, pp. 76-91, Feb. 26, 2017.
ClinicalTrials.gov (Oct. 22, 2015) Efficacy and Safety of Alirocumab Versus Placebo on Top of Maximally Tolerated Lipid Lowering Therapy in Patients With Hypercholesterolemia Who Have Type 1 or Type 2 Diabetes and Are Treated With Insulin (Odyssey DM—Insulin), ClinicalTrials.gov Identifier: NCT02585778.
ClinicalTrials.gov, (Apr. 6, 2015) "Study of Alirocumab (REGN727/SAR236553) in Patients With Heterozygous Familial Hypercholesterolemia (HeFH) Undergoing Low-density Lipoprotein (LDL) Apheresis Therapy (Odyssey Escape)ClinicalTrials.gov Identifier: NCT02326220", ClinicalTrials.gov Archive, Retrieve From: <<https://clinicaltriais.gov/archive/NCT02326220/2015_04_06>>.
ClinicalTrials.gov, (Aug. 8, 2012) "Open-Label Extension of Study R727-CL-1003 (NCT01266876) to Evaluate the Long-Term Safety and Efficacy of Alirocumab (REGN727) in Participants With Heterozygous Familial Hypercholesterolemia (HeFH)", ClinicalTrials.gov Identifier: NCT01663402, Retrieved From: <<https://clinicaltrials.gov/ct2/show/NCT01663402>>.
ClinicalTrials.gov, (Aug. 10, 2012) "Odyssey Outcomes: Evaluation of Cardiovascular Outcomes After an Acute Coronary Syndrome During Treatment With Alirocumab", ClinicalTrials.gov Identifier: NCT01663402, https://clinicaltrials.gov/archive/NCT01663402/2012_08_10.
ClinicalTrials.gov, (Aug. 12, 2013) "Efficacy and Safety of Alirocumab (SAR236553/REGN727) Versus Placebo on Top of Lipid-Modifying Therapy in Patients With Heterozygous Familial Hypercholesterolemia (Odyssey High FH)", ClinicalTrials.gov Identifier: NCT01617655, https://clinicaltrials.gov/archive/NCT01617655/2013_08_12.
ClinicalTrials.gov, (Aug. 20, 2014) "A Study of Alirocumab (REGN727/SAR236553) in Patients With ADH and GOFm of the PCSK9 Gene or LOFm of the apoB Gene", ClinicalTrials.gov Identifier: NCT01604824, https://clinicaltrials.gov/archive/NCT01604824/2014_08_20.
ClinicalTrials.gov, (Aug. 7, 2014) "Long-term Safety and Tolerability of Alirocumab (SAR236553/REGN727) Versus Placebo on Top of Lipid-Modifying Therapy in High Cardiovascular Risk Patients With Hypercholesterolemia (Odyssey Long Term)", ClinicalTrials.gov Identifier: NCT01507831, https://clinicaltrials.gov/archive/NCT01507831/2014_08_07.
ClinicalTrials.gov, (Dec. 22, 2014) "Study of Alirocumab (REGN727/SAR236553) in Patients With Heterozygous Familial Hypercholesterolemia (HeFH) Undergoing Low-density Lipoprotein (LDL) Apheresis Therapy (Odyssey Escape)", ClinicalTrials.gov Identifier: NCT02326220, https://clinicaltrials.gov/ct2/show/NCT02326220?term=NCT02326220&rank=1.
ClinicalTrials.gov, (Dec. 22, 2014) "Study of Alirocumab (REGN727/SAR236553) in Patients With Heterozygous Familial Hypercholesterolemia (HeFH) Undergoing Low-density Lipoprotein (LDL) Apheresis Therapy (Odyssey Escape)", ClinicalTrials.gov Identifier: NCT02326220, ClinicalTriais.gov Archive, Retrieved From:<<https://clinicaitriais.gov/archive/NCT02326220/2014_12_22>>.
ClinicalTrials.gov, (Dec. 23, 2010) "Study of the Safety and Efficacy of REGN727/SAR236553 in Patients with HeFH Hypercholesterolemia", ClinicalTrials.gov Identifier: NCT01266876, https://clinicaltrials.gov/archive/NCT01266876/2010_12_23.
ClinicalTrials.gov, (Dec. 27, 2013) "Phase III Study to Evaluate Alirocumab in Patients With Hypercholesterolemia Not Treated With a Statin (Odyssey Choice II)", ClinicalTrials.gov Identifier: NCT02023879, https://clinicaltrials.gov/archive/NCT02023879/2013_12_27.
ClinicalTrials.gov, (Feb. 1, 2011) "Efficacy and Safety Evaluation of Alirocumab (SAR236553/REGN727) in Patients with Primary Hypercholesterolemia on Stable Atorvastatin Therapy", ClinicalTrials.gov Identifier: NCT01288443, https://clinicaltrials.gov/archive/NCT01288443/2011_02_01.
ClinicalTrials.gov, (Feb. 1, 2011) "Efficacy and Safety Evaluation of Alirocumab (SAR236553/REGN727) When Co-administered With High Dose of Atorvastatin in Patients with Primary Hypercholesterolemia", ClinicalTrials.gov Identifier: NCT01288469, https://clinicaltrials.gov/archive/NCT01288469/2011_02_01.
ClinicalTrials.gov, (Feb. 1, 2015) "Study of Alirocumab (REGN727/SAR236553) in Patients With heFH (Heterozygous Familial Hypercholesterolemia) Who are Not Adequately Controlled with Their LMT (Lipid-Modifying Therapy) (Odyssey FH II)", ClinicalTrials.gov Identifier: NCT01709500, https://clinicaltrials.gov/archive/NCT01709500/2015_02_01.
ClinicalTrials.gov, (Feb. 1, 2015) "Study of Alirocumab (REGN727/SAR236553) in Patients with Primary Hypercholesterolemia and Moderate, High, or Very High Cardiovascular (CV) Risk, Who are Intolerant to Statins (Odyssey Alternative)", ClinicalTrials.gov Identifier: NCT01709513, https://clinicaltrials.gov/archive/NCT01709513/2015_02_01.
ClinicalTrials.gov, (Feb. 18, 2014) "A Study of Alirocumab (REGN727/SAR236553) in Patients with ADH and GOFm of the PCSK9 Gene or LOFm of the apoB Gene", ClinicalTrials.gov Identifier: NCT01604824, https://clinicaltrials.gov/archive/NCT01604824/2014_02_18.
ClinicalTrials.gov, (Feb. 18, 2015) "Odyssey Outcomes: Evaluation of Cardiovascular Outcomes After an Acute Coronary Syndrome During Treatment with Alirocumab", ClinicalTrials.gov Identifier: NCT01663402, https://clinicaltrials.gov/archive/NCT01663402/2015_02_18.
ClinicalTrials.gov, (Feb. 24, 2015) "Efficacy and Safety of Alirocumab (SAR236553/REGN727) Versus Placebo on Top of Lipid-Modifying Therapy in Patients with High Cardiovascular Risk and Hypercholesterolemia (Odyssey Combo I)", ClinicalTrials.gov Identifier: NCT01644175, https://clinicaltrials.gov/archive/NCT01644175/2015_02_24.
ClinicalTrials.gov, (Feb. 26, 2015) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/archive/NCT01644188/2015_02_26>>.
ClinicalTrials.gov, (Feb. 26, 2015) "Efficacy and Safety of Alirocumab (SAR236553/REGN727) Versus Placebo on Top of Lipid-Modifying Therapy in Patients with Heterozygous Familial Hypercholesterolemia (Odyssey High FH)", ClinicalTrials.gov Identifier: NCT01617655, https://clinicaltrials.gov/archive/NCT01617655/2015_02_26.
ClinicalTrials.gov, (Feb. 26, 2015) "Efficacy and Safety of Alirocumab (SAR236553/REGN727) Versus Placebo on Top of Lipid-Modifying Therapy in Patients with Heterozygous Familial Hypercholesterolemia Not Adequately Controlled With Their Lipid-Modifying Therapy", ClinicalTrials.gov Identifier: NCT01623115, https://clinicaltrials.gov/archive/NCT01623115/2015_02_26.
ClinicalTrials.gov, (Feb. 3, 2014) "Efficacy and Safety of Alirocumab (SAR236553/REGN727) Versus Ezetimibe on Top of Statin in High Cardiovascular Risk Patients with Hypercholesterolemia (Odyssey

(56) References Cited

OTHER PUBLICATIONS

Combo II)", ClinicalTrials.gov Identifier: NCT01644188, Retrieved from: <<https://clinicaltrials.gov/archive/NCT01644188/2014_02_03>>.
ClinicalTrials.gov, (Jan. 6, 2012) "Long-term Safety and Tolerability of Alirocumab (SAR236553/REGN727) Versus Placebo on Top of Lipid-Modifying Therapy in High Cardiovascular Risk Patients With Hypercholesterolemia (Odyssey Long Term)", ClinicalTrials.gov Identifier: NCT01507831, Retrieved From: <<https://clinicaltrials.gov/ct2/show/NCT01507831?term=NCT01507831&draw=2&rank=1>>.
ClinicalTrials.gov, (Jan. 12, 2012) "Efficacy and Safety Evaluation of Alirocumab (SAR236553/REGN727) in Patients with Primary Hypercholesterolemia on Stable Atorvastatin Therapy", ClinicalTrials.gov Identifier: NCT01288443, Retrieved from: <<https://clinicaltrials.gov/archive/NCT01288443/2012_01_12>>.
ClinicalTrials.gov, (Jan. 22, 2015) "Long-term Safety and Tolerability of Alirocumab (SAR236553/REGN727) Versus Placebo on Top of Lipid-Modifying Therapy in High Cardiovascular Risk Patients with Hypercholesterolemia (Odyssey Long Term)", ClinicalTrials.gov Identifier: NCT01507831, Retrieved from: <<https://clinicaltrials.gov/archive/NCT01507831/2015_01_22>>.
ClinicalTrials.gov, (Jan. 24, 2013) "A Study of Alirocumab (REGN727/SAR236553) in Patients with ADH and GOFm of the PCSK9 Gene or LOFm of the apoB Gene", ClinicalTrials.gov Identifier: NCT01604824, Retrieved from: <<https://clinicaltrials.gov/archive/NCT01604824/2013_01_24>>.
ClinicalTrials.gov, (Jan. 26, 2015) "Previous Study | Return to List | Next Study Ascending Multi-dose Study of REGN727(SAR236553) With and Without Concomitant Atorvastatin", ClinicalTrials.gov Identifier: NCT01161082, Retrieved from: <<https://clinicaltrials.gov/archive/NCT01161082/2015_01_26>>.
ClinicalTrials.gov, (Jan. 29, 2015) "A Study of Alirocumab (REGN727/SAR236553) in Patients with ADH and GOFm of the PCSK9 Gene or LOFm of the apoB Gene", ClinicalTrials.gov Identifier: NCT01604824, Retrieved from: <<https://clinicaltrials.gov/archive/NCT01604824/2015_01_29>>.
ClinicalTrials.gov, (Jan. 29, 2015) "Efficacy and Safety Evaluation of Alirocumab (SAR236553/REGN727) in Patients with Primary Hypercholesterolemia on Stable Atorvastatin Therapy in Japan", ClinicalTrials.gov Identifier: NCT01812707, Retrieved from: <<https://clinicaltrials.gov/archive/NCT01812707/2015_01_29>>.
ClinicalTrials.gov, (Jan. 29, 2015) "Efficacy and Safety Evaluation of Alirocumab (SAR236553/REGN727) in Patients with Primary Hypercholesterolemia on Stable Atorvastatin Therapy", ClinicalTrials.gov Identifier: NCT01288443, Retrieved from: <<https://clinicaltrials.gov/archive/NCT01288443/2015_01_29>>.
ClinicalTrials.gov, (Jan. 29, 2015) "Efficacy and Safety Evaluation of Alirocumab (SAR236553/REGN727) When Co-administered With High Dose of Atorvastatin in Patients with Primary Hypercholesterolemia", ClinicalTrials.gov Identifier: NCT01288469, Retrieved from: <<https://clinicaltrials.gov/archive/NCT01288469/2015_01_29>>.
ClinicalTrials.gov, (Jan. 29, 2015) "Study of the Safety and Efficacy of REGN727/SAR236553 in Patients with HeFH Hypercholesterolemia", ClinicalTrials.gov Identifier: NCT01266876, Retrieved from: <<https://clinicaltrials.gov/archive/NCT01266876/2015_01_29>>.
ClinicalTrials.gov, (Jan. 30, 2014) "Efficacy and Safety Evaluation of Alirocumab (SAR236553/REGN727) in Patients with Primary Hypercholesterolemia on Stable Atorvastatin Therapy in Japan", ClinicalTrials.gov Identifier: NCT01812707, Retrieved from: <<https://clinicaltrials.gov/archive/NCT01812707/2014_01_30>>.
ClinicalTrials.gov, (Jul. 10, 2015) "Odyssey Outcomes: Evaluation of Cardiovascular Outcomes After an Acute Coronary Syndrome During Treatment with Alirocumab", ClinicalTrials.gov Identifier: NCT01663402, Retrieved from: <<https://clinicaltrials.gov/archive/NCT01663402/2015_07_10>>.
ClinicalTrials.gov, (Jul. 13, 2010) "Ascending Multi-dose Study of REGN727(SAR236553) With and Without Concomitant Atorvastatin", ClinicalTrials.gov Identifier: NCT01161082, Retrieved from: <<https://clinicaltrials.gov/archive/NCT01161082>>.
ClinicalTrials.gov, (Jul. 16, 2012) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/archive/NCT01644188/2012_07_17>>.
ClinicalTrials.gov, (Jul. 17, 2012) "Efficacy and Safety of Alirocumab (SAR236553/REGN727) Versus Ezetimibe in Patients With Hypercholesterolemia (Odyssey Mono)", ClinicalTrials.gov Identifier: NCT01644474, Retrieved from: <<https://clinicaltrials.gov/ct2/show/NCT01644474?term=NCT01644474>>.
ClinicalTrials.gov, (Jul. 17, 2012) "Efficacy and Safety of Alirocumab (SAR236553/REGN727) Versus Placebo on Top of Lipid-Modifying Therapy in Patients with High Cardiovascular Risk and Hypercholesterolemia (Odyssey Combo I)", ClinicalTrials.gov Identifier: NCT01644175, Retrieved from: <<https://clinicaltrials.gov/archive/NCT01644175/2012_07_17>>.
ClinicalTrials.gov, (Jul. 18, 2013) "Efficacy and Safety of Alirocumab (SAR236553/REGN727) Versus Ezetimibe in Patients with Hypercholesterolemia (Odyssey Mono)", ClinicalTrials.gov Identifier: NCT01644474, Retrieved from: <<https://clinicaltrials.gov/archive/NCT01644474/2013_07_18>>.
ClinicalTrials.gov, (Jul. 18, 2013) "Efficacy and Safety of Alirocumab (SAR236553/REGN727) Versus Placebo on Top of Lipid-Modifying Therapy in Patients with High Cardiovascular Risk and Hypercholesterolemia (Odyssey Combo I)", ClinicalTrials.gov Identifier: NCT01644175, Retrieved from: <<https://clinicaltrials.gov/archive/NCT01644175/2013_07_18>>.
ClinicalTrials.gov, (Jul. 2, 2013) "Efficacy and Safety Evaluation of Alirocumab (SAR236553/REGN727) in Patients with Primary Hypercholesterolemia on Stable Atorvastatin Therapy", ClinicalTrials.gov Identifier: NCT01288443, Retrieved from: <<https://clinicaltrials.gov/archive/NCT01288443/2013_07_02>>.
ClinicalTrials.gov, (Jul. 2, 2013) "Efficacy and Safety Evaluation of Alirocumab (SAR236553/REGN727) When Co-administered with High Dose of Atorvastatin in Patients with Primary Hypercholesterolemia", ClinicalTrials.gov Identifier: NCT01288469, Retrieved from: <<https://clinicaltrials.gov/archive/NCT01288469/2013_07_02>>.
ClinicalTrials.gov, (Jul. 22, 2014) "Package Insert for Proplex T Factor IX Complex Heat Treated (Baxter)", ClinicalTrials.gov Identifier: NCT02023879, Retrieved from: <<https://clinicaltrials.gov/archive/NCT02023879/2014_07_22>>.
ClinicalTrials.gov, (Jul. 8, 2014) "Efficacy and Safety of Alirocumab (SAR236553/REGN727) Versus Ezetimibe in Patients with Hypercholesterolemia (Odyssey Mono)", ClinicalTrials.gov Identifier: NCT01644474, Retrieved from: <<https://clinicaltrials.gov/archive/NCT01644474/2014_07_08>>.
ClinicalTrials.gov, (Jun. 10, 2014) "Odyssey Outcomes: Evaluation of Cardiovascular Outcomes After an Acute Coronary Syndrome During Treatment with Alirocumab", ClinicalTrials.gov Identifier: NCT01663402, Retrieved from: <<https://clinicaltrials.gov/archive/NCT01663402/2014_06_10>>.
ClinicalTrials.gov, (Jun. 11, 2012) "Efficacy and Safety of Alirocumab (SAR236553/REGN727) Versus Placebo on Top of Lipid-Modifying Therapy in Patients with Heterozygous Familial Hypercholesterolemia (Odyssey High FH)", ClinicalTrials.gov Identifier: NCT01617655, Retrieved from: <<https://clinicaltrials.gov/archive/NCT01617655/2012_06_11>>.
ClinicalTrials.gov, (Jun. 18, 2012) "Efficacy and Safety of Alirocumab (SAR236553/REGN727) Versus Placebo on Top of Lipid-Modifying Therapy in Patients with Heterozygous Familial Hypercholesterolemia Not Adequately Controlled with Their Lipid-Modifying Therapy (Odyssey Fh I)", ClinicalTrials.gov Identifier: NCT01623115, Retrieved from: <<https://clinicaltrials.gov/archive/NCT01623115/2012_06_18>>.
ClinicalTrials.gov, (Jun. 18, 2015) "Efficacy and Safety of Alirocumab (SAR236553/REGN727) Versus Ezetimibe on Top of Statin in High Cardiovascular Risk Patients with Hypercholesterolemia (Odyssey

(56) References Cited

OTHER PUBLICATIONS

Combo II)", ClinicalTrials.gov Identifier: NCT01644188, Retrieved from: <<https://clinicaltrials.gov/archive/NCT01644188/2015_06_18>>.
ClinicalTrials.gov, (Jun. 18, 2015) "Study of the Safety and Efficacy of REGN727/SAR236553 in Patients with HeFH Hypercholesterolemia", ClinicalTrials.gov Identifier: NCT01266876, Retrieved from: <<https://clinicaltrials.gov/archive/NCT01266876/2015_06_18>>.
ClinicalTrials.gov, (Jun. 19, 2014) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/archive/NCT01644188/2014_06_19>>.
ClinicalTrials.gov, (Jun. 19, 2014) "Phase III Study to Evaluate Alirocumab in Patients with Hypercholesterolemia Not Treated With a Statin (Odyssey Choice II)", ClinicalTrials.gov Identifier: NCT02023879, Retrieved from: <<https://clinicaltrials.gov/archive/NCT02023879/2014_06_19>>.
ClinicalTrials.gov, (Jun. 27, 2013) "Efficacy and Safety Evaluation of Alirocumab (SAR236553/REGN727) in Patients with Primary Hypercholesterolemia on Stable Atorvastatin Therapy in Japan", ClinicalTrials.gov Identifier: NCT01812707, Retrieved from: <<https://clinicaltrials.gov/archive/NCT01812707/2013_06_27>>.
ClinicalTrials.gov, (Jun. 27, 2013) "Efficacy and Safety of Alirocumab (SAR236553/REGN727) Versus Placebo on Top of Lipid-Modifying Therapy in Patients with Heterozygous Familial Hypercholesterolemia Not Adequately Controlled with Their Lipid-Modifying Therapy (Odyssey FH I)", ClinicalTrials.gov Identifier: NCT01623115, Retrieved from: <<https://clinicaltrials.gov/archive/NCT01623115/2013_06_27>>.
ClinicalTrials.gov, (Jun. 27, 2013) "Long-term Safety and Tolerability of Alirocumab (SAR236553/REGN727) Versus Placebo on Top of Lipid-Modifying Therapy in High Cardiovascular Risk Patients with Hypercholesterolemia (ODYSSEY Long Term)", ClinicalTrials.gov Identifier: NCT01507831, Retrieved from: <<https://clinicaltrials.gov/archive/NCT01507831/2013_06_27>>.
ClinicalTrials.gov, (Mar. 10, 2014) "Phase III Study to Evaluate Alirocumab in Patients With Hypercholesterolemia Not Treated With a Statin (Odyssey Choice II)", ClinicalTrials.gov Identifier: NCT02023879, Retrieved from: <<https://clinicaltrials.gov/archive/NCT02023879/2014_03_10>>.
ClinicalTrials.gov, (Mar. 11, 2014) "Odyssey Outcomes: Evaluation of Cardiovascular Outcomes After an Acute Coronary Syndrome During Treatment with Alirocumab", ClinicalTrials.gov Identifier: NCT01663402, Retrieved from: <<https://clinicaltrials.gov/archive/NCT01663402/2014_03_11>>.
ClinicalTrials.gov, (Mar. 15, 2013) "Efficacy and Safety Evaluation of Alirocumab (SAR236553/REGN727) in Patients with Primary Hypercholesterolemia on Stable Atorvastatin Therapy in Japan", ClinicalTrials.gov Identifier: NCT01812707, Retrieved from: <<https://clinicaltrials.gov/archive/NCT01812707/2013_03_15>>.
ClinicalTrials.gov, (Mar. 16, 2012) "Study of the Safety and Efficacy of REGN727/SAR236553 in Patients with HeFH Hypercholesterolemia", ClinicalTrials.gov Identifier: NCT01266876, Retrieved from: <<https://clinicaltrials.gov/archive/NCT01266876/2012_03_16>>.
ClinicalTrials.gov, (Mar. 26, 2015) "Efficacy and Safety of Alirocumab (SAR236553/REGN727) Versus Placebo on Top of Lipid-Modifying Therapy in Patients with Heterozygous Familial Hypercholesterolemia (Odyssey High FH)", ClinicalTrials.gov Identifier: NCT01617655, Retrieved from: <<https://clinicaltrials.gov/archive/NCT01617655/2015_03_26>>.
ClinicalTrials.gov, (Mar. 26, 2015) "Efficacy and Safety of Alirocumab (SAR236553/REGN727) Versus Placebo on Top of Lipid-Modifying Therapy in Patients with Heterozygous Familial Hypercholesterolemia Not Adequately Controlled with Their Lipid-Modifying Therapy (Odyssey FH I)", ClinicalTrials.gov Identifier: NCT01623115, retrieved from: <<https://clinicaltrials.gov/archive/NCT01623115/2015_03_26>>.
ClinicalTrials.gov, (Mar. 9, 2015) "Study of Alirocumab (REGN727/SAR236553) in Patients With Heterozygous Familial Hypercholesterolemia (HeFH) Undergoing Low-density Lipoprotein (LDL) Apheresis Therapy (Odyssey Escape)", ClinicalTrials.gov Identifier: NCT02326220, ClinicalTriais.gov Archive, Retrieved from :<<https://clinicaitriais.gov/archive/NCT02326220/2015_03_09>>.
ClinicalTrials.gov, (May 20, 2015) "Previous Study | Return to List | Next Study Phase III Study to Evaluate Alirocumab in Patients With Hypercholesterolemia Not Treated with a Statin (Odyssey Choice II)", ClinicalTrials.gov Identifier: NCT02023879, Retrieved from: <<https://clinicaltrials.gov/archive/NCT02023879/2015_05_20>>.
ClinicalTrials.gov, (May 21, 2013) "Study of Alirocumab (REGN727/SAR236553) in Patients With heFH (Heterozygous Familial Hypercholesterolemia) Who are Not Adequately Controlled with Their LMT (Lipid-Modifying Therapy) (Odyssey FH II)", ClinicalTrials.gov Identifier: NCT01709500, Retrieved from: <<https://clinicaltrials.gov/archive/NCT01709500/2013_05_21>>.
ClinicalTrials.gov, (May 23, 2012) "A Study of Alirocumab (REGN727/SAR236553) in Patients with ADH and GOFm of the PCSK9 Gene or LOFm of the apoB Gene", ClinicalTrials.gov Identifier: NCT01604824, Retrieved from: <<https://clinicaltrials.gov/archive/NCT01604824/2012_05_23>>.
ClinicalTrials.gov, (May 28, 2014) "Efficacy and Safety of Alirocumab (SAR236553/REGN727) Versus Placebo on Top of Lipid-Modifying Therapy in Patients with High Cardiovascular Risk and Hypercholesterolemia (Odyssey Combo I)", ClinicalTrials.gov Identifier: NCT01644175, Retrieved from: <<https://clinicaltrials.gov/archive/NCT01644175/2014_05_28>>.
ClinicalTrials.gov, (Nov. 16, 2011) "Efficacy and Safety Evaluation of Alirocumab (SAR236553/REGN727) When Co-administered With High Dose of Atorvastatin in Patients with Primary Hypercholesterolemia", ClinicalTrials.gov Identifier: NCT01288469, Retrieved from: <<https://clinicaltrials.gov/archive/NCT01288469/2011_11_16>>.
ClinicalTrials.gov, (Nov. 18, 2011) "Study of the Safety and Efficacy of REGN727/SAR236553 in Patients with HeFH Hypercholesterolemia", ClinicalTrials.gov Identifier: NCT01266876, Retrieved from: <<https://clinicaltrials.gov/archive/NCT01266876/2011_11_18>>.
ClinicalTrials.gov, (Nov. 7, 2011) "Ascending Multi-dose Study of REGN727(SAR236553) With and Without Concomitant Atorvastatin", ClinicalTrials.gov Identifier: NCT01161082, Retrieved from: <<https://clinicaltrials.gov/archive/NCT01161082/2011_11_07>>.
ClinicalTrials.gov, (Oct. 8, 2012) "Study of Alirocumab (REGN727/SAR236553) in Patients With heFH (Heterozygous Familial Hypercholesterolemia) Who are Not Adequately Controlled With Their LMT (Lipid-Modifying Therapy) (Odyssey FH II)", ClinicalTrials.gov Identifier: NCT01709500, Retrieved from: <<https://clinicaltrials.gov/ct2/show/NCT01709500?term=NCT01709500>>.
ClinicalTrials.gov, (Oct. 1, 2014) "Efficacy and Safety of Alirocumab (SAR236553/REGN727) Versus Placebo on Top of Lipid-Modifying Therapy in Patients with High Cardiovascular Risk and Hypercholesterolemia (Odyssey Combo I)", ClinicalTrials.gov Identifier: NCT01644175, Retrieved from: <<https://clinicaltrials.gov/archive/NCT01644175/2014_10_01>>.
ClinicalTrials.gov, (Oct. 17, 2012) "Study of Alirocumab (REGN727/SAR236553) in Patients With heFH (Heterozygous Familial Hypercholesterolemia) Who are Not Adequately Controlled with Their LMT (Lipid-Modifying Therapy) (Odyssey FH II)", ClinicalTrials.gov Identifier: NCT01709500, Retrieved from: <<https://clinicaltrials.gov/archive/NCT01709500/2012_10_17>>.
ClinicalTrials.gov, (Oct. 17, 2012) "Study of Alirocumab (REGN727/SAR236553) in Patients with Primary Hypercholesterolemia and Moderate, High, or Very High Cardiovascular (CV) Risk, Who are Intolerant to Statins (Odyssey Alternative)", ClinicalTrials.gov Identifier: NCT01709513, Retrieved from: <<https://clinicaltrials.gov/archive/NCT01709513/2012_10_17>>.

(56) References Cited

OTHER PUBLICATIONS

ClinicalTrials.gov, (Oct. 22, 2013) "Odyssey Outcomes: Evaluation of Cardiovascular Outcomes After an Acute Coronary Syndrome During Treatment with Alirocumab", ClinicalTrials.gov Identifier: NCT01663402, Retrieved from: <<https://clinicaltrials.gov/archive/NCT01663402/2013_10_22>>.
ClinicalTrials.gov, (Oct. 25, 2013) "Study of Alirocumab (REGN727/SAR236553) in Patients With heFH (Heterozygous Familial Hypercholesterolemia) Who are Not Adequately Controlled with Their LMT (Lipid-Modifying Therapy) (Odyssey FH II)", ClinicalTrials.gov Identifier: NCT01709500, Retrieved from: <<https://clinicaltrials.gov/archive/NCT01709500/2013_10_25>>.
ClinicalTrials.gov, (Oct. 25, 2013) "Study to Evaluate the Efficacy and Safety of Every Four Weeks Treatment Regimen of Alirocumab (REGN727/ SAR236553) in Patients with Primary Hypercholesterolemia (Odyssey Choice 1)", ClinicalTrials.gov Identifier: NCT01926782, Retrieved from: <<https://clinicaltrials.gov/archive/NCT01926782/2013_10_25>>.
ClinicalTrials.gov, (Oct. 27, 2014) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/archive/NCT01644188/2014_10_27>>.
ClinicalTrials.gov, (Oct. 6, 2014) "Crystal Structure of The Complex of Rat Neonatal Fc Receptor With Fc", ClinicalTrials.gov Identifier: NCT01663402, Retrieved from: <<https://clinicaltrials.gov/archive/NCT01663402/2014_10_06>>.
ClinicalTrials.gov, (Oct. 6, 2014) "Efficacy and Safety of Alirocumab (SAR236553/REGN727) Versus Placebo on Top of Lipid-Modifying Therapy in Patients with Heterozygous Familial Hypercholesterolemia (Odyssey High FH)", ClinicalTrials.gov Identifier: NCT01617655, Retrieved from: <<https://clinicaltrials.gov/archive/NCT01617655/2014_10_06>>.
ClinicalTrials.gov, (Oct. 6, 2014) "Efficacy and Safety of Alirocumab (SAR236553/REGN727) Versus Placebo on Top of Lipid-Modifying Therapy in Patients with Heterozygous Familial Hypercholesterolemia Not Adequately Controlled with Their Lipid-Modifying Therapy (Odyssey FH I)", ClinicalTrials.gov Identifier: NCT01623115, Retrieved from: <<https://clinicaltrials.gov/archive/NCT01623115/2014_10_06>>.
ClinicalTrials.gov, (Oct. 7, 2013) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/archive/NCT01644188/2013_10_07>>.
ClinicalTrials.gov, (Oct. 7, 2013) "Odyssey Outcomes: Evaluation of Cardiovascular Outcomes After an Acute Coronary Syndrome During Treatment with Alirocumab", ClinicalTrials.gov Identifier: NCT01663402, Retrieved from: <<https://clinicaltrials.gov/archive/NCT01663402/2013_10_07>>.
ClinicalTrials.gov, (Oct. 7, 2013) "Study of Alirocumab (REGN727/SAR236553) in Patients with Primary Hypercholesterolemia and Moderate, High, or Very High Cardiovascular (CV) Risk, Who are Intolerant to Statins (Odyssey Alternative)", ClinicalTrials.gov Identifier: NCT01709513, Retrieved from: <<https://clinicaltrials.gov/archive/NCT01709513/2013_10_07>>.
ClinicalTrials.gov, (Sep. 22, 2014) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/archive/NCT01644188/2014_09_22>>.
Colhoun et al. (Sep. 20, 2014) "Efficacy and safety of alirocumab, a fully human PCSK9 monoclonal antibody, in high cardiovascular risk patients with poorly controlled hypercholesterolemia on maximally tolerated doses of statins: rationale and design of the Odyssey Combo I and II trials," BMC Cardiovasc Disord. 14(1):121.
Conroy, et al., "Estimation of Ten-Year Risk of Fatal Cardiovascular Disease in Europe: the Score Project", European Heart Journal, vol. 24, No. 11, pp. 987-1003. (2003).
Costet (May 1, 2012) "PCSK9 inhibitors as LDL cholesterol-lowering agents: Rationale, concerns and preliminary outcomes," Drugs of the Future. 37(5):331-341.
Daugherty et al. (2006) "Formulation and delivery issues for monoclonal antibody therapeutics," Advanced Drug Delivery Reviews 58:686-706.
Davidson et al. (2011) "Clinical utility of inflammatory markers and advanced lipoprotein testing: Advice from an expert panel of lipid specialists," Journal of Clinical Lipidology. 5:338-367.
Davignon, et al.(Jul. 11, 2010) "The Influence of PCSK9 Polymorphisms on Serum Low-Density Lipoprotein Cholesterol and Risk of Atherosclerosis", Current Atherosclerosis Reports, vol. 12, No. 5, pp. 308-315.
Defesche et al. (Jun. 2-5, 2013) "Natural history of autosomal dominant hypercholesterolemia caused by gain-of-function mutations in proprotein convertase subtilisin/kexin type 9 (PCSK9) (funded by Regeneron/Sanofi)," Abstract of a presentation presented at the 81st European Atherosclerosis Society (EAS) Congress, Jun. 2-5, 2013, Lyon, France.
Defesche et al. (Jun. 2-5, 2013) "Natural history of autosomal dominant hypercholesterolemia caused by gain-of-function mutations in proprotein convertase subtilisin/kexin type 9 (PCSK9) (funded by Regeneron/Sanofi)," Presentation presented at the 81st European Atherosclerosis Society (EAS) Congress, Jun. 2-5, 2013, Lyon, France.
Della, et al. (Jun. 2017) "Alirocumab For the Treatment of Hypercholesterolaemia", Expert Review of clinical Pharmacology, vol. 10, No. 6, pp. 571-582.
Demant et al. (2001) "The metabolism of lipoprotein(a) and other apolipoprotein B-containing lipoproteins: a kinetic study in humans," Atherosclerosis 157:325-339.
Denis, et al., "Gene Inactivation of Proprotein Convertase Subtilisin/Kexin Type 9 Reduces Atherosclerosis in Mice", Circulation, vol. 125, No. 7, pp. 894-901, Feb. 21, 2012.
Do, et al., "PCSK9 Inhibitors: Potential in Cardiovascular Therapeutics", Current Cardiology Reports, vol. 15, No. 3, p. 345, Jan. 22, 2013.
Dube et al. (Apr. 2012) "Lipoprotein(a): more interesting than ever after 50 years," Curr. Opin. Lipidol. 23:133-140.
Duff et al. (2009) "Antibody-mediated disruption of the interaction between PCSK9 and the low-density lipoprotein receptor," Biochem. J. 419(3):577-584.
Dufour et al. (2012) "Effect of REGN727/SAR236553 PCSK9 fully human monoclonal antibody in patients with elevated triglycerides/low high-density lipoprotein cholesterol: data from three phase 2 studies, " Circulation. 126:A16127.
Dufour et al. (Sep. 30, 2014) "One year open-label treatment with alirocumab 150 mg every two weeks in heterozygous familial hypercholesterolemic patients," Can J Cardiol. 30(10 suppl):S338. Abstract 546.
Edwards, et al. (Nov. 14, 2003) "The Remarkable Flexibility of the Human Antibody Repertoire; Isolation of Over One Thousand Different Antibodies to a Single Protein, BLyS", Journal of Molecular Biology, vol. 334, No. 1, 103-118.
EPG Health press release, "Odyssey Outcomes trial success for Praluent in reduction of Mace events.—Sanofi + Regeneron", available at: https://www.epgonline.org/global/news/odyssey-outcomes-trial success-for-praluent-inreduction-of-mace-events-sanofi- regeneron-.html, Mar. 11, 2018.
Epresspack, "Sanofi and Regeneron Report Positive Top-line Results with Alirocumab from First Phase 3 Study of a PCSK9 Inhibitor for LDL Cholesterol Reduction", Oct. 16, 2013, Retrieved from url: http://www.epresspack.net/mmr/sanofi-pcsk9-1st-phase3-results/.
European Office Action corresponding to European Patent Application No. 12701015.5, dated Apr. 24, 2015.
European Office Action corresponding to European Patent Application No. 12701015.5, dated May 30, 2014.
European Office Action corresponding to European Patent Application No. 12701742.4, dated Jun. 1, 2015.

(56) References Cited

OTHER PUBLICATIONS

European Office Action corresponding to European Patent Application No. 12701742.4, dated May 28, 2014.
European Public Assessment Report (EPAR) for Praluent™,European Medicines Agency, 3 Pages, 2016.
Extended European Search Report for European Patent Application No. 21151675.2, mailed Aug. 4, 2021.
Extended European Search Report received for European Application No. 19210918.9, dated Jun. 8, 2020.
Extended European Search Report received for European Application No. 19212291.9, dated May 18, 2020.
Extended European Search Report received for European Application No. 20174278.0, dated Nov. 10, 2020.
Extended European Search Report received in European Patent Application No. 16200305.7 dated Jun. 1, 2017.
Extended European Search Report received in European Patent Application No. 21185555.6 dated Mar. 21, 2022.
Fallon et al. (2000) "Increased endosomal sorting of ligand to recycling enhances potency of an intereukin-2 analog," J. Biological Chemistry 275(10):6790-6797.
Farnier (2011) "The role of proprotein convertase subtilisin/kexin type 9 in hyperlipidemia: Focus on therapeutic implications," American Journal of Cardiovascular Drugs 11(3):145-152.
Farnier et al. (2014) "Relationship between alirocumab, PCSK9 and LDL-C levels: results from the Odyssey Mono Phase 3 trial of alirocumab 75 mg every 2 weeks," Atherosclerosis. 235(2):e34-e35. Abstract EAS-0758.
Fasano et al. (2008) "45 Activity of Gain-of-Function PCSK9 Mutants on LDLR Correlates with Total-Cholesterol Values in ADH patients," Nutrition Metabolism and Cardiovascular Diseases. 18(1):S46.
Fasano, et al., "Degradation of LDLR Protein Mediated by 'Gain of Function' PCSK9 Mutants in Normal and ARH Cells", Atherosclerosis, vol. 203, Issue 1, pp. 166-171, Mar. 2009.
Ference, et al., Effect of Long-Term Exposure to Lower Low-Density Lipoprotein Cholesterol Beginning Early in Life on the Risk of Coronary Heart Disease, Journal of the American College of Cardiology, vol. 60, Issue 25, pp. 2631-2639, Dec. 25, 2012.
Ferrara, et al. (2015) "Recombinant Renewable Polyclonal Antibodies", mAbs, vol. 7, No. 1, pp. 32-41.
Foody et al. (2013) "Attainment of low-density lipoprotein cholesterol goals in patients at high cardiovascular risk: results from a managed care population study," Circulation. 128:A17254.
Foote et al. (1992) "Antibody Framework Residues Affecting the Conformation of the Hypervariable Loops," J. Mol. Biol. 224:487-499.
Gandek et al. (2004) "Psychometric evaluation of the SF-36 health survey in Medicare managed care," Health Care rinanc Rev. 25(4):5-25.
Gaudet et al. (2012) "Effect of SAR236553/REGN727 fully human monoclonal anti-proprotein convertase subtilisin/kexin type 9 antibody on plasma lipoprotein(a) concentrations: pooled analysis from three phase 2 studies (NCT:01266876; 01288469; 01288443)," Circulation. 126:A14725.
Gaudet et al. (Jun. 18, 2014) "Effect of Alirocumab, a Monoclonal Proprotein Convertase Subtilisin/Kexin 9 Antibody, on Lipoprotein(a) Concentrations (a Pooled Analysis of 150 mg Every 2 Weeks Dosing from Phase 2 Trials)," Am J Cardiol. 114(5):711-715.
Gaudet et al. (May 2013) "Alirocumab, a fully human monoclonal antibody to PCSK9, reduces high plasma Lp(a) concentration: pooled analysis of 352 patients from phase 2," J Clin Lipidol. 7(3):283-284. Abstract 178.
Gaudet et al. (Sep. 29, 2016) "Effect of Alirocumab on Lipoprotein(a) Over 1.5 Years (from the Phase 3 Odyssey Program)," Am. J. Cardiol. 119:40-46.
Genentech (2014) Actemra Subcutaneous Dosing & Administration Pocket Guide. pp. 1-40.
Gershoni et al. (Jan. 2007) "Epitope mapping—The first step in developing epitope-based vaccines," Biod, Adis International Ltd, NZ, vol. 21, No. 3, pp. 145-156.
Ginsberg et al. (2014) "Odyssey High FH: efficacy and safety of alirocumab in patients with severe heterozygous familial hypercholesterolemia," Circulation. 130:2119.
Giugliano, et al. (Oct. 28, 2017) "Clinical Efficacy and Safety of Achieving Very Low LDL-Cholesterol Concentrations with the PCSK9 Inhibitor Evolocumab: A Prespecified Secondary Analysis of the Fourier Trial", Lancet (North American Edition), vol. 390, No. 10106, pp. 1962-1971.
Gonnet et al. (1992) "Exhaustive Matching of the Entire Protein Sequence Database," Science. 256:1443-1445.
Goodson, et al., "Dental Applications", Medical Applications of Controlled Release, vol. 2pp, 115-138, 1984.
Gorcyca et al. (May 2015) "Prevalence of atherosclerotic cardiovascular disease and diabetes in the United States," J Clin Lipidol. 9(3):424. Abstract 118.
Gouni-Berthold, et al., "PCSK9 Antibodies for the Treatment of Hypercholesterolemia", Nutrients, vol. 6, No. 12, pp. 5517-5533. (2014).
Grozdanov et al. (2006) "Expression and localization of PCSK9 in rat hepatic cells," Biochem. Cell. Biol. 84:80-92.
Gusarova et al. (Jan. 18, 2017) "Reduction of LDL cholesterol by a monoclonal antibody to PCSK9 in rodents and nonhuman primates," Clin Lipidol. 7(6):737-743.
Gusarova et al. (Mar. 25-30, 2012) "Fully human antibody that blocks PCSK9 demonstrates reduction in LDL-C preclinically and in early clinical trials," Abstract of oral presentation at the Keystone Symposia on Molecular and Cellular Biology, Mar. 25-30, 2012, Montana, USA.
Haddley et al. (Apr. 1, 2013) "Alirocumab Anti-Proprotein Convertase 9 (PCSK9) Mab Treatment of Hypercholesterolemia," Drugs of the Future. 38(4):213-219.
healio.com, "PCSK9 inhibitors poised for breakthrough as new cholesterol-lowering therapy", Cardiology Today, Apr. 2013, Retrieved from url: https://www.healio.com/news/cardiology/20130411/10_3928_1081_597x_20130101_00_1098093.
Heap et al. (2005) "Analysis of a 17-amino acid residue, virus-neutralizing microantibody," Journal of General Virology. 86(6):1791-1800.
Himmler, et al., "Modelling the Societal Impact of Nirocumab in Patients with Severe Hypercholesterolemia Treated with Apheresis in Germany", Value in Health, vol. 20, Abstract No. PCV70, 1 Page. (2017).
Hiriyama et al. (Jan. 1, 2014) "Effects of evolocumab (AMG 145), a monoclonal antibody to PCSK9, in hypercholesterolemic, statin-treated Japanese patients at high cardiovascular risk—primary results from the phase 2 Yukawa study," Circulation Journal. 78(5):1073-1082.
Hirsch et al. (Mar. 2006) "ACC/AHA 2005 Practice Guidelines for the Management of Patients with Peripheral Arterial Disease (Lower Extremity, Renal, Mesenteric, and Abdominal Aortic)", Circulation, vol. 113, No. 11, pp. 1475-1547.
Hochleitner et al. (2000) "Characterization of a discontinuous epitope of the human immunodeficiency virus ~HIV! core protein p24 by epitope excision and differential chemical modification followed by mass spectrometric peptide mapping analysis," Protein Science. 9:487-496.
Holliger et al. (1993) "'Diabodies': small bivalent and bispecific antibody fragments," Proceedings of the National Academy of Sciences USA. 90(14):6444-6448.
Hopkins et al. (2007) "The Lund-Mackay staging system for chronic rhinosinusitis: How is it used and what does it predict?" Otolaryngology-Head and Neck Surgery. 137(4):555-561.
Hopkins et al. (2011) "Familial Hypercholesterolemias: Prevalence, genetics, diagnosis and screening recommendations from the National Lipid Association Expert Panel on Familial Hypercholesterolemia," Journal of Clinical Lipidology. 5(3):S9-S17.
Hopkins et al. (2013) "A randomized placebo-phase clinical trial with the monoclonal antibody alirocumab demonstrates reductions in low-density lipoprotein cholesterol in patients with proprotein convertase subtilisin/kexin type 9 gain-of-function mutations," Circulation. 128:A17156.
Hopkins et al. (Dec. 2015) "Characterization of Autosomal Dominant Hypercholesterolemia Caused by PCSK9 Gain of Function

(56) References Cited

OTHER PUBLICATIONS

Mutations and its Specific Treatment with Alirocumab, a PCSK9 Monoclonal Antibody," Circ Cardiovasc Genet. 8(6):823-831.
Horton et al. (2007) "Molecular biology of PCSK9: its role in LDL metabolism," Trends Biochem Sci. 32(2): 71-77.
Hovingh et al. (Feb. 13, 2013) "Diagnosis and treatment of familial hypercholesterolaemia," Eur Heart J. 34(13):962-971.
Huang et al. (Nov. 2016) "Clinical characteristics and unmet need among real-world atherosclerotic cardiovascular disease (ASCVD) patients stratified by statin use," J Clin Lipidol. 9(3):437-438. Abstract 134.
Huijgen et al. (2010) "Two years after molecular diagnosis of familial hypercholesterolemia: majority on cholesterol-lowering treatment but a minority reaches treatment goal," PLoS One. 5(2):e9220. pp. 1-7.
Huston et al. (1988) "Protein engineering of antibody binding sites: recovery of specific activity in an anti-digoxin single-chain Fv analogue produced in *Escherichia coli*," Proceedings of the National Academy of Sciences USA. 85(16):5879-5883.
Igawa et al. (2010) "Antibody recycling by engineered pH-dependent antigen binding improves the duration of antigen neutralization," Nature Biotechnology. 28(11):1203-1208.
International Nonproprietary Names for Pharmaceutical Substances (INN) WHO Drug Information, vol. 25, No. 4, 2011; 53 pages.
International Search Report and Written Opinion for PCT International Patent Application No. PCT/EP2009/063195, dated Feb. 13, 2014.
International Search Report and Written Opinion for PCT International Patent Application No. PCT/EP2012/051320, mailed Sep. 21, 2012.
International Search Report and Written Opinion for PCT International Patent Application No. PCT/EP2012/051321, mailed Apr. 19, 2012.
International Search Report and Written Opinion for PCT International Patent Application No. PCT/EP2012/057890, mailed Aug. 28, 2012.
International Search Report and Written Opinion for PCT International Patent Application No. PCT/EP2015/055369, mailed May 21, 2015.
International Search Report and Written Opinion for PCT International Patent Application No. PCT/IB2018/054182, dated Aug. 31, 2018.
International Search Report and Written Opinion for PCT International Patent Application No. PCT/US2009/068013, dated May 12, 2010.
International Search Report and Written Opinion for PCT International Patent Application No. PCT/US2012/042338, dated Aug. 23, 2012.
International Search Report and Written Opinion for PCT International Patent Application No. PCT/US2012/048574, dated Feb. 15, 2013.
International Search Report and Written Opinion for PCT International Patent Application No. PCT/US2013/023784, dated Jul. 10, 2013.
International Search Report and Written Opinion for PCT International Patent Application No. PCT/US2013/055747, dated Feb. 13, 2014.
International Search Report and Written Opinion for PCT International Patent Application No. PCT/US2013/057898, dated Feb. 13, 2014.
International Search Report and Written Opinion for PCT International Patent Application No. PCT/US2014/040050, mailed Oct. 6, 2014.
International Search Report and Written Opinion for PCT International Patent Application No. PCT/US2014/040695, dated Oct. 6, 2014.
International Search Report and Written Opinion for PCT International Patent Application No. PCT/US2014/041204, mailed Oct. 17, 2014.
International Search Report and Written Opinion for PCT International Patent Application No. PCT/US2014/046170, dated Oct. 2, 2014.
International Search Report and Written Opinion for PCT International Patent Application No. PCT/US2014/060109, mailed Apr. 16, 2015.
International Search Report and Written Opinion for PCT International Patent Application No. PCT/US2014/065149, mailed Feb. 3, 2015.
International Search Report and Written Opinion for PCT International Patent Application No. PCT/US2015/015633, mailed Aug. 19, 2015.
International Search Report and Written Opinion for PCT International Patent Application No. PCT/US2015/020564, mailed Jun. 12, 2015.
International Search Report and Written Opinion for PCT International Patent Application No. PCT/US2015/040754, mailed Oct. 14, 2015.
International Search Report and Written Opinion for PCT International Patent Application No. PCT/US2015/040765, mailed Nov. 26, 2015.
International Search Report and Written Opinion for PCT International Patent Application No. PCT/US2019/021034, dated Jun. 27, 2019.
Ito et al. (1992) "The His-probe method: effects of histidine residues introduced into the complementarity-determining regions of antibodies on antigen-antibody interactions at different pH values," Federation of European Biochemical Societies. 309(1):85-88.
Jefferis, et al., "Human Immunoglobulin Allotypesm", Abs, vol. 1, No. 4, pp. 332-338, Jul./Aug. 2009.
Jones et al. (2015) "Pooled safety and adverse events in nine randomized, placebo-controlled, phase 2 and 3 clinical trials of alirocumab," J Am Coll Cardiol. 65(10_S):A1363.
Jorgensen et al. (Dec. 17, 2012) "Genetically elevated non-fasting triglycerides and calculated remnant cholesterol as casual risk factors for myocardial infarction," European Heart Journal 34:1826-1833.
Julius, "Current Role of Lipoprotein Apheresis in the Treatment of High-Risk Patients", Journal of Cardiovascular Development and Disease, vol. 5, No. 27, pp. 1-11. (2018).
Julius, et al., "Effects of Lipoprotein Apheresis on PCSK9 Levels", Atherosclerosis Supplements, vol. 18, pp. 180-186. (2015).
Junghans et al. (1990) "Anti-Tac-H, a Humanized Antibody to the Interleukin 2 Receptor with New Features for Immunotherapy in Malignant and Immune Disorders," Cancer Research. 50:1495-1502.
Kastelein et al. (Aug. 31, 2014) "Efficacy and Safety of Alirocumab in Patients with Heterozygous Familial Hypercholesterolemia not Adequately Controlled with Current Lipid-Lowering Therapy: Results of Odyssey FH I and FH II Studies," Poster Presented at the ECS Congress 2014. Barcelona, Spain.
Kastelein et al. (Jun. 2014) "Efficacy and Safety of Alirocumab in Patients with Heterozygous Familial Hypercholesterolemia not Adequately Controlled with Current Lipid-Lowering Therapy: Design and Rationale of the Odyssey Fh Studies," Cardiovasc Drugs Ther. 28(3):281-289.
Kastelein et al. (Sep. 1, 2015) "Odyssey FH I and FH II: 78-week results with alirocumab treatment in 735 patients with heterozygous familial hypercholesterolemia," Eur Heart J. 36(43):2996-3003.
Kastner, et al. (2010) "Synergistic Effect of IL-6 and IL-4 in Driving Fate Revision of Natural Foxp3+ Regulatory T Cells", The Journal of Immunology, vol. 185, pp. 5778-5786.
Katayama et al. (2004) "Retrospective statistical analysis of lyophilized Protein Formulations of Progenipoietin Using PLS: Determination of the Critical Parameters for Long-Term Storage Stability," J. Pharm. Sci. 93(10):2609-2623.
Kawashiri et al. (2012) "Statin Therapy Improves Fractional Catabolic Rate of LDL without Affecting Impaired VLDL and VLDL Remnant Catabolismin Homozygous FH Patient Due to PCSK9 Gene Mutation: Evidence from Kinetic Study with Stable Isotope," Circulation 126(21):A13869.
Keene, et al. (Jul. 2014) "Effect on Cardiovascular Risk of High Density Lipoprotein Targeted Drug Treatments of Niacin, Fibrates,

(56) References Cited

OTHER PUBLICATIONS and CETP Inhibitors: Meta-Analysis of Randomised Controlled Trials Including 117411 Patients", British Medical Journal, vol. 349, No. g4379, pp. 1-13.

Kereiakes et al. (Dec. 2, 2014) "Efficacy and safety of alirocumab in high cardiovascular risk patients with suboptimally controlled hypercholesterolemia on maximally tolerated doses of statins: the Odyssey Combo I study," Circulation. 130:2119-2120.

Kereiakes, et al. (Jun. 2015) "Efficacy and Safety of The Proprotein Convertase Subtilisin/Kexin Type 9 Inhibitor Alirocumab Among High Cardiovascular Risk Patients on Maximally Tolerated Statin Therapy: The Odyssey Combo I Study", American Heart Journal, 169(6):906-915.e13.

Khawli, et al. (2010) "Charge Variants in IgG1: Isolation, Characterization, In Vitro Binding Properties and Pharmacokinetics in Rats", mAbs, vol. 2, No. 6, pp. 613-624.

Kolata (Jul. 27, 2015) "Praluent Looks Cheap to Those with Extreme Cholesterol" The New York Times. Accessible on the Internet at URL: www.nytimes.com/2015/07/28/health/praluent-looks-cheap-to-those-with-extreme-cholesterol.html. [Last Accessed on Sep. 5, 2017].

Konrad et al. (2011) "Effects of currently prescribed LDL-C-lowering drugs on PCSK9 and implications for the next generation of LDL-C-lowering agents," Lipids in Health and Disease. 10(1):38.

Koren et al. (2012) "Efficacy, safety and tolerability of 150 mg Q2W dose of the anti-PCSK9 mAb, REGN727/SAR236553: data from 3 phase 2 studies," Eur Heart J. 33(Abstract Supplement):37. Abstract 429.

Koren et al. (2014) "Effects of alirocumab, a fully human monoclonal antibody to proprotein convertase subtilisin/kexin type 9, on lipoprotein particle concentrations determined by nuclear magnetic resonance: substudy of a randomized double-blind phase II clinical trial," J Am Coll Cardiol. 63(12 Suppl 1):A1373.

Koren et al. (Jan. 22, 2015) "Safety and efficacy of alirocumab 150 mg every 2 weeks, a fully human proprotein convertase subtilisin/kexin type 9 monoclonal antibody: a Phase II pooled analysis," Postgrad Med. 22:1-8.

Koren et al. (May 2013) "Efficacy, safety and tolerability of alirocumab 150 mg Q2W, a fully human PCSK9 monoclonal antibody: a pooled analysis of 352 patients from phase 2," J Clin Lipidol. 7(3):279-280. Abstract 172.

Koschinsky et al. (2009) In; Clinical Lipidology: A Companion to Braunwald's Heart Disease. Ed: Ballantyne. pp. 136-143.

Koschinsky et al. (Dec. 2014) "Lipoprotein(a): an important cardiovascular risk factor and a clinical conundrum," Endocrinol. Metab. Clin. North Am. 43:949-962.

Kostner et al. (Jun. 4, 2013) "When should we measure lipoprotein (a)?" European Heart Journal. 34:3268-3276.

Krauss et al. (2014) "Alirocumab, a fully human monoclonal antibody to proprotein convertase subtilisin/kexin type 9, and its effects on lipoprotein subfractions determined by ion mobility," Circulation. 130:A15525.

Kühnast et al. (2012) "Aliskiren Inhibits Atherosclerosis Development and Imrpoves Plaque Stability in APOE*3Leiden.CETP Transgenic Mice with or without Treatment with Atorvastatin," J. Hypertens, 30(1):21-41.

Kuhnast et al. (2013) "PCSK-9 monoclonal antibody alirocumab dose-dependently decreases atherosclerosis development and enhances the effects of atorvastatin in APOE*3Leiden CETP mice," Circulation. 128:A15823.

Kühnast et al. (2013) "Niacin Reduces Atherosclerosis Development in APOE*3Leiden.CETP Mice Mainly by Reducing NonHDL-Cholesterol," PLOS ONE, 8(6):e66467, 13 pages.

Kuhnast et al. (Oct. 2014) "Alirocumab inhibits atherosclerosis, improves the plaque morphology, and enhances the effects of a statin," J Lipid Res. 55(10):2103-2112.

Kuiper et al. (May 2015) "Statin use and low density lipoprotein cholesterol goal attainment among a high cardiovascular risk population in the Netherlands," Pharmo ISA Poster.

Kwon, et al., "Molecular Basis for LDL Receptor Recognition by PCSK9" Proceedings of the National Academy of Sciences, vol. 105, No. 6, pp. 1820-1825, 2008.

Kyratsous, et al., "Reply to Dimitrov et al.: VelociSuite Technologies are a Foundation for Rapid Therapeutic Antibody Development", Proceedings of the National Academy of Sciences, vol. 112, No. 37, pp. E5116-E5116, 2015.

Lagace et al. (2006) "Secreted PCSK9 decreases the number of LDL receptors in hepatocytes and in liver of parabiotic mice," J Clin Invest Am Soc Clin Invest. 116(11):2995-3005.

Lalanne, et al., "Wild-Type PCSK9 Inhibits LDL Clearance but Does Not Affect apoB-Containing Lipoprotein Production in Mouse and Cultured Cells", Journal of Lipid Research, vol. 46, No. 6, pp. 1312-1319, 2005.

Lambert et al. (Jul. 17, 2012) "The PCSK9 decade," J Lipid Res. 53(12):2515-2524.

Lambert et al. (Nov. 24, 2014) "Normalization of Low-Density Lipoprotein Receptor Expression in Receptor Defective Homozygous Familial Hypercholesterolemia by Inhibition of PCSK9 With Alirocumab," J Am Coll Cardiol. 64(21):2299-2300.

Lambert, et al. (2009) "Review: Molecular Basis of PCSK9 Function", Atherosclerosis, vol. 203, No. 1, pp. 1-7.

Lamon-Fava et al. (Apr. 7, 2011) "Lipoprotein(a) levels, apo(a) isoform size, and coronary heart disease risk in the Framingham Offspring Study," J. Lipid Res. 52:1181-1187.

Langer et al. (1984) Medical Applications of Controlled Release, 2:115-138.

Langer et al. (1990) "New methods of drug delivery," Science. 249(4976):1527-1533.

Lederman, Lynne, Monoclonal Antibody to PCSK9 Offers New Approach to Treating Hypercholesterolemia, In MD Conference Express, vol. 13, No. 7, pp. 16-17, Aug. 31, 2013.

Lee et al. (2018) "How to Interpret Recent CV Outcome Trials and Future: PCSK9 Inhibitors", Journal of Lipid and Atherosclerosis, 7(1):1-11.

Leebmann et al. (Dec. 17, 2013) Circulation "Lipoprotein Apheresis in Patients With Maximally Tolerated Lipid-Lowering Therapy, Lipoprotein(a)—Hyperlipoproteinemia, and Progressive Cardiovascular Disease," Circulation. 128(24):2567-2576.

Lefranc et al. (2009) "IMGT®, the international ImMunoGeneTics information system®," Nucl. Acids Res. 37:D1006-D1012.

Leiter, et al. (Dec. 2017) "Efficacy and Safety of Alirocumab In Insulin-Treated Individuals with Type 1 or Type 2 Diabetes and High Cardiovascular Risk: The Odyssey DM-Insulin Randomized Trial", Diabetes, Obesity & metabolism, vol. 19, No. 12, pp. 1781-1792.

Leiter, et al. (Jul. 1, 2017) "Lipid-Lowering Efficacy and Safety of Alirocumab In Patients with or without Diabetes: A Sub-Analysis of Odyssey Combo II", Diabetes, Obesity & Metabolism, vol. 19, No. 7, pp. 989-996.

Leuenberger et al. (1996) "A Multilingual Glossary of Biotechnological Terms," Recueil des Travaux Chimiques des Pays Bas. 115(7):382.

Li et al. (2009) "Recent Patents on PCSK9: A New Target for Treating Hypercholesterolemia," Recent Patents on DNA and Gene Sequences. 3(3):201-212.

Lippi et al. (2000) "Lipoprotein(a): from ancestral benefit to modern pathogen?" QJ Med 93:75-84.

Lo, et al., "Pathogenicity and Epitope Characteristics Do Not Differ in IgG Subclass-Switched Anti-Desmoglein 3 IgG1 and IgG4 Autoantibodies in Pemphigus Vulgaris", PLoS One, vol. 11, No. 6, 2016.

Lopez (2008) "Inhibition of PCSK9 as a Novel Strategy for the Treatment of Hypercholesterolemia," Drug News & Perspectives Abstract. 21(6):323.

Lopez-Berestein et al., "Treatment of Systemic Fungal Infections with Liposomal-Amphotericin B", Liposomes in the Therapy of Infectious Diseases and Cancer, 1989, pp. 2533-2536.

Lose et al. (Apr. 2013) "Evaluation of Proprotein Convertase Subtilisin/Kexin Type 9: Focus on Potential Clinical and Therapeutic Implications for Low-Density Lipoprotein Cholesterol Lowering," Pharmacotherapy: The Journal of Human Pharmacology and Drug Therapy 33(4):447-460.

(56) References Cited

OTHER PUBLICATIONS

Lunven et al. (2014) "A randomized study of the relative bioavailability, pharmacodynamics, and safety of alirocumab, a fully human monoclonal antibody to proprotein convertase subtilison/ kexin type 9, after single subcutaneous administration at three different injection sites in healthy subjects," J Am Coll Cardiol 63(12 Suppl 1):A1377.
Lunven et al. (Dec. 2014) "A randomized study of the relative pharmacokinetics, pharmacodynamics and safety of alirocumab, a fully human monoclonal antibody to PCSK9, after single subcutaneous administration at three different injection sites in healthy subjects," Cardiovasc Ther. 32(6):297-301.
Maeda et al. (2002)"pH-dependent receptor/ligand dissociation as a determining factor for intracellular sorting of ligands for epidermal growth factor receptors in rat hepatocytes," J. Controlled Release 82:71-82.
Majumdar et al. (2011) "Evaluation of the effect of syringe surfaces on protein formulations," Journal of Pharmaceutical Sciences. 100(7):2563-2573.
Marcovina et al. (1998) "Lipoprotein(a) as a Risk Factor for Coronary Artery Disease," The American Journal of Cardiology 82(12A):57U-66U.
Maxwell et al. (2004) "Adenoviral-mediated expression of Pcsk9 in mice results in a low-density lipoprotein receptor knockout phenotype," Proc. Natl. Acad. Sci. USA. 101(18):7100-7105.
Maxwell, et al., Antibodies to PCSK9 A Superior Way to Lower LDL Cholesterol?, Circulation Research, vol. 111, No. 3, pp. 274-277, 2012.
McKee, "Praluent Slashes Need for Apheresis Treatment", PharmaTimes, 2 Pages. (Aug. 30, 2016).
McKenney et al. (Jun. 2-5, 2013) "Dynamics between the monoclonal antibody SAR236553/REGN727, proprotein convertase subtilisin/kexin type 9 (PCSK9) and low-density lipoprotein cholesterol (LDL-C) levels (funding: Regeneron/Sanofi)," Abstract of an oral presentation at the 81st European Atherosclerosis Society (EAS) Congress, Jun. 2-5, 2013, Lyon, France.
McKenney et al. (Jun. 2-5, 2013) "Dynamics between the monoclonal antibody SAR236553/REGN727, proprotein convertase subtilisin/kexin type 9 (PCSK9) and low-density lipoprotein cholesterol (LDL-C) levels (funding: Regeneron/Sanofi)," Presented as a poster presentation at the 81st European Atherosclerosis Society (EAS) Congress, Jun. 2-5, 2013, Lyon, France.
McKenney et al. (Mar. 2012) "A randomized, double-blind, placebo-controlled trial of the safety and efficacy of a monoclonal antibody to proprotein convertase subtilisin/kexin type 9 serine protease, REGN727/SAR236553, in patients with primary hypercholesterolemia (NCT: 01288443)," Presented as a late-breaking oral presentation at the American College of Cardiology (ACC) Annual Scientific Session, Mar. 24-27, 2012, Chicago, Illinois, USA.
McKenney et al. (Mar. 28, 2012) "Safety and efficacy of a monoclonal antibody to proprotein convertase subtilisin/kexin type 9 serine protease, SAR236553/REGN727, in patients with primary hypercholesterolemia receiving ongoing stable atorvastatin therapy," J Am Coll Cardiol. 59(25):2344-2353.
McNutt, et al. (Dec. 1, 2015) "So Far, PCSK9 Inhibitors Work for All Heterozygous FH Patients", Circulation: Cardiovascular Genetics, vol. 8, pp. 749-751.
McPherson (2013) "Remnant Cholesterol: Non-(HDL-C + LDL-C) as a Coronary Artery Disease Risk Factor," Journal of the American College of Cardiology. 61(4):437-439.
Meehan et al. (1996) "A microinfusor device for the delivery of therapeutic levels of peptides and macromolecules," J. Controlled Release 46:107-116.
Miettinen et al. (1971) "Cholesterol production in obesity," Circulation. 44(5):842-850.
Missouri DU Report (2003) "Statin Therapy" Drug Use Review Newsletter. 8(6) pp. 1-9.
Moon (2007) "Lipoprotein(a) and LDL Particle Size are Related to the Severity of Coronary Artery Disease", Cardiology 108:282-289.
Moriarty (May 2015) "PCSK9 Inhibitors and their Effect on Patients who are Statin Intolerant or Receiving Lipoprotein-apheresis," The 10th International Society for Apheresis Congress. May 13-16, 2015. Cancun, Mexico.
Moriarty et al. (2014) "Odyssey Alternative: Efficacy and safety of the proprotein convertase subtilisin/kexin type 9 monoclonal antibody, alirocumab, versus ezetimibe, in patients with statin intolerance as defined by a placebo run-in and statin rechallenge arm," Circulation. 130:2108-2109.
Moriarty et al. (Aug. 1, 2013) "Homogeneity of treatment effect of REGN727/SAR236553, a fully human monoclonal antibody against PCSK9, in lowering LDL-C: data from three phase 2 studies," Eur Heart J. 34(Suppl 1):18. Abstract 142.
Moriarty et al. (Aug. 29, 2015) "Efficacy and safety of alirocumab versus ezetimibe in statin-intolerant patients, with a statin-rechallenge arm: The Odyssey Alternative randomized trial," J Clin Lipidol. 9(6):758-769.
Moriarty et al. (Sep. 19, 2014) "Efficacy and safety of alirocumab, a monoclonal antibody to PCSK9, in statin-intolerant patients: Design and rationale of Odyssey Alternative, a randomized Phase 3 trial," J Clin Lipidol. 8(6):554-561.
Müller-Wieland, et al. (2017) "Design and Rationale of The Odyssey DM Dyslipidemia Trial: Lipid Lowering Efficacy and Safety of Alirocumab In Individuals with Type 2 Diabetes and Mixed Dyslipidaemia at High Cardiovascular Risk", Cardiovascular Diabetology, vol. 16, No. 70, pp. 1-10.
Murphy, et al., "Mice with Megabase Humanization of Their Immunoglobulin Genes Generate Antibodies as Efficiently as Normal Mice", Proceedings of the National Academy of Sciences, vol. 111, No. 14, pp. 5153-5158, 2014.
Nair, et al. (Jan. 1, 2016) "A simple practice guide for dose conversion between animals and human", Journal of Basic and Clinical Pharmacy, vol. 7, No. 2, pp. 27-31.
Nakasako et al. (1999)"The pH-dependent structural variation of complementarity-determining region H3 in the crystal structures of the Fv fragment from an anti- dansyl monoclonal antibody," J. Mol. Biol. 291:117-134.
Naureckiene et al. (2003) "Functional characterization of Narc 1, a novel proteinase related to proteinase K," Archives of Biochemistry and Biophysics 420:55-67.
Ned, et al. (2011) "Cascade Screening for Familial Hypercholesterolemia (FH)", PLoS Currents, vol. 3, 13 Pages.
Neil et al. (2004) "Established and emerging coronary risk factors in patients with heterozygous familial hypercholesterolaemia," Heart. 90(12):1431-1437.
Ni et al. (2010) "A proprotein convertase subtilisin-like/kexin type 9 (PCSK9) C-terminal domain antibody antigen-binding fragment inhibits PCSK9 internalization and restores low density lipoprotein uptake," J Biol Chem. 285(17):12882-91.
Noguchi et al. (2010) "The E32K variant of PCSK9 exacerbates the phenotype of familial hypercholesterolemia by increasing PCSK9 function and concentration in the circulation," Atherosclerosis 210(1):166-172.
Nordestgaard et al. (2010) "Lipoprotein(s) as cardiovascular risk factor: current status," European Heart Journal 31:2844-2853.
Opposition from EP Application No. 09793408.7 dated Oct. 11, 2017.
Padlan et al. (1995) "Identification of specificity-determining residues in antibodies," The FASEB Journal. 9(1):133-139.
Panka et al., "Variable Region Framework Differences Result in Decreased or Increased Affinity of Variant Anti-Digoxin Antibodies" Proc. Natl. Acad. Sci. USA (May 1988) 85:3080-3084.
Parhofer (2011) "Lipoprotein(a): Medical Treatment Options for an Elusive Molecule," Current Pharmaceutical Design 17:871-876.
Park et al. (2004) "Lipids and Lipoproteins: Post-transcriptional Regulation of Low Density Lipoprotein Receptor Protein by Proprotein Convertase Subtilisin/Kexin Type 9a in Mouse Liver," J. Biol. Chem. 279: 50630-50638.
Partial European Search Report received in European Patent Application No. 16200305.7 dated Feb. 28, 2017.
Partial European Search Report received in European Patent Application No. 21185555.6 dated Dec. 17, 2021.

(56) References Cited

OTHER PUBLICATIONS

Patro et al., "Protein formulation and fill-finish operations," Biotechnol Annu Rev, 8:55-84, (2002). Abstract only.
Pearson (1994) "Using the FASTA program to search protein and DNA sequence databases," Computer Analysis of Sequence Data. 1994:307-331.
Pfizer Inc. (Nov. 3, 2012) "Safety and Tolerability of Multiple Doses of PF-04950615 (RN316) In Subjects With Hypercholesterolemia," Accessible on the Internet at URL:http://clinicaltrials.gov/ct2/show?term=rn316&rank=2.
Pijlman et al. (2010) "Evaluation of cholesterol lowering treatment of patients with familial hypercholesterolemia: a large cross-sectional study in The Netherlands," Atherosclerosis. 209:189-194.
Pordy et al. (May 2013) "Alirocumab, a fully human monoclonal antibody to proprotein convertase subtilisin/kexin type 9: therapeutic dosing in phase 3 studies," J Clin Lipidol. 7(3):279.
Post et al. (1999) "Acyl-Coenzyme A:Cholesterol Acyltransferase Inhibitor, Avasimibe, Stimulates Bile Acid Synthesis and Cholesterol 7a-Hydroxylase in Cultured Rat Hepatocytes and In Vitro in the Rat," Hepatology, 30(2):491-500.
Post et al. (2003) "Increased Fecal Bile Acid Excretion in Transgenic Mice With Elevated Expression of Human Phospholipid Transfer Protein," Arterioscler Thromb Vasc Biol., 23:892-897.
Powchik (Jul. 15, 2010) Regeneron: Investor Day. pp. 1-19.
Powell et al. (1998) "Compendium of Excipients for Parenteral Formulations," PDA Journal of Pharmaceutical Science and Technology. 52(5):238-311.
Praluent® (Alirocumab), Highlights of Prescribing Information, United States Food and Drug Administration, 48 Pages, 2015.
Presta (2006) "Engineering of Therapeutic Antibodies to Minimize Immunogenicity and Optimize Function", Advanced Drug Delivery Reviews, pp. 640-656.
Qiu et al. (2007) "Small antibody mimetics comprising two complementarity-determining regions and a framework region for tumor targeting," Nature Biotechnology. 25(8):921-929.
QSM, "Essential Medicines and Health Products", WHO Drug Information, vol. 26, No. 2, 4 Pages, 2012.
Rader et al. (1995) "The Low Density Lipoprotein Receptor Is Not Required for Normal Catabolismof Lp(a) in Humans," The Journal of Clinical Investigation. 95:1403-1408.
Rahilly-Tierney et al. (2009) "Low-Density Lipoprotein Reduction and Magnitude of Cardiovascular Risk Reduction," Prev. Cardiol. 12(2):80-87.
Ramanathan et al. (2013) "Role of alirocumab (proprotein convertase subtilisin/kexin type 9 antibody) on CD81 levels and hepatitis C virus entry into hepatocytes," Circulation. 128:A12052.
Rashid et al. (2005) "Decreased plasma cholesterol and hypersensitivity to statins in mice lacking Pcsk9," Proc. Natl. Acad. Sci. USA. 102(15):5374-5379.
Ray (Jan. 2015) "Alirocumab: an investigational treatment for hypercholesterolemia," Clin Lipidol. 10(1):9-12.
Ray et al. (2013) "Attainment of low-density lipoprotein cholesterol goals in patients at very high cardiovascular risk in the United Kingdom: results from a general practice population study," Value Health. 16(7):A513.
Ray, et al. (Dec. 13, 2016) "Reductions in Atherogenic Lipids and Major Cardiovascular Events: A Pooled Analysis of 10 Odyssey Trials Comparing Alirocumab With Control", Circulation, vol. 134, No. 24, pp. 1931-1943.
Reddy et al. (2000) "Elimination of Fc receptor-dependent effector functions of a modified IgG4 monoclonal antibody to human CD4," The Journal of Immunology. 164(4):1925-1933.
Redlich et al., "Inflammatory bone loss: pathogenesis and therapeutic intervention", Nat Rev Drug Discov., Mar. 2012, 11(3): 234-250.
Regeneron and Sanofi (Nov. 5, 2012) "IR Conference Call on PCSK9: SAR236553/REGN727 PCSK9 Antibody for Hypercholesterolemia Phase 3 odyssey Program Underway," Accessible on the Internet at URL: www.sanofi.com/Images/31341_2012-11-05_PCSK9_call.pdf. pp. 1-30. [Last Accessed on Sep. 5, 2017].
Regeneron Newsroom, Sanofi and Regeneron Announce Collaboration with American College of Cardiology for PCSK9 Inhibitor Clinical Program, Retrieved From <<https://newsroom.regeneron.com./news-releases/news-release-details/sanofi-and-regeneron-announce-collaboration-american-college>>, 2 Pages., Dec. 19, 2013.
Regeneron Pharmaceuticals (Nov. 5, 2012) "Sanofi and Regeneron Announce Patient Enrollment in Cardiovascular Outcome Trial with Antibody to PCSK9 for Hypercholesterolemia," Press Release. Acquire Media.
Regeneron Pharmaceuticals, Inc. (Jun. 12, 2014) "Sanofi and Regeneron announce new, detailed data from positive sarilumab phase 3 rheumatoid arthritis trial at EULAR," Press Release. Acquire Media.
Reichert et al. (Jan. 1, 2011) "Antibody-based therapeutics to watch in 2011," MAbs. 3:76-99.
Reineke (2004) "Antibody epitope mapping using arrays of synthetic peptides," In; Antibody Engineering. Humana Press. pp. 443-463.
Response to Third Party Oppositions corresponding to European Patent Application No. 12761864.3, dated Dec. 9, 2016.
Rey et al. (2014) "Randomized, partial blind study of the pharmacodynamics, pharmacokinetics and safety of multiple subcutaneous doses of alirocumab, a fully human monoclonal antibody to proprotein convertase subtilisin/kexin type 9, administered every 4 weeks alone or in combination with ezetimibe or fenofibrate in healthy subjects," J Am Coll Cardiol. 63(12 Suppl 1):A1375.
Reyes-Soffer et al. (2015) "Abstract 129: Effects of a proprotein convertase subtilisin/kexin type 9 inhibitor, alirocumab, on lipid and lipoprotein metabolism in normal subjects," Arterioscler, Thromb Vasc Biol. 35:A129.
Reyes-Soffer et al. (Jan. 23, 2017) "Effects of PCSK9 Inhibition with Alirocumab on Lipoprotein Metabolism in Healthy Humans," Circulation 135:352-362.
Rhainds et al. (Dec. 2012) "PCSK9 inhibition and LDL cholesterol lowering: The biology of an attractive therapeutic target and critical review of the latest clinical trials," Clinical Lipidology 7(6):621-640.
Robinson (2002) "Protein Deamidation," Proc. Natl. Acad. Sci. USA. 99(8):5283-5288.
Robinson et al. (2013) "Management of Familial Hypercholesterolemia: A Review of the Recommendations from the National Lipid Association Expert Panel on Familial Hypercholesterolemia," J. Manag. Care Pharm. 19(2):139-149.
Robinson et al. (2015) "Adverse events in patients with low-density lipoprotein cholesterol levels <25 or <15 mg/dL on at least two consecutive visits in fourteen randomized, controlled, clinical trials of alirocumab," J Am Coll Cardiol. 65(10_S):A1350.
Robinson et al. (Apr. 16, 2015) "Odyssey Long Term Investigators. Efficacy and Safety of Alirocumab in Reducing Lipids and Cardiovascular Events.," N Eng J Med. 372:1489-1499.
Robinson et al. (Aug. 31, 2014) "Long-term safety, tolerability and efficacy of alirocumab versus placebo in high cardiovascular risk patients: first results from the Odyssey Long Term study in 2,341 patients," Highlights Presented at ESC Congress Aug. 31, 2014, Barcelona Spain, Circulation. 130:2120.
Robinson et al. (Sep. 30, 2014) "Efficacy and safety of alirocumab as add-on therapy in high-cardiovascular-risk patients with hypercholesterolemia not adequately controlled with atorvastatin (20 or 40 mg) or rosuvastatin (10 or 20mg): design and rationale of the Odyssey Options studies," Clin Cardiol. 37(10):597-604.
Robinson, et al. (Apr. 2015) "Supplementary Appendix: Efficacy and Safety of Alirocumab in Reducing Lipids and Cardiovascular Events", New England Journal of Medicine, pp. 60-61.
Romagnuolo et al. (Mar. 16, 2015) "Lipoprotein(a) Catabolismis Regulated by Proprotein Convertase Subtilisin/Kexin Type 9 through the Low Density Lipoprotein Receptor," The Journal of Biological Chemistry. 290(18):11649-11662.
Rose-John, et al. (May 17, 2006) "Interleukin-6 Biology is Coordinated by Membrane-Bound and Soluble Receptors: Role in Inflammation and Cancer", Journal of Leukocyte Biology, vol. 80, No. 2, pp. 227-236.

(56) References Cited

OTHER PUBLICATIONS

Roth et al. (Apr. 2014) "A 24-week study of alirocumab monotherapy versus ezetimibe: The first phase 3 data of a proprotein convertase subtilisin/kexin type 9 inhibitor," J Am Coll Cardiol. 63(12_S):A1370.
Roth et al. (Jan. 2015) "Odyssey Mono: effect of alirocumab 75 mg subcutaneously every 2 weeks as monotherapy versus ezetimibe over 24 weeks," Future Cardiol. 11(1):27-37.
Roth et al. (Jul. 2, 2014) "Monotherapy with the PCSK9 inhibitor alirocumab versus ezetimibe in patients with hypercholesterolemia: Results of a 24 week, double-blind, randomized Phase 3 trial," Int J Cardiol. 176(1):55-61.
Roth et al. (Mar. 2014) "Alirocumab for hyperlipidemia: physiology of PCSK9 inhibition, pharmacodynamics and Phase I and II clinical trial results of a PCSK9 monoclonal antibody," Future Cardiology. 10(2):183-199.
Roth et al. (Mar. 27, 2012) "The effects of co-administering a monoclonal antibody to proprotein convertase subtilisin/kexin type 9 serine protease, REGN727/SAR236553, with 10 and 80 mg atorvastatin compared to 80 mg atorvastatin alone in patients with primary hypercholesterolemia (NCT: 01288469)," J Am Coll Cardiol. 59:E1620.
Roth et al. (May 2015) "Patient and physician perspectives on administration of the PCSK9 monoclonal antibody alirocumab, an injectable medication to lower LDL-C levels," J. Clin. Lipidol. 37(9):1945-1954.
Roth et al. (May 23-26, 2015) "Phase 3 Randomized Trial Evaluating Alirocumab Every Four Weeks Dosing as Add-on to Statin or as Monotherapy: Odyssey Choice I," International Symposium on Atherosclerosis, Abstract No. 254.
Roth et al. (Nov. 15, 2012) "Atorvastatin with or without an antibody to PCSK9 in primary hypercholesterolemia," N Engl J Med. 367(20):1891-1900.
Rudikoff, et al. (Mar. 1, 1982) "Single Amino Acid Substitution Altering Antigen-Binding Specificity", Proceedings of the National Academy of Sciences of the United States of America, vol. 79, pp. 1979-1983.
Sabatine et al., "Evolocumab and Clinical Outcomes in Patients with Cardiovascular Disease", NEJM, May 4, 2017, 376(18): 1713-1722.
Sabatine, et al. (Dec. 2017) "Cardiovascular Safety and Efficacy of The PCSK9 Inhibitor Evolocumab In Patients with and without Diabetes and The Effect of Evolocumab on Glycaemia and Risk of New-Onset Diabetes: A Prespecified Analysis of The Fourier Randomised Controlled Trial", The Lancet Diabetes & Endocrinology, vol. 5, No. 12, pp. 941-950.
Saeedi et al. (Mar. 31, 2016) "Lipoprotein (a), an independent cardiovascular risk marker," Clinical Diabetes and Endocrinology. 2:7. pp. 1-6.
Sahebkar et al. (Aug. 8, 2013) "New LDL-Cholesterol Lowering Therapies: Pharmacology, Clinical Trials, and Relevance to Acute Coronary Syndromes," Clinical Therapeutics. 35(8):1082-1098.
Sanofi "Sanofi and Regeneron Report Positive Top-line Results with Alirocumab from First Phase 3 Study of a PCSK9 Inhibitor for LDL Cholesterol Reduction", Retrieved From: <<https://investor.regeneron.com/news-releases/news-release-details/sanofi-and-regeneron-report-positive-top-line-results-alirocumab>>, 3 Pages. (Dec. 5, 2018).
Sanofi, Press Release, Online, Sankyo Co., Ltd., Retrieved From: <<https://www.sanofi.co.jp/-/media/Project/One-Sanofi-Web/Websites/Asia-Pacific/Sanofi-JP/Home/press-releases/PDF/2012/20121112.pdf>>, Nov. 12, 2012.
Sarkar et al. (2002) Rational cytokine design for increased lifetime and enhanced potency using pH-activated "histidine switching," Nature Biotechnology 20:908-913.
Scaviner et al. (1999) "Protein Displays of the Human Immunoglobulin Heavy, Kappa and Lambda Variable and Joining Regions," Exp. Clin. Immunogenet. 16:234-240.
Schäfer et al. (Mar. 14-16, 2011) "Cholesterol lowering effect of SAR236553/REGN727, a fully human PCSK9 blocking monoclonal antibody in male Syrian hamster," Presented as a poster at the Drugs Affecting Lipid Metabolism (DALM)—XVII International Symposium, Mar. 14-16, 2011, Doha, Qatar.
Schafer, et al., "Failure is an Option: Learning from Unsuccessful Proof-of-Concept Trials", Drug Discovery Today, vol. 13, Issues 21-22, pp. 913-916, Nov. 2008.
Schiel, et al., "Four Years' Treatment Efficacy of Patients with Severe Hyperlipidemia. Lipid Lowering Drugs versus LDL-Apheresis", The International Journal of Artificial Organs, vol. 18, No. 12, pp. 786-793. (1995).
Schubert-Zsilavecz, et al., Better Blood Sugar Control In Diabetics. Insulin Glargin—A Long-Acting Insulin Analogue, Pharmazie in Unserer Zeit, vol. 30, No. 2 (English Translation), pp. 125-130, Jan. 2001.
Schwartz et al. (Aug. 7, 2014) "Effect of alirocumab, a monoclonal antibody to pcsk9, on long-term cardiovascular outcomes following acute coronary syndromes: Rationale and design of the odyssey outcomes trial" Am Heart J. 168(5):682-689.
Scott et al., "PCSK9 Inhibitors: Wearing FH Patients off Apheresis", MD Magazine, 2 Pages. (Aug. 29, 2016).
Sefton (1986) "Implantable Pumps," Critical Reviews in Biomedical Engineering. 14(3):201-240.
Seidah et al. (2003) "The secretory proprotein convertase neural apoptosis-regulated convertase 1 (NARC-1): liver regeneration and neuronal differentiation," Proc. Natl. Acad. Sci. USA. 100(3):928-933.
Shao (Apr. 26, 2014) "New Therapies for Lowering LDL-C: Targeting PCSK9," Abstract of oral presentation at the Sino-American Pharmaceutical Professionals Association—2014 Scientific Symposium, Apr. 26, 2014, New Jersey, USA.
Sharrett, et al., "Coronary Heart Disease Prediction From Lipoprotein Cholesterol Levels, Triglycerides, Lipoprotein(A), Apolipoproteins A-I and B, And HDL Density Subfractions", Circulation, vol. 104, No. 10, pp. 1108-1113. (2001).
Shields et al. (2002) "Lack of fucose on human IgG1 N-linked oligosaccharide improves binding to human FcγRIII and antibody-dependent cellular toxicity," Journal of Biological Chemistry. 277(30):26733-26740.
Shoji et al. (1998) "Intermediate-Density Lipoprotein as an Independent Risk Factor for Aortic Atherosclerosis in Hemodialysis Patients," J. Am. Soc. Nephrol. 9:1277-1284.
Sniderman, et al. (May 20, 2014) "The severe hypercholesterolemia phenotype: clinical diagnosis, management, and emerging therapies", Journal of the American College of Cardiology, vol. 3, No. 19, pp. 1935-1947.
Soutar (2011) "Unexpected Roles for PCSK9 in Lipid Metabolism," Current Opinion in Lipodology. 22:192-196.
Stahl (Jul. 15, 2010) "Early Clinical Development #1 REGN727: Anti-PCSK9", Regeneron Pharmaceuticals, pp. 1-21.
Stary et al. (1995) "A Definition of Advanced Types of Atherosclerotic Lesions and a Histological Classification of Atherosclerosis," Arterioscler Thromb Vase Biol., vol. 15, 47 pages.
Steen et al. (2014) "Attainment of Lipid Levels in Patients at High Cardiovascular Risk: Results from a U.S. Managed Care Population Study," Circulation. 130:A19949.
Steen et al. (Mar. 2015) "Cardiovascular Event Rates in a High-Risk Managed Care Population in the United States," J Am Coll Cardiol. 65(10_S):A1647.
Stein et al. (Jul. 2012) "Effect of a monoclonal antibody to PCSK9 on LDL cholesterol," Obstetrical and Gynecological Survey. 67(7):413-414.
Stein et al. (Mar. 2013) "Potential of proprotein Convertase Subtilisin/Kexin Type 9 Based Therapeutics," Current Atherosclerosis Reports. 15(310) pp. 1-14.
Stein et al. (Mar. 22, 2012) "Effect of a monoclonal antibody to PCSK9 on LDL cholesterol," N Engl J Med 366(12):1108-1118.
Stein et al. (Mar. 22, 2012) Clinical Study Protocol for "Effect of a monoclonal antibody to PCSK9 on LDL cholesterol," N Engl J Med 366(12):1108-1118.
Stein et al. (Mar. 22, 2012) Supplementary Appendix to "Effect of a monoclonal antibody to PCSK9 on LDL cholesterol," N Engl J Med 366(12):1108-1118.

(56) References Cited

OTHER PUBLICATIONS

Stein et al. (Mar. 30, 2014) "One year open-label treatment with alirocumab 150 mg every two weeks in heterozygous familial hypercholesterolemic patients," J Am Coll Cardiol. 63(12 Suppl 1):A1371.
Stein et al. (May 25-28, 2012) "Safety and efficacy of a monoclonal antibody to PCSK9, REGN727/SAR236553, in statin-treated heterozygous familial hypercholesterolemia patients," Presented as an oral presentation at the 80th European Atherosclerosis Society (EAS) Congress, May 25-28, 2012, Milan, Italy. Abstract 1398.
Stein et al. (May 26, 2012) "Effect of a monoclonal antibody to PCSK9, REGN727/SAR236553, to reduce low-density lipoprotein cholesterol in patients with heterozygous familial hypercholesterolaemia on stable statin dose with or without ezetimibe therapy: a phase 2 randomised controlled trial," Lancet. 380(9836):29-36.
Steinberg et al. (2009) "Inhibition of PCSK9: A powerful weapon for achieving ideal LDL cholesterol levels," Proceedings of the National Academy of Sciences USA. 106(24):9546-9547.
Stone et al. (2014) "2013 ACC/AHA Guideline on the Treatment of Blood Cholesterol to Reduce Atherosclerotic Cardiovascular Risk in Adults," Circulation. 129:S1-S48.
Stroes et al. (Jun. 17, 2014) "Anti-PCSK9 Antibody Effectively Lowers Cholesterol in Patients With Statin Intolerance," J. Am. Coll. Cardiol. 63(23):2541-2548.
Stroes et al. (Mar. 17, 2015) "Efficacy and safety of different dosing regimens of alirocumab (starting doses of 75 mg every two weeks and 150 mg every four weeks) versus placebo in patients with hypercholesterolemia not treated using statins: the Odyssey Choice II study," J Am Coll Cardiol. 65(10_S):A1370.
Sullivan et al. (Dec. 19, 2012) "Effect of a Monoclonal Antibody to PCSK9 on Low-Density Lipoprotein Cholesterol Levels in Statin-Intolerant Patients," JAMA. 308(23):2497-2506.
Swergold et al. (2010) "Safety, lipid, and lipoprotein effects of REGN727/SAR236553, a fully human proprotein convertase subtilisin kexin 9 (PCSK9) neutralizing monoclonal antibody administered intravenously to healthy volunteers," Circulation. 122:A23251.
Swergold et al. (2011) "Inhibition of proprotein convertase subtilisin/kexin type 9 with a monoclonal antibody REGN727/SAR236553, effectively reduces low-density-lipoprotein cholesterol, as mono or add-on therapy in heterozygous familial and non-familial hypercholesterolemia," Circulation 124:A16265.
Swergold et al. (2011) "REGN727/SAR236553, a fully human proprotein convertase subtilisin kexin 9 (PCSK9) monoclonal antibody: effects on safety and lipid and lipoprotein profiles when administered subcutaneously," J Am Coll Cardiol. 57(14):E2023.
Swergold et al. (2011) "REGN727/SAR236553, a fully-human monoclonal antibody to proprotein convertase subtilisin kexin 9 (PCSK9), decreases ApoB and non-HDL-C when administered intravenously to healthy volunteers," J Clin Lipidol. 5(3):219. Abstract 135.
Swergold et al. (Oct. 22-26, 2013) "Identification and characterization of patients with autosomal dominant hypercholesterolemia caused by gain-of-function mutations in proprotein convertase subtilisin/kexin type 9 and comparison with patients with Familial Hypercholesterolemia (FH) and Familial Defective apolipoprotein B (Fdb)," Abstract of a poster presentation at the American Society of Human Genetics (ASHG), Oct. 22-26, 2013, Boston, USA.
Tavori et al. (Oct. 11, 2013) "Loss of Plasma Proprotein Convertase Subtilisin/Kevin 9 (PCSK9) After Lipoprotein Apheresis," Circulation Research. 113(12):1290-1295.
Taylor et al. (1992) "A transgenic mouse that expresses a diversity of human sequence heavy and light chain immunoglobulins," Nucleic Acids Research, 20(23):6287-6295.
Teramoto et al. (2014) "Efficacy and safety of alirocumab in Japanese patients with hypercholesterolemia on stable statin therapy: first data with the 75 mg every two weeks dose," Circulation. 130:A13651.
The HPS2-Thrive Collaborative GR (Jul. 2014) "Effects of Extended-Release Niacin with Laropiprant in High-Risk Patients", The New England Journal of Medicine, vol. 371, No. 3, pp. 203-212.
Third Party Observations corresponding to European Patent Application No. 12761864.3, dated Feb. 24, 2016.
Third Party Observations corresponding to European Patent Application No. 12761864.3, dated Jul. 7, 2017.
Third Party Observations received for European Patent Application No. 12761864.3, dated Feb. 24, 2016.
Third Party Opposition received for Colombian Patent Application No. 13203072, dated Dec. 13, 2013.
Third Party Opposition received for Guatemalan Patent Application No. A-2013-0186, dated Sep. 18, 2014.
Thomas, et al., "Clinical Development Success Rates 2006-2015", BIO Industry Analysis, 28 Pages, Jun. 2016.
Thompsen et al. (2006) "A systematic review of LDL apheresis in the treatment of cardiovascular disease," Atherosclerosis. 189:31-38.
Thygesen et al. (Oct. 16, 2012) "Third Universal Definition of Myocardial Infarction", Journal of the American College of Cardiology, vol. 60, No. 16, pp. 1581-1598.
Timms et al. (2004) "A mutation in PCSK9 causing autosomal-dominant hypercholesterolemia in a Utah pedigree," Human Genetics 114(4):349-353.
Tiwari et al. (2011) "Statins therapy: a review on conventional and novel formulation approaches," Journal of Pharmacy and Pharmacology. 83(8):983-998.
Todo et al. (2004) "Detailed analysis of serum lipids and lipoproteins from Japanese type III hyperlipoproteinemia with apolipoprotein E2/2 phenotype," Clin. Chim. Acta. 348:35-40.
Toth et al. (2013) "Alirocumab, a proprotein convertase subtilisin/kexin type 9 monoclonal antibody, reduces cholesterol concentrations of all serum low-density lipoprotein cholesterol fractions," Circulation. 128:A17313.
Toth et al. (2013) "Alirocumab, a proprotein convertase subtilisin/kexin type 9 monoclonal antibody, reduces cholesterol concentrations of serum remnant lipoprotein fractions, very low-density lipoproteins and triglycerides," Circulation. 128:A17492.
Toth et al. (2014) "Proprotein convertase subtilisin/kexin 9 monoclonal antibody therapy significantly reduces apoprotein CII and CIII levels in serum," Atherosclerosis. 235(2):e107-e108. Abstract EAS-0750.
Tsimikas et al. (Jul. 22, 2015) "Antisense therapy targeting apolipoprotein(a): A randomised double-blind, placebo-controlled phase 1 study," Lancet. 386:1472-1483.
Tutt et al. (1991) "Trispecific F (ab') 3 derivatives that use cooperative signaling via the TCR/CD3 complex and CD2 to activate and redirect resting cytotoxic T cells," The Journal of Immunology. 147(1):60-69.
Uchiyama, et al. (2008) "Tocilizumab, A Humanized Anti-Interleukin-6 Receptor Antibody, Ameliorates Joint Swelling in Established Monkey Collagen-Induced Arthritis", Biological and Pharmaceutical Bulletin, vol. 31, No. 6, pp. 1159-1163.
Vajdos et al. (2002) "Comprehensive functional maps of the antigen-binding site of an anti-ErbB2 antibody obtained with shotgun scanning mutagenesis," Journal of Molecular Biology. 320(2):415-428.
Van Bruggen et al., "Evolocumab's Long-Term Mortality Risk Unlear Due to Shortened Follow-Up of Fourier", Amer Journ Cardio Drugs, 2022, 22: 5-8.
Van Der Hoorn et al. (2014) "Alirocumab, a monoclonal antibody to PCSK-9, dose-dependently decreases atherosclerosis, improves plaque stability and shows additive effects with atorvastatin in APOE*3Leiden.CETP mice," Atherosclerosis. 235(2):e19. Abstract WS16.
Van Wissen et al. (2003) "Long term statin treatment reduces lipoprotein(a) concentrations in heterozygous familial hypercholesterolaemia," Heart. 89(8):893-896.
Varbo et al. (2013) "Remnant Cholesterol as a Casual Risk Factor for Ischemic Heart Disease" Journal of the American College of Cardiology 61(4):427-436.
Varrett et al. (1999) "A third major locus for autosomal dominant hypercholesterolemia Maps to 1p34.1-p32," Am. J. Hum. Genet. 64:1378-1387.
Verschuren et al. (2005) "Effect of Low Dose Atorvastatin Versus Diet-Induced Cholesterol Lowering on Atherosclerotic Lesion Pro-

(56) References Cited

OTHER PUBLICATIONS gression and Inflammation in Apolipoprotein E*3-Leiden Transgenic Mice," Arterioscler Thromb Vasc. Biol., 25:161-167.

Villa, et al., "Ldl-C Lowering Efficacy of Evolocumab (Amg 145) Could Reduce Apheresis in Patients at High Risk for Cardiovascular Events in Germany", Value in Health, vol. 17, No. 7, pp. A504-A505. (2014).

Voet, et al., "Fundamentals of Biochemistry", Von Hoffmann Press, Inc., pp. 260-264. (1999).

Voet, et al., "Fundamentals of Biochemistry", Von Hoffman Press, Inc., pp. 80-81, 1999.

Walji (2013) "Lipoprotein Apheresis for the Treatment of Familial Hypercholesterolemia," Clinical Lipidology. 8(5):573-586.

Wang (1999) "Instability, stabilization, and formulation of liquid protein pharmaceuticals," International J. Pharmaceutics 185(2):129-188.

Wang (2009) "Fixed dosing versus body size-based dosing of monoclonal antibodies in adult clinical trials," J Clin Pharmacol. 49(9):1012-1024.

Wang et al. (2007) "Antibody Structure, Instability, and Formulation," Journal of Pharmaceutical Sciences. 96(1):1-26.

Ward et al. (1989) "Binding activities of a repertoire of single immunoglobulin variable domains secreted from *Escherichia coli*," Nature. 341(6242):544-546.

Warnick et al. (2008) "Standardization of Measurements for Cholesterol, Triglycerides, and Major Lipoproteins," Lab Med. 39(8):481-490.

Watanabe et al. (2009) "Optimizing pH response of affinity between protein G and IgG Fc," J. Biological Chemistry 284(18):12373-12383.

Webb et al. (2002) "A new mechanism for decreasing aggregation of Recombinant Human Interferon-Y by a Surfactant: Slowed Dissolution of Lyophilized Formulations in a Solution Containing 0.03% Polysorbate 20," J. Pharm. Sci. 91(2):543-558.

Westerterp et al. (2006) "Cholesteryl Ester Transfer Protein Decreases High-Density Lipoprotein and Severely Aggravates Atherosclerosis in APOE*3-Leiden Mice," Arterioscler Thromb. Vasc. Biol. Nov. 2006; 26(11):2552-2559.

Whalley et al. (1997) "Quality of life in rheumatoid arthritis," Br. J. Rheumatol. 36:884-888.

WHO (Jan. 1, 2012) "International Nonproprietary Names for Pharmaceutical Substances (INN)", World Health Organization, Drug Information, vol. 26, No. 4, pp. 401-471.

Winter et al. (1993) "Humanized Antibodies," Immunology Today 14(6):243-246.

Wong et al. (May 1-4, 2014) "Residual Dyslipidemia According to LDL-C, non-HDL-C and Apolipoprotein B by Cardiovascular Risk Category in Statin Treated US Adults, "J Clin Lipidol. 8:323-324. Presented as a poster presentation at the National Lipid Association Scientific Sessions, May 1-4, 2014, Orlando, Florida, USA.

Wu et al. (1987) "Receptor-mediated in vitro gene transformation by a soluble DNA carrier system," Journal of Biological Chemistry. 262(10):4429-4432.

Yamashita, "PCSK9 (Proprotein Convertase subtilisin/kexin Type 9)", Prevention of Arteriosclerosis, vol. 11, No. 4, pp. 101-105, 2013.

Yoshimura, et al. (2009) "Comprehensive Analysis of Inflammatory Immune Mediators in Vitreoretinal Diseases", PLoS One, vol. 4, No. 12, pp. 1-9.

Zhang, et al. (Apr. 11, 2018) "Usefulness of Alirocumab and Evolocumab for the Treatment of Patients with Diabetic Dyslipidemia", Proceedings, vol. 31, No. 2, pp. 180-184.

Zimmerman, "How Do PCSK9 Inhibitors Stack Up to Statins for Low-Density Lipoprotein Cholesterol Control?", American Health Drug Benefits, vol. 8, No. 8, pp. 436-442, Nov. 2015.

U.S. Appl. No. 14/896,196 2016/0115246 U.S. Pat. No. 10,494,442, filed Dec. 4, 2016 Apr. 28, 2016 Dec. 3, 2019, William J. Sasiela, Methods for Inhibiting Atherosclerosis by Administering an Inhibitor of PCSK9.

U.S. Appl. No. 16/505,074 2020/0071422 U.S. Pat. No. 10,995,150, filed Jul. 8, 2019 Mar. 5, 2020 May 4, 2021, William J. Sasiela, Methods for Inhibiting Atherosclerosis by Administering an Inhibitor of PCSK9.

U.S. Appl. No. 14/511,975 2015/0140002, filed Oct. 10, 2014 May 21, 2015, Marie Baccara-Dinet, Use of a PCSK9 Inhibitor to Treat Hyperlipidemia.

U.S. Appl. No. 13/982,381 2014/0178402 U.S. Pat. No. 9,682,013, filed Jul. 29, 2013 Jun. 26, 2014 Jun. 20, 2017, Corinne Hanotin, Pharmaceutical Compositions Compromising Human Antibodies to PCSK9.

U.S. Appl. No. 13/982,373 2014/0154262 U.S. Pat. No. 8,561,155, filed Jul. 29, 2013 Jun. 5, 2014 Feb. 7, 2017 Corinne Hanotin, Method of Reducing Cholesterol Levels Using a Human Anti-PCSK9 Antibody.

U.S. Appl. No. 16/365,317 2019/0343719 U.S. Pat. No. 11,246,925, filed Mar. 26, 2019 Nov. 14, 2019 Feb. 15, 2022, Corinne Hanotin, Human Antibodies to PCSK9 for Use In Methods of Treating Particular Groups of Subjects.

U.S. Appl. No. 17/560,402 2022/0218823, filed Dec. 23, 2021 Jul. 14, 2022, Corinne Hanotin, Human Antibodies to PCSK9 for Use In Methods of Treating Particular Groups of Subjects.

U.S. Appl. No. 18/790,032, filed Jul. 31, 2024, Corinne Hanotin, Human Antibodies to PCSK9 for Use In Methods of Treating Particular Groups of Subjects.

U.S. Appl. No. 14/539,199 2015/0152191 U.S. Pat. No. 10,428,157, filed Nov. 12, 2014 Jun. 4, 2015 Oct. 1, 2018, Marie Baccara-Dinet, Dosing Regimens for Use With PCSK9 Inhibitors.

U.S. Appl. No. 16/415,837 2020/0024364, filed May 17, 2019 Jan. 23, 2020, Marie Baccara-Dinet, Dosing Regimens for Use With PCSK9 Inhibitors.

U.S. Appl. No. 18/301,638 2023/0406957, filed Apr. 17, 2023 Dec. 21, 2023, Marie Baccara-Dinet, Dosing Regimens for Use With PCSK9 Inhibitors.

U.S. Appl. No. 14/801,384 2016/0137745 U.S. Pat. No. 10,544,232, filed Jul. 16, 2015 May 19, 2016 Jan. 28, 2020, Marie Baccara-Dinet, Methods for Treating Patients With Heterozygous Familial Hypercholesterolemia (heFH) With an Anti-PCSK9 Antibody.

U.S. Appl. No. 16/707,492 2020/0216565 U.S. Pat. No. 11,306,155, filed Dec. 9, 2019, Jul. 9, 2020 Apr. 19, 2022, Marie Baccara-Dinet, Methods for Treating Patients With Heterozygous Familial Hypercholesterolemia (heFH) With an Anti-PCSK9 Antibody.

U.S. Appl. No. 17/693,837 2022/0315669, filed Mar. 14, 2022 Oct. 6, 2022, Marie Baccara-Dinet, Methods for Treating Patients With Heterozygous Familial Hypercholesterolemia (hdFH) With an Anti-PCSK9 Antibody.

U.S. Appl. No. 18/786,917, filed Jul. 29, 2024, Marie Baccara-Dinet, Methods for Treating Patients With Heterozygous Familial Hypercholesterolemia (heFH) With an Anti-PCSK9 Antibody.

U.S. Appl. No. 14/657,192 2015/0284473, filed Mar. 13, 2015 Oct. 8, 2015, Laurence Bessac, Methods for Reducing Cardiovascular Risk.

U.S. Appl. No. 17/504,921 2022/0144969, filed Oct. 19, 2021 May 12, 2022, Laurence Bessac, Methods for Reducing Cardiovascular Risk.

U.S. Appl. No. 12/637,942 2010/0166768 U.S. Pat. No. 8,062,640, filed Dec. 15, 2009 Jul. 1, 2010 Nov. 22, 2011, Mark W. Sleeman, High Affinity Human Antibodies to PCSK9.

U.S. Appl. No. 13/095,234, 2011/0256148 U.S. Pat. No. 8,357,371, filed Apr. 27, 2011 Oct. 20, 2011 Jan. 22, 2013, Mark W. Sleeman, Methods for Treating Hypercholesterolemia Using Antibodies to PCSK9.

U.S. Appl. No. 14/100,992 2014/0099312 U.S. Pat. No. 9,724,411, filed Dec. 9, 2013 Apr. 10, 2014 Aug. 8, 2017, Mark W. Sleeman, Methods for Treating Hypercholesterolemia and Reducing LDL-C Using Antibodies to PCSK9.

U.S. Appl. No. 12/949,846 2011/00659002 U.S. Pat. No. 8,501,184, filed Nov. 19, 2010 Mar. 17, 2011 Aug. 6, 2013, Mark W. Sleeman, High Affinity Human Antibodies to PCSK9.

U.S. Appl. No. 14/737,488 2015/0284474 U.S. Pat. No. 9,550,837, filed Jun. 12, 2015 Oct. 8, 2015 Jan. 24, 2017, Mark W. Sleeman, Therapeutic Uses of Anti-PSCK9.

(56) References Cited

OTHER PUBLICATIONS

U.S. Appl. No. 15/377,364 2017/0096496 U.S. Pat. No. 10,023,654, filed Dec. 13, 2016 Apr. 6, 2017 Jul. 17, 2018, Mark W. Sleeman, Anti-PCSK9 Antibodies.
U.S. Appl. No. 15/996,773 2019/0135941 U.S. Pat. No. 10,941,210, filed Jun. 4, 2018 May 9, 2019 Mar. 9, 2021, Mark W. Sleeman, Anti-PCSK9 Antibodies.
U.S. Appl. No. 17/160,634 2021/0253735, filed Jan. 28, 2021 Aug. 19, 2021, Mark W. Sleeman, Anti-PCSK9 Antibodies.
U.S. Appl. No. 13/559,862 2013/0189277 U.S. Pat. No. 8,795,669, filed Jul. 27, 2012 Jul. 25, 2013 Aug. 5, 2014, Scott M. Walsh, Stabilized Formulations Containing Anti-PCSK9 Antibodies.
U.S. Appl. No. 14/319,730 2014/0341928 U.S. Pat. No. 9,193,801, filed Jun. 30, 2014 Nov. 20, 2014 Nov. 24, 2015, Scott M. Walsh, Stabilized Formulations Containing Anti-PCSK9 Antibodies.
U.S. Appl. No. 15/603,732 2018/0044436 U.S. Pat. No. 10,472,725, filed May 24, 2017 Feb. 15, 2018 Nov. 12, 2019, Scott M. Walsh, Stabilized Formulations Containing Anti-PCSK9 Antibodies.
U.S. Appl. No. 16/384,298 2019/0284301 U.S. Pat. No. 10,752,701, filed Apr. 15, 2019 Sep. 19, 2019 Aug. 25, 2020, Scott M. Walsh, Stabilized Formulations Containing Anti-PCSK9 Antibodies.
U.S. Appl. No. 16/930,595 2021/0054100 U.S. Pat. No. 11,673,967, filed Jul. 16, 2020 Feb. 25, 2021 Jun. 13, 2023, Scott M. Walsh, Stabilized Formulations Containing Anti-PCSK9 Antibodies.
U.S. Appl. No. 18/308,769 2023/0406959, filed Apr. 28, 2023 Dec. 21, 2023, Scott M. Walsh, Stabilized Formulations Containing Anti-PCSK9 Antibodies.
U.S. Appl. No. 13/611,405 2013/0243784 U.S. Pat. No. 10,076,571, filed Sep. 12, 2012 Sep. 19, 2013 Sep. 18, 2018, Gary Swergold, Methods for Reducing Lipoprotien(a) Levels by Administering an Inhibitor of Proprotein Convertase Subtilisin Kexin-9 (PCSK9).
U.S. Appl. No. 16/053,448 2018/0333490 U.S. Pat. No. 11,116,839, filed Aug. 2, 2018 Nov. 22, 2018 Sep. 14, 2021, Gary Swergold, Methods for Reducing Lipoprotein(a) Levels by Administering an Inhibitor of Proprotein Convertase Subtilisin Kexin-9 (PCSK9).
U.S. Appl. No. 14/290,544 2014/00356371 U.S. Pat. No. 10,111,953, filed May 29, 2014 Dec. 4, 2014 Oct. 30, 2018, Gary Swergold, Methods for reducing Remnant Cholesterol and Other Lipoprotein Fractions by Administering an Inhibitor of Proprotein Convertase Subtilisin Kexin-9 (PCSK9).
U.S. Appl. No. 16/662,313 2020/0255544, filed Oct. 24, 2019 Aug. 13, 2020, Corinne Hanotin, Methods for Treating High Cardiovascular Risk Patients With Hypercholesterolemia.
U.S. Appl. No. 16/004,126 2019/0031774, filed Jun. 8, 2018 Jan. 31, 2019, Maja Bujas-Bobanovic, Methods for Treating Hyperlipidemia In Diabetic Patients by Administering a PCSK9 Inhibitor.
U.S. Appl. No. 16/294,635 2019/0292273, filed Mar. 6, 2019 Sep. 26, 2019, Corinne Hanotin, Methods for Reducing Cardiovascular Risk.
U.S. Appl. No. 15/238,890 2017/0049886 U.S. Pat. No. 10,772,956, filed Aug. 17, 2016 Feb. 23, 2017 Sep. 15, 2020, Robert C. Pordy, Methods fro Reducing or Eliminating the Need for Lipoprotein Apheresis In Patients With Hyperlipidemia by Administering Alirocumab.
U.S. Appl. No. 16/991,269 2021/0100900 U.S. Pat. No. 11,904,017, filed Aug. 12, 2020 Apr. 8, 2021 Feb. 20, 2024, Robert C. Pordy, Methods for Reducing or Eliminating The Need for Lipoprotein Apheresis In Patients With Hyperlipidemia by Administering Alicrocumab.
U.S. Appl. No. 18/407,331 2024/0261400, filed Jan. 8, 2024 Aug. 8, 2024, Robert C. Pordy, Methods for Reducing or Eliminating The Need for Lipoprotein Apheresis In Patients With Hyperlipidemia by Administering Alirocumab.
Alexander, et al., "Coronary-Artery Bypass Grafting", The New England Journal of Medicine, May 2016, vol. 374, No. 20, pp. 1954-1964.
American College of Cardiology, "Alirocumab Reduces Cardiovascular Events after Acute Coronary Syndrome", Mar. 10, 2018.
Chen et al., "A Common PCSK9Haplotype, Encompassing the E670G Coding Single Nucleotide Polymorphism, Is a Novel Genetic Marker for Plasma Low-Density Lipoprotein Cholesterol Levels and Severity of Coronary Atherosclerosis", J. of the N. American College of Cardiol., May 17, 2005, 45(10): 1611-1619.
ClinicalTrials.gov, (Apr. 10, 2012) "Open-Label Extension of Study R7247-CL-1003 to Evaluate the Long-Term Safety of REGN727 (SAR236553) in Patients with Primary Hypercholesterolemia", ClinicalTrials.gov Identifier: NCT01576484, Retrieved from: <<https://clinicaltrials.gov/study/NCT01576484?term=NCT01576484&rank=1&tab=hi story&a=1#version-content-panel>>.
ClinicalTrials.gov, (Aug. 10, 2012) "Odyssey Outcomes: Evaluation of Cardiovascular Outcomes After an Acute Coronary Syndrome During Treatment with Alirocumab", Version 1, ClinicalTrials.gov Identifier: NCT01663402.
Dufour et al., "Open-label therapy with alirocumab in patients with heterozygous familial hypercholesterolemia: Results from three years of treatment", International Journal of Cardiology, Feb. 2017, 228: 754-760.
Extended European Search Report for European Patent Application No. 24160083.2, dated Sep. 25, 2024.
Jacobson, "Lipoprotein(a), Cardiovascular Disease, and Contemporary Management", Mayo Clinic Proceedings, Nov. 2013, 88(11): 1294-1311.
Lupattelli et al., "Lipoprotein(a) in peripheral arterial occlusive disease", Vasa, 1994, 23(4): 321-324.
Marcucci et al., "Increased plasma levels of lipoprotein(a) and the risk of idiopathic and recurrent venous thromboembolism", Clinical Study, Dec. 2003, 115(8): 601-605.
Murata et al., "Plasma lipoprotein(a) levels are high in patients with central retinal artery occlusion", Regular Article, Aug. 15, 1998, 91(4): 169-174.
Nenseter et al., "Lipoprotein(a) levels in coronary heart disease-susceptible and -resistant patients with familial hypercholesterolemia", Atherosclerosis, Jun. 2011, 216(2): 426-432.
Partial International Search Report received for PCT Patent Application No. PCT/US2014/040163, mailed on Nov. 6, 2014, 6 pages.
Reiner et al., "ESC/EAS Guidelines for the management of dyslipidaemias: The Task Force for the management of dyslipidaemias of the European Society of Cardiology (ESC) and the European Atherosclerosis Society (EAS)", European Heart Journal, Jul. 2011, 32(14): 1769-1818.
Rossebo et al., "Intensive Lipid Lowering with Simvastatin and Ezetimibe in Aortic Stenosis", NEJM, Sep. 25, 2008, 359(13): 1343-1356.
Standards of Medical Care in Diabetes—2012, Diabetes Care, Jan. 1, 2012, 35(Suppl. 1): S11-S63.
Tsimikas S., "A Test in Context: Lipoprotein(a): Diagnosis, Prognosis, Controversies, and Emerging Therapies", JACC, Feb. 14, 2017, 69(6): 692-711.
Willeit et al., "Evidence of a Prominent Role in the Evolution of Advanced Carotid Plaques: The Bruneck Study", Stroke, Sep. 1995, 26: 1582-1587.

* cited by examiner

```
H1H316P VH (SEQ ID NO:90)    EVQLVESGGGLVQPGGSLRLSCAASGFTFNNYAMNWVRQAPGKG
H1M300N VH (SEQ ID NO:218)   EMQLVESGGGLVQPGGSLRLSCAASGFTFSSHWMKWVRQAPGKG
                                                     |_____|
                                                        CDR1

H1H316P VH (SEQ ID NO:90)    LDWVSTISGSGGTTNYADSVKGRFIISRDSSKHTLYLQMNSLRA
H1M300N VH (SEQ ID NO:218)   LEWVANINQDGSEKYYVVDSVKGRFTISRDNAKNSLFLQMNSLRA
                                  |_____|
                                      CDR2

H1H316P VH (SEQ ID NO:90)    EDTAVYYCAKDSNWGNFDL------WGRGTLVTVSS
H1M300N VH (SEQ ID NO:218)   EDTAVYYCARDIVLMVYDMDYYYYGMDVWGQGTTVTVSS
                                     |_____|
                                             CDR3

H1H316P VK (SEQ ID NO:92)    DIVMTQSPDSLAVSLGERATINCKSSQSVLYRSNNRNFLGWYQQ
H1M300N VK (SEQ ID NO:226)   DIVMTQSPLSLPVTPGEPASISCRSSQSLLHSNGNNY-LDWYLQ
                                                       |_____|
                                                            CDR1

H1H316P VK (SEQ ID NO:92)    KPGQPPNLLIYWASTRESGVPDRFSGSGSGTDFTLTISSLQAED
H1M300N VK (SEQ ID NO:226)   KPGQSPQLLIYLGSNRASGVPDRFSGSGSGTDFTLKISRVEAED
                                       |___|
                                       CDR2

H1H316P VK (SEQ ID NO:92)    VAVYYCQQYYTTPYTFGQGTKLEIK
H1M300N VK (SEQ ID NO:226)   VGVYYCMQTLQTPLTFGGGTKVEIK
                                   |_____|
                                       CDR3
```

Fig. 1

SEQUENCE LISTING

```
Sequence total quantity: 763
SEQ ID NO: 1                moltype = DNA   length = 351
FEATURE                     Location/Qualifiers
misc_feature                1..351
                            note = Synthetic
source                      1..351
                            mol_type = other DNA
                            organism = synthetic construct
SEQUENCE: 1
caggtccagc tggtgcagtc tggggggagc ttggtacagc ctggggggtc cctgagactc    60
tcctgtgcag cctctggatt tactctaagt agttacgaca tgcactgggt ccgccaatct   120
acaggaaaag gtctggagtg ggtctcagct attggttcta ccgtgacaca atactatcca   180
ggctccgtga aggccgatt caccatcacc agagaaaaag ccaagaactc cgtgtatctt   240
caaatgaaca gcctgagagc cggggacacg gctgtgtatt actgtgtaag agaggggtgg   300
gaggtacccT ttgactactg gggccaggga accctggtca ctgtctcctc a            351

SEQ ID NO: 2                moltype = AA    length = 117
FEATURE                     Location/Qualifiers
REGION                      1..117
                            note = Synthetic
source                      1..117
                            mol_type = protein
                            organism = synthetic construct
SEQUENCE: 2
QVQLVQSGGG LVQPGGSLRL SCAASGFTLS SYDMHWVRQS TGKGLEWVSA IGSTGDTYYP    60
GSVKGRFTIT REKAKNSVYL QMNSLRAGDT AVYYCVREGW EVPFDYWGQG TLVTVSS      117

SEQ ID NO: 3                moltype = DNA   length = 24
FEATURE                     Location/Qualifiers
misc_feature                1..24
                            note = Synthetic
source                      1..24
                            mol_type = other DNA
                            organism = synthetic construct
SEQUENCE: 3
ggatttactc taagtagtta cgac                                            24

SEQ ID NO: 4                moltype = AA    length = 8
FEATURE                     Location/Qualifiers
REGION                      1..8
                            note = Synthetic
source                      1..8
                            mol_type = protein
                            organism = synthetic construct
SEQUENCE: 4
GFTLSSYD                                                              8

SEQ ID NO: 5                moltype = DNA   length = 21
FEATURE                     Location/Qualifiers
misc_feature                1..21
                            note = Synthetic
source                      1..21
                            mol_type = other DNA
                            organism = synthetic construct
SEQUENCE: 5
attggttcta ccgtgacaca a                                               21

SEQ ID NO: 6                moltype = AA    length = 7
FEATURE                     Location/Qualifiers
REGION                      1..7
                            note = Synthetic
source                      1..7
                            mol_type = protein
                            organism = synthetic construct
SEQUENCE: 6
IGSTGDT                                                               7

SEQ ID NO: 7                moltype = DNA   length = 33
FEATURE                     Location/Qualifiers
misc_feature                1..33
                            note = Synthetic
source                      1..33
                            mol_type = other DNA
                            organism = synthetic construct
SEQUENCE: 7
gtaagagagg ggtgggaggt acccTttgac tac                                  33

SEQ ID NO: 8                moltype = AA    length = 11
```

| FEATURE | Location/Qualifiers |
|---|---|
| REGION | 1..11<br>note = Synthetic |
| source | 1..11<br>mol_type = protein<br>organism = synthetic construct |

SEQUENCE: 8
VREGWEVPFD Y                                                              11

| SEQ ID NO: 9 | moltype = DNA  length = 327 |
|---|---|
| FEATURE | Location/Qualifiers |
| misc_feature | 1..327<br>note = Synthetic |
| source | 1..327<br>mol_type = other DNA<br>organism = synthetic construct |

SEQUENCE: 9
gacatccaga tgacccagtc tccagccacc ctgtctgtgt ctccagggga aagagccgcc    60
ctctcctgca gggccagtca gagtgttagc agcaacttag cctggtacca ccagaaacct   120
ggccaggctc ccaggctcct catctatggt gcatccacca gggccactgg tatcccagcc   180
aggttcagtg gcattgggtc tgggacagag ttcactctca ttatcagcag cctgcagtct   240
gaagattttg catttattt ctgtcagcag tataataact ggcctccatt cactttcggc   300
cctgggacca aggtggagat caaacga                                      327

| SEQ ID NO: 10 | moltype = AA  length = 109 |
|---|---|
| FEATURE | Location/Qualifiers |
| REGION | 1..109<br>note = Synthetic |
| source | 1..109<br>mol_type = protein<br>organism = synthetic construct |

SEQUENCE: 10
DIQMTQSPAT LSVSPGERAA LSCRASQSVS SNLAWYHQKP GQAPRLLIYG ASTRATGIPA     60
RFSGIGSGTE FTLIISSLQS EDFAFYFCQQ YNNWPPFTFG PGTKVEIKR               109

| SEQ ID NO: 11 | moltype = DNA  length = 18 |
|---|---|
| FEATURE | Location/Qualifiers |
| misc_feature | 1..18<br>note = Synthetic |
| source | 1..18<br>mol_type = other DNA<br>organism = synthetic construct |

SEQUENCE: 11
cagagtgtta gcagcaac                                                 18

| SEQ ID NO: 12 | moltype = AA  length = 6 |
|---|---|
| FEATURE | Location/Qualifiers |
| REGION | 1..6<br>note = Synthetic |
| source | 1..6<br>mol_type = protein<br>organism = synthetic construct |

SEQUENCE: 12
QSVSSN                                                               6

| SEQ ID NO: 13 | moltype =   length = |
|---|---|

SEQUENCE: 13
000

| SEQ ID NO: 14 | moltype =   length = |
|---|---|

SEQUENCE: 14
000

| SEQ ID NO: 15 | moltype = DNA  length = 30 |
|---|---|
| FEATURE | Location/Qualifiers |
| misc_feature | 1..30<br>note = Synthetic |
| source | 1..30<br>mol_type = other DNA<br>organism = synthetic construct |

SEQUENCE: 15
cagcagtata ataactggcc tccattcact                                    30

| SEQ ID NO: 16 | moltype = AA  length = 10 |
|---|---|
| FEATURE | Location/Qualifiers |
| REGION | 1..10<br>note = Synthetic |
| source | 1..10<br>mol_type = protein |

```
                    organism = synthetic construct
SEQUENCE: 16
QQYNNWPPFT                                                                  10

SEQ ID NO: 17            moltype = DNA   length = 351
FEATURE                  Location/Qualifiers
misc_feature             1..351
                         note = Synthetic
source                   1..351
                         mol_type = other DNA
                         organism = synthetic construct
SEQUENCE: 17
gaggtgcagc tggtggagtc tgggggaggc ttggtacagc ctggggggtc cctgagactc     60
tcctgtgcag cctctggatt tactctaagt agttacgaca tgcactgggt ccgccaatct    120
acaggaaaag gtctggagtg ggtctcagct attggttcta ccggtgacac atactatcca    180
ggctccgtga agggccgatt caccatcacc agagaaaaag ccaagaactc cgtgtatctt    240
caaatgaaca gcctgagagc cggggacacg gctgtgtatt actgtgtaag agaggggtgg    300
gaggtacccct ttgactactg gggccaggga accctggtca ccgtctcctc a            351

SEQ ID NO: 18            moltype = AA   length = 117
FEATURE                  Location/Qualifiers
REGION                   1..117
                         note = Synthetic
source                   1..117
                         mol_type = protein
                         organism = synthetic construct
SEQUENCE: 18
EVQLVESGGG LVQPGGSLRL SCAASGFTLS SYDMHWVRQS TGKGLEWVSA IGSTGDTYYP     60
GSVKGRFTIT REKAKNSVYL QMNSLRAGDT AVYYCVREGW EVPFDYWGQG TLVTVSS       117

SEQ ID NO: 19            moltype = DNA   length = 324
FEATURE                  Location/Qualifiers
misc_feature             1..324
                         note = Synthetic
source                   1..324
                         mol_type = other DNA
                         organism = synthetic construct
SEQUENCE: 19
gaaatagtga tgacgcagtc tccagccacc ctgtctgtgt ctccagggga aagagccgcc     60
ctctcctgca gggccagtca gagtgttagc agcaacttag cctggtacca ccagaaacct    120
ggccaggctc ccaggctcct catctatggt gcatccacca gggccactgg tatcccagcc    180
aggttcagtg gcattgggtc tgggacagag ttcactctca ttatcagcag cctgcagtct    240
gaagattttg catttattt ctgtcagcag tataataact ggcctccatt cactttcggc     300
cctgggacca aagtggatat caaa                                           324

SEQ ID NO: 20            moltype = AA   length = 108
FEATURE                  Location/Qualifiers
REGION                   1..108
                         note = Synthetic
source                   1..108
                         mol_type = protein
                         organism = synthetic construct
SEQUENCE: 20
EIVMTQSPAT LSVSPGERAA LSCRASQSVS SNLAWYHQKP GQAPRLLIYG ASTRATGIPA     60
RFSGIGSGTE FTLIISSLQS EDFAFYFCQQ YNNWPPFTFG PGTKVDIK                 108

SEQ ID NO: 21            moltype = DNA   length = 351
FEATURE                  Location/Qualifiers
misc_feature             1..351
                         note = Synthetic
source                   1..351
                         mol_type = other DNA
                         organism = synthetic construct
SEQUENCE: 21
gaggtgcagc tggtggagtc tgggggaggc ttggtacagc ctggggggtc cctgagactc     60
tcctgtgcag cctctggatt tactctaagt agttacgaca tgcactgggt ccgccaagct    120
acaggaaaag gtctggagtg ggtctcagct attggttcta ccggtgacac atactatcca    180
ggctccgtga agggccgatt caccatctcc agagaaaatg ccaagaactc cttgtatctt    240
caaatgaaca gcctgagagc cggggacacg gctgtgtatt actgtgtaag agaggggtgg    300
gaggtacccct ttgactactg gggccaggga accctggtca ccgtctcctc a            351

SEQ ID NO: 22            moltype = AA   length = 117
FEATURE                  Location/Qualifiers
REGION                   1..117
                         note = Synthetic
source                   1..117
                         mol_type = protein
                         organism = synthetic construct
SEQUENCE: 22
```

```
EVQLVESGGG LVQPGGSLRL SCAASGFTLS SYDMHWVRQA TGKGLEWVSA IGSTGDTYYP    60
GSVKGRFTIS RENAKNSLYL QMNSLRAGDT AVYYCVREGW EVPFDYWGQG TLVTVSS     117

SEQ ID NO: 23           moltype = DNA   length = 324
FEATURE                 Location/Qualifiers
misc_feature            1..324
                        note = Synthetic
source                  1..324
                        mol_type = other DNA
                        organism = synthetic construct
SEQUENCE: 23
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagatttg cagtttatta ctgtcagcag tataataact ggcctccatt cactttcggc    300
cctgggacca agtggatat caaa                                           324

SEQ ID NO: 24           moltype = AA   length = 108
FEATURE                 Location/Qualifiers
REGION                  1..108
                        note = Synthetic
source                  1..108
                        mol_type = protein
                        organism = synthetic construct
SEQUENCE: 24
EIVMTQSPAT LSVSPGERAT LSCRASQSVS SNLAWYQQKP GQAPRLLIYG ASTRATGIPA    60
RFSGSGSGTE FTLTISSLQS EDFAVYYCQQ YNNWPPFTFG PGTKVDIK              108

SEQ ID NO: 25           moltype = DNA   length = 342
FEATURE                 Location/Qualifiers
misc_feature            1..342
                        note = Synthetic
source                  1..342
                        mol_type = other DNA
                        organism = synthetic construct
SEQUENCE: 25
caggtgcagc tggtgcagtc tggggggaggc gtggtccagc ctggagggtc cctgagactc    60
tcctgtgcag cgtctggatt cacccttcagt agctatggca tgcactgggt ccgccaggct   120
ccaggcaagg ggctggagtg ggtggcgttt ataggatttg atggaagtaa tacattat    180
ggagactccg tgaggggccg aatcatcata tccagagaca attccgagaa cacgttgtat   240
ctggaaatga acagcctgag agccgaggac acggcaatgt actattgtgc gagagagaag   300
ggttagact ggggccaggg aaccacggtc accgtctcct ca                      342

SEQ ID NO: 26           moltype = AA   length = 114
FEATURE                 Location/Qualifiers
REGION                  1..114
                        note = Synthetic
source                  1..114
                        mol_type = protein
                        organism = synthetic construct
SEQUENCE: 26
QVQLVQSGGG VVQPGRSLRL SCAASGFTFS SYGMHWVRQA PGKGLEWVAF IGFDGSNIHY    60
GDSVRGRIII SRDNSENTLY LEMNSLRAED TAMYYCAREK GLDWGQGTTV TVSS         114

SEQ ID NO: 27           moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 27
ggattcacct tcagtagcta tggc                                           24

SEQ ID NO: 28           moltype = AA   length = 8
FEATURE                 Location/Qualifiers
REGION                  1..8
                        note = Synthetic
source                  1..8
                        mol_type = protein
                        organism = synthetic construct
SEQUENCE: 28
GFTFSSYG                                                              8

SEQ ID NO: 29           moltype = DNA   length = 24
FEATURE                 Location/Qualifiers
misc_feature            1..24
                        note = Synthetic
```

```
                        source          1..24
                                        mol_type = other DNA
                                        organism = synthetic construct
                        SEQUENCE: 29
                        ataggatttg atggaagtaa tata                                           24

SEQ ID NO: 30   moltype = AA  length = 8
                        FEATURE         Location/Qualifiers
                        REGION          1..8
                                        note = Synthetic
                        source          1..8
                                        mol_type = protein
                                        organism = synthetic construct
                        SEQUENCE: 30
                        IGFDGSNI                                                             8

SEQ ID NO: 31   moltype = DNA  length = 21
                        FEATURE         Location/Qualifiers
                        misc_feature    1..21
                                        note = Synthetic
                        source          1..21
                                        mol_type = other DNA
                                        organism = synthetic construct
                        SEQUENCE: 31
                        gcgagagaga agggtttaga c                                              21

SEQ ID NO: 32   moltype = AA  length = 7
                        FEATURE         Location/Qualifiers
                        REGION          1..7
                                        note = Synthetic
                        source          1..7
                                        mol_type = protein
                                        organism = synthetic construct
                        SEQUENCE: 32
                        AREKGLD                                                              7

SEQ ID NO: 33   moltype = DNA  length = 321
                        FEATURE         Location/Qualifiers
                        misc_feature    1..321
                                        note = Synthetic
                        source          1..321
                                        mol_type = other DNA
                                        organism = synthetic construct
                        SEQUENCE: 33
                        gccatccaga tgacccagtc tccttccacc ctgtctgcat ctgtaggaga cagagtcacc     60
                        atcacttgcc gggccagtca gagtattagt agctggttgg cctggtatca gcagaaacca    120
                        gggaaagccc ctaagctcct gatctataag gcgtctagtt tagaaagtgg ggtcccatca    180
                        aggttcagcg gcagtggatc tgggacagaa ttcactctca ccatcagcag cctgcagcct    240
                        gatgattttg caacttatta ctgccaacag tataatagtt attacacttt tggccagggg    300
                        accaaggtgg aaatcaaacg a                                             321

SEQ ID NO: 34   moltype = AA  length = 107
                        FEATURE         Location/Qualifiers
                        REGION          1..107
                                        note = Synthetic
                        source          1..107
                                        mol_type = protein
                                        organism = synthetic construct
                        SEQUENCE: 34
                        AIQMTQSPST LSASVGDRVT ITCRASQSIS SWLAWYQQKP GKAPKLLIYK ASSLESGVPS     60
                        RFSGSGSGTE FTLTISSLQP DDFATYYCQQ YNSYYTFGQG TKVEIKR                  107

SEQ ID NO: 35   moltype = DNA  length = 18
                        FEATURE         Location/Qualifiers
                        misc_feature    1..18
                                        note = Synthetic
                        source          1..18
                                        mol_type = other DNA
                                        organism = synthetic construct
                        SEQUENCE: 35
                        cagagtatta gtagctgg                                                  18

SEQ ID NO: 36   moltype = AA  length = 6
                        FEATURE         Location/Qualifiers
                        REGION          1..6
                                        note = Synthetic
                        source          1..6
                                        mol_type = protein
                                        organism = synthetic construct
```

```
SEQUENCE: 36
QSISSW                                                                   6

SEQ ID NO: 37              moltype =    length =
SEQUENCE: 37
000

SEQ ID NO: 38              moltype =    length =
SEQUENCE: 38
000

SEQ ID NO: 39              moltype = DNA   length = 24
FEATURE                    Location/Qualifiers
misc_feature               1..24
                           note = Synthetic
source                     1..24
                           mol_type = other DNA
                           organism = synthetic construct
SEQUENCE: 39
caacagtata atagttatta cact                                               24

SEQ ID NO: 40              moltype = AA   length = 8
FEATURE                    Location/Qualifiers
REGION                     1..8
                           note = Synthetic
source                     1..8
                           mol_type = protein
                           organism = synthetic construct
SEQUENCE: 40
QQYNSYYT                                                                 8

SEQ ID NO: 41              moltype = DNA   length = 342
FEATURE                    Location/Qualifiers
misc_feature               1..342
                           note = Synthetic
source                     1..342
                           mol_type = other DNA
                           organism = synthetic construct
SEQUENCE: 41
caggtgcagc tggtggagtc tgggggaggc gtggtccagc ctgggaggtc cctgagactc         60
tcctgtgcag cgtctggatt caccttcagt agctatggca tgcactgggt ccgccaggct        120
ccaggcaagg ggctggagtg ggtggcgttt ataggatttg atggaagtaa tatacattat        180
ggagactccg tgagggccg aatcatcata tccagagaca attccgagaa cacgttgtat         240
ctggaaatga acagcctgag agccgaggac acggcaatgt actattgtgc gagagagaag        300
ggtttagact ggggccaggg aaccctggtc accgtctcct ca                           342

SEQ ID NO: 42              moltype = AA   length = 114
FEATURE                    Location/Qualifiers
REGION                     1..114
                           note = Synthetic
source                     1..114
                           mol_type = protein
                           organism = synthetic construct
SEQUENCE: 42
QVQLVESGGG VVQPGRSLRL SCAASGFTFS SYGMHWVRQA PGKGLEWVAF IGFDGSNIHY         60
GDSVRGRIII SRDNSENTLY LEMNSLRAED TAMYYCAREK GLDWGQGTLV TVSS              114

SEQ ID NO: 43              moltype = DNA   length = 318
FEATURE                    Location/Qualifiers
misc_feature               1..318
                           note = Synthetic
source                     1..318
                           mol_type = other DNA
                           organism = synthetic construct
SEQUENCE: 43
gacatccaga tgacccagtc tccttccacc ctgtctgcat ctgtaggaga cagagtcacc         60
atcacttgcc gggccagtca gagtattagt agctggttgg cctggtatca gcagaaacca       120
gggaaagccc ctaagctcct gatctataag gcgtctagtt tagaaagtgg ggtcccatca       180
aggttcagcg gcagtggatc tgggacagaa ttcactctca ccatcagcag cctgcagcct       240
gatgattttg caacttatta ctgccaacag tataatagtt attacacttt tggccagggg       300
accaagctgg agatcaaa                                                     318

SEQ ID NO: 44              moltype = AA   length = 106
FEATURE                    Location/Qualifiers
REGION                     1..106
                           note = Synthetic
source                     1..106
                           mol_type = protein
                           organism = synthetic construct
```

```
SEQUENCE: 44
DIQMTQSPST LSASVGDRVT ITCRASQSIS SWLAWYQQKP GKAPKLLIYK ASSLESGVPS    60
RFSGSGSGTE FTLTISSLQP DDFATYYCQQ YNSYYTFGQG TKLEIK                  106

SEQ ID NO: 45           moltype = DNA   length = 342
FEATURE                 Location/Qualifiers
misc_feature            1..342
                        note = Synthetic
source                  1..342
                        mol_type = other DNA
                        organism = synthetic construct
SEQUENCE: 45
caggtgcagc tggtggagtc tgggggaggc gtggtccagc ctggggaggtc cctgagactc    60
tcctgtgcag cctctggatt caccttcagt agctatggca tgcactgggt ccgccaggct   120
ccaggcaagg gctgagtg gtggcagtt ataggatttg atggaagtaa tatatactat       180
gcagactccg tgaagggccg attcaccatc tccagagaca attccaagaa cacgctgtat   240
ctgcaaatga acagcctgag agctgaggac acggctgtgt attactgtgc gagagagaag   300
ggtttagact ggggccaggg aaccctggtc accgtctcct ca                      342

SEQ ID NO: 46           moltype = AA   length = 114
FEATURE                 Location/Qualifiers
REGION                  1..114
                        note = Synthetic
source                  1..114
                        mol_type = protein
                        organism = synthetic construct
SEQUENCE: 46
QVQLVESGGG VVQPGRSLRL SCAASGFTFS SYGMHWVRQA PGKGLEWVAV IGFDGSNIYY    60
ADSVKGRFTI SRDNSKNTLY LQMNSLRAED TAVYYCAREK GLDWGQGTLV TVSS         114

SEQ ID NO: 47           moltype = DNA   length = 319
FEATURE                 Location/Qualifiers
misc_feature            1..319
                        note = Synthetic
source                  1..319
                        mol_type = other DNA
                        organism = synthetic construct
SEQUENCE: 47
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attcactttt tggccagggg   300
accaagctgg agatcaaac                                                319

SEQ ID NO: 48           moltype = AA   length = 106
FEATURE                 Location/Qualifiers
REGION                  1..106
                        note = Synthetic
source                  1..106
                        mol_type = protein
                        organism = synthetic construct
SEQUENCE: 48
DIQMTQSPST LSASVGDRVT ITCRASQSIS SWLAWYQQKP GKAPKLLIYK ASSLESGVPS    60
RFSGSGSGTE FTLTISSLQP DDFATYYCQQ YNSYYTFGQG TKLEIK                  106

SEQ ID NO: 49           moltype = DNA   length = 342
FEATURE                 Location/Qualifiers
misc_feature            1..342
                        note = Synthetic
source                  1..342
                        mol_type = other DNA
                        organism = synthetic construct
SEQUENCE: 49
caggtgcagc tgcaggagtc tgggggaggc gtggtccagc ctggggaggtc cctgagactc    60
tcctgtgcag cgtctggatt caccttcagt agctatggca tgcactgggt ccgccaggct   120
ccaggcaagg gctggagtg gtggcgtttt ataggatttg atggaagtaa tatatattat    180
ggagactccg tgaggggccg aatcatcata tccagagaca attccgagaa cacgttgtat   240
ctggaaatga acagcctgag agccgaggac acggcagtgt attattgtgc gagagagaag   300
ggtttagact ggggccaggg aaccctggtc actgtctcct ca                      342

SEQ ID NO: 50           moltype = AA   length = 114
FEATURE                 Location/Qualifiers
REGION                  1..114
                        note = Synthetic
source                  1..114
                        mol_type = protein
                        organism = synthetic construct
SEQUENCE: 50
```

```
QVQLQESGGG VVQPGRSLRL SCAASGFTFS SYGMHWVRQA PGKGLEWVAF IGFDGSNIYY    60
GDSVRGRIII SRDNSENTLY LEMNSLRAED TAVYYCAREK GLDWGQGTLV TVSS         114

SEQ ID NO: 51              moltype = DNA   length = 24
FEATURE                    Location/Qualifiers
misc_feature               1..24
                           note = Synthetic
source                     1..24
                           mol_type = other DNA
                           organism = synthetic construct
SEQUENCE: 51
ggattcacct tcagtagcta tggc                                          24

SEQ ID NO: 52              moltype = AA    length = 8
FEATURE                    Location/Qualifiers
REGION                     1..8
                           note = Synthetic
source                     1..8
                           mol_type = protein
                           organism = synthetic construct
SEQUENCE: 52
GFTFSSYG                                                             8

SEQ ID NO: 53              moltype = DNA   length = 24
FEATURE                    Location/Qualifiers
misc_feature               1..24
                           note = Synthetic
source                     1..24
                           mol_type = other DNA
                           organism = synthetic construct
SEQUENCE: 53
ataggatttg atggaagtaa tata                                          24

SEQ ID NO: 54              moltype = AA    length = 8
FEATURE                    Location/Qualifiers
REGION                     1..8
                           note = Synthetic
source                     1..8
                           mol_type = protein
                           organism = synthetic construct
SEQUENCE: 54
IGFDGSNI                                                             8

SEQ ID NO: 55              moltype = DNA   length = 21
FEATURE                    Location/Qualifiers
misc_feature               1..21
                           note = Synthetic
source                     1..21
                           mol_type = other DNA
                           organism = synthetic construct
SEQUENCE: 55
gcgagagaga agggtttaga c                                             21

SEQ ID NO: 56              moltype = AA    length = 7
FEATURE                    Location/Qualifiers
REGION                     1..7
                           note = Synthetic
source                     1..7
                           mol_type = protein
                           organism = synthetic construct
SEQUENCE: 56
AREKGLD                                                              7

SEQ ID NO: 57              moltype = DNA   length = 342
FEATURE                    Location/Qualifiers
misc_feature               1..342
                           note = Synthetic
source                     1..342
                           mol_type = other DNA
                           organism = synthetic construct
SEQUENCE: 57
gccatccaga tgacccagtc tccagactcc ctggctgtgt ctctgggcga gagggccacc   60
atcaactgca agtccagcca gagtgttttt cacacctcca acaataagaa ctacttagtt  120
tggtatcagc agaaaccagg acagcctcct aagttgctcc tttactgggc ctctacccgg  180
gaatccgggg tccctgaccg attcagtggc agcgggtctg ggacagattt cactctcacc  240
atcagcagcc tgcaggctga agatgtggca aattattact gtcaccaata ttacagtatt  300
ccgtggacgt tcggccaagg gaccaaggtg gagatcaaac ga                     342

SEQ ID NO: 58              moltype = AA    length = 114
```

```
FEATURE              Location/Qualifiers
REGION               1..114
                     note = Synthetic
source               1..114
                     mol_type = protein
                     organism = synthetic construct
SEQUENCE: 58
AIQMTQSPDS LAVSLGERAT INCKSSQSVF HTSNNKNYLV WYQQKPGQPP KLLLYWASTR   60
ESGVPDRFSG SGSGTDFTLT ISSLQAEDVA NYYCHQYYSI PWTFGQGTKV EIKR        114

SEQ ID NO: 59        moltype = DNA   length = 36
FEATURE              Location/Qualifiers
misc_feature         1..36
                     note = Synthetic
source               1..36
                     mol_type = other DNA
                     organism = synthetic construct
SEQUENCE: 59
cagagtgttt ttcacacctc caacaataag aactac                             36

SEQ ID NO: 60        moltype = AA   length = 12
FEATURE              Location/Qualifiers
REGION               1..12
                     note = Synthetic
source               1..12
                     mol_type = protein
                     organism = synthetic construct
SEQUENCE: 60
QSVFHTSNNK NY                                                       12

SEQ ID NO: 61        moltype =   length =
SEQUENCE: 61
000

SEQ ID NO: 62        moltype =   length =
SEQUENCE: 62
000

SEQ ID NO: 63        moltype = DNA   length = 27
FEATURE              Location/Qualifiers
misc_feature         1..27
                     note = Synthetic
source               1..27
                     mol_type = other DNA
                     organism = synthetic construct
SEQUENCE: 63
caccaatatt acagtattcc gtggacg                                       27

SEQ ID NO: 64        moltype = AA   length = 9
FEATURE              Location/Qualifiers
REGION               1..9
                     note = Synthetic
source               1..9
                     mol_type = protein
                     organism = synthetic construct
SEQUENCE: 64
HQYYSIPWT                                                            9

SEQ ID NO: 65        moltype = DNA   length = 342
FEATURE              Location/Qualifiers
misc_feature         1..342
                     note = Synthetic
source               1..342
                     mol_type = other DNA
                     organism = synthetic construct
SEQUENCE: 65
caggtgcagc tggtggagtc tgggggaggc gtggtccagc ctggggaggtc cctgagactc   60
tcctgtgcag cgtctggatt cacccttcagt agctatggca tgcactgggt ccgccaggct  120
ccaggcaagg ggctggagtg ggtggcgttt ataggatttg atggaagtaa tatatattat  180
ggagactccg tgaggggccg aatcatcata tccagagaca attccgagaa cacgttgtat  240
ctggaaatga acagcctgag agccgaggac acggcagtgt attattgtgc gagagagaag  300
ggtttagact ggggccaggg aaccctggtc accgtctcct ca                     342

SEQ ID NO: 66        moltype = AA   length = 114
FEATURE              Location/Qualifiers
REGION               1..114
                     note = Synthetic
source               1..114
                     mol_type = protein
```

```
                            organism = synthetic construct
SEQUENCE: 66
QVQLVESGGG VVQPGRSLRL SCAASGFTFS SYGMHWVRQA PGKGLEWVAF IGFDGSNIYY    60
GDSVRGRIII SRDNSENTLY LEMNSLRAED TAVYYCAREK GLDWGQGTLV TVSS         114

SEQ ID NO: 67           moltype = DNA   length = 339
FEATURE                 Location/Qualifiers
misc_feature            1..339
                        note = Synthetic
source                  1..339
                        mol_type = other DNA
                        organism = synthetic construct
SEQUENCE: 67
gacatcgtga tgacccagtc tccagactcc ctggctgtgt ctctgggcga gagggccacc    60
atcaactgca agtccagcca gagtgttttt cacacctcca acaataagaa ctacttagtt   120
tggtatcagc agaaaccagg acagcctcct aagttgctcc tttactgggc ctctacccgg   180
gaatccgggg tccctgaccg attcagtggc agcgggtctg ggacagattt cactctcacc   240
atcagcagcc tgcaggctga agatgtggca aattattact gtcaccaata ttacagtatt   300
ccgtggacgt tcggccaagg gaccaaggtg gaaatcaaa                          339

SEQ ID NO: 68           moltype = AA    length = 113
FEATURE                 Location/Qualifiers
REGION                  1..113
                        note = Synthetic
source                  1..113
                        mol_type = protein
                        organism = synthetic construct
SEQUENCE: 68
DIVMTQSPDS LAVSLGERAT INCKSSQSVF HTSNNKNYLV WYQQKPGQPP KLLLYWASTR    60
ESGVPDRFSG SGSGTDFTLT ISSLQAEDVA NYYCHQYYSI PWTFGQGTKV EIK          113

SEQ ID NO: 69           moltype = DNA   length = 342
FEATURE                 Location/Qualifiers
misc_feature            1..342
                        note = Synthetic
source                  1..342
                        mol_type = other DNA
                        organism = synthetic construct
SEQUENCE: 69
caggtgcagc tggtggagtc tgggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt ataggatttg atggaagtaa tatatactat   180
gcagactccg tgaagggccg attcaccatc tccagagaca attccaagaa cacgctgtat   240
ctgcaaatga acagcctgag agctgaggac acggctgtgt attactgtgc gagagagaag   300
ggtttagact ggggccaggg aaccctggtc accgtctcct ca                      342

SEQ ID NO: 70           moltype = AA    length = 114
FEATURE                 Location/Qualifiers
REGION                  1..114
                        note = Synthetic
source                  1..114
                        mol_type = protein
                        organism = synthetic construct
SEQUENCE: 70
QVQLVESGGG VVQPGRSLRL SCAASGFTFS SYGMHWVRQA PGKGLEWVAV IGFDGSNIYY    60
ADSVKGRFTI SRDNSKNTLY LQMNSLRAED TAVYYCAREK GLDWGQGTLV TVSS         114

SEQ ID NO: 71           moltype = DNA   length = 339
FEATURE                 Location/Qualifiers
misc_feature            1..339
                        note = Synthetic
source                  1..339
                        mol_type = other DNA
                        organism = synthetic construct
SEQUENCE: 71
gacatcgtga tgacccagtc tccagactcc ctggctgtgt ctctgggcga gagggccacc    60
atcaactgca agtccagcca gagtgttttt cacacctcca acaataagaa ctacttagct   120
tggtaccagc agaaaccagg acagcctcct aagctgctca tttactgggc ctctacccgg   180
gaatccgggg tccctgaccg attcagtggc agcgggtctg ggacagattt cactctcacc   240
atcagcagcc tgcaggctga agatgtggca gtttattact gtcaccaata ttacagtatt   300
ccgtggacgt tcggccaagg gaccaaggtg gaaatcaaa                          339

SEQ ID NO: 72           moltype = AA    length = 113
FEATURE                 Location/Qualifiers
REGION                  1..113
                        note = Synthetic
source                  1..113
                        mol_type = protein
                        organism = synthetic construct
```

```
SEQUENCE: 72
DIVMTQSPDS LAVSLGERAT INCKSSQSVF HTSNNKNYLA WYQQKPGQPP KLLIYWASTR    60
ESGVPDRFSG SGSGTDFTLT ISSLQAEDVA VYYCHQYYSI PWTFGQGTKV EIK          113

SEQ ID NO: 73               moltype = DNA   length = 354
FEATURE                     Location/Qualifiers
misc_feature                1..354
                            note = Synthetic
source                      1..354
                            mol_type = other DNA
                            organism = synthetic construct
SEQUENCE: 73
gaagtgcagc tggtgcagtc tgggggaggc ttggtacagc ctggggggtc cctgagactc    60
tcctgtgcag cctctggatt cacctttaac aactatgcca tgaactgggt ccgccaggct   120
ccaggaaagg gactgactg gtctcaact attagtggta gcggtggtac tacaaactac    180
gcagactccg tgaagggccg tttcattatt tcccgagaca gttccaaaca cacgctgtat   240
ctgcaaatga acagcctgag agccgaggac acggccgtat attactgtgc gaaagattct   300
aactggggaa atttcgatct ctggggccgt ggcaccacgg tcactgtctc ctca         354

SEQ ID NO: 74               moltype = AA    length = 118
FEATURE                     Location/Qualifiers
REGION                      1..118
                            note = Synthetic
source                      1..118
                            mol_type = protein
                            organism = synthetic construct
SEQUENCE: 74
EVQLVQSGGG LVQPGGSLRL SCAASGFTFN NYAMNWVRQA PGKGLDWVST ISGSGGTTNY    60
ADSVKGRFII SRDSSKHTLY LQMNSLRAED TAVYYCAKDS NWGNFDLWGR GTTVTVSS    118

SEQ ID NO: 75               moltype = DNA   length = 24
FEATURE                     Location/Qualifiers
misc_feature                1..24
                            note = Synthetic
source                      1..24
                            mol_type = other DNA
                            organism = synthetic construct
SEQUENCE: 75
ggattcacct taacaactat gcc                                            24

SEQ ID NO: 76               moltype = AA    length = 8
FEATURE                     Location/Qualifiers
REGION                      1..8
                            note = Synthetic
source                      1..8
                            mol_type = protein
                            organism = synthetic construct
SEQUENCE: 76
GFTFNNYA                                                              8

SEQ ID NO: 77               moltype = DNA   length = 24
FEATURE                     Location/Qualifiers
misc_feature                1..24
                            note = Synthetic
source                      1..24
                            mol_type = other DNA
                            organism = synthetic construct
SEQUENCE: 77
attagtggta gcggtggtac taca                                           24

SEQ ID NO: 78               moltype = AA    length = 8
FEATURE                     Location/Qualifiers
REGION                      1..8
                            note = Synthetic
source                      1..8
                            mol_type = protein
                            organism = synthetic construct
SEQUENCE: 78
ISGSGGTT                                                              8

SEQ ID NO: 79               moltype = DNA   length = 33
FEATURE                     Location/Qualifiers
misc_feature                1..33
                            note = Synthetic
source                      1..33
                            mol_type = other DNA
                            organism = synthetic construct
SEQUENCE: 79
gcgaaagatt ctaactgggg aaatttcgat ctc                                 33
```

```
SEQ ID NO: 80          moltype = AA   length = 11
FEATURE                Location/Qualifiers
REGION                 1..11
                       note = Synthetic
source                 1..11
                       mol_type = protein
                       organism = synthetic construct
SEQUENCE: 80
AKDSNWGNFD L                                                          11

SEQ ID NO: 81          moltype = DNA  length = 342
FEATURE                Location/Qualifiers
misc_feature           1..342
                       note = Synthetic
source                 1..342
                       mol_type = other DNA
                       organism = synthetic construct
SEQUENCE: 81
gacatccaga tgacccagtc tccagactcc ctggctgtgt ctctgggcga gagggccacc     60
atcaactgca agtccagcca gagtgtttta tacaggtcca acaataggaa cttcttaggt    120
tggtaccagc agaaaccagg gcagcctcct aatctactca tttactgggc atctacccgg    180
gaatccgggg tccctgaccg attcagtggc agcgggtctg ggacagattt cactctcacc    240
atcagcagcc tgcaggctga agatgtggca gtttattact gtcaacaata ttatactact    300
ccgtacactt ttggccaggg gaccaaggtg gaaatcaaac ga                       342

SEQ ID NO: 82          moltype = AA   length = 114
FEATURE                Location/Qualifiers
REGION                 1..114
                       note = Synthetic
source                 1..114
                       mol_type = protein
                       organism = synthetic construct
SEQUENCE: 82
DIQMTQSPDS LAVSLGERAT INCKSSQSVL YRSNNRNFLG WYQQKPGQPP NLLIYWASTR     60
ESGVPDRFSG SGSGTDFTLT ISSLQAEDVA VYYCQQYYTT PYTFGQGTKV EIKR          114

SEQ ID NO: 83          moltype = DNA  length = 36
FEATURE                Location/Qualifiers
misc_feature           1..36
                       note = Synthetic
source                 1..36
                       mol_type = other DNA
                       organism = synthetic construct
SEQUENCE: 83
cagagtgttt tatacaggtc caacaatagg aacttc                               36

SEQ ID NO: 84          moltype = AA   length = 12
FEATURE                Location/Qualifiers
REGION                 1..12
                       note = Synthetic
source                 1..12
                       mol_type = protein
                       organism = synthetic construct
SEQUENCE: 84
QSVLYRSNNR NF                                                         12

SEQ ID NO: 85          moltype =     length =
SEQUENCE: 85
000

SEQ ID NO: 86          moltype =     length =
SEQUENCE: 86
000

SEQ ID NO: 87          moltype = DNA  length = 27
FEATURE                Location/Qualifiers
misc_feature           1..27
                       note = Synthetic
source                 1..27
                       mol_type = other DNA
                       organism = synthetic construct
SEQUENCE: 87
caacaatatt atactactcc gtacact                                         27

SEQ ID NO: 88          moltype = AA   length = 9
FEATURE                Location/Qualifiers
REGION                 1..9
                       note = Synthetic
```

```
source                        1..9
                              mol_type = protein
                              organism = synthetic construct
SEQUENCE: 88
QQYYTTPYT                                                                    9

SEQ ID NO: 89                 moltype = DNA   length = 354
FEATURE                       Location/Qualifiers
misc_feature                  1..354
                              note = Synthetic
source                        1..354
                              mol_type = other DNA
                              organism = synthetic construct
SEQUENCE: 89
gaggtgcagc tggtggagtc tgggggaggc ttggtacagc ctgggggtc cctgagactc         60
tcctgtgcag cctctggatt cacctttaac aactatgcca tgaactgggt ccgccaggct        120
ccaggaaagg gactggactg ggtctcaact attagtggta gcggtggtac tacaaactac        180
gcagactccg tgaagggccg tttcattatt tcccgagaca gttccaaaca cacgctgtat        240
ctgcaaatga acagcctgag agccgaggac acggccgtat attactgtgc gaaagattct        300
aactggggaa atttcgatct ctggggccgt ggcaccctgg tcactgtctc ctca              354

SEQ ID NO: 90                 moltype = AA   length = 118
FEATURE                       Location/Qualifiers
REGION                        1..118
                              note = Synthetic
source                        1..118
                              mol_type = protein
                              organism = synthetic construct
SEQUENCE: 90
EVQLVESGGG LVQPGGSLRL SCAASGFTFN NYAMNWVRQA PGKGLDWVST ISGSGGTTNY         60
ADSVKGRFII SRDSSKHTLY LQMNSLRAED TAVYYCAKDS NWGNFDLWGR GTLVTVSS         118

SEQ ID NO: 91                 moltype = DNA   length = 339
FEATURE                       Location/Qualifiers
misc_feature                  1..339
                              note = Synthetic
source                        1..339
                              mol_type = other DNA
                              organism = synthetic construct
SEQUENCE: 91
gacatcgtga tgacccagtc tccagactcc ctggctgtgt ctctgggcga gagggccacc         60
atcaactgca agtccagcca gagtgtttta tacaggtcca acaataggaa cttcttaggt        120
tggtaccagc agaaaccagg gcagcctcct aatctactac tttactgggc atctacccgg        180
gaatccgggg tccctgaccg attcagtggc agcgggtctg ggacagattt cactctcacc        240
atcagcagcc tgcaggctga agatgtggca gtttattact gtcaacaata ttatactact        300
ccgtacactt ttggccaggg gaccaagctg gagatcaaa                               339

SEQ ID NO: 92                 moltype = AA   length = 113
FEATURE                       Location/Qualifiers
REGION                        1..113
                              note = Synthetic
source                        1..113
                              mol_type = protein
                              organism = synthetic construct
SEQUENCE: 92
DIVMTQSPDS LAVSLGERAT INCKSSQSVL YRSNNRNFLG WYQQKPGQPP NLLIYWASTR         60
ESGVPDRFSG SGSGTDFTLT ISSLQAEDVA VYYCQQYYTT PYTFGQGTKL EIK               113

SEQ ID NO: 93                 moltype = DNA   length = 354
FEATURE                       Location/Qualifiers
misc_feature                  1..354
                              note = Synthetic
source                        1..354
                              mol_type = other DNA
                              organism = synthetic construct
SEQUENCE: 93
gaggtgcagc tggtggagtc tgggggaggc ttggtacagc ctgggggtc cctgagactc         60
tcctgtgcag cctctggatt cacctttaac aactatgcca tgagctgggt ccgccaggct        120
ccagggaagg ggctggagtg ggtctcagct attagtggta gcggtggtac tacatactac        180
gcagactccg tgaagggccg gttcaccatc tccagagaca attccaagaa cacgctgtat        240
ctgcaaatga acagcctgag agccgaggac acggccgtat attactgtgc gaaagattct        300
aactggggaa atttcgatct ctggggccgt ggcaccctgg tcactgtctc ctca              354

SEQ ID NO: 94                 moltype = AA   length = 118
FEATURE                       Location/Qualifiers
REGION                        1..118
                              note = Synthetic
source                        1..118
                              mol_type = protein
```

```
                            organism = synthetic construct
SEQUENCE: 94
EVQLVESGGG LVQPGGSLRL SCAASGFTFN NYAMSWVRQA PGKGLEWVSA ISGSGGTTYY    60
ADSVKGRFTI SRDNSKNTLY LQMNSLRAED TAVYYCAKDS NWGNFDLWGR GTLVTVSS    118

SEQ ID NO: 95           moltype = DNA   length = 339
FEATURE                 Location/Qualifiers
misc_feature            1..339
                        note = Synthetic
source                  1..339
                        mol_type = other DNA
                        organism = synthetic construct
SEQUENCE: 95
gacatcgtga tgacccagtc tccagactcc ctggctgtgt ctctgggcga gagggccacc    60
atcaactgca agtccagcca gagtgtttta tacaggtcca acaataggaa cttcttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcaacaata ttatactact   300
ccgtacactt ttggccaggg gaccaagctg gagatcaaa                          339

SEQ ID NO: 96           moltype = AA    length = 113
FEATURE                 Location/Qualifiers
REGION                  1..113
                        note = Synthetic
source                  1..113
                        mol_type = protein
                        organism = synthetic construct
SEQUENCE: 96
DIVMTQSPDS LAVSLGERAT INCKSSQSVL YRSNNRNFLA WYQQKPGQPP KLLIYWASTR    60
ESGVPDRFSG SGSGTDFTLT ISSLQAEDVA VYYCQQYYTT PYTFGQGTKL EIK          113

SEQ ID NO: 97           moltype = DNA   length = 351
FEATURE                 Location/Qualifiers
misc_feature            1..351
                        note = Synthetic
source                  1..351
                        mol_type = other DNA
                        organism = synthetic construct
SEQUENCE: 97
caggtgcagc tggtgcagtc tgggggaggc ttggtacagc ctggggggtc cctgagactc    60
tcctgtgcag tctctggatt caccctcagt agctacgata tgcactgggt ccgccaacct   120
acaggaaaag gtctggagtg ggtctcagct attggttcta ctggtgacac atactatcca   180
ggctccgtga agggccgatt caccatctcc agagaaaatg ccaagaactc cttgtatctt   240
caaatgaaca gcctgagagc cggggacacg gctgtgtatt actgtgcaag agagggatgg   300
gacgtacccc ttgacttctg gggccaggga accctggtca ccgtctcctc a            351

SEQ ID NO: 98           moltype = AA    length = 117
FEATURE                 Location/Qualifiers
REGION                  1..117
                        note = Synthetic
source                  1..117
                        mol_type = protein
                        organism = synthetic construct
SEQUENCE: 98
QVQLVQSGGG LVQPGGSLRL SCAVSGFTLS SYDMHWVRQP TGKGLEWVSA IGSTGDTYYP    60
GSVKGRFTIS RENAKNSLYL QMNSLRAGDT AVYYCAREGW DVPFDFWGQG TLVTVSS      117

SEQ ID NO: 99           moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 99
ggattcaccc tcagtagcta cgat                                           24

SEQ ID NO: 100          moltype = AA    length = 8
FEATURE                 Location/Qualifiers
REGION                  1..8
                        note = Synthetic
source                  1..8
                        mol_type = protein
                        organism = synthetic construct
SEQUENCE: 100
GFTLSSYD                                                              8

SEQ ID NO: 101          moltype = DNA   length = 21
FEATURE                 Location/Qualifiers
```

```
misc_feature            1..21
                        note = Synthetic
source                  1..21
                        mol_type = other DNA
                        organism = synthetic construct
SEQUENCE: 101
attggttcta ctggtgacac a                                              21

SEQ ID NO: 102          moltype = AA  length = 7
FEATURE                 Location/Qualifiers
REGION                  1..7
                        note = Synthetic
source                  1..7
                        mol_type = protein
                        organism = synthetic construct
SEQUENCE: 102
IGSTGDT                                                              7

SEQ ID NO: 103          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 103
gcaagagagg gatgggacgt acccctttgac ttc                                33

SEQ ID NO: 104          moltype = AA  length = 11
FEATURE                 Location/Qualifiers
REGION                  1..11
                        note = Synthetic
source                  1..11
                        mol_type = protein
                        organism = synthetic construct
SEQUENCE: 104
AREGWDVPFD F                                                         11

SEQ ID NO: 105          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 105
gccatccagt tgacccagtc tccatcctcc ctgtctgcat ctgtaggaga cagagtcacc    60
atcacttgcc gggcaagtca ggacattaga aatgatttag ctggtatca gcagaaacca   120
gggaaagccc ctaagctcct gatctatgct gcatccagtt tacaaagtgg ggtcccatca   180
cggttcagcg gcagtggatc tggcacagat ttcactctca ccatcagcag cctgcagcct   240
gaagattttg caacttatta ctgtctacaa gattacaatt acccgtggac gttcggccaa   300
gggaccaagg tggagatcaa acga                                          324

SEQ ID NO: 106          moltype = AA  length = 108
FEATURE                 Location/Qualifiers
REGION                  1..108
                        note = Synthetic
source                  1..108
                        mol_type = protein
                        organism = synthetic construct
SEQUENCE: 106
AIQLTQSPSS LSASVGDRVT ITCRASQDIR NDLGWYQQKP GKAPKLLIYA ASSLQSGVPS    60
RFSGSGSGTD FTLTISSLQP EDFATYYCLQ DYNYPWTFGQ GTKVEIKR                108

SEQ ID NO: 107          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 107
caggacatta gaaatgat                                                  18

SEQ ID NO: 108          moltype = AA  length = 6
FEATURE                 Location/Qualifiers
REGION                  1..6
                        note = Synthetic
source                  1..6
```

```
                        mol_type = protein
                        organism = synthetic construct
SEQUENCE: 108
QDIRND                                                                  6

SEQ ID NO: 109          moltype =    length =
SEQUENCE: 109
000

SEQ ID NO: 110          moltype =    length =
SEQUENCE: 110
000

SEQ ID NO: 111          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 111
ctacaagatt acaattaccc gtggacg                                          27

SEQ ID NO: 112          moltype = AA   length = 9
FEATURE                 Location/Qualifiers
REGION                  1..9
                        note = Synthetic
source                  1..9
                        mol_type = protein
                        organism = synthetic construct
SEQUENCE: 112
LQDYNYPWT                                                               9

SEQ ID NO: 113          moltype = DNA   length = 351
FEATURE                 Location/Qualifiers
misc_feature            1..351
                        note = Synthetic
source                  1..351
                        mol_type = other DNA
                        organism = synthetic construct
SEQUENCE: 113
gaggtgcagc tggtggagtc tgggggaggc ttggtacagc ctggggggtc cctgagactc       60
tcctgtgcag tctctggatt caccctcagt agctacgata tgcactgggt ccgccaacct      120
acaggaaaag gtctgagtg gtctcagct attggttcta ctggtgacac atactatcca       180
ggctccgtga aggccgatt caccatctcc agagaaaatg ccaagaactc cttgtatctt      240
caaatgaaca gcctgagagc cggggacacg gctgtgtatt actgtgcaag agagggatgg     300
gacgtacccctt tgacttctg gggccaggga accctggtca ccgtctcctc a             351

SEQ ID NO: 114          moltype = AA   length = 117
FEATURE                 Location/Qualifiers
REGION                  1..117
                        note = Synthetic
source                  1..117
                        mol_type = protein
                        organism = synthetic construct
SEQUENCE: 114
EVQLVESGGG LVQPGGSLRL SCAVSGFTLS SYDMHWVRQP TGKGLEWVSA IGSTGDTYYP       60
GSVKGRFTIS RENAKNSLYL QMNSLRAGDT AVYYCAREGW DVPFDFWGQG TLVTVSS         117

SEQ ID NO: 115          moltype = DNA   length = 321
FEATURE                 Location/Qualifiers
misc_feature            1..321
                        note = Synthetic
source                  1..321
                        mol_type = other DNA
                        organism = synthetic construct
SEQUENCE: 115
gccatccaga tgacccagtc tccatcctcc ctgtctgcat ctgtaggaga cagagtcacc       60
atcacttgcc gggcaagtca ggacattaga aatgatttag ctgtatca gcagaaacca      120
gggaaagccc ctaagctcct gatctatgct gcatccagtt tacaaagtgg ggtcccatca     180
cggttcagcg gcagtggatc tggcacagat tcactctca ccatcagcag cctgcagcct     240
gaagattttg caacttatta ctgtctacaa gattacaatt accgtggac gttcggccaa     300
gggaccaagg tggaaatcaa a                                               321

SEQ ID NO: 116          moltype = AA   length = 107
FEATURE                 Location/Qualifiers
REGION                  1..107
                        note = Synthetic
source                  1..107
```

```
                        mol_type = protein
                        organism = synthetic construct
SEQUENCE: 116
AIQMTQSPSS LSASVGDRVT ITCRASQDIR NDLGWYQQKP GKAPKLLIYA ASSLQSGVPS    60
RFSGSGSGTD FTLTISSLQP EDFATYYCLQ DYNYPWTFGQ GTKVEIK                 107

SEQ ID NO: 117          moltype = DNA   length = 351
FEATURE                 Location/Qualifiers
misc_feature            1..351
                        note = Synthetic
source                  1..351
                        mol_type = other DNA
                        organism = synthetic construct
SEQUENCE: 117
gaggtgcagc tggtggagtc tgggggaggc ttggtacagc ctgggggtc cctgagactc     60
tcctgtgcag cctctggatt caccctcagt agctacgata tgcactgggt ccgccaagct   120
acaggaaaag gtctggagtg gtctcagct attggttcta ctggtgacac atactatcca   180
ggctccgtga agggccgatt caccatctcc agagaaaatg ccaagaactc cttgtatctt   240
caaatgaaca gcctgagagc cggggacacg ctgtgtatt actgtgcaag agagggatgg   300
gacgtaccct ttgacttctg gggccaggga accctggtca ccgtctcctc a            351

SEQ ID NO: 118          moltype = AA    length = 117
FEATURE                 Location/Qualifiers
REGION                  1..117
                        note = Synthetic
source                  1..117
                        mol_type = protein
                        organism = synthetic construct
SEQUENCE: 118
EVQLVESGGG LVQPGGSLRL SCAASGFTLS SYDMHWVRQA TGKGLEWVSA IGSTGDTYYP    60
GSVKGRFTIS RENAKNSLYL QMNSLRAGDT AVYYCAREGW DVPFDFWGQG TLVTVSS      117

SEQ ID NO: 119          moltype = DNA   length = 321
FEATURE                 Location/Qualifiers
misc_feature            1..321
                        note = Synthetic
source                  1..321
                        mol_type = other DNA
                        organism = synthetic construct
SEQUENCE: 119
gccatccaga tgacccagtc tccatcctcc ctgtctgcat ctgtaggaga cagagtcacc    60
atcacttgcc gggcaagtca ggacattaga aatgatttag ctggtatca gcagaaacca   120
gggaaagccc ctaagctcct gatctatgct gcatccagtt tacaaagtgg ggtcccatca   180
aggttcagcg gcagtggatc tgggacagat ttcactctca ccatcagcag cctgcagcct   240
gaagattttg caacttatta ctgtctacaa gattacaatt acccgtggac gttcggccaa   300
gggaccaagg tggaaatcaa a                                             321

SEQ ID NO: 120          moltype = AA    length = 107
FEATURE                 Location/Qualifiers
REGION                  1..107
                        note = Synthetic
source                  1..107
                        mol_type = protein
                        organism = synthetic construct
SEQUENCE: 120
AIQMTQSPSS LSASVGDRVT ITCRASQDIR NDLGWYQQKP GKAPKLLIYA ASSLQSGVPS    60
RFSGSGSGTD FTLTISSLQP EDFATYYCLQ DYNYPWTFGQ GTKVEIK                 107

SEQ ID NO: 121          moltype = DNA   length = 384
FEATURE                 Location/Qualifiers
misc_feature            1..384
                        note = Synthetic
source                  1..384
                        mol_type = other DNA
                        organism = synthetic construct
SEQUENCE: 121
caggtgcagc tgcaggagtc ggggccagga ctggtgaagc cttcggagac cctgtccctc    60
acctgcactg tctctgggga ctccatcaat acttactggg gagctggtt ccggcagccc   120
ccagggaagg gactggagtg gattgggtat atctattata gtgggaccac caactacaac   180
ccctccctca gagtcgagt caccatatca atagacacgc ccaggaacca gttctccctg   240
aagctgatct ctgtgaccgc agcggacacg gccgtgtatt actgtgcgag agagggatt   300
actatgattc ggggagttac cctctactat tactcctacg gtatggacgt ctggggccaa   360
gggaccacgg tcaccgtctc ctca                                          384

SEQ ID NO: 122          moltype = AA    length = 128
FEATURE                 Location/Qualifiers
REGION                  1..128
                        note = Synthetic
source                  1..128
```

```
                               mol_type = protein
                               organism = synthetic construct
SEQUENCE: 122
QVQLQESGPG LVKPSETLSL TCTVSGDSIN TYYWSWFRQP PGKGLEWIGY IYYSGTTNYN   60
PSLKSRVTIS IDTPRNQFSL KLISVTAADT AVYYCARERI TMIRGVTLYY YSYGMDVWGQ  120
GTTVTVSS                                                          128

SEQ ID NO: 123           moltype = DNA   length = 24
FEATURE                  Location/Qualifiers
misc_feature             1..24
                         note = Synthetic
source                   1..24
                         mol_type = other DNA
                         organism = synthetic construct
SEQUENCE: 123
ggggactcca tcaatactta ctac                                         24

SEQ ID NO: 124           moltype = AA   length = 8
FEATURE                  Location/Qualifiers
REGION                   1..8
                         note = Synthetic
source                   1..8
                         mol_type = protein
                         organism = synthetic construct
SEQUENCE: 124
GDSINTYY                                                            8

SEQ ID NO: 125           moltype = DNA   length = 21
FEATURE                  Location/Qualifiers
misc_feature             1..21
                         note = Synthetic
source                   1..21
                         mol_type = other DNA
                         organism = synthetic construct
SEQUENCE: 125
atctattata gtggaaccac c                                            21

SEQ ID NO: 126           moltype = AA   length = 7
FEATURE                  Location/Qualifiers
REGION                   1..7
                         note = Synthetic
source                   1..7
                         mol_type = protein
                         organism = synthetic construct
SEQUENCE: 126
IYYSGTT                                                             7

SEQ ID NO: 127           moltype = DNA   length = 66
FEATURE                  Location/Qualifiers
misc_feature             1..66
                         note = Synthetic
source                   1..66
                         mol_type = other DNA
                         organism = synthetic construct
SEQUENCE: 127
gcgagagaga ggattactat gattcgggga gttaccctct actattactc ctacggtatg  60
gacgtc                                                             66

SEQ ID NO: 128           moltype = AA   length = 22
FEATURE                  Location/Qualifiers
REGION                   1..22
                         note = Synthetic
source                   1..22
                         mol_type = protein
                         organism = synthetic construct
SEQUENCE: 128
ARERITMIRG VTLYYYSYGM DV                                           22

SEQ ID NO: 129           moltype = DNA   length = 324
FEATURE                  Location/Qualifiers
misc_feature             1..324
                         note = Synthetic
source                   1..324
                         mol_type = other DNA
                         organism = synthetic construct
SEQUENCE: 129
gacatccaga tgacccagtc tccatccttc ctgtctgcat ctgtaggaga cagagtcacc  60
atcacttgct gggccagtca ggacattagc agttatttag cctggtatca gcaaaaacca 120
gggatagccc ctaagctcct gatctatgct gcatccactt tgcaaagtgg ggtcccatca 180
```

```
aggttcggcg gcagtggatc tgggacagaa ttcactctca caatcagcag cctgcagcct    240
gaagattttg caacttatta ctgtcaacag cttaatagtt accctcggac gttcggccaa    300
gggaccaagg tggaaatcaa acga                                          324

SEQ ID NO: 130            moltype = AA  length = 108
FEATURE                   Location/Qualifiers
REGION                    1..108
                          note = Synthetic
source                    1..108
                          mol_type = protein
                          organism = synthetic construct
SEQUENCE: 130
DIQMTQSPSF LSASVGDRVT ITCWASQDIS SYLAWYQQKP GIAPKLLIYA ASTLQSGVPS    60
RFGGSGSGTE FTLTISSLQP EDFATYYCQQ LNSYPRTFGQ GTKVEIKR                108

SEQ ID NO: 131            moltype = DNA  length = 18
FEATURE                   Location/Qualifiers
misc_feature              1..18
                          note = Synthetic
source                    1..18
                          mol_type = other DNA
                          organism = synthetic construct
SEQUENCE: 131
caggacatta gcagttat                                                  18

SEQ ID NO: 132            moltype = AA  length = 6
FEATURE                   Location/Qualifiers
REGION                    1..6
                          note = Synthetic
source                    1..6
                          mol_type = protein
                          organism = synthetic construct
SEQUENCE: 132
QDISSY                                                               6

SEQ ID NO: 133            moltype =   length =
SEQUENCE: 133
000

SEQ ID NO: 134            moltype =   length =
SEQUENCE: 134
000

SEQ ID NO: 135            moltype = DNA  length = 27
FEATURE                   Location/Qualifiers
misc_feature              1..27
                          note = Synthetic
source                    1..27
                          mol_type = other DNA
                          organism = synthetic construct
SEQUENCE: 135
caacagctta atagttaccc tcggacg                                        27

SEQ ID NO: 136            moltype = AA  length = 9
FEATURE                   Location/Qualifiers
REGION                    1..9
                          note = Synthetic
source                    1..9
                          mol_type = protein
                          organism = synthetic construct
SEQUENCE: 136
QQLNSYPRT                                                            9

SEQ ID NO: 137            moltype = DNA  length = 384
FEATURE                   Location/Qualifiers
misc_feature              1..384
                          note = Synthetic
source                    1..384
                          mol_type = other DNA
                          organism = synthetic construct
SEQUENCE: 137
caggtgcagc tgcaggagtc ggggccagga ctggtgaagc cttcggagac cctgtccctc    60
acctgcactg tctctgggga ctccatcaat acttactact ggagctggtt ccggcagccc    120
ccagggaagg gactggagtg gattgggtat atcattata gtggaaccac caactacaac    180
ccctccctca agagtcgagt caccatatca atagacacgc caggaaccag gttctccctg    240
aagctgatct ctgtgaccgc agcggacacg gccgtgtatt actgtgcgag agaggatt     300
actatgattc ggggagttac cctctactat tactcctacg gtatggacgt ctggggccaa   360
gggaccacgg tcaccgtctc ctca                                          384
```

```
SEQ ID NO: 138            moltype = AA   length = 128
FEATURE                   Location/Qualifiers
REGION                    1..128
                          note = Synthetic
source                    1..128
                          mol_type = protein
                          organism = synthetic construct
SEQUENCE: 138
QVQLQESGPG LVKPSETLSL TCTVSGDSIN TYYWSWFRQP PGKGLEWIGY IYYSGTTNYN    60
PSLKSRVTIS IDTPRNQFSL KLISVTAADT AVYYCARERI TMIRGVTLYY YSYGMDVWGQ   120
GTTVTVSS                                                            128

SEQ ID NO: 139            moltype = DNA   length = 321
FEATURE                   Location/Qualifiers
misc_feature              1..321
                          note = Synthetic
source                    1..321
                          mol_type = other DNA
                          organism = synthetic construct
SEQUENCE: 139
gacatccaga tgacccagtc tccatccttc ctgtctgcat ctgtaggaga cagagtcacc    60
atcacttgct gggccagtca ggacattagc agttatttag cctggtatca gcaaaaacca   120
gggatagccc ctaagctcct gatctatgct gcatccactt tgcaaagtgg ggtcccatca   180
aggttcggcg gcagtggatc tgggacagaa ttcactctca caatcagcag cctgcagcct   240
gaagattttg caacttatta ctgtcaacag cttaatagtt accctcggac gttcggccaa   300
gggaccaagg tggaaatcaa a                                             321

SEQ ID NO: 140            moltype = AA   length = 107
FEATURE                   Location/Qualifiers
REGION                    1..107
                          note = Synthetic
source                    1..107
                          mol_type = protein
                          organism = synthetic construct
SEQUENCE: 140
DIQMTQSPSF LSASVGDRVT ITCWASQDIS SYLAWYQQKP GIAPKLLIYA ASTLQSGVPS    60
RFGGSGSGTE FTLTISSLQP EDFATYYCQQ LNSYPRTFGQ GTKVEIK                 107

SEQ ID NO: 141            moltype = DNA   length = 384
FEATURE                   Location/Qualifiers
misc_feature              1..384
                          note = Synthetic
source                    1..384
                          mol_type = other DNA
                          organism = synthetic construct
SEQUENCE: 141
caggtgcagc tgcaggagtc gggcccagga ctggtgaagc cttcggagac cctgtccctc    60
acctgcactg tctctgggga ctccatcaat acttactact ggagctggat ccggcagccc   120
ccagggaagg gactggagtg gattgggtat atctattata gtggaaccac caactacaac   180
ccctccctca gagtcgagt caccatatca gtagacacg ccaagaacca gttctccctg   240
aagctgagct ctgtgaccgc tgcggacacg gccgtgtatt actgtgcgag agagaggatt   300
actatgattc ggggagttac cctctactat tactcctacg gtatggacgt ctggggccaa   360
gggaccacgg tcaccgtctc ctca                                          384

SEQ ID NO: 142            moltype = AA   length = 128
FEATURE                   Location/Qualifiers
REGION                    1..128
                          note = Synthetic
source                    1..128
                          mol_type = protein
                          organism = synthetic construct
SEQUENCE: 142
QVQLQESGPG LVKPSETLSL TCTVSGDSIN TYYWSWIRQP PGKGLEWIGY IYYSGTTNYN    60
PSLKSRVTIS VDTSKNQFSL KLSSVTAADT AVYYCARERI TMIRGVTLYY YSYGMDVWGQ   120
GTTVTVSS                                                            128

SEQ ID NO: 143            moltype = DNA   length = 321
FEATURE                   Location/Qualifiers
misc_feature              1..321
                          note = Synthetic
source                    1..321
                          mol_type = other DNA
                          organism = synthetic construct
SEQUENCE: 143
gacatccaga tgacccagtc tccatcctcc ctgtctgcat ctgtaggaga cagagtcacc    60
atcacttgcc gggcaagtca ggacattagc agttatttag ctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtcaacag cttaatagtt accctcggac gttcggccaa   300
```

```
gggaccaagg tggaaatcaa a                                              321

SEQ ID NO: 144           moltype = AA  length = 107
FEATURE                  Location/Qualifiers
REGION                   1..107
                         note = Synthetic
source                   1..107
                         mol_type = protein
                         organism = synthetic construct
SEQUENCE: 144
DIQMTQSPSS LSASVGDRVT ITCRASQDIS SYLGWYQQKP GKAPKRLIYA ASSLQSGVPS    60
RFSGSGSGTE FTLTISSLQP EDFATYYCQQ LNSYPRTFGQ GTKVEIK                  107

SEQ ID NO: 145           moltype = DNA  length = 378
FEATURE                  Location/Qualifiers
misc_feature             1..378
                         note = Synthetic
source                   1..378
                         mol_type = other DNA
                         organism = synthetic construct
SEQUENCE: 145
caggtgcagc tggtgcagtc tggagctgag gtgaagaagc ctggggcctc agtgaaggtc    60
tcctgcaagg cttctggtta cacctttacc aactatggta tcagctgggt gcgacaggcc   120
cctggacaag gacttgagtt aatgggatgg attagtggtt acaatggtaa cacaaactat   180
gcacaagaac tccaggccag agtcaccatg accacagaca catccacgag cacagcctac   240
atggagctga ggaacctgag atctgacgac acggccgtat attactgtgc gagagataga   300
gtcgttgtag cagctgctaa ttactacttt tattctatgg acgtctgggg ccaagggacc   360
acggtcaccg tctcctca                                                 378

SEQ ID NO: 146           moltype = AA  length = 126
FEATURE                  Location/Qualifiers
REGION                   1..126
                         note = Synthetic
source                   1..126
                         mol_type = protein
                         organism = synthetic construct
SEQUENCE: 146
QVQLVQSGAE VKKPGASVKV SCKASGYTFT NYGISWVRQA PGQGLELMGW ISGYNGNTNY    60
AQELQARVTM TTDTSTSTAY MELRNLRSDD TAVYYCARDR VVVAAANYYF YSMDVWGQGT   120
TVTVSS                                                              126

SEQ ID NO: 147           moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 147
ggttacacct ttaccaacta tggt                                           24

SEQ ID NO: 148           moltype = AA  length = 8
FEATURE                  Location/Qualifiers
REGION                   1..8
                         note = Synthetic
source                   1..8
                         mol_type = protein
                         organism = synthetic construct
SEQUENCE: 148
GYTFTNYG                                                             8

SEQ ID NO: 149           moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 149
attagtggtt acaatggtaa caca                                           24

SEQ ID NO: 150           moltype = AA  length = 8
FEATURE                  Location/Qualifiers
REGION                   1..8
                         note = Synthetic
source                   1..8
                         mol_type = protein
                         organism = synthetic construct
SEQUENCE: 150
```

```
ISGYNGNT                                                                    8

SEQ ID NO: 151           moltype = DNA   length = 57
FEATURE                  Location/Qualifiers
misc_feature             1..57
                         note = Synthetic
source                   1..57
                         mol_type = other DNA
                         organism = synthetic construct
SEQUENCE: 151
gcgagagata gagtcgttgt agcagctgct aattactact tttattctat ggacgtc      57

SEQ ID NO: 152           moltype = AA    length = 19
FEATURE                  Location/Qualifiers
REGION                   1..19
                         note = Synthetic
source                   1..19
                         mol_type = protein
                         organism = synthetic construct
SEQUENCE: 152
ARDRVVVAAA NYYFYSMDV                                                        19

SEQ ID NO: 153           moltype = DNA   length = 339
FEATURE                  Location/Qualifiers
misc_feature             1..339
                         note = Synthetic
source                   1..339
                         mol_type = other DNA
                         organism = synthetic construct
SEQUENCE: 153
gccatccaga tgacccagtc tccactctcc ctgtccgtca cccttggaca gccggcctcc    60
atctcctgca ggtctagtca aagcctcgta tacagtgatg agacacctta cttgaattgg   120
tttcagcaga ggccaggcca atctccaagg cgcctaattt ataaggtttc taaccgggac   180
tctggggtcc cagacagatt cagcggcagt gggtcaggca ctgctttcac actgaaaatc   240
agcggggtgg aggccgagga tgttggggtt tactactgca tgcaagctac acactggcct   300
cggacgttcg gccaagggac caaggtggaa atcaaacga                          339

SEQ ID NO: 154           moltype = AA    length = 113
FEATURE                  Location/Qualifiers
REGION                   1..113
                         note = Synthetic
source                   1..113
                         mol_type = protein
                         organism = synthetic construct
SEQUENCE: 154
AIQMTQSPLS LSVTLGQPAS ISCRSSQSLV YSDGDTYLNW FQQRPGQSPR RLIYKVSNRD    60
SGVPDRFSGS GSGTAFTLKI SGVEAEDVGV YYCMQATHWP RTFGQGTKVE IKR          113

SEQ ID NO: 155           moltype = DNA   length = 33
FEATURE                  Location/Qualifiers
misc_feature             1..33
                         note = Synthetic
source                   1..33
                         mol_type = other DNA
                         organism = synthetic construct
SEQUENCE: 155
caaagcctcg tatacagtga tggagacacc tac                                 33

SEQ ID NO: 156           moltype = AA    length = 11
FEATURE                  Location/Qualifiers
REGION                   1..11
                         note = Synthetic
source                   1..11
                         mol_type = protein
                         organism = synthetic construct
SEQUENCE: 156
QSLVYSDGDT Y                                                         11

SEQ ID NO: 157           moltype =    length =
SEQUENCE: 157
000

SEQ ID NO: 158           moltype =    length =
SEQUENCE: 158
000

SEQ ID NO: 159           moltype = DNA   length = 27
FEATURE                  Location/Qualifiers
misc_feature             1..27
```

```
                        note = Synthetic
source                  1..27
                        mol_type = other DNA
                        organism = synthetic construct
SEQUENCE: 159
atgcaagcta cacactggcc tcggacg                                               27

SEQ ID NO: 160          moltype = AA  length = 9
FEATURE                 Location/Qualifiers
REGION                  1..9
                        note = Synthetic
source                  1..9
                        mol_type = protein
                        organism = synthetic construct
SEQUENCE: 160
MQATHWPRT                                                                    9

SEQ ID NO: 161          moltype = DNA  length = 378
FEATURE                 Location/Qualifiers
misc_feature            1..378
                        note = Synthetic
source                  1..378
                        mol_type = other DNA
                        organism = synthetic construct
SEQUENCE: 161
caggttcagc tggtgcagtc tggagctgag gtgaagaagc ctggggcctc agtgaaggtc            60
tcctgcaagg cttctggtta cacctttacc aactatggta tcagctgggt gcgacaggcc          120
cctggacaag gacttgagtt aatgggatgg attagtggtt acaatggtaa cacaaactat          180
gcacaagaac tccaggccag agtcaccatg accacagaca catccacgag cacagcctac          240
atggagctga ggaacctgag atctgacgac acggccgtat attactgtgc gagagataga          300
gtcgttgtag cagctgctaa ttactacttt tattctatgg acgtctgggg ccaagggacc          360
acggtcaccg tctcctca                                                        378

SEQ ID NO: 162          moltype = AA  length = 126
FEATURE                 Location/Qualifiers
REGION                  1..126
                        note = Synthetic
source                  1..126
                        mol_type = protein
                        organism = synthetic construct
SEQUENCE: 162
QVQLVQSGAE VKKPGASVKV SCKASGYTFT NYGISWVRQA PGQGLELMGW ISGYNGNTNY            60
AQELQARVTM TTDTSTSTAY MELRNLRSDD TAVYYCARDR VVVAAANYYF YSMDVWGQGT          120
TVTVSS                                                                     126

SEQ ID NO: 163          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 163
gatgttgtga tgactcagtc tccactctcc ctgtccgtca cccttggaca gccggcctcc            60
atctcctgca ggtctagtca aagcctcgta tacagtgatg gagacaccta cttgaattgg          120
tttcagcaga ggccaggcca atctccaagg cgcctaattt ataaggtttc taaccgggac          180
tctggggtcc cagacagatt cagcggcagt gggtcaggca ctgctttcac actgaaaatc          240
agcggggtgg aggccgagga tgttggggtt tactactgca tgcaagctac acactggcct          300
cggacgttcg gccaagggac caaggtggaa atcaaa                                    336

SEQ ID NO: 164          moltype = AA  length = 112
FEATURE                 Location/Qualifiers
REGION                  1..112
                        note = Synthetic
source                  1..112
                        mol_type = protein
                        organism = synthetic construct
SEQUENCE: 164
DVVMTQSPLS LSVTLGQPAS ISCRSSQSLV YSDGDTYLNW FQQRPGQSPR RLIYKVSNRD            60
SGVPDRFSGS GSGTAFTLKI SGVEAEDVGV YYCMQATHWP RTFGQGTKVE IK                  112

SEQ ID NO: 165          moltype = DNA  length = 378
FEATURE                 Location/Qualifiers
misc_feature            1..378
                        note = Synthetic
source                  1..378
                        mol_type = other DNA
                        organism = synthetic construct
SEQUENCE: 165
```

```
caggttcagc tggtgcagtc tggagctgag gtgaagaagc ctggggcctc agtgaaggtc    60
tcctgcaagg cttctggtta cacctttacc aactatggta tcagctgggt gcgacaggcc   120
cctggacaag gccttgagtg gatgggatgg attagtggtt acaatggtaa cacaaactat   180
gcacagaagc tccagggcag agtcaccatg accacagaca catccacgag cacagcctac   240
atgctgctga ggagcctgag atctgacgac acggccgtgt attactgtgc gagagataga   300
gtcgttgtag cagctgctaa ttactacttt tattctatgg acgtctgggg ccaagggacc   360
acggtcaccg tctcctca                                                 378

SEQ ID NO: 166          moltype = AA  length = 126
FEATURE                 Location/Qualifiers
REGION                  1..126
                        note = Synthetic
source                  1..126
                        mol_type = protein
                        organism = synthetic construct
SEQUENCE: 166
QVQLVQSGAE VKKPGASVKV SCKASGYTFT NYGISWVRQA PGQGLEWMGW ISGYNGNTNY    60
AQKLQGRVTM TTDTSTSTAY MELRSLRSDD TAVYYCARDR VVVAAANYYF YSMDVWGQGT   120
TVTVSS                                                              126

SEQ ID NO: 167          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 167
gatgttgtga tgactcagtc tccactctcc ctgcccgtca cccttggaca gccggcctcc    60
atctcctgca ggtctagtca aagcctcgta tacagtgatg gagacaccta cttgaattgg   120
tttcagcaga ggccaggcca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaagctac acactggcct   300
cggacgttcg gccaagggac caaggtggaa atcaaa                             336

SEQ ID NO: 168          moltype = AA  length = 112
FEATURE                 Location/Qualifiers
REGION                  1..112
                        note = Synthetic
source                  1..112
                        mol_type = protein
                        organism = synthetic construct
SEQUENCE: 168
DVVMTQSPLS LPVTLGQPAS ISCRSSQSLV YSDGDTYLNW FQQRPGQSPR RLIYKVSNRD    60
SGVPDRFSGS GSGTDFTLKI SRVEAEDVGV YYCMQATHWP RTFGQGTKVE IK           112

SEQ ID NO: 169          moltype = DNA  length = 375
FEATURE                 Location/Qualifiers
misc_feature            1..375
                        note = Synthetic
source                  1..375
                        mol_type = other DNA
                        organism = synthetic construct
SEQUENCE: 169
caggtccact tgaaggagtc tggtcctacg ctggtgaaac ccacacagac cctcacgctg    60
acctgcacct ctctggcatt ctcactcatc actagtggag tgggtgtggg ctggattcgt   120
cagccccccg gaaaggccct ggagtggctt gcactcattt attggaatgg tgataagcgc   180
tacagcccat ctctgaagag caggctcacc atcaccaagg acacctccaa aaaccaggtg   240
gtccttacaa tgaccaacat ggaccctgtg gacacagcca catattactg tgcacacagg   300
ataactgaaa ctagttacta cttctactac ggtatggacg tctggggcca agggaccacg   360
gtcaccgtct cctca                                                    375

SEQ ID NO: 170          moltype = AA  length = 125
FEATURE                 Location/Qualifiers
REGION                  1..125
                        note = Synthetic
source                  1..125
                        mol_type = protein
                        organism = synthetic construct
SEQUENCE: 170
QVHLKESGPT LVKPTQTLTL TCTFSGFSLI TSGVGVGWIR QPPGKALEWL ALIYWNGDKR    60
YSPSLKSRLT ITKDTSKNQV VLTMTNMDPV DTATYYCAHR ITETSYYFYY GMDVWGQGTT   120
VTVSS                                                               125

SEQ ID NO: 171          moltype = DNA  length = 30
FEATURE                 Location/Qualifiers
misc_feature            1..30
                        note = Synthetic
source                  1..30
```

```
                        mol_type = other DNA
                        organism = synthetic construct
SEQUENCE: 171
ggattctcac tcatcactag tggagtgggt                                30

SEQ ID NO: 172          moltype = AA   length = 10
FEATURE                 Location/Qualifiers
REGION                  1..10
                        note = Synthetic
source                  1..10
                        mol_type = protein
                        organism = synthetic construct
SEQUENCE: 172
GFSLITSGVG                                                      10

SEQ ID NO: 173          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 173
atttattgga atggtgataa g                                         21

SEQ ID NO: 174          moltype = AA   length = 7
FEATURE                 Location/Qualifiers
REGION                  1..7
                        note = Synthetic
source                  1..7
                        mol_type = protein
                        organism = synthetic construct
SEQUENCE: 174
IYWNGDK                                                         7

SEQ ID NO: 175          moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 175
gcacacagga taactgaaac tagttactac ttctactacg gtatggacgt c         51

SEQ ID NO: 176          moltype = AA   length = 17
FEATURE                 Location/Qualifiers
REGION                  1..17
                        note = Synthetic
source                  1..17
                        mol_type = protein
                        organism = synthetic construct
SEQUENCE: 176
AHRITETSYY FYYGMDV                                              17

SEQ ID NO: 177          moltype = DNA  length = 339
FEATURE                 Location/Qualifiers
misc_feature            1..339
                        note = Synthetic
source                  1..339
                        mol_type = other DNA
                        organism = synthetic construct
SEQUENCE: 177
gacatccaga tgacccagtc tccactctcc ctgcccgtca cccctggaga gccggcctcc 60
atctcctgca ggtctagtca gagcctcctg catagtcatg gatacgacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactccg 300
ctcactttcg gcggagggac caaggtggaa atcaaacga                      339

SEQ ID NO: 178          moltype = AA   length = 113
FEATURE                 Location/Qualifiers
REGION                  1..113
                        note = Synthetic
source                  1..113
                        mol_type = protein
                        organism = synthetic construct
SEQUENCE: 178
DIQMTQSPLS LPVTPGEPAS ISCRSSQSLL HSHGYDYLDW YLQKPGQSPQ LLIYLGSNRA 60
```

```
SGVPDRFSGS GSGTDFTLKI SRVEAEDVGV YYCMQALQTP LTFGGGTKVE IKR              113

SEQ ID NO: 179          moltype = DNA   length = 33
FEATURE                 Location/Qualifiers
misc_feature            1..33
                        note = Synthetic
source                  1..33
                        mol_type = other DNA
                        organism = synthetic construct
SEQUENCE: 179
cagagcctcc tgcatagtca tggatacgac tat                                    33

SEQ ID NO: 180          moltype = AA    length = 11
FEATURE                 Location/Qualifiers
REGION                  1..11
                        note = Synthetic
source                  1..11
                        mol_type = protein
                        organism = synthetic construct
SEQUENCE: 180
QSLLHSHGYD Y                                                            11

SEQ ID NO: 181          moltype =   length =
SEQUENCE: 181
000

SEQ ID NO: 182          moltype =   length =
SEQUENCE: 182
000

SEQ ID NO: 183          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 183
atgcaagctc tacaaactcc gctcact                                           27

SEQ ID NO: 184          moltype = AA    length = 9
FEATURE                 Location/Qualifiers
REGION                  1..9
                        note = Synthetic
source                  1..9
                        mol_type = protein
                        organism = synthetic construct
SEQUENCE: 184
MQALQTPLT                                                               9

SEQ ID NO: 185          moltype = DNA   length = 375
FEATURE                 Location/Qualifiers
misc_feature            1..375
                        note = Synthetic
source                  1..375
                        mol_type = other DNA
                        organism = synthetic construct
SEQUENCE: 185
cagatcacct tgaaggagtc tggtcctacg ctggtgaaac ccacacagac cctcacgctg       60
acctgcacct tctctggatt ctcactcatc actagtggag tgggtgtggg ctggattcgt       120
cagccccccg gaaaggccct ggagtggctt gcactcattt attggaatgg tgataagcgc       180
tacagcccat ctctgaagag caggctcacc atcaccaagg acacctccaa aaaccaggtg       240
gtccttacaa tgaccaacat ggaccctgtg acacagcca catattactg tgcacacagg        300
ataactgaaa ctagttacta cttctactac ggtatggacg tctggggcca agggaccacg       360
gtcaccgtct cctca                                                        375

SEQ ID NO: 186          moltype = AA    length = 125
FEATURE                 Location/Qualifiers
REGION                  1..125
                        note = Synthetic
source                  1..125
                        mol_type = protein
                        organism = synthetic construct
SEQUENCE: 186
QITLKESGPT LVKPTQTLTL TCTFSGFSLI TSGVGVGWIR QPPGKALEWL ALIYWNGDKR       60
YSPSLKSRLT ITKDTSKNQV VLTMTNMDPV DTATYYCAHR ITETSYYFYY GMDVWGQGTT       120
VTVSS                                                                   125

SEQ ID NO: 187          moltype = DNA   length = 336
```

```
FEATURE                 Location/Qualifiers
misc_feature            1..336
                        note = Synthetic
source                  1..336
                        mol_type = other DNA
                        organism = synthetic construct
SEQUENCE: 187
gatattgtga tgactcagtc tccactctcc ctgcccgtca cccctggaga gccggcctcc    60
atctcctgca ggtctagtca gagcctcctg catagtcatg gatacgacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactccg   300
ctcacttccg gcggagggac caaggtggag atcaaa                             336

SEQ ID NO: 188          moltype = AA  length = 112
FEATURE                 Location/Qualifiers
REGION                  1..112
                        note = Synthetic
source                  1..112
                        mol_type = protein
                        organism = synthetic construct
SEQUENCE: 188
DIVMTQSPLS LPVTPGEPAS ISCRSSQSLL HSHGYDYLDW YLQKPGQSPQ LLIYLGSNRA    60
SGVPDRFSGS GSGTDFTLKI SRVEAEDVGV YYCMQALQTP LTFGGGTKVE IK           112

SEQ ID NO: 189          moltype = DNA  length = 375
FEATURE                 Location/Qualifiers
misc_feature            1..375
                        note = Synthetic
source                  1..375
                        mol_type = other DNA
                        organism = synthetic construct
SEQUENCE: 189
cagatcacct tgaaggagtc tggtcctacg ctggtgaaac ccacacagac cctcacgctg    60
acctgcacct ctctctggatt ctcactcatc actagtggag tgggtgtggg ctggatccgt  120
cagcccccag gaaaggccct ggagtggctt gcactcattt attggaatgg tgataagcgc   180
tacagcccct ctctgaagag caggctcacc atcaccaagg acacctccaa aaaccaggtg   240
gtccttacaa tgaccaacat ggaccctgtg acacagccca tatattactg tgcacacagg   300
ataactgaaa ctagttacta cttctactac ggtatggacg tctggggcca agggaccacg   360
gtcaccgtct cctca                                                    375

SEQ ID NO: 190          moltype = AA  length = 125
FEATURE                 Location/Qualifiers
REGION                  1..125
                        note = Synthetic
source                  1..125
                        mol_type = protein
                        organism = synthetic construct
SEQUENCE: 190
QITLKESGPT LVKPTQTLTL TCTFSGFSLI TSGVGVGWIR QPPGKALEWL ALIYWNGDKR    60
YSPSLKSRLT ITKDTSKNQV VLTMTNMDPV DTATYYCAHR ITETSYYFYY GMDVWGQGTT   120
VTVSS                                                               125

SEQ ID NO: 191          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 191
gatattgtga tgactcagtc tccactctcc ctgcccgtca cccctggaga gccggcctcc    60
atctcctgca ggtctagtca gagcctcctg catagtcatg gatacgacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactccg   300
ctcacttccg gcggagggac caaggtggag atcaaa                             336

SEQ ID NO: 192          moltype = AA  length = 112
FEATURE                 Location/Qualifiers
REGION                  1..112
                        note = Synthetic
source                  1..112
                        mol_type = protein
                        organism = synthetic construct
SEQUENCE: 192
DIVMTQSPLS LPVTPGEPAS ISCRSSQSLL HSHGYDYLDW YLQKPGQSPQ LLIYLGSNRA    60
SGVPDRFSGS GSGTDFTLKI SRVEAEDVGV YYCMQALQTP LTFGGGTKVE IK           112
```

```
SEQ ID NO: 193            moltype = DNA  length = 375
FEATURE                   Location/Qualifiers
misc_feature              1..375
                          note = Synthetic
source                    1..375
                          mol_type = other DNA
                          organism = synthetic construct
SEQUENCE: 193
cagatcacct tgaaggagtc tggtcctact ctggtgaaac cctcacagac cctcacgctg     60
acctgcacct tctctgggtt ctcactcagc actagtggag tgggtgtggg ctggatccgt    120
cagcccccag gaaaggccct ggagtggctt gcactcattt attggaattc tgataagcgc    180
tacagcccca ctctgaagag caggctcacc atcaccaagg acacctccaa aaaccaggta    240
gtccttacaa tgaccaacat ggaccctgtg acacagcca catattactg tgcacacaga     300
catgacagct cgtcctacta cttctactac ggtatggacg tctggggcca agggatcacg    360
gtcaccgtct cctca                                                     375

SEQ ID NO: 194            moltype = AA  length = 125
FEATURE                   Location/Qualifiers
REGION                    1..125
                          note = Synthetic
source                    1..125
                          mol_type = protein
                          organism = synthetic construct
SEQUENCE: 194
QITLKESGPT LVKPSQTLTL TCTFSGFSLS TSGVGVGWIR QPPGKALEWL ALIYWNSDKR     60
YSPSLKSRLT ITKDTSKNQV VLTMTNMDPV DTATYYCAHR HDSSSYYFYY GMDVWGQGIT    120
VTVSS                                                                125

SEQ ID NO: 195            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 195
gggttctcac tcagcactag tggagtgggt                                      30

SEQ ID NO: 196            moltype = AA  length = 10
FEATURE                   Location/Qualifiers
REGION                    1..10
                          note = Synthetic
source                    1..10
                          mol_type = protein
                          organism = synthetic construct
SEQUENCE: 196
GFSLSTSGVG                                                            10

SEQ ID NO: 197            moltype = DNA  length = 21
FEATURE                   Location/Qualifiers
misc_feature              1..21
                          note = Synthetic
source                    1..21
                          mol_type = other DNA
                          organism = synthetic construct
SEQUENCE: 197
atttattgga attctgataa g                                               21

SEQ ID NO: 198            moltype = AA  length = 7
FEATURE                   Location/Qualifiers
REGION                    1..7
                          note = Synthetic
source                    1..7
                          mol_type = protein
                          organism = synthetic construct
SEQUENCE: 198
IYWNSDK                                                               7

SEQ ID NO: 199            moltype = DNA  length = 51
FEATURE                   Location/Qualifiers
misc_feature              1..51
                          note = Synthetic
source                    1..51
                          mol_type = other DNA
                          organism = synthetic construct
SEQUENCE: 199
gcacacagac atgacagctc gtcctactac ttctactacg gtatggacgt c              51

SEQ ID NO: 200            moltype = AA  length = 17
```

```
FEATURE              Location/Qualifiers
REGION               1..17
                     note = Synthetic
source               1..17
                     mol_type = protein
                     organism = synthetic construct
SEQUENCE: 200
AHRHDSSSYY FYYGMDV                                                    17

SEQ ID NO: 201       moltype = DNA  length = 339
FEATURE              Location/Qualifiers
misc_feature         1..339
                     note = Synthetic
source               1..339
                     mol_type = other DNA
                     organism = synthetic construct
SEQUENCE: 201
gacatccaga tgacccagtc tccgctctcc ctgcccgtca cccctggaga gccggcctcc      60
atctcctgca ggtctagtca gagcctcctc catagtcatg gatacaacta tttggattgg    120
tacctgcaga agccagggca gtctccacaa ctcctgatct atttgggttc taatcgggcc    180
tccgggtgtcc ctgacaggtt cagtggcggt ggatcaggca cagatttttac actgaaaatc   240
agcagagtgg aggctgagga tgttgggatt tattactgca tgcaagctct acagactcct    300
ctcactttcg gcggagggac caaggtggag atcaaacga                            339

SEQ ID NO: 202       moltype = AA  length = 113
FEATURE              Location/Qualifiers
REGION               1..113
                     note = Synthetic
source               1..113
                     mol_type = protein
                     organism = synthetic construct
SEQUENCE: 202
DIQMTQSPLS LPVTPGEPAS ISCRSSQSLL HSHGYNYLDW YLQKPGQSPQ LLIYLGSNRA     60
SGVPDRFSGG GSGTDFTLKI SRVEAEDVGI YYCMQALQTP LTFGGGTKVE IKR           113

SEQ ID NO: 203       moltype = DNA  length = 33
FEATURE              Location/Qualifiers
misc_feature         1..33
                     note = Synthetic
source               1..33
                     mol_type = other DNA
                     organism = synthetic construct
SEQUENCE: 203
cagagcctcc tccatagtca tggatacaac tat                                  33

SEQ ID NO: 204       moltype = AA  length = 11
FEATURE              Location/Qualifiers
REGION               1..11
                     note = Synthetic
source               1..11
                     mol_type = protein
                     organism = synthetic construct
SEQUENCE: 204
QSLLHSHGYN Y                                                          11

SEQ ID NO: 205       moltype =   length =
SEQUENCE: 205
000

SEQ ID NO: 206       moltype =   length =
SEQUENCE: 206
000

SEQ ID NO: 207       moltype = DNA  length = 27
FEATURE              Location/Qualifiers
misc_feature         1..27
                     note = Synthetic
source               1..27
                     mol_type = other DNA
                     organism = synthetic construct
SEQUENCE: 207
atgcaagctc tacagactcc tctcact                                         27

SEQ ID NO: 208       moltype = AA  length = 9
FEATURE              Location/Qualifiers
REGION               1..9
                     note = Synthetic
source               1..9
                     mol_type = protein
```

```
                        organism = synthetic construct
SEQUENCE: 208
MQALQTPLT                                                            9

SEQ ID NO: 209          moltype = DNA  length = 375
FEATURE                 Location/Qualifiers
misc_feature            1..375
                        note = Synthetic
source                  1..375
                        mol_type = other DNA
                        organism = synthetic construct
SEQUENCE: 209
cagatcacct tgaaggagtc tggtcctact ctggtgaaac cctcacagac cctcacgctg    60
acctgcacct tctctgggtt ctcactcagc actagtggag tgggtgtggg ctggatccgt   120
cagcccccag gaaaggccct ggagtggctt gcactcattt attggaattc tgataagcgc   180
tacagcccct ctctgaagag caggctcacc atcaccaagg acacctccaa aaaccaggta   240
gtccttacaa tgaccaacat ggaccctgtg gacacagcca catattactg tgcacacaga   300
catgacagct cgtcctacta cttctactac ggtatggacg tctggggcca agggaccacg   360
gtcaccgtct cctca                                                   375

SEQ ID NO: 210          moltype = AA  length = 125
FEATURE                 Location/Qualifiers
REGION                  1..125
                        note = Synthetic
source                  1..125
                        mol_type = protein
                        organism = synthetic construct
SEQUENCE: 210
QITLKESGPT LVKPSQTLTL TCTFSGFSLS TSGVGVGWIR QPPGKALEWL ALIYWNSDKR    60
YSPSLKSRLT ITKDTSKNQV VLTMTNMDPV DTATYYCAHR HDSSSYYFYY GMDVWGQGTT   120
VTVSS                                                              125

SEQ ID NO: 211          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 211
gatattgtga tgactcagtc tccgctctcc ctgcccgtca cccctggaga gccggcctcc    60
atctcctgca ggtctagtca gagcctcctc catagtcatg gatacaacta tttggattgg   120
tacctgcaga agccagggca gtctccacaa ctcctgatct atttgggttc taatcgggcc   180
tccggggtcc ctgacaggtt cagtggcggt ggatcaggca cagattttac actgaaaatc   240
agcagagtgg aggctgagga tgttggggatt tattactgca tgcaagctct acagactcct   300
ctcacttttcg gcggagggac caaggtggag atcaaa                           336

SEQ ID NO: 212          moltype = AA  length = 112
FEATURE                 Location/Qualifiers
REGION                  1..112
                        note = Synthetic
source                  1..112
                        mol_type = protein
                        organism = synthetic construct
SEQUENCE: 212
DIVMTQSPLS LPVTPGEPAS ISCRSSQSLL HSHGYNYLDW YLQKPGQSPQ LLIYLGSNRA    60
SGVPDRFSGG GSGTDFTLKI SRVEAEDVGI YYCMQALQTP LTFGGGTKVE IK           112

SEQ ID NO: 213          moltype = DNA  length = 375
FEATURE                 Location/Qualifiers
misc_feature            1..375
                        note = Synthetic
source                  1..375
                        mol_type = other DNA
                        organism = synthetic construct
SEQUENCE: 213
cagatcaccct tgaaggagtc tggtcctacg ctggtgaaac ccacacagac cctcacgctg   60
acctgcacct tctctgggtt ctcactcagc actagtggag tgggtgtggg ctggatccgt   120
cagcccccag gaaaggccct ggagtggctt gcactcattt attggaattc tgataagcgc   180
tacagcccat ctctgaagag caggctcacc atcaccaagg acacctccaa aaaccaggta   240
gtccttacaa tgaccaacat ggaccctgtg gacacagcca catattactg tgcacacaga   300
catgacagct cgtcctacta cttctactac ggtatggacg tctggggcca agggaccacg   360
gtcaccgtct cctca                                                   375

SEQ ID NO: 214          moltype = AA  length = 125
FEATURE                 Location/Qualifiers
REGION                  1..125
                        note = Synthetic
source                  1..125
```

```
                        mol_type = protein
                        organism = synthetic construct
SEQUENCE: 214
QITLKESGPT LVKPTQTLTL TCTFSGFSLS TSGVGVGWIR QPPGKALEWL ALIYWNSDKR    60
YSPSLKSRLT ITKDTSKNQV VLTMTNMDPV DTATYYCAHR HDSSSYYFYY GMDVWGQGTT   120
VTVSS                                                               125

SEQ ID NO: 215          moltype = DNA   length = 336
FEATURE                 Location/Qualifiers
misc_feature            1..336
                        note = Synthetic
source                  1..336
                        mol_type = other DNA
                        organism = synthetic construct
SEQUENCE: 215
gatattgtga tgactcagtc tccactctcc ctgcccgtca cccctggaga gccggcctcc    60
atctcctgca ggtctagtca gagcctcctc catagtcatg gatacaacta tttggattgg   120
tacctgcaga agccagggca gtctccacag ctcctgatct atttgggttc taatcgggcc   180
tccggggtcc ctgacaggtt cagtggcagt ggatcaggca cagatttttac actgaaaatc   240
agcagagtgg aggctgagga tgttggggtt tattactgca tgcaagctct acagactcct   300
ctcactttcg gcggagggac caaggtggag atcaaa                             336

SEQ ID NO: 216          moltype = AA    length = 112
FEATURE                 Location/Qualifiers
REGION                  1..112
                        note = Synthetic
source                  1..112
                        mol_type = protein
                        organism = synthetic construct
SEQUENCE: 216
DIVMTQSPLS LPVTPGEPAS ISCRSSQSLL HSHGYNYLDW YLQKPGQSPQ LLIYLGSNRA    60
SGVPDRFSGS GSGTDFTLKI SRVEAEDVGV YYCMQALQTP LTFGGGTKVE IK           112

SEQ ID NO: 217          moltype = DNA   length = 381
FEATURE                 Location/Qualifiers
misc_feature            1..381
                        note = Synthetic
source                  1..381
                        mol_type = other DNA
                        organism = synthetic construct
SEQUENCE: 217
gagatgcaac tggtggagtc tgggggaggc ttggtccagc ctggggggtc cctgagactc    60
tcctgtgcag cctctggatt cacctttagt agtcactgga tgaagtgggt ccgccaggct   120
ccagggaagg ggctggagtg ggtggccaac ataaaccaag atggaagtga aaaatactat   180
gtggactctg tgaagggccg attcaccatc tccagagaca cgccaagaa ctcactgttt    240
ctgcaaatga acagcctgag agccgaggac acggctgtgt attactgtgc gagagatatt   300
gtactaatgg tctatgatat ggactactac tactacggta tggacgtctg ggggccaaggg   360
accacggtca ccgtctcctc a                                             381

SEQ ID NO: 218          moltype = AA    length = 127
FEATURE                 Location/Qualifiers
REGION                  1..127
                        note = Synthetic
source                  1..127
                        mol_type = protein
                        organism = synthetic construct
SEQUENCE: 218
EMQLVESGGG LVQPGGSLRL SCAASGFTFS SHWMKWVRQA PGKGLEWVAN INQDGSEKYY    60
VDSVKGRFTI SRDNAKNSLF LQMNSLRAED TAVYYCARDI VLMVYDMDYY YYGMDVWGQG   120
TTVTVSS                                                             127

SEQ ID NO: 219          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 219
ggattcacct ttagtagtca ctgg                                           24

SEQ ID NO: 220          moltype = AA    length = 8
FEATURE                 Location/Qualifiers
REGION                  1..8
                        note = Synthetic
source                  1..8
                        mol_type = protein
                        organism = synthetic construct
SEQUENCE: 220
```

```
GFTFSSHW                                                                       8

SEQ ID NO: 221         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 221
ataaaccaag atggaagtga gaaa                                                    24

SEQ ID NO: 222         moltype = AA  length = 8
FEATURE                Location/Qualifiers
REGION                 1..8
                       note = Synthetic
source                 1..8
                       mol_type = protein
                       organism = synthetic construct
SEQUENCE: 222
INQDGSEK                                                                       8

SEQ ID NO: 223         moltype = DNA  length = 60
FEATURE                Location/Qualifiers
misc_feature           1..60
                       note = Synthetic
source                 1..60
                       mol_type = other DNA
                       organism = synthetic construct
SEQUENCE: 223
gcgagagata ttgtactaat ggtctatgat atggactact actactacgg tatggacgtc            60

SEQ ID NO: 224         moltype = AA  length = 20
FEATURE                Location/Qualifiers
REGION                 1..20
                       note = Synthetic
source                 1..20
                       mol_type = protein
                       organism = synthetic construct
SEQUENCE: 224
ARDIVLMVYD MDYYYYGMDV                                                         20

SEQ ID NO: 225         moltype = DNA  length = 336
FEATURE                Location/Qualifiers
misc_feature           1..336
                       note = Synthetic
source                 1..336
                       mol_type = other DNA
                       organism = synthetic construct
SEQUENCE: 225
gatattgtga tgactcagtc tccactctcc ctgcccgtca cccctggaga gccggcctcc            60
atctcctgca ggtctagtca gagcctcctg catagtaatg gaaacaacta tttggattgg           120
tacctgcaga agccagggca gtctccacag ctcctgatct atttgggttc taatcgggcc           180
tccggggtcc ctgacaggtt cagtggcagt ggatcaggca cagattttac actgaaaatc           240
agcagagtgg aggctgagga tgttggggtt tattactgca tgcaaactct acaaactccg           300
ctcactttcg gcggagggac caaggtggag atcaaa                                    336

SEQ ID NO: 226         moltype = AA  length = 112
FEATURE                Location/Qualifiers
REGION                 1..112
                       note = Synthetic
source                 1..112
                       mol_type = protein
                       organism = synthetic construct
SEQUENCE: 226
DIVMTQSPLS LPVTPGEPAS ISCRSSQSLL HSNGNNYLDW YLQKPGQSPQ LLIYLGSNRA            60
SGVPDRFSGS GSGTDFTLKI SRVEAEDVGV YYCMQTLQTP LTFGGGTKVE IK                   112

SEQ ID NO: 227         moltype = DNA  length = 33
FEATURE                Location/Qualifiers
misc_feature           1..33
                       note = Synthetic
source                 1..33
                       mol_type = other DNA
                       organism = synthetic construct
SEQUENCE: 227
cagagcctcc tgcatagtaa tggaaacaac tat                                          33

SEQ ID NO: 228         moltype = AA  length = 11
```

```
FEATURE                 Location/Qualifiers
REGION                  1..11
                        note = Synthetic
source                  1..11
                        mol_type = protein
                        organism = synthetic construct
SEQUENCE: 228
QSLLHSNGNN Y                                                          11

SEQ ID NO: 229          moltype =    length =
SEQUENCE: 229
000

SEQ ID NO: 230          moltype =    length =
SEQUENCE: 230
000

SEQ ID NO: 231          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 231
atgcaaactc tacaaactcc gctcact                                         27

SEQ ID NO: 232          moltype = AA   length = 9
FEATURE                 Location/Qualifiers
REGION                  1..9
                        note = Synthetic
source                  1..9
                        mol_type = protein
                        organism = synthetic construct
SEQUENCE: 232
MQTLQTPLT                                                             9

SEQ ID NO: 233          moltype = DNA   length = 381
FEATURE                 Location/Qualifiers
misc_feature            1..381
                        note = Synthetic
source                  1..381
                        mol_type = other DNA
                        organism = synthetic construct
SEQUENCE: 233
gaggtgcagc tggtggagtc tgggggaggc ttggtccagc ctgggggtc cctgagactc      60
tcctgtgcag cctctggatt cacctttagt agtcactgga tgaagtgggt ccgccaggct    120
ccagggaagg ggctggagtg ggtggccaac ataaaccaag atggaagtga aaaatactat    180
gtggactctg tgaagggccg attcaccatc tccagagaca cgccaagaa ctcactgttt     240
ctgcaaatga acagcctgag agccgaggac acggctgtgt attactgtgc gagagatatt   300
gtactaatgg tctatgatat ggactactac tactacggta tggacgtctg gggccaaggg   360
accacggtca ccgtctcctc a                                              381

SEQ ID NO: 234          moltype = AA   length = 127
FEATURE                 Location/Qualifiers
REGION                  1..127
                        note = Synthetic
source                  1..127
                        mol_type = protein
                        organism = synthetic construct
SEQUENCE: 234
EVQLVESGGG LVQPGGSLRL SCAASGFTFS SHWMKWVRQA PGKGLEWVAN INQDGSEKYY     60
VDSVKGRFTI SRDNAKNSLF LQMNSLRAED TAVYYCARDI VLMVYDMDYY YYGMDVWGQG   120
TTVTVSS                                                              127

SEQ ID NO: 235          moltype = DNA   length = 336
FEATURE                 Location/Qualifiers
misc_feature            1..336
                        note = Synthetic
source                  1..336
                        mol_type = other DNA
                        organism = synthetic construct
SEQUENCE: 235
gatattgtga tgactcagtc tccactctcc ctgcccgtca cccctggaga gccggcctcc    60
atctcctgca ggtctagtca gagcctcctg catagtaatg aaacaacta tttggattgg    120
tacctgcaga agccagggca gtctccacag ctcctgatct atttgggttc taatcgggcc   180
tccggggtcc ctgacaggtt cagtggcagt ggatcaggca cagatttac actgaaaatc   240
agcagagtgg aggctgagga tgttgggggtt tattactgca tgcaaactct acaaactccg  300
ctcactttcg gcggagggac caaggtggag atcaaa                              336
```

```
SEQ ID NO: 236         moltype = AA  length = 112
FEATURE                Location/Qualifiers
REGION                 1..112
                       note = Synthetic
source                 1..112
                       mol_type = protein
                       organism = synthetic construct
SEQUENCE: 236
DIVMTQSPLS LPVTPGEPAS ISCRSSQSLL HSNGNNYLDW YLQKPGQSPQ LLIYLGSNRA    60
SGVPDRFSGS GSGTDFTLKI SRVEAEDVGV YYCMQTLQTP LTFGGGTKVE IK           112

SEQ ID NO: 237         moltype = DNA  length = 381
FEATURE                Location/Qualifiers
misc_feature           1..381
                       note = Synthetic
source                 1..381
                       mol_type = other DNA
                       organism = synthetic construct
SEQUENCE: 237
gaggtgcagc tggtggagtc tgggggaggc ttggtccagc ctgggggtc cctgagactc     60
tcctgtgcag cctctggatt cacctttagt agtcactgta tgagctgggt ccgccaggct   120
ccagggaagg ggctgagtg gtggccaac ataaaccaag atggaagtga aaatactat      180
gtggactctg tgaagggccg attcaccatc tccagagaca cgccaagaa ctcactgtat    240
ctgcaaatga acagcctgag agccgaggac acggctgtgt attactgtgc gagagatatt   300
gtactaatgg tctatgatat ggactactac tactacggta tggacgtctg ggggcaaggg   360
accacggtca ccgtctcctc a                                             381

SEQ ID NO: 238         moltype = AA  length = 127
FEATURE                Location/Qualifiers
REGION                 1..127
                       note = Synthetic
source                 1..127
                       mol_type = protein
                       organism = synthetic construct
SEQUENCE: 238
EVQLVESGGG LVQPGGSLRL SCAASGFTFS SHWMSWVRQA PGKGLEWVAN INQDGSEKYY    60
VDSVKGRFTI SRDNAKNSLY LQMNSLRAED TAVYYCARDI VLMVYDMDYY YYGMDVWGQG   120
TTVTVSS                                                             127

SEQ ID NO: 239         moltype = DNA  length = 336
FEATURE                Location/Qualifiers
misc_feature           1..336
                       note = Synthetic
source                 1..336
                       mol_type = other DNA
                       organism = synthetic construct
SEQUENCE: 239
gatattgtga tgactcagtc tccactctcc ctgcccgtca cccctggaga gccggcctcc    60
atctcctgca ggtctagtca gagcctcctg catagtaatg gaaacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaaactct acaaactccg   300
ctcacttttcg gcggagggac caaggtggag atcaaa                            336

SEQ ID NO: 240         moltype = AA  length = 112
FEATURE                Location/Qualifiers
REGION                 1..112
                       note = Synthetic
source                 1..112
                       mol_type = protein
                       organism = synthetic construct
SEQUENCE: 240
DIVMTQSPLS LPVTPGEPAS ISCRSSQSLL HSNGNNYLDW YLQKPGQSPQ LLIYLGSNRA    60
SGVPDRFSGS GSGTDFTLKI SRVEAEDVGV YYCMQTLQTP LTFGGGTKVE IK           112

SEQ ID NO: 241         moltype = DNA  length = 381
FEATURE                Location/Qualifiers
misc_feature           1..381
                       note = Synthetic
source                 1..381
                       mol_type = other DNA
                       organism = synthetic construct
SEQUENCE: 241
caggtgcagc tggtggagtc tgggggaggc gtggtccagc ctggggaggtc cctgagactc    60
tcctgtgcag tctctggatt caccttcagt agctatggca tgcactgggt ccgccaggct   120
ccaggcaagg ggctggagtg gtggcagct atatcatatg atggaagtaa taatactat     180
gtagactccg tgaagggccg attcaccatc tccagagaca attccaagaa aacgctgtat   240
ctgcaaatga acagcctgag agctgaggac acggctgtgt ataattgtgc gaaaaatatt   300
```

```
gtactagtga tgtatgatat agactatcac tactatggga tggacgtctg gggccaaggg    360
accacggtca ccgtctcctc a                                              381

SEQ ID NO: 242        moltype = AA   length = 127
FEATURE               Location/Qualifiers
REGION                1..127
                      note = Synthetic
source                1..127
                      mol_type = protein
                      organism = synthetic construct
SEQUENCE: 242
QVQLVESGGG VVQPGRSLRL SCAVSGFTFS SYGMHWVRQA PGKGLEWVAA ISYDGSNKYY    60
VDSVKGRFTI SRDNSKKTLY LQMNSLRAED TAVYNCAKNI VLVMYDIDYH YYGMDVWGQG    120
TTVTVSS                                                              127

SEQ ID NO: 243        moltype = DNA   length = 24
FEATURE               Location/Qualifiers
misc_feature          1..24
                      note = Synthetic
source                1..24
                      mol_type = other DNA
                      organism = synthetic construct
SEQUENCE: 243
ggattcacct tcagtagcta tggc                                           24

SEQ ID NO: 244        moltype = AA   length = 8
FEATURE               Location/Qualifiers
REGION                1..8
                      note = Synthetic
source                1..8
                      mol_type = protein
                      organism = synthetic construct
SEQUENCE: 244
GFTFSSYG                                                             8

SEQ ID NO: 245        moltype = DNA   length = 24
FEATURE               Location/Qualifiers
misc_feature          1..24
                      note = Synthetic
source                1..24
                      mol_type = other DNA
                      organism = synthetic construct
SEQUENCE: 245
atatcatatg atggaagtaa taaa                                           24

SEQ ID NO: 246        moltype = AA   length = 8
FEATURE               Location/Qualifiers
REGION                1..8
                      note = Synthetic
source                1..8
                      mol_type = protein
                      organism = synthetic construct
SEQUENCE: 246
ISYDGSNK                                                             8

SEQ ID NO: 247        moltype = DNA   length = 60
FEATURE               Location/Qualifiers
misc_feature          1..60
                      note = Synthetic
source                1..60
                      mol_type = other DNA
                      organism = synthetic construct
SEQUENCE: 247
gcgaaaaata ttgtactagt gatgtatgat atagactatc actactatgg gatggacgtc    60

SEQ ID NO: 248        moltype = AA   length = 20
FEATURE               Location/Qualifiers
REGION                1..20
                      note = Synthetic
source                1..20
                      mol_type = protein
                      organism = synthetic construct
SEQUENCE: 248
AKNIVLVMYD IDYHYYGMDV                                                20

SEQ ID NO: 249        moltype = DNA   length = 336
FEATURE               Location/Qualifiers
misc_feature          1..336
                      note = Synthetic
```

```
                          source           1..336
                                           mol_type = other DNA
                                           organism = synthetic construct
           SEQUENCE: 249
           gatattgtga tgactcagtc tccactctcc ctgcccgtca cccctggaga gccggcctcc   60
           atctcctgca ggtctagtca gagcctcctg catagtaatg gatacaacta tttggattgg  120
           tacctgcaga agccagggca gtctccacaa ctcctgatct atttgggttt taatcgggcc  180
           tccggggtcc ctgacaggtt cagtggcagt ggatcaggca cagattttac actgaaaatc  240
           agcagagtgg aggctgagga tgttggggtt tattactgca tgcaagctct acaaactcct  300
           ctcactttcg gcggagggac caaggtggag atcaga                            336

SEQ ID NO: 250       moltype = AA   length = 112
           FEATURE              Location/Qualifiers
           REGION               1..112
                                note = Synthetic
           source               1..112
                                mol_type = protein
                                organism = synthetic construct
           SEQUENCE: 250
           DIVMTQSPLS LPVTPGEPAS ISCRSSQSLL HSNGYNYLDW YLQKPGQSPQ LLIYLGFNRA    60
           SGVPDRFSGS GSGTDFTLKI SRVEAEDVGV YYCMQALQTP LTFGGGTKVE IR            112

SEQ ID NO: 251       moltype = DNA   length = 33
           FEATURE              Location/Qualifiers
           misc_feature         1..33
                                note = Synthetic
           source               1..33
                                mol_type = other DNA
                                organism = synthetic construct
           SEQUENCE: 251
           cagagcctcc tgcatagtaa tggatacaac tat                                33

SEQ ID NO: 252       moltype = AA   length = 11
           FEATURE              Location/Qualifiers
           REGION               1..11
                                note = Synthetic
           source               1..11
                                mol_type = protein
                                organism = synthetic construct
           SEQUENCE: 252
           QSLLHSNGYN Y                                                        11

SEQ ID NO: 253       moltype =    length =
           SEQUENCE: 253
           000

SEQ ID NO: 254       moltype =    length =
           SEQUENCE: 254
           000

SEQ ID NO: 255       moltype = DNA   length = 27
           FEATURE              Location/Qualifiers
           misc_feature         1..27
                                note = Synthetic
           source               1..27
                                mol_type = other DNA
                                organism = synthetic construct
           SEQUENCE: 255
           atgcaagctc tacaaactcc tctcact                                       27

SEQ ID NO: 256       moltype = AA   length = 9
           FEATURE              Location/Qualifiers
           REGION               1..9
                                note = Synthetic
           source               1..9
                                mol_type = protein
                                organism = synthetic construct
           SEQUENCE: 256
           MQALQTPLT                                                           9

SEQ ID NO: 257       moltype = DNA   length = 381
           FEATURE              Location/Qualifiers
           misc_feature         1..381
                                note = Synthetic
           source               1..381
                                mol_type = other DNA
                                organism = synthetic construct
           SEQUENCE: 257
           caggtgcagc tggtggagtc tgggggaggc gtggtccagc ctgggaggtc cctgagactc   60
```

```
tcctgtgcag tctctggatt caccttcagt agctatggca tgcactgggt ccgccaggct    120
ccaggcaagg ggctggagtg ggtggcagct atatcatatg atggaagtaa taaatactat    180
gtagactccg tgaagggccg attcaccatc tccagagaca attccaagaa aacgctatat    240
ctgcaaatga acagcctgag agctgaggac acggctgtgt ataattgtgc gaaaaatatt    300
gtactagtga tgtatgatat agactatcac tactatggga tggacgtctg ggggcaaggg    360
accacggtca ccgtctcctc a                                               381

SEQ ID NO: 258           moltype = AA   length = 127
FEATURE                  Location/Qualifiers
REGION                   1..127
                         note = Synthetic
source                   1..127
                         mol_type = protein
                         organism = synthetic construct
SEQUENCE: 258
QVQLVESGGG VVQPGRSLRL SCAVSGFTFS SYGMHWVRQA PGKGLEWVAA ISYDGSNKYY    60
VDSVKGRFTI SRDNSKKTLY LQMNSLRAED TAVYNCAKNI VLVMYDIDYH YYGMDVWGQG    120
TTVTVSS                                                               127

SEQ ID NO: 259           moltype = DNA   length = 336
FEATURE                  Location/Qualifiers
misc_feature             1..336
                         note = Synthetic
source                   1..336
                         mol_type = other DNA
                         organism = synthetic construct
SEQUENCE: 259
gatattgtga tgactcagtc tccactctcc ctgcccgtca cccctggaga gccggcctcc    60
atctcctgca ggtctagtca gagcctcctg catagtaatg gatacaacta tttggattgg    120
tacctgcaga agccagggca gtctccacaa ctcctgatct atttgggttt taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
ctcactttcg gcggagggac caaggtggag atcaaa                                336

SEQ ID NO: 260           moltype = AA   length = 112
FEATURE                  Location/Qualifiers
REGION                   1..112
                         note = Synthetic
source                   1..112
                         mol_type = protein
                         organism = synthetic construct
SEQUENCE: 260
DIVMTQSPLS LPVTPGEPAS ISCRSSQSLL HSNGYNYLDW YLQKPGQSPQ LLIYLGFNRA    60
SGVPDRFSGS GSGTDFTLKI SRVEAEDVGV YYCMQALQTP LTFGGGTKVE IK             112

SEQ ID NO: 261           moltype = DNA   length = 381
FEATURE                  Location/Qualifiers
misc_feature             1..381
                         note = Synthetic
source                   1..381
                         mol_type = other DNA
                         organism = synthetic construct
SEQUENCE: 261
caggtgcagc tggtggagtc tgggggaggc gtggtccagc ctgggaggtc cctgagactc    60
tcctgtgcag cctctggatt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctatat    240
ctgcaaatga acagcctgag agctgaggac acggctgtgt attactgtgc gaaaaatatt    300
gtactagtga tgtatgatat agactatcac tactatggga tggacgtctg ggggcaaggg    360
accacggtca ccgtctcctc a                                               381

SEQ ID NO: 262           moltype = AA   length = 127
FEATURE                  Location/Qualifiers
REGION                   1..127
                         note = Synthetic
source                   1..127
                         mol_type = protein
                         organism = synthetic construct
SEQUENCE: 262
QVQLVESGGG VVQPGRSLRL SCAASGFTFS SYGMHWVRQA PGKGLEWVAV ISYDGSNKYY    60
ADSVKGRFTI SRDNSKNTLY LQMNSLRAED TAVYYCAKNI VLVMYDIDYH YYGMDVWGQG    120
TTVTVSS                                                               127

SEQ ID NO: 263           moltype = DNA   length = 336
FEATURE                  Location/Qualifiers
misc_feature             1..336
                         note = Synthetic
source                   1..336
                         mol_type = other DNA
```

```
                        organism = synthetic construct
SEQUENCE: 263
gatattgtga tgactcagtc tccactctcc ctgcccgtca ccctggaga gccggcctcc    60
atctcctgca ggtctagtca gagcctcctg catagtaatg gatacaacta tttggattgg   120
tacctgcaga agccagggca gtctccacag ctcctgatct atttgggttt taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300
ctcacttttcg gcggagggac caaggtggag atcaaa                            336

SEQ ID NO: 264          moltype = AA   length = 112
FEATURE                 Location/Qualifiers
REGION                  1..112
                        note = Synthetic
source                  1..112
                        mol_type = protein
                        organism = synthetic construct
SEQUENCE: 264
DIVMTQSPLS LPVTPGEPAS ISCRSSQSLL HSNGYNYLDW YLQKPGQSPQ LLIYLGFNRA    60
SGVPDRFSGS GSGTDFTLKI SRVEAEDVGV YYCMQALQTP LTFGGGTKVE IK           112

SEQ ID NO: 265          moltype = DNA   length = 381
FEATURE                 Location/Qualifiers
misc_feature            1..381
                        note = Synthetic
source                  1..381
                        mol_type = other DNA
                        organism = synthetic construct
SEQUENCE: 265
caggtgcagc tggtggagtc tgggggaggc gtggtccagc ctgggaggtc cctgagactc    60
tcctgtgcag tctctggatt cacccttcagt agctatggc tgcactgggt ccgccaggct   120
ccaggcaagg ggctggagtg ggtggcagct atatcatatg atggaagtaa taaatactat   180
gtagactccg tgaagggccg attcaccatc tccagagaca attccaagaa aacgctgtat   240
ctgcaaatga acagcctgag agctgaggac acggctgtgt ataattgtgc gaaaaatatt   300
gtactagtga tgtatgatat agactatcac tactatggga tggacgtctg gggccaaggg   360
accacggtca ccgtctcctc a                                             381

SEQ ID NO: 266          moltype = AA   length = 127
FEATURE                 Location/Qualifiers
REGION                  1..127
                        note = Synthetic
source                  1..127
                        mol_type = protein
                        organism = synthetic construct
SEQUENCE: 266
QVQLVESGGG VVQPGRSLRL SCAVSGFTFS SYGMHWVRQA PGKGLEWVAA ISYDGSNKYY    60
VDSVKGRFTI SRDNSKKTLY LQMNSLRAED TAVYNCAKNI VLVMYDIDYH YYGMDVWGQG   120
TTVTVSS                                                             127

SEQ ID NO: 267          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 267
ggattcacct tcagtagcta tggc                                           24

SEQ ID NO: 268          moltype = AA   length = 8
FEATURE                 Location/Qualifiers
REGION                  1..8
                        note = Synthetic
source                  1..8
                        mol_type = protein
                        organism = synthetic construct
SEQUENCE: 268
GFTFSSYG                                                              8

SEQ ID NO: 269          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 269
atatcatatg atggaagtaa taaa                                           24

SEQ ID NO: 270          moltype = AA   length = 8
```

```
FEATURE                 Location/Qualifiers
REGION                  1..8
                        note = Synthetic
source                  1..8
                        mol_type = protein
                        organism = synthetic construct
SEQUENCE: 270
ISYDGSNK                                                               8

SEQ ID NO: 271          moltype = DNA   length = 60
FEATURE                 Location/Qualifiers
misc_feature            1..60
                        note = Synthetic
source                  1..60
                        mol_type = other DNA
                        organism = synthetic construct
SEQUENCE: 271
gcgaaaaata ttgtactagt gatgtatgat atagactatc actactatgg gatggacgtc      60

SEQ ID NO: 272          moltype = AA   length = 20
FEATURE                 Location/Qualifiers
REGION                  1..20
                        note = Synthetic
source                  1..20
                        mol_type = protein
                        organism = synthetic construct
SEQUENCE: 272
AKNIVLVMYD IDYHYYGMDV                                                  20

SEQ ID NO: 273          moltype = DNA   length = 336
FEATURE                 Location/Qualifiers
misc_feature            1..336
                        note = Synthetic
source                  1..336
                        mol_type = other DNA
                        organism = synthetic construct
SEQUENCE: 273
gatattgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccaggcca gtctccacaa ctcctgatct atttgggttt taatcgggcc     180
tccgggtgtcc ctgacaggtt cagtggcagt ggatcaggca cagattttac actgaaaatc    240
agcagagtgg aggctgagga tgttggggtt tattactgca tgcaagctct acaaactcct     300
ctcactttcg gcggagggac caaggtggag atcaga                               336

SEQ ID NO: 274          moltype = AA   length = 112
FEATURE                 Location/Qualifiers
REGION                  1..112
                        note = Synthetic
source                  1..112
                        mol_type = protein
                        organism = synthetic construct
SEQUENCE: 274
DIVMTQSPLS LPVTPGEPAS ISCRSSQSLL HSNGYNYLDW YLQKPGQSPQ LLIYLGFNRA      60
SGVPDRFSGS GSGTDFTLKI SRVEAEDVGV YYCMQALQTP LTFGGGTKVE IR             112

SEQ ID NO: 275          moltype = DNA   length = 33
FEATURE                 Location/Qualifiers
misc_feature            1..33
                        note = Synthetic
source                  1..33
                        mol_type = other DNA
                        organism = synthetic construct
SEQUENCE: 275
cagagcctcc tgcatagtaa tggatacaac tat                                   33

SEQ ID NO: 276          moltype = AA   length = 11
FEATURE                 Location/Qualifiers
REGION                  1..11
                        note = Synthetic
source                  1..11
                        mol_type = protein
                        organism = synthetic construct
SEQUENCE: 276
QSLLHSNGYN Y                                                           11

SEQ ID NO: 277          moltype =    length =
SEQUENCE: 277
000
```

-continued

```
SEQ ID NO: 278          moltype =    length =
SEQUENCE: 278
000

SEQ ID NO: 279          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 279
atgcaagctc tacaaactcc tctcact                                              27

SEQ ID NO: 280          moltype = AA   length = 9
FEATURE                 Location/Qualifiers
REGION                  1..9
                        note = Synthetic
source                  1..9
                        mol_type = protein
                        organism = synthetic construct
SEQUENCE: 280
MQALQTPLT                                                                   9

SEQ ID NO: 281          moltype = DNA   length = 381
FEATURE                 Location/Qualifiers
misc_feature            1..381
                        note = Synthetic
source                  1..381
                        mol_type = other DNA
                        organism = synthetic construct
SEQUENCE: 281
caggtgcagc tggtggagtc tgggggaggc gtggtccagc ctgggaggtc cctgagactc           60
tcctgtgcag tctctggatt caccttcagt agctatggca tgcactgggt ccgccaggct          120
ccaggcaagg ggctggagtg ggtggcagct atatcatatg atggaagtaa taaatactat          180
gtagactccg tgaagggccg attcaccatc tccagagaca attccaagaa aacgctgtat          240
ctgcaaatga acagcctgag agctgaggac acggctgtgt ataattgtgc gaaaaatatt          300
gtactagtga tgtatgatat agactatcac tactatggga tggacgtctg gggccaaggg          360
accacggtca ccgtctcctc a                                                   381

SEQ ID NO: 282          moltype = AA   length = 127
FEATURE                 Location/Qualifiers
REGION                  1..127
                        note = Synthetic
source                  1..127
                        mol_type = protein
                        organism = synthetic construct
SEQUENCE: 282
QVQLVESGGG VVQPGRSLRL SCAVSGFTFS SYGMHWVRQA PGKGLEWVAA ISYDGSNKYY           60
VDSVKGRFTI SRDNSKKTLY LQMNSLRAED TAVYNCAKNI VLVMYDIDYH YYGMDVWGQG          120
TTVTVSS                                                                   127

SEQ ID NO: 283          moltype = DNA   length = 336
FEATURE                 Location/Qualifiers
misc_feature            1..336
                        note = Synthetic
source                  1..336
                        mol_type = other DNA
                        organism = synthetic construct
SEQUENCE: 283
gatattgtga tgactcagtc tccactctcc ctgcccgtca cccctggaga gccggcctcc           60
atctcctgca ggtctagtca gagcctcctg catagtaatg gatacaacta tttggattgg          120
tacctgcaga agccagggca gtctccacaa ctcctgatct atttgggttt taatcgggcc          180
tccggggtcc ctgacaggtt cagtggcagt ggatcaggca cagattttac actgaaaatc          240
agcagagtgg aggctgagga tgttggggtt tattactgca tgcaagctct acaaactcct          300
ctcactttcg gcggagggac caaggtggag atcaaa                                   336

SEQ ID NO: 284          moltype = AA   length = 112
FEATURE                 Location/Qualifiers
REGION                  1..112
                        note = Synthetic
source                  1..112
                        mol_type = protein
                        organism = synthetic construct
SEQUENCE: 284
DIVMTQSPLS LPVTPGEPAS ISCRSSQSLL HSNGYNYLDW YLQKPGQSPQ LLIYLGFNRA           60
SGVPDRFSGS GSGTDFTLKI SRVEAEDVGV YYCMQALQTP LTFGGGTKVE IK                  112

SEQ ID NO: 285          moltype = DNA   length = 381
```

```
FEATURE                 Location/Qualifiers
misc_feature            1..381
                        note = Synthetic
source                  1..381
                        mol_type = other DNA
                        organism = synthetic construct
SEQUENCE: 285
caggtgcagc tggtggagtc tgggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgc gaaaaatatt   300
gtactagtga tgtatgatat agactatcac tactatggga tggacgtctg ggggcaaggg   360
accacggtca ccgtctcctc a                                             381

SEQ ID NO: 286          moltype = AA  length = 127
FEATURE                 Location/Qualifiers
REGION                  1..127
                        note = Synthetic
source                  1..127
                        mol_type = protein
                        organism = synthetic construct
SEQUENCE: 286
QVQLVESGGG VVQPGRSLRL SCAASGFTFS SYGMHWVRQA PGKGLEWVAV ISYDGSNKYY     60
ADSVKGRFTI SRDNSKNTLY LQMNSLRAED TAVYYCAKNI VLVMYDIDYH YYGMDVWGQG    120
TTVTVSS                                                             127

SEQ ID NO: 287          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 287
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttt taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300
ctcactttcg gcggagggac caaggtggag atcaaa                             336

SEQ ID NO: 288          moltype = AA  length = 112
FEATURE                 Location/Qualifiers
REGION                  1..112
                        note = Synthetic
source                  1..112
                        mol_type = protein
                        organism = synthetic construct
SEQUENCE: 288
DIVMTQSPLS LPVTPGEPAS ISCRSSQSLL HSNGYNYLDW YLQKPGQSPQ LLIYLGFNRA     60
SGVPDRFSGS GSGTDFTLKI SRVEAEDVGV YYCMQALQTP LTFGGGTKVE IK            112

SEQ ID NO: 289          moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 289
cagatcacct tgaaggagtc tggtcctacg ctggtaaaac ccacacagac cctcacgctg    60
acctgcacct tctctgggtt ctcactcagc gctagtggag tgggtgtggg ctggttccgt   120
cagccccag gaaaggccct ggagtggctt gcactcattt attggaatga tgataagcgt   180
tacagcccat ctctaaagaa cagcctcacc atcaccaagg acacctccaa aaaccaggtg   240
gtccttacaa tgaccaacat ggaccctgtg gacacagcca catattactg tgcacacaga   300
atacatctat ggtcctactt ctactacggt atggacgtct ggggccaagg gaccacggtc   360
accgtctcct ca                                                       372

SEQ ID NO: 290          moltype = AA  length = 124
FEATURE                 Location/Qualifiers
REGION                  1..124
                        note = Synthetic
source                  1..124
                        mol_type = protein
                        organism = synthetic construct
SEQUENCE: 290
QITLKESGPT LVKPTQTLTL TCTFSGFSLS ASGVGVGWFR QPPGKALEWL ALIYWNDDKR     60
YSPSLKNSLT ITKDTSKNQV VLTMTNMDPV DTATYYCAHR IHLWSYFYYG MDVWGQGTTV   120
```

TVSS                                                                           124

SEQ ID NO: 291          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 291
gggttctcac tcagcgctag tggagtgggt                                                30

SEQ ID NO: 292          moltype = AA  length = 10
FEATURE                 Location/Qualifiers
REGION                  1..10
                        note = Synthetic
source                  1..10
                        mol_type = protein
                        organism = synthetic construct
SEQUENCE: 292
GFSLSASGVG                                                                     10

SEQ ID NO: 293          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 293
atttattgga atgatgataa g                                                        21

SEQ ID NO: 294          moltype = AA  length = 7
FEATURE                 Location/Qualifiers
REGION                  1..7
                        note = Synthetic
source                  1..7
                        mol_type = protein
                        organism = synthetic construct
SEQUENCE: 294
IYWNDDK                                                                        7

SEQ ID NO: 295          moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 295
gcacacagaa tacatctatg gtcctacttc tactacggta tggacgtc                           48

SEQ ID NO: 296          moltype = AA  length = 16
FEATURE                 Location/Qualifiers
REGION                  1..16
                        note = Synthetic
source                  1..16
                        mol_type = protein
                        organism = synthetic construct
SEQUENCE: 296
AHRIHLWSYF YYGMDV                                                              16

SEQ ID NO: 297          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 297
gatattgtga tgactcagtc tccactctcc ctgcccgtca cccctggaga gccggcctcc               60
atctcctgca ggtctagtca gactctcctg catagtaatg gatacaacta tttcgattgg              120
tacctgcaga agccagggca gtctccacag ctcctgatct atttgggttc taatcgggcc              180
tccggggtcc ctgacagatt cagtggcagt ggatcaggca cagatttac actgaaaatc               240
agcagagtgg aggctgagga tgttggaatt tattactgca tgcaagctct acaaactcct              300
ctcactttcg gcggagggac caaggtggag atcaga                                       336

SEQ ID NO: 298          moltype = AA  length = 112
FEATURE                 Location/Qualifiers

```
REGION                  1..112
                        note = Synthetic
source                  1..112
                        mol_type = protein
                        organism = synthetic construct
SEQUENCE: 298
DIVMTQSPLS LPVTPGEPAS ISCRSSQTLL HSNGYNYFDW YLQKPGQSPQ LLIYLGSNRA    60
SGVPDRFSGS GSGTDFTLKI SRVEAEDVGI YYCMQALQTP LTFGGGTKVE IR           112

SEQ ID NO: 299          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 299
cagactctcc tgcatagtaa tggatacaac tat                                 33

SEQ ID NO: 300          moltype = AA  length = 11
FEATURE                 Location/Qualifiers
REGION                  1..11
                        note = Synthetic
source                  1..11
                        mol_type = protein
                        organism = synthetic construct
SEQUENCE: 300
QTLLHSNGYN Y                                                         11

SEQ ID NO: 301          moltype =     length =
SEQUENCE: 301
000

SEQ ID NO: 302          moltype =     length =
SEQUENCE: 302
000

SEQ ID NO: 303          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 303
atgcaagctc tacaaactcc tctcact                                        27

SEQ ID NO: 304          moltype = AA  length = 9
FEATURE                 Location/Qualifiers
REGION                  1..9
                        note = Synthetic
source                  1..9
                        mol_type = protein
                        organism = synthetic construct
SEQUENCE: 304
MQALQTPLT                                                             9

SEQ ID NO: 305          moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 305
cagatcaccT tgaaggagtc tggtcctacg ctggtaaaac ccacacagac cctcacgctg    60
acctgcacct tctctgggtt ctcactcagc gctagtggag tgggtgtggg ctggttccgt   120
cagccccag gaaaggccct ggagtggctt gcactcattt attggaatga tgataagcgt   180
tacagcccat ctctaaagaa cagcctcacc atcaccaagg acacctccaa aaaccaggtg   240
gtccttacaa tgaccaacat ggaccctgtg gacacagcca catattactg tgcacacaga   300
atacatctat ggtcctactt ctactacggt atggacgtct ggggccaagg gaccacggtc   360
accgtctcct ca                                                       372

SEQ ID NO: 306          moltype = AA  length = 124
FEATURE                 Location/Qualifiers
REGION                  1..124
                        note = Synthetic
source                  1..124
                        mol_type = protein
```

```
                    organism = synthetic construct
SEQUENCE: 306
QITLKESGPT LVKPTQTLTL TCTFSGFSLS ASGVGVGWFR QPPGKALEWL ALIYWNDDKR    60
YSPSLKNSLT ITKDTSKNQV VLTMTNMDPV DTATYYCAHR IHLWSYFYYG MDVWGQGTTV   120
TVSS                                                                124

SEQ ID NO: 307            moltype = DNA   length = 336
FEATURE                   Location/Qualifiers
misc_feature              1..336
                          note = Synthetic
source                    1..336
                          mol_type = other DNA
                          organism = synthetic construct
SEQUENCE: 307
gatattgtga tgactcagtc tccactctcc ctgcccgtca cccctggaga gccggcctcc    60
atctcctgca ggtctagtca gactctcctg catagtaatg gatacaacta tttcgattgg   120
tacctgcaga agccagggca gtctccacag ctcctgatct atttgggttc taatcgggcc   180
tccggggtcc ctgacagatt cagtggcagt ggatcaggca cagattttac actgaaaatc   240
agcagagtgg aggctgagga tgttggaatt tattactgca tgcaagctct acaaactcct   300
ctcactttcg gcggagggac caaggtggag atcaaa                             336

SEQ ID NO: 308            moltype = AA    length = 112
FEATURE                   Location/Qualifiers
REGION                    1..112
                          note = Synthetic
source                    1..112
                          mol_type = protein
                          organism = synthetic construct
SEQUENCE: 308
DIVMTQSPLS LPVTPGEPAS ISCRSSQTLL HSNGYNYFDW YLQKPGQSPQ LLIYLGSNRA    60
SGVPDRFSGS GSGTDFTLKI SRVEAEDVGI YYCMQALQTP LTFGGGTKVE IK           112

SEQ ID NO: 309            moltype = DNA   length = 372
FEATURE                   Location/Qualifiers
misc_feature              1..372
                          note = Synthetic
source                    1..372
                          mol_type = other DNA
                          organism = synthetic construct
SEQUENCE: 309
cagatcacct tgaaggagtc tggtcctacg ctggtgaaac ccacacagac cctcacgctg    60
acctgcacct tctctgggtt ctcactcagc gctagtggag tgggtgtggg ctggatccgt   120
cagccccag gaaaggccct ggagtggctt gcactcattt attggaatga tgataagcgc   180
tacagcccat ctctgaagag caggctcacc atcaccaagg acacctccaa aaaccaggtg   240
gtccttacaa tgaccaacat ggaccctgtg acacagcca catattactg tgcacacaga   300
atacatctat ggtcctactt ctactacggt atggacgtct gggggcaagg gaccacggtc   360
accgtctcct ca                                                       372

SEQ ID NO: 310            moltype = AA    length = 124
FEATURE                   Location/Qualifiers
REGION                    1..124
                          note = Synthetic
source                    1..124
                          mol_type = protein
                          organism = synthetic construct
SEQUENCE: 310
QITLKESGPT LVKPTQTLTL TCTFSGFSLS ASGVGVGWIR QPPGKALEWL ALIYWNDDKR    60
YSPSLKSRLT ITKDTSKNQV VLTMTNMDPV DTATYYCAHR IHLWSYFYYG MDVWGQGTTV   120
TVSS                                                                124

SEQ ID NO: 311            moltype = DNA   length = 336
FEATURE                   Location/Qualifiers
misc_feature              1..336
                          note = Synthetic
source                    1..336
                          mol_type = other DNA
                          organism = synthetic construct
SEQUENCE: 311
gatattgtga tgactcagtc tccactctcc ctgcccgtca cccctggaga gccggcctcc    60
atctcctgca ggtctagtca gactctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300
ctcactttcg gcggagggac caaggtggag atcaaa                             336

SEQ ID NO: 312            moltype = AA    length = 112
FEATURE                   Location/Qualifiers
REGION                    1..112
                          note = Synthetic
```

```
source                      1..112
                            mol_type = protein
                            organism = synthetic construct
SEQUENCE: 312
DIVMTQSPLS LPVTPGEPAS ISCRSSQTLL HSNGYNYLDW YLQKPGQSPQ LLIYLGSNRA    60
SGVPDRFSGS GSGTDFTLKI SRVEAEDVGV YYCMQALQTP LTFGGGTKVE IK           112

SEQ ID NO: 313              moltype = DNA   length = 381
FEATURE                     Location/Qualifiers
misc_feature                1..381
                            note = Synthetic
source                      1..381
                            mol_type = other DNA
                            organism = synthetic construct
SEQUENCE: 313
caggttcagc tggtgcagtc tggacctgag gtgaagaacc ctggggcctc agtgaaggtc    60
tcctgcaagg cttctggtta cacctttacc acctatggta tcagttgggt acgacaggcc   120
cctggacaag ggcttgagtg gatgggatgg atcagcggtt acaatggtaa aacaaacgat   180
gcacagaagt tccaggacag agtcgccatg accacagaca catccacgag cacagcctac   240
atggagctga ggagcctgag atctgacgac acggccattt attactgttc gagagatcgt   300
ttagtagtac cacctgccct taattattcc tactacgtta tggacgtctg gggccaaggg   360
accacggtca ccgtctcctc a                                             381

SEQ ID NO: 314              moltype = AA   length = 127
FEATURE                     Location/Qualifiers
REGION                      1..127
                            note = Synthetic
source                      1..127
                            mol_type = protein
                            organism = synthetic construct
SEQUENCE: 314
QVQLVQSGPE VKNPGASVKV SCKASGYTFT TYGISWVRQA PGQGLEWMGW ISGYNGKTND    60
AQKFQDRVAM TTDTSTSTAY MELRSLRSDD TAIYYCSRDR LVVPPALNYS YYVMDVWGQG   120
TTVTVSS                                                             127

SEQ ID NO: 315              moltype = DNA   length = 24
FEATURE                     Location/Qualifiers
misc_feature                1..24
                            note = Synthetic
source                      1..24
                            mol_type = other DNA
                            organism = synthetic construct
SEQUENCE: 315
ggttacacct ttaccaccta tggt                                           24

SEQ ID NO: 316              moltype = AA   length = 8
FEATURE                     Location/Qualifiers
REGION                      1..8
                            note = Synthetic
source                      1..8
                            mol_type = protein
                            organism = synthetic construct
SEQUENCE: 316
GYTFTTYG                                                              8

SEQ ID NO: 317              moltype = DNA   length = 24
FEATURE                     Location/Qualifiers
misc_feature                1..24
                            note = Synthetic
source                      1..24
                            mol_type = other DNA
                            organism = synthetic construct
SEQUENCE: 317
atcagcggtt acaatggtaa aaca                                           24

SEQ ID NO: 318              moltype = AA   length = 8
FEATURE                     Location/Qualifiers
REGION                      1..8
                            note = Synthetic
source                      1..8
                            mol_type = protein
                            organism = synthetic construct
SEQUENCE: 318
ISGYNGKT                                                              8

SEQ ID NO: 319              moltype = DNA   length = 60
FEATURE                     Location/Qualifiers
misc_feature                1..60
                            note = Synthetic
```

```
                        source          1..60
                                        mol_type = other DNA
                                        organism = synthetic construct
SEQUENCE: 319
tcgagagatc gtttagtagt accacctgcc cttaattatt cctactacgt tatggacgtc    60

SEQ ID NO: 320          moltype = AA   length = 20
FEATURE                 Location/Qualifiers
REGION                  1..20
                        note = Synthetic
source                  1..20
                        mol_type = protein
                        organism = synthetic construct
SEQUENCE: 320
SRDRLVVPPA LNYSYYVMDV                                                20

SEQ ID NO: 321          moltype = DNA   length = 336
FEATURE                 Location/Qualifiers
misc_feature            1..336
                        note = Synthetic
source                  1..336
                        mol_type = other DNA
                        organism = synthetic construct
SEQUENCE: 321
gatgttgtga tgactcagtc tccactctcc ctgcccgtca cccttggaca gccggcctcc    60
atctcctgca ggtctagtca aagcctcgta tacagtgatg gaaacaccta cttgaattgg   120
tctcagcaga ggccaggtca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggccg   300
tacactttg gccaggggac caagctggag atcaaa                              336

SEQ ID NO: 322          moltype = AA   length = 112
FEATURE                 Location/Qualifiers
REGION                  1..112
                        note = Synthetic
source                  1..112
                        mol_type = protein
                        organism = synthetic construct
SEQUENCE: 322
DVVMTQSPLS LPVTLGQPAS ISCRSSQSLV YSDGNTYLNW SQQRPGQSPR RLIYKVSNRD    60
SGVPDRFSGS GSGTDFTLKI SRVEAEDVGV YYCMQGTHWP YTFGQGTKLE IK           112

SEQ ID NO: 323          moltype = DNA   length = 33
FEATURE                 Location/Qualifiers
misc_feature            1..33
                        note = Synthetic
source                  1..33
                        mol_type = other DNA
                        organism = synthetic construct
SEQUENCE: 323
caaagcctcg tatacagtga tggaaacacc tac                                 33

SEQ ID NO: 324          moltype = AA   length = 11
FEATURE                 Location/Qualifiers
REGION                  1..11
                        note = Synthetic
source                  1..11
                        mol_type = protein
                        organism = synthetic construct
SEQUENCE: 324
QSLVYSDGNT Y                                                         11

SEQ ID NO: 325          moltype =     length =
SEQUENCE: 325
000

SEQ ID NO: 326          moltype =     length =
SEQUENCE: 326
000

SEQ ID NO: 327          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 327
atgcaaggta cacactggcc gtacact                                        27
```

```
SEQ ID NO: 328          moltype = AA   length = 9
FEATURE                 Location/Qualifiers
REGION                  1..9
                        note = Synthetic
source                  1..9
                        mol_type = protein
                        organism = synthetic construct
SEQUENCE: 328
MQGTHWPYT                                                                    9

SEQ ID NO: 329          moltype = DNA  length = 381
FEATURE                 Location/Qualifiers
misc_feature            1..381
                        note = Synthetic
source                  1..381
                        mol_type = other DNA
                        organism = synthetic construct
SEQUENCE: 329
caggttcagc tggtgcagtc tggacctgag gtgaagaacc ctggggcctc agtgaaggtc    60
tcctgcaagg cttctggtta cacctttacc acctatggta tcagttgggt acgacaggcc   120
cctggacaag gccttgagtg gatgggatgg atcagcggt acaatggtaa aacaaacgat   180
gcacagaagt tccaggacag agtcgccatg accacagaca catccacgag cacagcctac   240
atggagctga ggagcctgag atctgacgac acggccattt attactgttc gagagatcgt   300
ttagtagtac cacctgccct taattattcc tactacgtta tggacgtctg gggccaaggg   360
accacggtca ccgtctcctc a                                             381

SEQ ID NO: 330          moltype = AA   length = 127
FEATURE                 Location/Qualifiers
REGION                  1..127
                        note = Synthetic
source                  1..127
                        mol_type = protein
                        organism = synthetic construct
SEQUENCE: 330
QVQLVQSGPE VKNPGASVKV SCKASGYTFT TYGISWVRQA PGQGLEWMGW ISGYNGKTND    60
AQKFQDRVAM TTDTSTSTAY MELRSLRSDD TAIYYCSRDR LVVPPALNYS YYVMDVWGQG   120
TTVTVSS                                                             127

SEQ ID NO: 331          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 331
gatgttgtga tgactcagtc tccactctcc ctgcccgtca cccttggaca gccggcctcc    60
atctcctgca ggtctagtca aagcctcgta tacagtgatg gaaacaccta cttgaattgg   120
tctcagcaga ggccaggtca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggccg   300
tacacttttg gccaggggac caagctggag atcaaa                             336

SEQ ID NO: 332          moltype = AA   length = 112
FEATURE                 Location/Qualifiers
REGION                  1..112
                        note = Synthetic
source                  1..112
                        mol_type = protein
                        organism = synthetic construct
SEQUENCE: 332
DVVMTQSPLS LPVTLGQPAS ISCRSSQSLV YSDGNTYLNW SQQRPGQSPR RLIYKVSNRD    60
SGVPDRFSGS GSGTDFTLKI SRVEAEDVGV YYCMQGTHWP YTFGQGTKLE IK           112

SEQ ID NO: 333          moltype = DNA  length = 381
FEATURE                 Location/Qualifiers
misc_feature            1..381
                        note = Synthetic
source                  1..381
                        mol_type = other DNA
                        organism = synthetic construct
SEQUENCE: 333
caggttcagc tggtgcagtc tggagctgag gtgaagaagc tggggcctc agtgaaggtc    60
tcctgcaagg cttctggtta cacctttacc acctatggta tcagctgggt gcgacaggcc   120
cctggacaag gccttgagtg gatgggatgg atcagcggtt acaatggtaa aacaaactat   180
gcacagaagc tccagggcag agtcaccatg accacagaca tccacgag cacagcctac    240
atggagctga ggagcctgag atctgacgac acggccgtgt attactgttc gagagatcgt   300
ttagtagtac cacctgccct taattattcc tactacgtta tggacgtctg ggggcaaggg   360
```

```
accacggtca ccgtctcctc a                                               381

SEQ ID NO: 334          moltype = AA   length = 127
FEATURE                 Location/Qualifiers
REGION                  1..127
                        note = Synthetic
source                  1..127
                        mol_type = protein
                        organism = synthetic construct
SEQUENCE: 334
QVQLVQSGAE VKKPGASVKV SCKASGYTFT TYGISWVRQA PGQGLEWMGW ISGYNGKTNY    60
AQKLQGRVTM TTDTSTSTAY MELRSLRSDD TAVYYCSRDR LVVPPALNYS YYVMDVWGQG   120
TTVTVSS                                                             127

SEQ ID NO: 335          moltype = DNA   length = 336
FEATURE                 Location/Qualifiers
misc_feature            1..336
                        note = Synthetic
source                  1..336
                        mol_type = other DNA
                        organism = synthetic construct
SEQUENCE: 335
gatgttgtga tgactcagtc tccactctcc ctgcccgtca cccttggaca gccggcctcc    60
atctcctgca ggtctagtca aagcctcgta tacagtgatg gaaacaccta cttgaattgg   120
tttcagcaga ggccaggcca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggccg   300
tacacttttg gccaggggac caagctggag atcaaa                             336

SEQ ID NO: 336          moltype = AA   length = 112
FEATURE                 Location/Qualifiers
REGION                  1..112
                        note = Synthetic
source                  1..112
                        mol_type = protein
                        organism = synthetic construct
SEQUENCE: 336
DVVMTQSPLS LPVTLGQPAS ISCRSSQSLV YSDGNTYLNW FQQRPGQSPR RLIYKVSNRD    60
SGVPDRFSGS GSGTDFTLKI SRVEAEDVGV YYCMQGTHWP YTFGQGTKLE IK           112

SEQ ID NO: 337          moltype = DNA   length = 354
FEATURE                 Location/Qualifiers
misc_feature            1..354
                        note = Synthetic
source                  1..354
                        mol_type = other DNA
                        organism = synthetic construct
SEQUENCE: 337
gaggtgcagc tggtggagtc tgggggaggc ctggtcaagc ctggggggtc cctgagactc    60
tcctgtgcag cctctggatt caccttcagt agctatagca tggactgggt ccgccaggct   120
ccagggaagg ggctggagtg ggtctcatcc attagtagta gtagttatat catatactac   180
gcagactctg tgaagggccg attcaccatc tccagagaca ccgccaagaa ctcactgtat   240
ctgcaaatga acagcctgag agacgaggac acggctgttt attactgtgc gagagaggc   300
agtagcagac tttttgacta ctggggccag ggaaccctgg tcaccgtctc ctca        354

SEQ ID NO: 338          moltype = AA   length = 118
FEATURE                 Location/Qualifiers
REGION                  1..118
                        note = Synthetic
source                  1..118
                        mol_type = protein
                        organism = synthetic construct
SEQUENCE: 338
EVQLVESGGG LVKPGGSLRL SCAASGFTFS SYSMDWVRQA PGKGLEWVSS ISSSSSYIYY    60
ADSVKGRFTI SRDTAKNSLY LQMNSLRDED TAVYYCAREG SSRLFDYWGQ GTLVTVSS    118

SEQ ID NO: 339          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 339
ggattcacct tcagtagcta tagc                                           24

SEQ ID NO: 340          moltype = AA   length = 8
FEATURE                 Location/Qualifiers
REGION                  1..8
```

```
                         note = Synthetic
source                   1..8
                         mol_type = protein
                         organism = synthetic construct
SEQUENCE: 340
GFTFSSYS                                                                 8

SEQ ID NO: 341           moltype = DNA   length = 24
FEATURE                  Location/Qualifiers
misc_feature             1..24
                         note = Synthetic
source                   1..24
                         mol_type = other DNA
                         organism = synthetic construct
SEQUENCE: 341
attagtagta gtagtagtta cata                                              24

SEQ ID NO: 342           moltype = AA   length = 8
FEATURE                  Location/Qualifiers
REGION                   1..8
                         note = Synthetic
source                   1..8
                         mol_type = protein
                         organism = synthetic construct
SEQUENCE: 342
ISSSSSYI                                                                 8

SEQ ID NO: 343           moltype = DNA   length = 33
FEATURE                  Location/Qualifiers
misc_feature             1..33
                         note = Synthetic
source                   1..33
                         mol_type = other DNA
                         organism = synthetic construct
SEQUENCE: 343
gcgagagagg gcagtagcag acttttttgac tac                                   33

SEQ ID NO: 344           moltype = AA   length = 11
FEATURE                  Location/Qualifiers
REGION                   1..11
                         note = Synthetic
source                   1..11
                         mol_type = protein
                         organism = synthetic construct
SEQUENCE: 344
AREGSSRLFD Y                                                            11

SEQ ID NO: 345           moltype = DNA   length = 321
FEATURE                  Location/Qualifiers
misc_feature             1..321
                         note = Synthetic
source                   1..321
                         mol_type = other DNA
                         organism = synthetic construct
SEQUENCE: 345
gacatccaga tgacccagtc tccttccacc ctgtctgcat ctgtaggaga cagagtcacc       60
atcacttgcc gggccagtca gagtattagt agctggttgg cctggtatca gcagagacca      120
gggaaagccc ctaagctcct gatctataag gcgtctagtt tagaaggtgg agtcccatca      180
aggttcagcg gcagtggatc tgggacagaa ttcactctca ccatcagcag cctgcagcct      240
gaggattttg caacttatta ctgccaacag tataatagtt attggtacac ttttggccag      300
gggaccaagc tggagatcaa a                                                321

SEQ ID NO: 346           moltype = AA   length = 107
FEATURE                  Location/Qualifiers
REGION                   1..107
                         note = Synthetic
source                   1..107
                         mol_type = protein
                         organism = synthetic construct
SEQUENCE: 346
DIQMTQSPST LSASVGDRVT ITCRASQSIS SWLAWYQQRP GKAPKLLIYK ASSLEGGVPS       60
RFSGSGSGTE FTLTISSLQP EDFATYYCQQ YNSYWYTFGQ GTKLEIK                    107

SEQ ID NO: 347           moltype = DNA   length = 18
FEATURE                  Location/Qualifiers
misc_feature             1..18
                         note = Synthetic
source                   1..18
                         mol_type = other DNA
```

```
                        organism = synthetic construct
SEQUENCE: 347
cagagtatta gtagctgg                                                       18

SEQ ID NO: 348          moltype = AA   length = 6
FEATURE                 Location/Qualifiers
REGION                  1..6
                        note = Synthetic
source                  1..6
                        mol_type = protein
                        organism = synthetic construct
SEQUENCE: 348
QSISSW                                                                     6

SEQ ID NO: 349          moltype =   length =
SEQUENCE: 349
000

SEQ ID NO: 350          moltype =   length =
SEQUENCE: 350
000

SEQ ID NO: 351          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 351
caacagtata atagttattg gtacact                                             27

SEQ ID NO: 352          moltype = AA   length = 9
FEATURE                 Location/Qualifiers
REGION                  1..9
                        note = Synthetic
source                  1..9
                        mol_type = protein
                        organism = synthetic construct
SEQUENCE: 352
QQYNSYWYT                                                                  9

SEQ ID NO: 353          moltype = DNA   length = 354
FEATURE                 Location/Qualifiers
misc_feature            1..354
                        note = Synthetic
source                  1..354
                        mol_type = other DNA
                        organism = synthetic construct
SEQUENCE: 353
gaggtgcagc tggtggagtc tgggggaggc ctggtcaagc ctggggggtc cctgagactc          60
tcctgtgcag cctctggatt cacccttcag agctatagca tggactgggt ccgccaggct         120
ccagggaagg ggctggagtg ggtctcatcc attagtagta gtagtagtta catatactac         180
gcagactctg tgaagggccg attcaccatc tccagagaca ccgccaagaa ctcactgtat         240
ctgcaaatga acagcctgag agacgaggac acggctgttt attactgtgc gagagagggc         300
agtagcgagc ttttttgacta ctggggccag ggaaccctgg tcaccgtctc ctca             354

SEQ ID NO: 354          moltype = AA   length = 118
FEATURE                 Location/Qualifiers
REGION                  1..118
                        note = Synthetic
source                  1..118
                        mol_type = protein
                        organism = synthetic construct
SEQUENCE: 354
EVQLVESGGG LVKPGGSLRL SCAASGFTFS SYSMDWVRQA PGKGLEWVSS ISSSSSYIYY          60
ADSVKGRFTI SRDTAKNSLY LQMNSLRDED TAVYYCAREG SSRLFDYWGQ GTLVTVSS          118

SEQ ID NO: 355          moltype = DNA   length = 321
FEATURE                 Location/Qualifiers
misc_feature            1..321
                        note = Synthetic
source                  1..321
                        mol_type = other DNA
                        organism = synthetic construct
SEQUENCE: 355
gacatccaga tgacccagtc tccttccacc ctgtctgcat ctgtaggaga cagagtcacc          60
atcacttgcc gggccagtca gagtattagt agctggttgg cctggtatca gcagagacca        120
gggaaagccc ctaagctcct gatctataag gcgtctagtt tagaaggtgg agtcccatca        180
```

```
aggttcagcg gcagtggatc tgggacagaa ttcactctca ccatcagcag cctgcagcct    240
gaggattttg caacttatta ctgccaacag tataatagtt attggtacac ttttggccag    300
gggaccaagc tggagatcaa a                                              321

SEQ ID NO: 356          moltype = AA   length = 107
FEATURE                 Location/Qualifiers
REGION                  1..107
                        note = Synthetic
source                  1..107
                        mol_type = protein
                        organism = synthetic construct
SEQUENCE: 356
DIQMTQSPST LSASVGDRVT ITCRASQSIS SWLAWYQQRP GKAPKLLIYK ASSLEGGVPS     60
RFSGSGSGTE FTLTISSLQP EDFATYYCQQ YNSYWYTFGQ GTKLEIK                  107

SEQ ID NO: 357          moltype = DNA   length = 354
FEATURE                 Location/Qualifiers
misc_feature            1..354
                        note = Synthetic
source                  1..354
                        mol_type = other DNA
                        organism = synthetic construct
SEQUENCE: 357
gaggtgcagc tggtggagtc tgggggaggc ctggtcaagc ctggggggtc cctgagactc     60
tcctgtgcag cctctggatt caccttcagt agctatagca tgaactgggt ccgccaggct    120
ccagggaagg ggctggagtg ggtctcatcc attagtagta gtagttacat atactacgca    180
gcagactcag tgaagggccg attcaccatc tccagagaca acgccaagaa ctcactgtat    240
ctgcaaatga acagcctgag agccgaggac acggctgtgt attactgtgc gagagaggggc    300
agtagcagac ttttgactac tggggccaa ggaaccctgg tcaccgtctc ctca            354

SEQ ID NO: 358          moltype = AA   length = 118
FEATURE                 Location/Qualifiers
REGION                  1..118
                        note = Synthetic
source                  1..118
                        mol_type = protein
                        organism = synthetic construct
SEQUENCE: 358
EVQLVESGGG LVKPGGSLRL SCAASGFTFS SYSMNWVRQA PGKGLEWVSS ISSSSSYIYY     60
ADSVKGRFTI SRDNAKNSLY LQMNSLRAED TAVYYCAREG SSRLFDYWGQ GTLVTVSS     118

SEQ ID NO: 359          moltype = DNA   length = 321
FEATURE                 Location/Qualifiers
misc_feature            1..321
                        note = Synthetic
source                  1..321
                        mol_type = other DNA
                        organism = synthetic construct
SEQUENCE: 359
gacatccaga tgacccagtc tccttccacc ctgtctgcat ctgtaggaga cagagtcacc     60
atcacttgcc gggccagtca gagtattagt agctggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attggtacac ttttggccag    300
gggaccaagc tggagatcaa a                                              321

SEQ ID NO: 360          moltype = AA   length = 107
FEATURE                 Location/Qualifiers
REGION                  1..107
                        note = Synthetic
source                  1..107
                        mol_type = protein
                        organism = synthetic construct
SEQUENCE: 360
DIQMTQSPST LSASVGDRVT ITCRASQSIS SWLAWYQQKP GKAPKLLIYK ASSLESGVPS     60
RFSGSGSGTE FTLTISSLQP DDFATYYCQQ YNSYWYTFGQ GTKLEIK                  107

SEQ ID NO: 361          moltype = DNA   length = 384
FEATURE                 Location/Qualifiers
misc_feature            1..384
                        note = Synthetic
source                  1..384
                        mol_type = other DNA
                        organism = synthetic construct
SEQUENCE: 361
caggtgcacc tggtggagtc tgggggaggc ttggtcaagc ctggagggtc cctgagactc     60
tcctgtgcag cctctggatt caccttcagt gaccactaca tgagctggat ccgccaggct    120
ccagggaagg ggctggagtg gatttcatac attagtaatg atggtggtac aaatactat    180
gtggactctg tgagggccg attcatcatt tccagggaca acgccaagaa ctcattgtat    240
```

```
ctacatatga acagcctcag agccgacgac acggccgtgt attactgtgc gagagatcag    300
ggatatattg gctacgactc gtattattac tattcctacg gtatggacgt ctggggccaa    360
gggaccacgg tcaccgtcgc ctca                                           384

SEQ ID NO: 362          moltype = AA   length = 128
FEATURE                 Location/Qualifiers
REGION                  1..128
                        note = Synthetic
source                  1..128
                        mol_type = protein
                        organism = synthetic construct
SEQUENCE: 362
QVHLVESGGG LVKPGGSLRL SCAASGFTFS DHYMSWIRQA PGKGLEWISY ISNDGGTKYY    60
VDSVEGRFII SRDNAKNSLY LHMNSLRADD TAVYYCARDQ GYIGYDSYYY YSYGMDVWGQ    120
GTTVTVAS                                                             128

SEQ ID NO: 363          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 363
ggattcacct tcagtgacca ctac                                           24

SEQ ID NO: 364          moltype = AA   length = 8
FEATURE                 Location/Qualifiers
REGION                  1..8
                        note = Synthetic
source                  1..8
                        mol_type = protein
                        organism = synthetic construct
SEQUENCE: 364
GFTFSDHY                                                             8

SEQ ID NO: 365          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 365
attagtaatg atggtggtac caaa                                           24

SEQ ID NO: 366          moltype = AA   length = 8
FEATURE                 Location/Qualifiers
REGION                  1..8
                        note = Synthetic
source                  1..8
                        mol_type = protein
                        organism = synthetic construct
SEQUENCE: 366
ISNDGGTK                                                             8

SEQ ID NO: 367          moltype = DNA   length = 63
FEATURE                 Location/Qualifiers
misc_feature            1..63
                        note = Synthetic
source                  1..63
                        mol_type = other DNA
                        organism = synthetic construct
SEQUENCE: 367
gcgagagatc aggatatat tggctacgac tcgtattatt actattccta cggtatggac     60
gtc                                                                  63

SEQ ID NO: 368          moltype = AA   length = 21
FEATURE                 Location/Qualifiers
REGION                  1..21
                        note = Synthetic
source                  1..21
                        mol_type = protein
                        organism = synthetic construct
SEQUENCE: 368
ARDQGYIGYD SYYYYSYGMD V                                              21

SEQ ID NO: 369          moltype = DNA   length = 321
FEATURE                 Location/Qualifiers
```

```
misc_feature            1..321
                        note = Synthetic
source                  1..321
                        mol_type = other DNA
                        organism = synthetic construct
SEQUENCE: 369
aaaattgtgt tgacgcagtc tccaggcacc ctgcctttgt ttccagggga aagagccacc    60
ctctcctgta gggccagtca gagtgttaac aacaaattct tagcctggta ccagcagaaa   120
tctggccagg ctcccaggct cctcatctat ggtgcatcca gcagggccac tggcatccca   180
gacaggttca gtggcagtgg gtctgggacc gacttcactc tcaccactcag cggactggag   240
cctgaagatt ttgaagtgta ttattgtcaa gtatatggta actcactcac tctcggcgga   300
gggaccaagg tggagatcaa g                                              321

SEQ ID NO: 370          moltype = AA   length = 107
FEATURE                 Location/Qualifiers
REGION                  1..107
                        note = Synthetic
source                  1..107
                        mol_type = protein
                        organism = synthetic construct
SEQUENCE: 370
KIVLTQSPGT LPLFPGERAT LSCRASQSVN NKFLAWYQQK SGQAPRLLIY GASSRATGIP    60
DRFSGSGSGT DFTLTISGLE PEDFEVYYCQ VYGNSLTLGG GTKVEIK                 107

SEQ ID NO: 371          moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 371
cagagtgtta acaacaaatt c                                              21

SEQ ID NO: 372          moltype = AA   length = 7
FEATURE                 Location/Qualifiers
REGION                  1..7
                        note = Synthetic
source                  1..7
                        mol_type = protein
                        organism = synthetic construct
SEQUENCE: 372
QSVNNKF                                                               7

SEQ ID NO: 373          moltype =   length =
SEQUENCE: 373
000

SEQ ID NO: 374          moltype =   length =
SEQUENCE: 374
000

SEQ ID NO: 375          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 375
caagtatatg gtaactcact cact                                           24

SEQ ID NO: 376          moltype = AA   length = 8
FEATURE                 Location/Qualifiers
REGION                  1..8
                        note = Synthetic
source                  1..8
                        mol_type = protein
                        organism = synthetic construct
SEQUENCE: 376
QVYGNSLT                                                              8

SEQ ID NO: 377          moltype = DNA   length = 384
FEATURE                 Location/Qualifiers
misc_feature            1..384
                        note = Synthetic
source                  1..384
                        mol_type = other DNA
                        organism = synthetic construct
```

```
SEQUENCE: 377
caggtgcagc tggtggagtc tgggggaggc ttggtcaagc ctggagggtc cctgagactc    60
tcctgtgcag cctctggatt caccttcagt gaccactaca tgagctggat ccgccaggct   120
ccagggaagg ggctggagtg gatttcatac attagtaatg atggtggtac caaatactat   180
gtggactctg tggagggccg attcatcatt tccaggggac agccaagaa ctcattgtat    240
ctacatatga acagcctcag agccgacgac acggccgtgt attactgtgc gagagatcag   300
ggatatattg gctacgactc gtattattac tattcctacg gtatggacgt ctggggccaa   360
gggaccacgg tcaccgtctc ctca                                          384
```

| SEQ ID NO: 378 | moltype = AA  length = 128 |
|---|---|
| FEATURE | Location/Qualifiers |
| REGION | 1..128 |
|  | note = Synthetic |
| source | 1..128 |
|  | mol_type = protein |
|  | organism = synthetic construct |

```
SEQUENCE: 378
QVQLVESGGG LVKPGGSLRL SCAASGFTFS DHYMSWIRQA PGKGLEWISY ISNDGGTKYY    60
VDSVEGRFII SRDNAKNSLY LHMNSLRADD TAVYYCARDQ GYIGYDSYYY YSYGMDVWGQ   120
GTTVTVSS                                                            128
```

| SEQ ID NO: 379 | moltype = DNA  length = 321 |
|---|---|
| FEATURE | Location/Qualifiers |
| misc_feature | 1..321 |
|  | note = Synthetic |
| source | 1..321 |
|  | mol_type = other DNA |
|  | organism = synthetic construct |

```
SEQUENCE: 379
gaaattgtgt tgacgcagtc tccaggcacc ctgcctttgt ttccagggga aagagccacc    60
ctctcctgta gggccagtca gagtgttaac aacaaattct tagcctggta ccagcagaaa   120
tctggccagg ctcccaggct cctcatctat ggtgcatcca gcaggccac tggcatccca    180
gacaggttca gtggcagtgg gtctgggacc gacttcactc tcaccatcag cggactggag   240
cctgaagatt ttgaagtgta ttattgtcaa gtatatggta actcactcac tctcggcgga   300
gggaccaagg tggagatcaa a                                             321
```

| SEQ ID NO: 380 | moltype = AA  length = 107 |
|---|---|
| FEATURE | Location/Qualifiers |
| REGION | 1..107 |
|  | note = Synthetic |
| source | 1..107 |
|  | mol_type = protein |
|  | organism = synthetic construct |

```
SEQUENCE: 380
EIVLTQSPGT LPLFPGERAT LSCRASQSVN NKFLAWYQQK SGQAPRLLIY GASSRATGIP    60
DRFSGSGSGT DFTLTISGLE PEDFEVYYCQ VYGNSLTLGG GTKVEIK                 107
```

| SEQ ID NO: 381 | moltype = DNA  length = 384 |
|---|---|
| FEATURE | Location/Qualifiers |
| misc_feature | 1..384 |
|  | note = Synthetic |
| source | 1..384 |
|  | mol_type = other DNA |
|  | organism = synthetic construct |

```
SEQUENCE: 381
caggtgcagc tggtggagtc tgggggaggc ttggtcaagc ctggagggtc cctgagactc    60
tcctgtgcag cctctggatt caccttcagt gaccactaca tgagctggat ccgccaggct   120
ccagggaagg ggctggagtg ggtttcatac attagtaatg atggtggtac caaatactac   180
gcagactctg tgaagggccg attcaccatc tccagggaca acgccaagaa ctcactgtat   240
ctgcaaatga acagcctgag agccgaggac acggccgtgt attactgtgc gagagatcag   300
ggatatattg gctacgactc gtattattac tattcctacg gtatggacgt ctggggccaa   360
gggaccacgg tcaccgtctc ctca                                          384
```

| SEQ ID NO: 382 | moltype = AA  length = 128 |
|---|---|
| FEATURE | Location/Qualifiers |
| REGION | 1..128 |
|  | note = Synthetic |
| source | 1..128 |
|  | mol_type = protein |
|  | organism = synthetic construct |

```
SEQUENCE: 382
QVQLVESGGG LVKPGGSLRL SCAASGFTFS DHYMSWIRQA PGKGLEWVSY ISNDGGTKYY    60
ADSVKGRFTI SRDNAKNSLY LQMNSLRAED TAVYYCARDQ GYIGYDSYYY YSYGMDVWGQ   120
GTTVTVSS                                                            128
```

| SEQ ID NO: 383 | moltype = DNA  length = 321 |
|---|---|
| FEATURE | Location/Qualifiers |
| misc_feature | 1..321 |
|  | note = Synthetic |

```
source                  1..321
                        mol_type = other DNA
                        organism = synthetic construct
SEQUENCE: 383
gaaattgtgt tgacgcagtc tccaggcacc ctgtctttgt ctccagggga aagagccacc    60
ctctcctgca gggccagtca gagtgttaac aacaaattct tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcaa gtatatggta actcactcac tttcggcgga   300
gggaccaagg tggagatcaa a                                             321

SEQ ID NO: 384          moltype = AA  length = 107
FEATURE                 Location/Qualifiers
REGION                  1..107
                        note = Synthetic
source                  1..107
                        mol_type = protein
                        organism = synthetic construct
SEQUENCE: 384
EIVLTQSPGT LSLSPGERAT LSCRASQSVN NKFLAWYQQK PGQAPRLLIY GASSRATGIP    60
DRFSGSGSGT DFTLTISRLE PEDFAVYYCQ VYGNSLTFGG GTKVEIK                 107

SEQ ID NO: 385          moltype = DNA  length = 360
FEATURE                 Location/Qualifiers
misc_feature            1..360
                        note = Synthetic
source                  1..360
                        mol_type = other DNA
                        organism = synthetic construct
SEQUENCE: 385
gaggtgcaga aggtggagtc tgggggaggc ctggtcaagc cggggggtc cctgagactc     60
tcctgtacag cctctggatt caccttcagt acttataaca tgaattgggt ccgccaggct   120
ccagggaagg gactggagtg ggtctcatcc attaggagta gtagtaatta catatactac   180
gcagactcag tgaagggccg attcaccatc tccagagaca acgccaagaa ttcactgtat   240
ctgcaaatga acagcctgag agccgatgac acggctgtgt attactgtgc gagagatggc   300
agcagttggt acgactactc tgactactgg ggccagggaa ccctggtcac cgtctcctca   360

SEQ ID NO: 386          moltype = AA  length = 120
FEATURE                 Location/Qualifiers
REGION                  1..120
                        note = Synthetic
source                  1..120
                        mol_type = protein
                        organism = synthetic construct
SEQUENCE: 386
EVQKVESGGG LVKPGGSLRL SCTASGFTFS TYNMNWVRQA PGKGLEWVSS IRSSSNYIYY    60
ADSVKGRFTI SRDNAKNSLY LQMNSLRADD TAVYYCARDS SWYDYSDYW GQGTLVTVSS    120

SEQ ID NO: 387          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 387
ggattcacct tcagtactta taac                                          24

SEQ ID NO: 388          moltype = AA  length = 8
FEATURE                 Location/Qualifiers
REGION                  1..8
                        note = Synthetic
source                  1..8
                        mol_type = protein
                        organism = synthetic construct
SEQUENCE: 388
GFTFSTYN                                                             8

SEQ ID NO: 389          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 389
attaggagta gtagtaatta cata                                          24

SEQ ID NO: 390          moltype = AA  length = 8
```

```
FEATURE              Location/Qualifiers
REGION               1..8
                     note = Synthetic
source               1..8
                     mol_type = protein
                     organism = synthetic construct
SEQUENCE: 390
IRSSSNYI                                                                    8

SEQ ID NO: 391       moltype = DNA  length = 39
FEATURE              Location/Qualifiers
misc_feature         1..39
                     note = Synthetic
source               1..39
                     mol_type = other DNA
                     organism = synthetic construct
SEQUENCE: 391
gcgagagatg gcagcagttg gtacgactac tctgactac                                 39

SEQ ID NO: 392       moltype = AA  length = 13
FEATURE              Location/Qualifiers
REGION               1..13
                     note = Synthetic
source               1..13
                     mol_type = protein
                     organism = synthetic construct
SEQUENCE: 392
ARDGSSWYDY SDY                                                             13

SEQ ID NO: 393       moltype = DNA  length = 321
FEATURE              Location/Qualifiers
misc_feature         1..321
                     note = Synthetic
source               1..321
                     mol_type = other DNA
                     organism = synthetic construct
SEQUENCE: 393
gacatccaga tgacccagtc tccttccacc ctgtctgcat ctgtaggaga cagagtcacc          60
atcacttgcc gggccagtca gagtattagt agctggttgg cctggtatca acagatacca        120
gggaaagccc ctaaactcct gatctataag gcgtctagtt tagaaaatgg ggtcccatca        180
aggttcagcg gcagtggatc tgggacagaa ttcactctca tcatcagcag cctgcagcct        240
gatgattttg caacttatta ctgccaacag tatattagtt attctcggac gttcggccaa        300
gggaccaagg tggaaatcaa a                                                  321

SEQ ID NO: 394       moltype = AA  length = 107
FEATURE              Location/Qualifiers
REGION               1..107
                     note = Synthetic
source               1..107
                     mol_type = protein
                     organism = synthetic construct
SEQUENCE: 394
DIQMTQSPST LSASVGDRVT ITCRASQSIS SWLAWYQQIP GKAPKLLIYK ASSLENGVPS          60
RFSGSGSGTE FTLIISSLQP DDFATYYCQQ YISYSRTFGQ GTKVEIK                      107

SEQ ID NO: 395       moltype = DNA  length = 18
FEATURE              Location/Qualifiers
misc_feature         1..18
                     note = Synthetic
source               1..18
                     mol_type = other DNA
                     organism = synthetic construct
SEQUENCE: 395
cagagtatta gtagctgg                                                        18

SEQ ID NO: 396       moltype = AA  length = 6
FEATURE              Location/Qualifiers
REGION               1..6
                     note = Synthetic
source               1..6
                     mol_type = protein
                     organism = synthetic construct
SEQUENCE: 396
QSISSW                                                                      6

SEQ ID NO: 397       moltype =   length =
SEQUENCE: 397
000
```

```
SEQ ID NO: 398          moltype =    length =
SEQUENCE: 398
000

SEQ ID NO: 399          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 399
caacagtata ttagttattc tcggacg                                           27

SEQ ID NO: 400          moltype = AA   length = 9
FEATURE                 Location/Qualifiers
REGION                  1..9
                        note = Synthetic
source                  1..9
                        mol_type = protein
                        organism = synthetic construct
SEQUENCE: 400
QQYISYSRT                                                               9

SEQ ID NO: 401          moltype = DNA   length = 360
FEATURE                 Location/Qualifiers
misc_feature            1..360
                        note = Synthetic
source                  1..360
                        mol_type = other DNA
                        organism = synthetic construct
SEQUENCE: 401
gaggtgcagc tggtggagtc tgggggaggc ctggtcaagc cggggggtc cctgagactc        60
tcctgtacag cctctggatt caccttcagt acttataaca tgaattgggt ccgccaggct       120
ccagggaagg gactggagtg ggtctcatcc attaggagta gtagtaatta catatactac       180
gcagactcag tgaaggggcg attcaccatc tccagagaca acgccaagaa ttcactgtat       240
ctgcaaatga acagcctgag agccgatgac acggctgtgt attactgtgc gagagatggc       300
agcagttggt acgactactc tgactactgg ggccagggaa ccctggtcac cgtctcctca       360

SEQ ID NO: 402          moltype = AA   length = 120
FEATURE                 Location/Qualifiers
REGION                  1..120
                        note = Synthetic
source                  1..120
                        mol_type = protein
                        organism = synthetic construct
SEQUENCE: 402
EVQLVESGGG LVKPGGSLRL SCTASGFTFS TYNMNWVRQA PGKGLEWVSS IRSSSNYIYY       60
ADSVKGRFTI SRDNAKNSLY LQMNSLRADD TAVYYCARDG SSWYDYSDYW GQGTLVTVSS       120

SEQ ID NO: 403          moltype = DNA   length = 321
FEATURE                 Location/Qualifiers
misc_feature            1..321
                        note = Synthetic
source                  1..321
                        mol_type = other DNA
                        organism = synthetic construct
SEQUENCE: 403
gacatccaga tgacccagtc tccttccacc ctgtctgcat ctgtaggaga cagagtcacc       60
atcacttgcc gggccagtca gagtattagt agctggttgg cctggtatca acagatacca      120
gggaaagccc ctaaactcct gatctataag gcgtctagtt tagaaaatgg ggtcccatca       180
aggttcagcg gcagtggatc tgggacagaa ttcactctca tcatcagcag cctgcagcct      240
gatgattttg caacttatta ctgccaacag tatattagtt attctcggac gttcggccaa      300
gggaccaagg tggaaatcaa a                                                 321

SEQ ID NO: 404          moltype = AA   length = 107
FEATURE                 Location/Qualifiers
REGION                  1..107
                        note = Synthetic
source                  1..107
                        mol_type = protein
                        organism = synthetic construct
SEQUENCE: 404
DIQMTQSPST LSASVGDRVT ITCRASQSIS SWLAWYQQIP GKAPKLLIYK ASSLENGVPS       60
RFSGSGSGTE FTLIISSLQP DDFATYYCQQ YISYSRTFGQ GTKVEIK                    107

SEQ ID NO: 405          moltype = DNA   length = 360
FEATURE                 Location/Qualifiers
misc_feature            1..360
```

```
                        note = Synthetic
source                  1..360
                        mol_type = other DNA
                        organism = synthetic construct
SEQUENCE: 405
gaggtgcagc tggtggagtc tggggggaggc ctggtcaagc ctgggggggtc cctgagactc    60
tcctgtgcag cctctggatt caccttcagt acttataaca tgaactgggt ccgccaggct    120
ccagggaagg ggctggagtg ggtctcatcc attaggagta gtagtaatta catatactac    180
gcagactcag tgaagggccg attcaccatc tccagagaca cgccaagaa ctcactgtat    240
ctgcaaatga acagcctgag agccgaggac acggctgtgt attactgtgc gagagatggc    300
agcagttggt acgactactc tgactactgg ggccaaggaa ccctggtcac cgtctcctca    360

SEQ ID NO: 406          moltype = AA   length = 120
FEATURE                 Location/Qualifiers
REGION                  1..120
                        note = Synthetic
source                  1..120
                        mol_type = protein
                        organism = synthetic construct
SEQUENCE: 406
EVQLVESGGG LVKPGGSLRL SCAASGFTFS TYNMNWVRQA PGKGLEWVSS IRSSSNYIYY     60
ADSVKGRFTI SRDNAKNSLY LQMNSLRAED TAVYYCARDG SSWYDYSDYW GQGTLVTVSS   120

SEQ ID NO: 407          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 407
gacatccaga tgacccagtc tccttccacc ctgtctgcat ctgtaggaga cagagtcacc     60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tatattagtt attctcggac gttcggccaa   300
gggaccaagg tggaaatcaa a                                             321

SEQ ID NO: 408          moltype = AA   length = 107
FEATURE                 Location/Qualifiers
REGION                  1..107
                        note = Synthetic
source                  1..107
                        mol_type = protein
                        organism = synthetic construct
SEQUENCE: 408
DIQMTQSPST LSASVGDRVT ITCRASQSIS SWLAWYQQKP GKAPKLLIYK ASSLESGVPS     60
RFSGSGSGTE FTLTISSLQP DDFATYYCQQ YISYSRTFGQ GTKVEIK                 107

SEQ ID NO: 409          moltype = DNA  length = 360
FEATURE                 Location/Qualifiers
misc_feature            1..360
                        note = Synthetic
source                  1..360
                        mol_type = other DNA
                        organism = synthetic construct
SEQUENCE: 409
gaggtgcagc tggtggagtc tgggggaggc ctggtcaagc cggggggggtc cctgagactc     60
tcctgtacag cctctggatt caccttcagt acttataaca tgaattgggt ccgccaggct    120
ccagggaagg gactggagtg ggtctcatcc attaggagta gtagtaatta catatactac   180
gcagactcag tgaagggccg attcaccatc tccagagaca cgccaagaa ttcactgtat    240
ctgcaaatga acagcctgag agccgatgac acggctgtgt attactgtgc gagagatggc   300
agcagttggt acgactactc tgactactgg ggccagggaa ccctggtcac cgtctcctca   360

SEQ ID NO: 410          moltype = AA   length = 120
FEATURE                 Location/Qualifiers
REGION                  1..120
                        note = Synthetic
source                  1..120
                        mol_type = protein
                        organism = synthetic construct
SEQUENCE: 410
EVQLVESGGG LVKPGGSLRL SCTASGFTFS TYNMNWVRQA PGKGLEWVSS IRSSSNYIYY     60
ADSVKGRFTI SRDNAKNSLY LQMNSLRADD TAVYYCARDG SSWYDYSDYW GQGTLVTVSS   120

SEQ ID NO: 411          moltype = DNA  length = 24
FEATURE                 Location/Qualifiers
misc_feature            1..24
                        note = Synthetic
```

```
source                  1..24
                        mol_type = other DNA
                        organism = synthetic construct
SEQUENCE: 411
ggattcacct tcagtactta taac                                         24

SEQ ID NO: 412          moltype = AA   length = 8
FEATURE                 Location/Qualifiers
REGION                  1..8
                        note = Synthetic
source                  1..8
                        mol_type = protein
                        organism = synthetic construct
SEQUENCE: 412
GFTFSTYN                                                            8

SEQ ID NO: 413          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 413
attaggagta gtagtaatta cata                                         24

SEQ ID NO: 414          moltype = AA   length = 8
FEATURE                 Location/Qualifiers
REGION                  1..8
                        note = Synthetic
source                  1..8
                        mol_type = protein
                        organism = synthetic construct
SEQUENCE: 414
IRSSSNYI                                                            8

SEQ ID NO: 415          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 415
gcgagagatg gcagcagttg gtacgactac tctgactac                         39

SEQ ID NO: 416          moltype = AA   length = 13
FEATURE                 Location/Qualifiers
REGION                  1..13
                        note = Synthetic
source                  1..13
                        mol_type = protein
                        organism = synthetic construct
SEQUENCE: 416
ARDGSSWYDY SDY                                                     13

SEQ ID NO: 417          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 417
gacatccaga tgacccagtc tccttccacc ctgtctgcat ctgtaggaga cagagtcacc   60
atcacttgcc gggccagtca gagtattagt agctggttgg cctggtatca acagatacca  120
gggaaagccc ctaaactcct gatctataag gcgtctagtt tagaaaatgg ggtcccatca  180
aggttcagcg gcagtggatc tgggacagaa ttcactctca tcatcagcag cctgcagcct  240
gatgattttg caacttatta ctgccaacag tatattagtt attctcggac gttcggccaa  300
gggaccaagg tggaaatcaa a                                           321

SEQ ID NO: 418          moltype = AA   length = 107
FEATURE                 Location/Qualifiers
REGION                  1..107
                        note = Synthetic
source                  1..107
                        mol_type = protein
                        organism = synthetic construct
SEQUENCE: 418
```

```
DIQMTQSPST LSASVGDRVT ITCRASQSIS SWLAWYQQIP GKAPKLLIYK ASSLENGVPS    60
RFSGSGSGTE FTLIISSLQP DDFATYYCQQ YISYSRTFGQ GTKVEIK                107

SEQ ID NO: 419          moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 419
cagagtatta gtagctgg                                                 18

SEQ ID NO: 420          moltype = AA   length = 6
FEATURE                 Location/Qualifiers
REGION                  1..6
                        note = Synthetic
source                  1..6
                        mol_type = protein
                        organism = synthetic construct
SEQUENCE: 420
QSISSW                                                              6

SEQ ID NO: 421          moltype =    length =
SEQUENCE: 421
000

SEQ ID NO: 422          moltype =    length =
SEQUENCE: 422
000

SEQ ID NO: 423          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 423
caacagtata ttagttattc tcggacg                                       27

SEQ ID NO: 424          moltype = AA   length = 9
FEATURE                 Location/Qualifiers
REGION                  1..9
                        note = Synthetic
source                  1..9
                        mol_type = protein
                        organism = synthetic construct
SEQUENCE: 424
QQYISYSRT                                                           9

SEQ ID NO: 425          moltype = DNA   length = 360
FEATURE                 Location/Qualifiers
misc_feature            1..360
                        note = Synthetic
source                  1..360
                        mol_type = other DNA
                        organism = synthetic construct
SEQUENCE: 425
gaggtgcagc tggtggagtc tgggggaggc ctggtcaagc cggggggtc cctgagactc    60
tcctgtacag cctctggatt caccttcagt acttataaca tgaattgggt ccgccaggct   120
ccagggaagg gactggagtg ggtctcatcc attaggagta gtagtaatta catatactac   180
gcagactcag tgaagggccg attcaccatc tccagagaca cgccaagaa ttcactgtat    240
ctgcaaatga acagcctgag agccgatgac acggctgtgt attactgtgc gagagatggc   300
agcagttggt acgactactc tgactactgg ggccaggaa ccctggtcac cgtctcctca    360

SEQ ID NO: 426          moltype = AA   length = 120
FEATURE                 Location/Qualifiers
REGION                  1..120
                        note = Synthetic
source                  1..120
                        mol_type = protein
                        organism = synthetic construct
SEQUENCE: 426
EVQLVESGGG LVKPGGSLRL SCTASGFTFS TYNMNWVRQA PGKGLEWVSS IRSSSNYIYY    60
ADSVKGRFTI SRDNAKNSLY LQMNSLRADD TAVYYCARDG SSWYDYSDYW GQGTLVTVSS   120

SEQ ID NO: 427          moltype = DNA   length = 321
FEATURE                 Location/Qualifiers
```

```
misc_feature           1..321
                       note = Synthetic
source                 1..321
                       mol_type = other DNA
                       organism = synthetic construct
SEQUENCE: 427
gacatccaga tgacccagtc tccttccacc ctgtctgcat ctgtaggaga cagagtcacc   60
atcacttgcc gggccagtca gagtattagt agctggttgg cctggtatca acagatacca  120
gggaaagccc ctaaactcct gatctataag gcgtctagtt tagaaaatgg ggtcccatca  180
aggttcagcg gcagtggatc tgggacagaa ttcactctca tcatcagcag cctgcagcct  240
gatgattttg caacttatta ctgccaacag tatattagtt attctcggac gttcggccaa  300
gggaccaagg tggaaatcaa a                                            321

SEQ ID NO: 428         moltype = AA    length = 107
FEATURE                Location/Qualifiers
REGION                 1..107
                       note = Synthetic
source                 1..107
                       mol_type = protein
                       organism = synthetic construct
SEQUENCE: 428
DIQMTQSPST LSASVGDRVT ITCRASQSIS SWLAWYQQIP GKAPKLLIYK ASSLENGVPS    60
RFSGSGSGTE FTLIISSLQP DDFATYYCQQ YISYSRTFGQ GTKVEIK                 107

SEQ ID NO: 429         moltype = DNA   length = 360
FEATURE                Location/Qualifiers
misc_feature           1..360
                       note = Synthetic
source                 1..360
                       mol_type = other DNA
                       organism = synthetic construct
SEQUENCE: 429
gaggtgcagc tggtggagtc tgggggaggc ctggtcaagc ctgggggtc cctgagactc    60
tcctgtgcag cctctggatt caccttcagt acttataaca tgaactgggt ccgccaggct  120
ccagggaagg ggctggagtg ggtctcatcc attaggagta gtagtaatta catatactac  180
gcagactcag tgaagggccg attcaccatc tccagagaca cgccaagaa ctcactgtat   240
ctgcaaatga acagcctgag agccgaggac acggctgtgt attactgtgc gagagatggc  300
agcagttggt acgactactc tgactactgg ggccaaggaa ccctggtcac cgtctcctca  360

SEQ ID NO: 430         moltype = AA    length = 120
FEATURE                Location/Qualifiers
REGION                 1..120
                       note = Synthetic
source                 1..120
                       mol_type = protein
                       organism = synthetic construct
SEQUENCE: 430
EVQLVESGGG LVKPGGSLRL SCAASGFTFS TYNMNWVRQA PGKGLEWVSS IRSSSNYIYY    60
ADSVKGRFTI SRDNAKNSLY LQMNSLRAED TAVYYCARDG SSWYDYSDYW GQGTLVTVSS   120

SEQ ID NO: 431         moltype = DNA   length = 321
FEATURE                Location/Qualifiers
misc_feature           1..321
                       note = Synthetic
source                 1..321
                       mol_type = other DNA
                       organism = synthetic construct
SEQUENCE: 431
gacatccaga tgacccagtc tccttccacc ctgtctgcat ctgtaggaga cagagtcacc   60
atcacttgcc gggccagtca gagtattagt agctggttgg cctggtatca gcagaaacca  120
gggaaagccc ctaagctcct gatctataag gcgtctagtt tagaaagtgg ggtcccatca  180
aggttcagcg gcagtggatc tgggacagaa ttcactctca ccatcagcag cctgcagcct  240
gatgattttg caacttatta ctgccaacag tatattagtt attctcggac gttcggccaa  300
gggaccaagg tggaaatcaa a                                            321

SEQ ID NO: 432         moltype = AA    length = 107
FEATURE                Location/Qualifiers
REGION                 1..107
                       note = Synthetic
source                 1..107
                       mol_type = protein
                       organism = synthetic construct
SEQUENCE: 432
DIQMTQSPST LSASVGDRVT ITCRASQSIS SWLAWYQQKP GKAPKLLIYK ASSLESGVPS    60
RFSGSGSGTE FTLTISSLQP DDFATYYCQQ YISYSRTFGQ GTKVEIK                 107

SEQ ID NO: 433         moltype = DNA   length = 360
FEATURE                Location/Qualifiers
misc_feature           1..360
```

```
                        note = Synthetic
source                  1..360
                        mol_type = other DNA
                        organism = synthetic construct
SEQUENCE: 433
gaggtgcagc tggtggagtc tgggggaggc ctggtcaagc cggggggtc cctgagactc    60
tcctgtacag cctctggatt caccttcagt acttataaca tgaattgggt ccgccaggct   120
ccagggaagg gactggagtg gtctcatcc attaggagta gtagtaatta catatactac   180
gcagactcag tgaagggccg attcaccatc tccagagaca acgccaagag ttcactgtat   240
ctgcaaatga acagcctgag agccgaggac acggctgtgt attactgtgc gagagatggc   300
agcagttggt acgactactc tgactactgg ggccagggaa ccctggtcac cgtctcctca   360

SEQ ID NO: 434          moltype = AA   length = 120
FEATURE                 Location/Qualifiers
REGION                  1..120
                        note = Synthetic
source                  1..120
                        mol_type = protein
                        organism = synthetic construct
SEQUENCE: 434
EVQLVESGGG LVKPGGSLRL SCTASGFTFS TYNMNWVRQA PGKGLEWVSS IRSSSNYIYY    60
ADSVKGRFTI SRDNAKSSLY LQMNSLRAED TAVYYCARDG SSWYDYSDYW GQGTLVTVSS   120

SEQ ID NO: 435          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 435
ggattcacct tcagtactta taac                                           24

SEQ ID NO: 436          moltype = AA   length = 8
FEATURE                 Location/Qualifiers
REGION                  1..8
                        note = Synthetic
source                  1..8
                        mol_type = protein
                        organism = synthetic construct
SEQUENCE: 436
GFTFSTYN                                                              8

SEQ ID NO: 437          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 437
attaggagta gtagtaatta cata                                           24

SEQ ID NO: 438          moltype = AA   length = 8
FEATURE                 Location/Qualifiers
REGION                  1..8
                        note = Synthetic
source                  1..8
                        mol_type = protein
                        organism = synthetic construct
SEQUENCE: 438
IRSSSNYI                                                              8

SEQ ID NO: 439          moltype = DNA   length = 39
FEATURE                 Location/Qualifiers
misc_feature            1..39
                        note = Synthetic
source                  1..39
                        mol_type = other DNA
                        organism = synthetic construct
SEQUENCE: 439
gcgagagatg gcagcagttg gtacgactac tctgactac                           39

SEQ ID NO: 440          moltype = AA   length = 13
FEATURE                 Location/Qualifiers
REGION                  1..13
                        note = Synthetic
source                  1..13
                        mol_type = protein
```

```
                           organism = synthetic construct
SEQUENCE: 440
ARDGSSWYDY SDY                                                            13

SEQ ID NO: 441             moltype = DNA  length = 321
FEATURE                    Location/Qualifiers
misc_feature               1..321
                           note = Synthetic
source                     1..321
                           mol_type = other DNA
                           organism = synthetic construct
SEQUENCE: 441
gacatccaga tgacccagtc tccttccacc ctgtctgcat ctgtaggaga cagagtcacc    60
atcacttgcc gggccagtca gagtattagt agctggttgg cctggtatca acaggtacca   120
gggaaagccc ctaaactcct gatctataag gcgtctagtt tagaaaatgg ggtcccatca   180
aggttcagcg gcagtggatc tgggacagaa ttcactctca tcatcagcag cctgcagcct   240
gatgattttg caacttatta ctgccaacag tatattagtt attctcggac gttcggccaa   300
gggaccaagg tggaaatcaa a                                             321

SEQ ID NO: 442             moltype = AA  length = 107
FEATURE                    Location/Qualifiers
REGION                     1..107
                           note = Synthetic
source                     1..107
                           mol_type = protein
                           organism = synthetic construct
SEQUENCE: 442
DIQMTQSPST LSASVGDRVT ITCRASQSIS SWLAWYQQVP GKAPKLLIYK ASSLENGVPS    60
RFSGSGSGTE FTLIISSLQP DDFATYYCQQ YISYSRTFGQ GTKVEIK                 107

SEQ ID NO: 443             moltype = DNA  length = 18
FEATURE                    Location/Qualifiers
misc_feature               1..18
                           note = Synthetic
source                     1..18
                           mol_type = other DNA
                           organism = synthetic construct
SEQUENCE: 443
cagagtatta gtagctgg                                                  18

SEQ ID NO: 444             moltype = AA  length = 6
FEATURE                    Location/Qualifiers
REGION                     1..6
                           note = Synthetic
source                     1..6
                           mol_type = protein
                           organism = synthetic construct
SEQUENCE: 444
QSISSW                                                                6

SEQ ID NO: 445             moltype =   length =
SEQUENCE: 445
000

SEQ ID NO: 446             moltype =   length =
SEQUENCE: 446
000

SEQ ID NO: 447             moltype = DNA  length = 27
FEATURE                    Location/Qualifiers
misc_feature               1..27
                           note = Synthetic
source                     1..27
                           mol_type = other DNA
                           organism = synthetic construct
SEQUENCE: 447
caacagtata ttagttattc tcggacg                                        27

SEQ ID NO: 448             moltype = AA  length = 9
FEATURE                    Location/Qualifiers
REGION                     1..9
                           note = Synthetic
source                     1..9
                           mol_type = protein
                           organism = synthetic construct
SEQUENCE: 448
QQYISYSRT                                                             9

SEQ ID NO: 449             moltype = DNA  length = 360
```

| FEATURE | Location/Qualifiers |
|---|---|
| misc_feature | 1..360 |
| | note = Synthetic |
| source | 1..360 |
| | mol_type = other DNA |
| | organism = synthetic construct |

SEQUENCE: 449
```
gaggtgcagc tggtggagtc tgggggaggc ctggtcaagc cggggggggtc cctgagactc   60
tcctgtacag cctctggatt caccttcagt acttataaca tgaattgggt ccgccaggct  120
ccagggaagg gactggagtg ggtctcatcc attaggagta gtagtaatta catatactac  180
gcagactcag tgaagggccg attcaccatc tccagagaca acgccaagag ttcactgtat  240
ctgcaaatga acagcctgag agccgaggac acggctgtgt attactgtgc gagagatggc  300
agcagttggt acgactactc tgactactgg ggccaggaa ccctggtcac cgtctcctca  360
```

| SEQ ID NO: 450 | moltype = AA  length = 120 |
|---|---|
| FEATURE | Location/Qualifiers |
| REGION | 1..120 |
| | note = Synthetic |
| source | 1..120 |
| | mol_type = protein |
| | organism = synthetic construct |

SEQUENCE: 450
```
EVQLVESGGG LVKPGGSLRL SCTASGFTFS TYNMNWVRQA PGKGLEWVSS IRSSSNYIYY   60
ADSVKGRFTI SRDNAKSSLY LQMNSLRAED TAVYYCARDG SSWYDYSDYW GQGTLVTVSS  120
```

| SEQ ID NO: 451 | moltype = DNA  length = 321 |
|---|---|
| FEATURE | Location/Qualifiers |
| misc_feature | 1..321 |
| | note = Synthetic |
| source | 1..321 |
| | mol_type = other DNA |
| | organism = synthetic construct |

SEQUENCE: 451
```
gacatccaga tgacccagtc tccttccacc ctgtctgcat ctgtaggaga cagagtcacc   60
atcacttgcc gggccagtca gagtattagt agctggttgg cctggtatca acaggtacca  120
gggaaagccc ctaaactcct gatctataag gcgtctagtt tagaaaatgg ggtcccatca  180
aggttcagcg gcagtggatc tgggacagaa ttcactctca tcatcagcag cctgcagcct  240
gatgattttg caacttatta ctgccaacag tatattagtt attctcggac gttcggccaa  300
gggaccaagg tggaaatcaa a                                            321
```

| SEQ ID NO: 452 | moltype = AA  length = 107 |
|---|---|
| FEATURE | Location/Qualifiers |
| REGION | 1..107 |
| | note = Synthetic |
| source | 1..107 |
| | mol_type = protein |
| | organism = synthetic construct |

SEQUENCE: 452
```
DIQMTQSPST LSASVGDRVT ITCRASQSIS SWLAWYQQVP GKAPKLLIYK ASSLENGVPS   60
RFSGSGSGTE FTLIISSLQP DDFATYYCQQ YISYSRTFGQ GTKVEIK                107
```

| SEQ ID NO: 453 | moltype = DNA  length = 360 |
|---|---|
| FEATURE | Location/Qualifiers |
| misc_feature | 1..360 |
| | note = Synthetic |
| source | 1..360 |
| | mol_type = other DNA |
| | organism = synthetic construct |

SEQUENCE: 453
```
gaggtgcagc tggtggagtc tgggggaggc ctggtcaagc ctgggggggtc cctgagactc   60
tcctgtgcag cctctggatt caccttcagt acttataaca tgaactgggt ccgccaggct  120
ccagggaagg ggctggagtg ggtctcatcc attaggagta gtagtaatta catatactac  180
gcagactcag tgaagggccg attcaccatc tccagagaca acgccaagaa ctcactgtat  240
ctgcaaatga acagcctgag agccgaggac acggctgtgt attactgtgc gagagatggc  300
agcagttggt acgactactc tgactactgg ggccaggaa ccctggtcac cgtctcctca  360
```

| SEQ ID NO: 454 | moltype = AA  length = 120 |
|---|---|
| FEATURE | Location/Qualifiers |
| REGION | 1..120 |
| | note = Synthetic |
| source | 1..120 |
| | mol_type = protein |
| | organism = synthetic construct |

SEQUENCE: 454
```
EVQLVESGGG LVKPGGSLRL SCAASGFTFS TYNMNWVRQA PGKGLEWVSS IRSSSNYIYY   60
ADSVKGRFTI SRDNAKNSLY LQMNSLRAED TAVYYCARDG SSWYDYSDYW GQGTLVTVSS  120
```

| SEQ ID NO: 455 | moltype = DNA  length = 321 |
|---|---|
| FEATURE | Location/Qualifiers |

| | | |
|---|---|---|
| misc_feature | 1..321 | |
| | note = Synthetic | |
| source | 1..321 | |
| | mol_type = other DNA | |
| | organism = synthetic construct | |

SEQUENCE: 455
```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tatattagtt attctcggac gttcggccaa   300
gggaccaagg tggaaatcaa a                                             321
```

| | | |
|---|---|---|
| SEQ ID NO: 456 | moltype = AA   length = 107 | |
| FEATURE | Location/Qualifiers | |
| REGION | 1..107 | |
| | note = Synthetic | |
| source | 1..107 | |
| | mol_type = protein | |
| | organism = synthetic construct | |

SEQUENCE: 456
```
DIQMTQSPST LSASVGDRVT ITCRASQSIS SWLAWYQQKP GKAPKLLIYK ASSLESGVPS    60
RFSGSGSGTE FTLTISSLQP DDFATYYCQQ YISYSRTFGQ GTKVEIK                107
```

| | | |
|---|---|---|
| SEQ ID NO: 457 | moltype = DNA   length = 360 | |
| FEATURE | Location/Qualifiers | |
| misc_feature | 1..360 | |
| | note = Synthetic | |
| source | 1..360 | |
| | mol_type = other DNA | |
| | organism = synthetic construct | |

SEQUENCE: 457
```
gaggtgcagc tggtggagtc tgggggaggc ctggtcaagc cggggggggtc cctgagactc    60
tcctgtacag cctctggatt caccttcagt acttataaca tgaattgggt ccgccaggct   120
ccagggaagg gactggagtg ggtctcatcc attaggagta gtagtaatta catatactac   180
gcagactcag tgaagggccg attcaccatc tccagagaca cgccaagaa ttcactgtat   240
ctgcaaatga acagcctgag agccgatgac acggctgtgt attactgtgc gagagatggc   300
agcagttggt acgactactc tgactactgg ggccagggaa ccctggtcac cgtctcctca   360
```

| | | |
|---|---|---|
| SEQ ID NO: 458 | moltype = AA   length = 120 | |
| FEATURE | Location/Qualifiers | |
| REGION | 1..120 | |
| | note = Synthetic | |
| source | 1..120 | |
| | mol_type = protein | |
| | organism = synthetic construct | |

SEQUENCE: 458
```
EVQLVESGGG LVKPGGSLRL SCTASGFTFS TYNMNWVRQA PGKGLEWVSS IRSSSNYIYY    60
ADSVKGRFTI SRDNAKNSLY LQMNSLRADD TAVYYCARDG SSWYDYSDYW GQGTLVTVSS   120
```

| | | |
|---|---|---|
| SEQ ID NO: 459 | moltype = DNA   length = 24 | |
| FEATURE | Location/Qualifiers | |
| misc_feature | 1..24 | |
| | note = Synthetic | |
| source | 1..24 | |
| | mol_type = other DNA | |
| | organism = synthetic construct | |

SEQUENCE: 459
```
ggattcacct tcagtactta taac                                            24
```

| | | |
|---|---|---|
| SEQ ID NO: 460 | moltype = AA   length = 8 | |
| FEATURE | Location/Qualifiers | |
| REGION | 1..8 | |
| | note = Synthetic | |
| source | 1..8 | |
| | mol_type = protein | |
| | organism = synthetic construct | |

SEQUENCE: 460
```
GFTFSTYN                                                              8
```

| | | |
|---|---|---|
| SEQ ID NO: 461 | moltype = DNA   length = 24 | |
| FEATURE | Location/Qualifiers | |
| misc_feature | 1..24 | |
| | note = Synthetic | |
| source | 1..24 | |
| | mol_type = other DNA | |
| | organism = synthetic construct | |

SEQUENCE: 461
```
attaggagta gtagtaatta cata                                            24
```

```
SEQ ID NO: 462            moltype = AA  length = 8
FEATURE                   Location/Qualifiers
REGION                    1..8
                          note = Synthetic
source                    1..8
                          mol_type = protein
                          organism = synthetic construct
SEQUENCE: 462
IRSSSNYI                                                                   8

SEQ ID NO: 463            moltype = DNA  length = 39
FEATURE                   Location/Qualifiers
misc_feature              1..39
                          note = Synthetic
source                    1..39
                          mol_type = other DNA
                          organism = synthetic construct
SEQUENCE: 463
gcgagagatg gcagcagttg gtacgactac tctgactac                                39

SEQ ID NO: 464            moltype = AA  length = 13
FEATURE                   Location/Qualifiers
REGION                    1..13
                          note = Synthetic
source                    1..13
                          mol_type = protein
                          organism = synthetic construct
SEQUENCE: 464
ARDGSSWYDY SDY                                                            13

SEQ ID NO: 465            moltype = DNA  length = 321
FEATURE                   Location/Qualifiers
misc_feature              1..321
                          note = Synthetic
source                    1..321
                          mol_type = other DNA
                          organism = synthetic construct
SEQUENCE: 465
gacatccaga tgacccagtc tccttccacc ctgtctgcat ctgtaggaga cagagtcacc          60
atcacttgcc gggccagtca gagtattagt agctggttgg cctggtatca acagatacca        120
gggaaagccc ctaaactcct gatctataag gcgtctagtt tagaaaatgg ggtcccatca        180
aggttcagcg gcagtggatc tgggacagaa ttcactctca tcatcagcag cctgcagcct        240
gatgattttg caacttatta ctgccaacag tatattagtt attctcggac gttcggccaa        300
gggaccaagg tggaaatcaa a                                                  321

SEQ ID NO: 466            moltype = AA  length = 107
FEATURE                   Location/Qualifiers
REGION                    1..107
                          note = Synthetic
source                    1..107
                          mol_type = protein
                          organism = synthetic construct
SEQUENCE: 466
DIQMTQSPST LSASVGDRVT ITCRASQSIS SWLAWYQQIP GKAPKLLIYK ASSLENGVPS          60
RFSGSGSGTE FTLIISSLQP DDFATYYCQQ YISYSRTFGQ GTKVEIK                      107

SEQ ID NO: 467            moltype = DNA  length = 18
FEATURE                   Location/Qualifiers
misc_feature              1..18
                          note = Synthetic
source                    1..18
                          mol_type = other DNA
                          organism = synthetic construct
SEQUENCE: 467
cagagtatta gtagctgg                                                       18

SEQ ID NO: 468            moltype = AA  length = 6
FEATURE                   Location/Qualifiers
REGION                    1..6
                          note = Synthetic
source                    1..6
                          mol_type = protein
                          organism = synthetic construct
SEQUENCE: 468
QSISSW                                                                     6

SEQ ID NO: 469            moltype =     length =
SEQUENCE: 469
```

```
000

SEQ ID NO: 470         moltype =    length =
SEQUENCE: 470
000

SEQ ID NO: 471         moltype = DNA   length = 27
FEATURE                Location/Qualifiers
misc_feature           1..27
                       note = Synthetic
source                 1..27
                       mol_type = other DNA
                       organism = synthetic construct
SEQUENCE: 471
caacagtata ttagttattc tcggacg                                     27

SEQ ID NO: 472         moltype = AA    length = 9
FEATURE                Location/Qualifiers
REGION                 1..9
                       note = Synthetic
source                 1..9
                       mol_type = protein
                       organism = synthetic construct
SEQUENCE: 472
QQYISYSRT                                                         9

SEQ ID NO: 473         moltype = DNA   length = 360
FEATURE                Location/Qualifiers
misc_feature           1..360
                       note = Synthetic
source                 1..360
                       mol_type = other DNA
                       organism = synthetic construct
SEQUENCE: 473
gaggtgcagc tggtggagtc tgggggaggc ctggtcaagc cggggggtc cctgagactc   60
tcctgtacag cctctggatt caccttcagt acttataaca tgaattgggt ccgccaggct  120
ccagggaagg gactggagtg ggtctcatcc attaggagta gtagtaatta catatactac  180
gcagactcag tgaagggccg attcaccatc tccagagaca cgccaagaa ttcactgtat   240
ctgcaaatga acagcctgag agccgatgac acggctgtgt attactgtgc gagagatggc  300
agcagttggt acgactactc tgactactgg ggccaggga cctggtcac cgtctcctca   360

SEQ ID NO: 474         moltype = AA    length = 120
FEATURE                Location/Qualifiers
REGION                 1..120
                       note = Synthetic
source                 1..120
                       mol_type = protein
                       organism = synthetic construct
SEQUENCE: 474
EVQLVESGGG LVKPGGSLRL SCTASGFTFS TYNMNWVRQA PGKGLEWVSS IRSSSNYIYY  60
ADSVKGRFTI SRDNAKNSLY LQMNSLRADD TAVYYCARDG SSWYDYSDYW GQGTLVTVSS 120

SEQ ID NO: 475         moltype = DNA   length = 321
FEATURE                Location/Qualifiers
misc_feature           1..321
                       note = Synthetic
source                 1..321
                       mol_type = other DNA
                       organism = synthetic construct
SEQUENCE: 475
gacatccaga tgacccagtc tccttccacc ctgtctgcat ctgtaggaga cagagtcacc  60
atcacttgcc gggccagtca gagtattagt agctggttgg cctggtatca acagatacca 120
gggaaagccc ctaaactcct gatctataag gcgtctagtt tagaaaatgg ggtcccatca 180
aggttcagcg gcagtggatc tgggacagaa ttcactctca tcatcagcag cctgcagcct 240
gatgattttg caacttatta ctgccaacag tatattagtt attctcggac gttcggccaa 300
gggaccaagg tggaaatcaa a                                           321

SEQ ID NO: 476         moltype = AA    length = 107
FEATURE                Location/Qualifiers
REGION                 1..107
                       note = Synthetic
source                 1..107
                       mol_type = protein
                       organism = synthetic construct
SEQUENCE: 476
DIQMTQSPST LSASVGDRVT ITCRASQSIS SWLAWYQQIP GKAPKLLIYK ASSLENGVPS  60
RFSGSGSGTE FTLIISSLQP DDFATYYCQQ YISYSRTFGQ GTKVEIK              107

SEQ ID NO: 477         moltype = DNA   length = 360
```

```
FEATURE                 Location/Qualifiers
misc_feature            1..360
                        note = Synthetic
source                  1..360
                        mol_type = other DNA
                        organism = synthetic construct
SEQUENCE: 477
gaggtgcagc tggtgagtc tgggggaggc ctggtcaagc ctgggggtc cctgagactc      60
tcctgtgcag cctctggatt caccttcagt acttataaca tgaactgggt ccgccaggct    120
ccagggaagg ggctggagtg ggtctcatcc attaggagta gtagtaatta catatactac    180
gcagactcag tgaagggccg attcaccatc tccagagaca acgccaagaa ctcactgtat    240
ctgcaaatga acagcctgag agccgaggac acggctgtgt attactgtgc gagagatggc    300
agcagttggt acgactactc tgactactgg ggccaaggaa ccctggtcac cgtctcctca    360

SEQ ID NO: 478          moltype = AA  length = 120
FEATURE                 Location/Qualifiers
REGION                  1..120
                        note = Synthetic
source                  1..120
                        mol_type = protein
                        organism = synthetic construct
SEQUENCE: 478
EVQLVESGGG LVKPGGSLRL SCAASGFTFS TYNMNWVRQA PGKGLEWVSS IRSSSNYIYY    60
ADSVKGRFTI SRDNAKNSLY LQMNSLRAED TAVYYCARDG SSWYDYSDYW GQGTLVTVSS    120

SEQ ID NO: 479          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 479
gacatccaga tgacccagtc tccttccacc ctgtctgcat ctgtaggaga cagagtcacc    60
atcacttgcc gggccagtca gagtattagt agctggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tatattagtt attctcggac gttcggccaa    300
gggaccaagg tggaaatcaa a                                              321

SEQ ID NO: 480          moltype = AA  length = 107
FEATURE                 Location/Qualifiers
REGION                  1..107
                        note = Synthetic
source                  1..107
                        mol_type = protein
                        organism = synthetic construct
SEQUENCE: 480
DIQMTQSPST LSASVGDRVT ITCRASQSIS SWLAWYQQKP GKAPKLLIYK ASSLESGVPS    60
RFSGSGSGTE FTLTISSLQP DDFATYYCQQ YISYSRTFGQ GTKVEIK                  107

SEQ ID NO: 481          moltype = DNA  length = 354
FEATURE                 Location/Qualifiers
misc_feature            1..354
                        note = Synthetic
source                  1..354
                        mol_type = other DNA
                        organism = synthetic construct
SEQUENCE: 481
gaggtgcaac tagtggagtc tgggggaggc ttggtacagc ctgggggtc cctgagactc     60
tcctgtgtag tctctggatt caccttcggt gactacgaca tgcactgggt ccgtcaagct    120
acaggaaagg gtctggagtg ggtctcaggt attgctcctg ctggtgacac atcctataca    180
ggctccgtga agggccgatt caccatctcc agagagaatg ccaagaactc cttgcatctt    240
caaatgaaca gcctgacaac cggggacacg gctatatatt attgtgctag agaggatata    300
gcagtgcctg gttttgatta ctggggccag ggaaccctgg tcaccgtctc ctca          354

SEQ ID NO: 482          moltype = AA  length = 118
FEATURE                 Location/Qualifiers
REGION                  1..118
                        note = Synthetic
source                  1..118
                        mol_type = protein
                        organism = synthetic construct
SEQUENCE: 482
EVQLVESGGG LVQPGGSLRL SCVVSGFTFG DYDMHWVRQA TGRGLEWVSG IAPAGDTSYT    60
GSVKGRFTIS RENAKNSLHL QMNSLTTGDT AIYYCAREDI AVPGFDYWGQ GTLVTVSS     118

SEQ ID NO: 483          moltype = DNA  length = 24
FEATURE                 Location/Qualifiers
```

```
misc_feature            1..24
                        note = Synthetic
source                  1..24
                        mol_type = other DNA
                        organism = synthetic construct
SEQUENCE: 483
ggattcacct tcggtgacta cgac                                              24

SEQ ID NO: 484          moltype = AA   length = 8
FEATURE                 Location/Qualifiers
REGION                  1..8
                        note = Synthetic
source                  1..8
                        mol_type = protein
                        organism = synthetic construct
SEQUENCE: 484
GFTFGDYD                                                                 8

SEQ ID NO: 485          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 485
attgctcctg ctggtgacac a                                                 21

SEQ ID NO: 486          moltype = AA   length = 7
FEATURE                 Location/Qualifiers
REGION                  1..7
                        note = Synthetic
source                  1..7
                        mol_type = protein
                        organism = synthetic construct
SEQUENCE: 486
IAPAGDT                                                                  7

SEQ ID NO: 487          moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 487
gctagagagg atatagcagt gcctggtttt gattac                                 36

SEQ ID NO: 488          moltype = AA   length = 12
FEATURE                 Location/Qualifiers
REGION                  1..12
                        note = Synthetic
source                  1..12
                        mol_type = protein
                        organism = synthetic construct
SEQUENCE: 488
AREDIAVPGF DY                                                           12

SEQ ID NO: 489          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 489
gaaatagtga tgacgcagtc tccagccacc ctgtctgtgt ctccagggga acgaggcacc        60
ctctcctgca gggccagtca gagtgttagc agcaactrag cctggtacca gcagaaacct       120
ggccaggctc ccagactcct catctatggt gcatccacga gggcactgg cttcccagcc        180
aggttcagtg gcagtgggtc tgggacagag ttcactctca ccatcagcag cctgcagtct       240
gaagattttg cagtttatta ctgtcagcag tataataagt ggcctccgtt cactttcggc       300
cctgggacca aagtggattt caaa                                             324

SEQ ID NO: 490          moltype = AA   length = 108
FEATURE                 Location/Qualifiers
REGION                  1..108
                        note = Synthetic
source                  1..108
                        mol_type = protein
```

```
                        organism = synthetic construct
SEQUENCE: 490
EIVMTQSPAT LSVSPGERGT LSCRASQSVS SNLAWYQQKP GQAPRLLIYG ASTRATGFPA    60
RFSGSGSGTE FTLTISSLQS EDFAVYYCQQ YNKWPPFTFG PGTKVDFK                108

SEQ ID NO: 491          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 491
cagagtgtta gcagcaac                                                  18

SEQ ID NO: 492          moltype = AA  length = 6
FEATURE                 Location/Qualifiers
REGION                  1..6
                        note = Synthetic
source                  1..6
                        mol_type = protein
                        organism = synthetic construct
SEQUENCE: 492
QSVSSN                                                               6

SEQ ID NO: 493          moltype =   length =
SEQUENCE: 493
000

SEQ ID NO: 494          moltype =   length =
SEQUENCE: 494
000

SEQ ID NO: 495          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 495
cagcagtata ataagtggcc tccgttcact                                     30

SEQ ID NO: 496          moltype = AA  length = 10
FEATURE                 Location/Qualifiers
REGION                  1..10
                        note = Synthetic
source                  1..10
                        mol_type = protein
                        organism = synthetic construct
SEQUENCE: 496
QQYNKWPPFT                                                           10

SEQ ID NO: 497          moltype = DNA  length = 354
FEATURE                 Location/Qualifiers
misc_feature            1..354
                        note = Synthetic
source                  1..354
                        mol_type = other DNA
                        organism = synthetic construct
SEQUENCE: 497
gaggtgcaac tagtggagtc tgggggaggc ttggtacagc ctgggggtc cctgagactc     60
tcctgtgtag tctctggatt caccttcggt gactacgaca tgcactgggt ccgtcaagct   120
acaggaagag gtctggagtg ggtctcaggt attgctcctg ctggtgacac atcctataca   180
ggctccgtga agggccgatt caccatctcc agagagaatg ccaagaactc cttgcatctt   240
caaatgaaca gcctgacaac cggggacacg gctatatatt attgtgctag agaggatata   300
gcagtgcctg gttttgatta ctggggccag ggaaccctgg tcaccgtctc ctca         354

SEQ ID NO: 498          moltype = AA  length = 118
FEATURE                 Location/Qualifiers
REGION                  1..118
                        note = Synthetic
source                  1..118
                        mol_type = protein
                        organism = synthetic construct
SEQUENCE: 498
EVQLVESGGG LVQPGGSLRL SCVVSGFTFG DYDMHWVRQA TGRGLEWVSG IAPAGDTSYT    60
GSVKGRFTIS RENAKNSLHL QMNSLTTGDT AIYYCAREDI AVPGFDYWGQ GTLVTVSS    118
```

| SEQ ID NO: 499 | moltype = DNA length = 324 |
|---|---|
| FEATURE | Location/Qualifiers |
| misc_feature | 1..324 |
| | note = Synthetic |
| source | 1..324 |
| | mol_type = other DNA |
| | organism = synthetic construct |

SEQUENCE: 499
```
gaaatagtga tgacgcagtc tccagccacc ctgtctgtgt ctccagggga acgaggcacc   60
ctctcctgca gggccagtca gagtgttagc agcaacttag cctggtacca gcagaaacct  120
ggccaggctc ccagactcct catctatggt gcatccacga gggccactgg cttcccagcc  180
aggttcagtg gcagtgggtc tgggacagag ttcactctca ccatcagcag cctgcagtct  240
gaagattttg cagtttatta ctgtcagcag tataataagt ggcctccgtt cactttcggc  300
cctgggacca aagtggatat caaa                                         324
```

| SEQ ID NO: 500 | moltype = AA length = 108 |
|---|---|
| FEATURE | Location/Qualifiers |
| REGION | 1..108 |
| | note = Synthetic |
| source | 1..108 |
| | mol_type = protein |
| | organism = synthetic construct |

SEQUENCE: 500
```
EIVMTQSPAT LSVSPGERGT LSCRASQSVS SNLAWYQQKP GQAPRLLIYG ASTRATGFPA   60
RFSGSGSGTE FTLTISSLQS EDFAVYYCQQ YNKWPPFTFG PGTKVDIK              108
```

| SEQ ID NO: 501 | moltype = DNA length = 354 |
|---|---|
| FEATURE | Location/Qualifiers |
| misc_feature | 1..354 |
| | note = Synthetic |
| source | 1..354 |
| | mol_type = other DNA |
| | organism = synthetic construct |

SEQUENCE: 501
```
gaggtgcagc tggtggagtc tgggggaggc ttggtacagc ctggggggtc cctgagactc   60
tcctgtgcag cctctggatt caccttcggt gactacgaca tgcactgggt ccgccaagct  120
acaggaaaag gtctggagtg ggtctcagct attgctcctg ctggtgacac atactatcca  180
ggctccgtga agggccgatt caccatctcc agagaaaatg ccaagaactc cttgtatctt  240
caaatgaaca gcctgagagc cggggacacg gctgtgtatt actgtgctag agaggatata  300
gcagtgcctg gttttgatta ctggggccaa ggaaccctgg tcaccgtctc ctca       354
```

| SEQ ID NO: 502 | moltype = AA length = 118 |
|---|---|
| FEATURE | Location/Qualifiers |
| REGION | 1..118 |
| | note = Synthetic |
| source | 1..118 |
| | mol_type = protein |
| | organism = synthetic construct |

SEQUENCE: 502
```
EVQLVESGGG LVQPGGSLRL SCAASGFTFG DYDMHWVRQA TGKGLEWVSA IAPAGDTYYP   60
GSVKGRFTIS RENAKNSLYL QMNSLRAGDT AVYYCAREDI AVPGFDYWGQ GTLVTVSS   118
```

| SEQ ID NO: 503 | moltype = DNA length = 324 |
|---|---|
| FEATURE | Location/Qualifiers |
| misc_feature | 1..324 |
| | note = Synthetic |
| source | 1..324 |
| | mol_type = other DNA |
| | organism = synthetic construct |

SEQUENCE: 503
```
gaaatagtga tgacgcagtc tccagccacc ctgtctgtgt ctccagggga aagagccacc   60
ctctcctgca gggccagtca gagtgttagc agcaacttag cctggtacca gcagaaacct  120
ggccaggctc ccaggctcct catctatggt gcatccacca gggccactgg tatcccagcc  180
aggttcagtg gcagtgggtc tgggacagag ttcactctca ccatcagcag cctgcagtct  240
gaagattttg cagtttatta ctgtcagcag tataataagt ggcctccgtt cactttcggc  300
cctgggacca aagtggatat caaa                                         324
```

| SEQ ID NO: 504 | moltype = AA length = 108 |
|---|---|
| FEATURE | Location/Qualifiers |
| REGION | 1..108 |
| | note = Synthetic |
| source | 1..108 |
| | mol_type = protein |
| | organism = synthetic construct |

SEQUENCE: 504
```
EIVMTQSPAT LSVSPGERAT LSCRASQSVS SNLAWYQQKP GQAPRLLIYG ASTRATGIPA   60
RFSGSGSGTE FTLTISSLQS EDFAVYYCQQ YNKWPPFTFG PGTKVDIK              108
```

| SEQ ID NO: 505 | moltype = DNA length = 378 |
|---|---|

```
FEATURE                 Location/Qualifiers
misc_feature            1..378
                        note = Synthetic
source                  1..378
                        mol_type = other DNA
                        organism = synthetic construct
SEQUENCE: 505
caaattctgc tggtgcaatc tggacctgag gtgaaggagc ctggggcctc agtgaaggtc    60
tcctgcaagg cttctggtta caccttacc aactacgcta tcagctgggt gcgacaggtc   120
cctggacaag gcttgagtg gatgggatgg gtcagcgctt acaatggtca cacaaactat   180
gcacatgaag tccagggcag agtcaccatg accacagaca catccacgac cacagcctac   240
atggagctga ggagcctgag atctgacgac acggccatgt attactgtgc gagaggggt   300
gtagtcgtgc cagttgctcc ccacttctac aacggtatgg acgtctgggg ccaagggacc   360
acggtcaccg tctcctca                                                378

SEQ ID NO: 506          moltype = AA  length = 126
FEATURE                 Location/Qualifiers
REGION                  1..126
                        note = Synthetic
source                  1..126
                        mol_type = protein
                        organism = synthetic construct
SEQUENCE: 506
QILLVQSGPE VKEPGASVKV SCKASGYTFT NYAISWVRQV PGQGLEWMGW VSAYNGHTNY    60
AHEVQGRVTM TTDTSTTTAY MELRSLRSDD TAMYYCARGG VVVPVAPHFY NGMDVWGQGT   120
TVTVSS                                                             126

SEQ ID NO: 507          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 507
ggttacacct ttaccaacta cgct                                          24

SEQ ID NO: 508          moltype = AA  length = 8
FEATURE                 Location/Qualifiers
REGION                  1..8
                        note = Synthetic
source                  1..8
                        mol_type = protein
                        organism = synthetic construct
SEQUENCE: 508
GYTFTNYA                                                            8

SEQ ID NO: 509          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 509
gtcagcgctt acaatggtca caca                                          24

SEQ ID NO: 510          moltype = AA  length = 8
FEATURE                 Location/Qualifiers
REGION                  1..8
                        note = Synthetic
source                  1..8
                        mol_type = protein
                        organism = synthetic construct
SEQUENCE: 510
VSAYNGHT                                                            8

SEQ ID NO: 511          moltype = DNA  length = 57
FEATURE                 Location/Qualifiers
misc_feature            1..57
                        note = Synthetic
source                  1..57
                        mol_type = other DNA
                        organism = synthetic construct
SEQUENCE: 511
gcgagagggg gtgtagtcgt gccagttgct ccccacttct acaacggtat ggacgtc      57

SEQ ID NO: 512          moltype = AA  length = 19
FEATURE                 Location/Qualifiers
```

```
REGION                  1..19
                        note = Synthetic
source                  1..19
                        mol_type = protein
                        organism = synthetic construct
SEQUENCE: 512
ARGGVVVPVA PHFYNGMDV                                                    19

SEQ ID NO: 513          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 513
gatattgtga tgactcagtt tccactctcc ctgcccgtca cccctggaga gccggcctcc        60
atctcctgca ggtctagtca gagcctcctg catattaatg aatacaacta tttggattgg      120
tacctaaaga agccagggca gtctccacac ctcctgatct atttgggttt taatcgggcc      180
tccgggggtcc ctgacaggtt cagtggcagt ggatcaggca cagattttac actgaaaatc     240
agcagagtgg aggctgagga tgttggggtc tattactgca tgcaagctct tcaaactccg      300
tggacgttag gccaagggac caaggtggaa atcaaa                                336

SEQ ID NO: 514          moltype = AA  length = 112
FEATURE                 Location/Qualifiers
REGION                  1..112
                        note = Synthetic
source                  1..112
                        mol_type = protein
                        organism = synthetic construct
SEQUENCE: 514
DIVMTQFPPLS LPVTPGEPAS ISCRSSQSLL HINEYNYLDW YLKKPGQSPQ LLIYLGFNRA       60
SGVPDRFSGS GSGTDFTLKI SRVEAEDVGV YYCMQALQTP WTLGQGTKVE IK              112

SEQ ID NO: 515          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 515
cagagcctcc tgcatattaa tgaatacaac tat                                    33

SEQ ID NO: 516          moltype = AA  length = 11
FEATURE                 Location/Qualifiers
REGION                  1..11
                        note = Synthetic
source                  1..11
                        mol_type = protein
                        organism = synthetic construct
SEQUENCE: 516
QSLLHINEYN Y                                                            11

SEQ ID NO: 517          moltype =   length =
SEQUENCE: 517
000

SEQ ID NO: 518          moltype =   length =
SEQUENCE: 518
000

SEQ ID NO: 519          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 519
atgcaagctc ttcaaactcc gtggacg                                           27

SEQ ID NO: 520          moltype = AA  length = 9
FEATURE                 Location/Qualifiers
REGION                  1..9
                        note = Synthetic
source                  1..9
                        mol_type = protein
                        organism = synthetic construct
```

-continued

```
SEQUENCE: 520
MQALQTPWT                                                              9

SEQ ID NO: 521          moltype = DNA  length = 378
FEATURE                 Location/Qualifiers
misc_feature            1..378
                        note = Synthetic
source                  1..378
                        mol_type = other DNA
                        organism = synthetic construct
SEQUENCE: 521
caggttcagc tggtgcagtc tggacctgag gtgaaggagc ctggggcctc agtgaaggtc   60
tcctgcaagg cttctggtta cacctttacc aactacgcta tcagctgggt gcgacaggtc  120
cctggacaag ggcttgagtg gatgggatgg gtcagcgctt acaatggtca cacaaactat  180
gcacatgaag tccagggcag agtcaccatg accacagaca catccacgac cacagcctac  240
atggagctga ggagcctgag atctgacgac acggccatgt attactgtgc gagagggggt  300
gtagtcgtgc cagttgctcc ccacttctac aacggtatgg acgtctgggg ccaagggacc  360
acggtcaccg tctcctca                                                 378

SEQ ID NO: 522          moltype = AA  length = 126
FEATURE                 Location/Qualifiers
REGION                  1..126
                        note = Synthetic
source                  1..126
                        mol_type = protein
                        organism = synthetic construct
SEQUENCE: 522
QVQLVQSGPE VKEPGASVKV SCKASGYTFT NYAISWVRQV PGQGLEWMGW VSAYNGHTNY   60
AHEVQGRVTM TTDTSTTTAY MELRSLRSDD TAMYYCARGG VVVPVAPHFY NGMDVWGQGT  120
TVTVSS                                                             126

SEQ ID NO: 523          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 523
gatattgtga tgactcagtc tccactctcc ctgcccgtca cccctggaga gccggcctcc   60
atctcctgca ggtctagtca gagcctcctg catattaatg aatacaacta tttggattgg  120
tacctaaaga agcagggca gtctccacag ctcctgatct atttgggttt taatcgggcc  180
tccggggtcc ctgacaggtt cagtggcagt ggatcaggca cagattttac actgaaaatc  240
agcagagtgg aggctgagga tgttggggtc tattactgca tgcaagctct tcaaactccg  300
tggacgttag gccaagggac caaggtggaa atcaaa                            336

SEQ ID NO: 524          moltype = AA  length = 112
FEATURE                 Location/Qualifiers
REGION                  1..112
                        note = Synthetic
source                  1..112
                        mol_type = protein
                        organism = synthetic construct
SEQUENCE: 524
DIVMTQSPLS LPVTPGEPAS ISCRSSQSLL HINEYNYLDW YLKKPGQSPQ LLIYLGFNRA   60
SGVPDRFSGS GSGTDFTLKI SRVEAEDVGV YYCMQALQTP WTLGQGTKVE IK          112

SEQ ID NO: 525          moltype = DNA  length = 378
FEATURE                 Location/Qualifiers
misc_feature            1..378
                        note = Synthetic
source                  1..378
                        mol_type = other DNA
                        organism = synthetic construct
SEQUENCE: 525
caggttcagc tggtgcagtc tggagctgag gtgaagaagc ctggggcctc agtgaaggtc   60
tcctgcaagg cttctggtta cacctttacc aactacgcta tcagctgggt gcgacaggcc  120
cctggacaag ggcttgagtg gatgggatgg gtcagcgctt acaatggtca cacaaactat  180
gcacagaagt tccagggcag agtcaccatg accacagaca catccacgac cacagcctat  240
atggagctga ggagcctgag atctgacgac acggccgtgt attactgtgc gagagggggt  300
gtagtcgtgc cagttgctcc ccacttctac aacggtatgg acgtctgggg caagggacc   360
acggtcaccg tctcctca                                                 378

SEQ ID NO: 526          moltype = AA  length = 126
FEATURE                 Location/Qualifiers
REGION                  1..126
                        note = Synthetic
source                  1..126
                        mol_type = protein
```

```
                        organism = synthetic construct
SEQUENCE: 526
QVQLVQSGAE VKKPGASVKV SCKASGYTFT NYAISWVRQA PGQGLEWMGW VSAYNGHTNY    60
AQKLQGRVTM TTDTSTSTAY MELRSLRSDD TAVYYCARGG VVVPVAPHFY NGMDVWGQGT   120
TVTVSS                                                              126

SEQ ID NO: 527          moltype = DNA   length = 336
FEATURE                 Location/Qualifiers
misc_feature            1..336
                        note = Synthetic
source                  1..336
                        mol_type = other DNA
                        organism = synthetic construct
SEQUENCE: 527
gatattgtga tgactcagtc tccactctcc ctgcccgtca ccctggaga gccggcctcc     60
atctcctgca ggtctagtca gagcctcctg catattaatg aatacaacta tttggattgg  120
tacctgcaga agccagggca gtctccacag ctcctgatct atttgggttc taatcgggcc  180
tccggggtcc ctgacaggtt cagtggcagt ggatcaggca cagattttac actgaaaatc  240
agcagagtgg aggctgagga tgttggggtt tattactgca tgcaagctct tcaaactccg  300
tggacgttcg gccaagggac caaggtggaa atcaaa                            336

SEQ ID NO: 528          moltype = AA   length = 112
FEATURE                 Location/Qualifiers
REGION                  1..112
                        note = Synthetic
source                  1..112
                        mol_type = protein
                        organism = synthetic construct
SEQUENCE: 528
DIVMTQSPLS LPVTPGEPAS ISCRSSQSLL HINEYNYLDW YLQKPGQSPQ LLIYLGSNRA    60
SGVPDRFSGS GSGTDFTLKI SRVEAEDVGV YYCMQALQTP WTFGQGTKVE IK           112

SEQ ID NO: 529          moltype = DNA   length = 351
FEATURE                 Location/Qualifiers
misc_feature            1..351
                        note = Synthetic
source                  1..351
                        mol_type = other DNA
                        organism = synthetic construct
SEQUENCE: 529
gaggtgcagc tggtggagtc tgggggaggc ttggtacagc ctggggggtc cctgagactc    60
tcctgtgcag cctctggatt caccctaagt agctacgaca tgcactgggt ccgccaagca  120
acaggaaaag gtctgagtg gtctcagct attggcagac ctggtgacac atactataca   180
ggctccgtga tgggccgatt caccatctcc agagacgctg ccaaaaactc cttctatctt  240
gaaatgaaca gcctgagagt cggggacacg gctgtatatt actgtgcaag agagggaata  300
agaacaccct atgattattg gggccaggga gcccgggtca ccgtctcctc a           351

SEQ ID NO: 530          moltype = AA   length = 117
FEATURE                 Location/Qualifiers
REGION                  1..117
                        note = Synthetic
source                  1..117
                        mol_type = protein
                        organism = synthetic construct
SEQUENCE: 530
EVQLVESGGG LVQPGGSLRL SCAASGFTLS SYDMHWVRQA TGKGLEWVSA IGSTGDTYYT    60
GSVMGRFTIS RDAAKNSFYL EMNSLRVGDT AVYYCAREGI RTPYDYWGQG ARVTVSS     117

SEQ ID NO: 531          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 531
ggattcaccc taagtagcta cgac                                           24

SEQ ID NO: 532          moltype = AA   length = 8
FEATURE                 Location/Qualifiers
REGION                  1..8
                        note = Synthetic
source                  1..8
                        mol_type = protein
                        organism = synthetic construct
SEQUENCE: 532
GFTLSSYD                                                              8

SEQ ID NO: 533          moltype = DNA   length = 21
```

```
FEATURE                 Location/Qualifiers
misc_feature            1..21
                        note = Synthetic
source                  1..21
                        mol_type = other DNA
                        organism = synthetic construct
SEQUENCE: 533
attggcagta ctggtgacac a                                              21

SEQ ID NO: 534          moltype = AA  length = 7
FEATURE                 Location/Qualifiers
REGION                  1..7
                        note = Synthetic
source                  1..7
                        mol_type = protein
                        organism = synthetic construct
SEQUENCE: 534
IGSTGDT                                                               7

SEQ ID NO: 535          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 535
gcaagagagg gaataagaac accctatgat tat                                 33

SEQ ID NO: 536          moltype = AA  length = 11
FEATURE                 Location/Qualifiers
REGION                  1..11
                        note = Synthetic
source                  1..11
                        mol_type = protein
                        organism = synthetic construct
SEQUENCE: 536
AREGIRTPYD Y                                                         11

SEQ ID NO: 537          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 537
gaaatagtga tgacgcagtc tccagccacc ctgtctgtgt ctccagggga aagagccacc     60
ctctcctgca gggccagtca gagtgttagc agcaatgtag cctggtacca gcagaaacct   120
ggccaggctc ccaggctcct catctatggt gcatccacca gggccactgg tatcccagcc   180
aggttcagtg gcagtgggtc tgggacagaa ttcactctca ccatcagcag cctgcagtct   240
gaagattttg cagtttatta ctgtcagcag tataataatt ggcctccatt cactttcggc   300
cctgggacca agtggatat caaa                                           324

SEQ ID NO: 538          moltype = AA  length = 108
FEATURE                 Location/Qualifiers
REGION                  1..108
                        note = Synthetic
source                  1..108
                        mol_type = protein
                        organism = synthetic construct
SEQUENCE: 538
EIVMTQSPAT LSVSPGERAT LSCRASQSVS SNVAWYQQKP GQAPRLLIYG ASTRATGIPA    60
RFSGSGSGTE FTLTISSLQS EDFAVYYCQQ YNNWPPFTFG PGTKVDIK                108

SEQ ID NO: 539          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 539
cagagtgtta gcagcaat                                                  18

SEQ ID NO: 540          moltype = AA  length = 6
FEATURE                 Location/Qualifiers
REGION                  1..6
                        note = Synthetic
```

```
source                  1..6
                        mol_type = protein
                        organism = synthetic construct
SEQUENCE: 540
QSVSSN                                                                      6

SEQ ID NO: 541          moltype =   length =
SEQUENCE: 541
000

SEQ ID NO: 542          moltype =   length =
SEQUENCE: 542
000

SEQ ID NO: 543          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 543
cagcagtata ataattggcc tccattcact                                            30

SEQ ID NO: 544          moltype = AA  length = 10
FEATURE                 Location/Qualifiers
REGION                  1..10
                        note = Synthetic
source                  1..10
                        mol_type = protein
                        organism = synthetic construct
SEQUENCE: 544
QQYNNWPPFT                                                                  10

SEQ ID NO: 545          moltype = DNA  length = 351
FEATURE                 Location/Qualifiers
misc_feature            1..351
                        note = Synthetic
source                  1..351
                        mol_type = other DNA
                        organism = synthetic construct
SEQUENCE: 545
gaggtgcagc tggtggagtc tgggggaggc ttggtacagc ctggggggtc cctgagactc           60
tcctgtgcag cctctggatt caccctaagt agctacgaca tgcactgggt ccgccaagca          120
acaggaaaag gtctggagtg ggtctcagct attggcagta ctggtgacac atactataca          180
ggctccgtga tgggccgatt caccatctcc agagacgctg ccaaaaactc cttctatctt          240
gaaatgaaca gcctgagagt cggggacacg gctgtatatt actgtgcaag agagggaata          300
agaacaccct atgattattg gggccaggga accctggtca ccgtctcctc a                   351

SEQ ID NO: 546          moltype = AA  length = 117
FEATURE                 Location/Qualifiers
REGION                  1..117
                        note = Synthetic
source                  1..117
                        mol_type = protein
                        organism = synthetic construct
SEQUENCE: 546
EVQLVESGGG LVQPGGSLRL SCAASGFTLS SYDMHWVRQA TGKGLEWVSA IGSTGDTYYT           60
GSVMGRFTIS RDAAKNSFYL EMNSLRVGDT AVYYCAREGI RTPYDYWGQG TLVTVSS             117

SEQ ID NO: 547          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 547
gaaatagtga tgacgcagtc tccagccacc ctgtctgtgt ctccagggga aagagccacc           60
ctctcctgca gggccagtca gagtgttagc agcaatgtag cctggtacca gcagaaacct          120
ggccaggctc ccaggctcct catctatggt gcatccacca gggccactgg tatcccagcc          180
aggttcagtg gcagtgggtc tgggacagaa ttcactctca ccatcagcag cctgcagtct          240
gaagattttg cagtttatta ctgtcagcag tataataatt ggcctccatt cactttcggc          300
cctgggacca aagtggatat caaa                                                 324

SEQ ID NO: 548          moltype = AA  length = 108
FEATURE                 Location/Qualifiers
REGION                  1..108
                        note = Synthetic
```

```
source                  1..108
                        mol_type = protein
                        organism = synthetic construct
SEQUENCE: 548
EIVMTQSPAT LSVSPGERAT LSCRASQSVS SNVAWYQQKP GQAPRLLIYG ASTRATGIPA    60
RFSGSGSGTE FTLTISSLQS EDFAVYYCQQ YNNWPPFTFG PGTKVDIK                108

SEQ ID NO: 549          moltype = DNA  length = 351
FEATURE                 Location/Qualifiers
misc_feature            1..351
                        note = Synthetic
source                  1..351
                        mol_type = other DNA
                        organism = synthetic construct
SEQUENCE: 549
gaggtgcagc tggtggagtc tgggggaggc ttggtacagc ctggggggtc cctgagactc    60
tcctgtgcag cctctggatt caccctaagt agctacgaca tgcactgggt ccgccaagct   120
acaggaaaag gtctggagtg ggtctcagct attggcagta ctggtgacac atactatcca   180
ggctccgtga agggccgatt caccatctcc agagaaaatg ccaagaactc cttgtatctt   240
caaatgaaca gcctgagagc cggggacacg gctgtgtatt actgtgcaag agagggaata   300
agaacaccct atgattattg gggccaagga accctggtca ccgtctcctc a            351

SEQ ID NO: 550          moltype = AA  length = 117
FEATURE                 Location/Qualifiers
REGION                  1..117
                        note = Synthetic
source                  1..117
                        mol_type = protein
                        organism = synthetic construct
SEQUENCE: 550
EVQLVESGGG LVQPGGSLRL SCAASGFTLS SYDMHWVRQA TGKGLEWVSA IGSTGDTYYP    60
GSVKGRFTIS RENAKNSLYL QMNSLRAGDT AVYYCAREGI RTPYDYWGQG TLVTVSS      117

SEQ ID NO: 551          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 551
gaaatagtga tgacgcagtc tccagccacc ctgtctgtgt ctccagggga aagagccacc    60
ctctcctgca gggccagtca gagtgttagc agcaatttga actggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataatt ggcctccatt cactttcggc   300
cctgggacca aagtggatat caaa                                          324

SEQ ID NO: 552          moltype = AA  length = 108
FEATURE                 Location/Qualifiers
REGION                  1..108
                        note = Synthetic
source                  1..108
                        mol_type = protein
                        organism = synthetic construct
SEQUENCE: 552
EIVMTQSPAT LSVSPGERAT LSCRASQSVS SNLAWYQQKP GQAPRLLIYG ASTRATGIPA    60
RFSGSGSGTE FTLTISSLQS EDFAVYYCQQ YNNWPPFTFG PGTKVDIK                108

SEQ ID NO: 553          moltype = DNA  length = 351
FEATURE                 Location/Qualifiers
misc_feature            1..351
                        note = Synthetic
source                  1..351
                        mol_type = other DNA
                        organism = synthetic construct
SEQUENCE: 553
gaggtgcagc tggtggagtc tgggggaggc ttggtacagc ctggggggtc cctgagactc    60
tcctgtgcag cctctggatt caccctaagt agctacgaca tgcactgggt ccgccaagca   120
acaggaaaag gtctggagtg ggtctcagct attggcagta ctggtgacac atactataca   180
ggctccgtga agggccgatt caccatctcc agagacgctg ccaaaaactc cttctatctt   240
gaaatgaaca gcctgagagt cggggacacg gctgtatatt actgtgcaag agagggaata   300
agaacaccct atgattattg gggccaggga cccgggtca ccgtctcctc a              351

SEQ ID NO: 554          moltype = AA  length = 117
FEATURE                 Location/Qualifiers
REGION                  1..117
                        note = Synthetic
source                  1..117
```

```
                        mol_type = protein
                        organism = synthetic construct
SEQUENCE: 554
EVQLVESGGG LVQPGGSLRL SCAASGFTLS SYDMHWVRQA TGKGLEWVSA IGSTGDTYYT   60
GSVMGRFTIS RDAAKNSFYL EMNSLRVGDT AVYYCAREGI RTPYDYWGQG ARVTVSS      117

SEQ ID NO: 555          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 555
ggattcaccc taagtagcta cgac                                           24

SEQ ID NO: 556          moltype = AA   length = 8
FEATURE                 Location/Qualifiers
REGION                  1..8
                        note = Synthetic
source                  1..8
                        mol_type = protein
                        organism = synthetic construct
SEQUENCE: 556
GFTLSSYD                                                             8

SEQ ID NO: 557          moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 557
attggcagta ctggtgacac a                                              21

SEQ ID NO: 558          moltype = AA   length = 7
FEATURE                 Location/Qualifiers
REGION                  1..7
                        note = Synthetic
source                  1..7
                        mol_type = protein
                        organism = synthetic construct
SEQUENCE: 558
IGSTGDT                                                              7

SEQ ID NO: 559          moltype = DNA   length = 33
FEATURE                 Location/Qualifiers
misc_feature            1..33
                        note = Synthetic
source                  1..33
                        mol_type = other DNA
                        organism = synthetic construct
SEQUENCE: 559
gcaagagagg gaataagaac accctatgat tat                                 33

SEQ ID NO: 560          moltype = AA   length = 11
FEATURE                 Location/Qualifiers
REGION                  1..11
                        note = Synthetic
source                  1..11
                        mol_type = protein
                        organism = synthetic construct
SEQUENCE: 560
AREGIRTPYD Y                                                         11

SEQ ID NO: 561          moltype = DNA   length = 324
FEATURE                 Location/Qualifiers
misc_feature            1..324
                        note = Synthetic
source                  1..324
                        mol_type = other DNA
                        organism = synthetic construct
SEQUENCE: 561
gaaatagtga tgacgcagtc tccagccacc ctgtctgtgt ctccagggga aagagccacc   60
ctctcctgca gggccagtca gagtgttagc agcaatgtag cctggtacca gcagaaacct  120
ggccaggctc ccaggctcct catctatggt gcatccacca gggccactgg tatcccagcc  180
aggttcagtg gcagtgggtc tgggacagaa ttcactctca ccatcagcag cctgcagtct  240
gaagattttg cagtttatta ctgtcagcag tataataatt ggcctccatt cactttcggc  300
```

```
cctgggacca aagtggatat caaa                                              324

SEQ ID NO: 562          moltype = AA   length = 108
FEATURE                 Location/Qualifiers
REGION                  1..108
                        note = Synthetic
source                  1..108
                        mol_type = protein
                        organism = synthetic construct
SEQUENCE: 562
EIVMTQSPAT LSVSPGERAT LSCRASQSVS SNVAWYQQKP GQAPRLLIYG ASTRATGIPA        60
RFSGSGSGTE FTLTISSLQS EDFAVYYCQQ YNNWPPFTFG PGTKVDIK                    108

SEQ ID NO: 563          moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 563
cagagtgtta gcagcaat                                                      18

SEQ ID NO: 564          moltype = AA   length = 6
FEATURE                 Location/Qualifiers
REGION                  1..6
                        note = Synthetic
source                  1..6
                        mol_type = protein
                        organism = synthetic construct
SEQUENCE: 564
QSVSSN                                                                    6

SEQ ID NO: 565          moltype =    length =
SEQUENCE: 565
000

SEQ ID NO: 566          moltype =    length =
SEQUENCE: 566
000

SEQ ID NO: 567          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 567
cagcagtata ataattggcc tccattcact                                         30

SEQ ID NO: 568          moltype = AA   length = 10
FEATURE                 Location/Qualifiers
REGION                  1..10
                        note = Synthetic
source                  1..10
                        mol_type = protein
                        organism = synthetic construct
SEQUENCE: 568
QQYNNWPPFT                                                               10

SEQ ID NO: 569          moltype = DNA   length = 351
FEATURE                 Location/Qualifiers
misc_feature            1..351
                        note = Synthetic
source                  1..351
                        mol_type = other DNA
                        organism = synthetic construct
SEQUENCE: 569
gaggtgcagc tggtggagtc tgggggaggc ttggtacagc ctggggggtc cctgagactc        60
tcctgtgcag cctctggatt caccctaagt agctacgaca tgcactgggt ccgccaagca       120
acaggaaaag gtctggagtg ggtctcagct attggcagta ctggtgacac atactataca       180
ggctccgtga tgggccgatt caccatctcc agagacgctg ccaaaaactc cttctatctt       240
gaaatgaaca gcctgagagt cggggacacg gctgtatatt actgtgcaag agagggaata       300
agaacaccct atgattattg gggccaggga acctggtca ccgtctcctc a                351

SEQ ID NO: 570          moltype = AA   length = 117
FEATURE                 Location/Qualifiers
REGION                  1..117
```

```
                            note = Synthetic
source                      1..117
                            mol_type = protein
                            organism = synthetic construct
SEQUENCE: 570
EVQLVESGGG LVQPGGSLRL SCAASGFTLS SYDMHWVRQA TGKGLEWVSA IGSTGDTYYT    60
GSVMGRFTIS RDAAKNSFYL EMNSLRVGDT AVYYCAREGI RTPYDYWGQG TLVTVSS      117

SEQ ID NO: 571              moltype = DNA   length = 324
FEATURE                     Location/Qualifiers
misc_feature                1..324
                            note = Synthetic
source                      1..324
                            mol_type = other DNA
                            organism = synthetic construct
SEQUENCE: 571
gaaatagtga tgacgcagtc tccagccacc ctgtctgtgt ctccagggga agagccacc     60
ctctcctgca gggccagtca gagtgttagc agcaatgtag cctggtacca gcagaaacct  120
ggccaggctc ccaggctcct catctatggt gcatccacca gggccactgg tatcccagcc  180
aggttcagtg gcagtgggtc tgggacagaa ttcactctca ccatcagcag cctgcagtct  240
gaagattttg cagtttatta ctgtcagcag tataataatt ggcctccatt cactttcggc  300
cctgggacca aagtggatat caaa                                          324

SEQ ID NO: 572              moltype = AA   length = 108
FEATURE                     Location/Qualifiers
REGION                      1..108
                            note = Synthetic
source                      1..108
                            mol_type = protein
                            organism = synthetic construct
SEQUENCE: 572
EIVMTQSPAT LSVSPGERAT LSCRASQSVS SNVAWYQQKP GQAPRLLIYG ASTRATGIPA    60
RFSGSGSGTE FTLTISSLQS EDFAVYYCQQ YNNWPPFTFG PGTKVDIK                108

SEQ ID NO: 573              moltype = DNA   length = 351
FEATURE                     Location/Qualifiers
misc_feature                1..351
                            note = Synthetic
source                      1..351
                            mol_type = other DNA
                            organism = synthetic construct
SEQUENCE: 573
gaggtgcagc tggtggagtc tgggggaggc ttggtacagc ctggggggtc cctgagactc     60
tcctgtgcag cctctggatt caccctaagt agctacgaca tgcactgggt ccgccaagct   120
acaggaaaag gtctggagtg ggtctcagct attggcagta ctggtgacac atactatcca   180
ggctccgtga agggccgatt caccatctcc agagaaaatg ccaagaactc cttgtatctt   240
caaatgaaca gcctgagagc cggggacacg gctgtgtatt actgtgcaag agagggaata   300
agaacaccct atgattattg gggccaagga accctggtca ccgtctcctc a             351

SEQ ID NO: 574              moltype = AA   length = 117
FEATURE                     Location/Qualifiers
REGION                      1..117
                            note = Synthetic
source                      1..117
                            mol_type = protein
                            organism = synthetic construct
SEQUENCE: 574
EVQLVESGGG LVQPGGSLRL SCAASGFTLS SYDMHWVRQA TGKGLEWVSA IGSTGDTYYP    60
GSVKGRFTIS RENAKNSLYL QMNSLRAGDT AVYYCAREGI RTPYDYWGQG TLVTVSS      117

SEQ ID NO: 575              moltype = DNA   length = 324
FEATURE                     Location/Qualifiers
misc_feature                1..324
                            note = Synthetic
source                      1..324
                            mol_type = other DNA
                            organism = synthetic construct
SEQUENCE: 575
gaaatagtga tgacgcagtc tccagccacc ctgtctgtgt ctccagggga agagccacc     60
ctctcctgca gggccagtca gagtgttagc agcaatttag cctggtacca gcagaaacct  120
ggccaggctc ccaggctcct catctatggt gcatccacca gggccactgg tatcccagcc  180
aggttcagtg gcagtgggtc tgggacagag ttcactctca ccatcagcag cctgcagtct  240
gaagattttg cagtttatta ctgtcagcag tataataatt ggcctccatt cactttcggc  300
cctgggacca aagtggatat caaa                                          324

SEQ ID NO: 576              moltype = AA   length = 108
FEATURE                     Location/Qualifiers
REGION                      1..108
                            note = Synthetic
```

```
                        -continued source                  1..108
                        mol_type = protein
                        organism = synthetic construct
SEQUENCE: 576
EIVMTQSPAT LSVSPGERAT LSCRASQSVS SNLAWYQQKP GQAPRLLIYG ASTRATGIPA    60
RFSGSGSGTE FTLTISSLQS EDFAVYYCQQ YNNWPPFTFG PGTKVDIK                108

SEQ ID NO: 577          moltype = DNA   length = 363
FEATURE                 Location/Qualifiers
misc_feature            1..363
                        note = Synthetic
source                  1..363
                        mol_type = other DNA
                        organism = synthetic construct
SEQUENCE: 577
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccaggaaagg gcctggagtg ggtctcaggt attaattgga acagtggtag cataggctat   180
gcggactctg tgaagggccg attcaccatc tccagagaca cgccaagca ctccctgtat    240
ctgcaaatga acagtctgag acctgaggac acggccttgt attactgtgt aaaagaggtg   300
actacgggat actactacgg tatggacgtc tggggccaag gaccacggt caccgtctcc    360
tca                                                                 363

SEQ ID NO: 578          moltype = AA    length = 121
FEATURE                 Location/Qualifiers
REGION                  1..121
                        note = Synthetic
source                  1..121
                        mol_type = protein
                        organism = synthetic construct
SEQUENCE: 578
EVQLVESGGG LVQPGRSLRL SCAASGFTFD DYAMHWVRQA PGKGLEWVSG INWNSGSIGY    60
ADSVKGRFTI SRDNAKHSLY LQMNSLRPED TALYYCVKEV TTGYYYGMDV WGQGTTVTVS   120
S                                                                   121

SEQ ID NO: 579          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 579
ggattcacct ttgatgatta tgcc                                           24

SEQ ID NO: 580          moltype = AA    length = 8
FEATURE                 Location/Qualifiers
REGION                  1..8
                        note = Synthetic
source                  1..8
                        mol_type = protein
                        organism = synthetic construct
SEQUENCE: 580
GFTFDDYA                                                              8

SEQ ID NO: 581          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 581
attaattgga acagtggtag cata                                           24

SEQ ID NO: 582          moltype = AA    length = 8
FEATURE                 Location/Qualifiers
REGION                  1..8
                        note = Synthetic
source                  1..8
                        mol_type = protein
                        organism = synthetic construct
SEQUENCE: 582
INWNSGSI                                                              8

SEQ ID NO: 583          moltype = DNA   length = 42
FEATURE                 Location/Qualifiers
misc_feature            1..42
                        note = Synthetic
```

```
source                  1..42
                        mol_type = other DNA
                        organism = synthetic construct
SEQUENCE: 583
gtaaaagagg tgactacggg atactactac ggtatggacg tc              42

SEQ ID NO: 584          moltype = AA  length = 14
FEATURE                 Location/Qualifiers
REGION                  1..14
                        note = Synthetic
source                  1..14
                        mol_type = protein
                        organism = synthetic construct
SEQUENCE: 584
VKEVTTGYYY GMDV                                             14

SEQ ID NO: 585          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 585
gacatccagt tgacccagtc tccatccttc ctgtctgcat ctgtaggaga cagagtcacc   60
atcacttgct gggccagtca gggcattagc agttatttag cctggtatca gaaaaaacca  120
gggaaagccc ctaacctcct gatctatgat gcatccactt tgcaaagtgg ggtcccatca  180
aggttcagcg gcagtggatc tgggacagaa ttcactctca cactcagcag cctgcagcct  240
gaagattttg caacttatta ctgtcaacag cttaatattt acccattcac tttcggccct  300
gggaccaaag tggatatcaa a                                            321

SEQ ID NO: 586          moltype = AA  length = 107
FEATURE                 Location/Qualifiers
REGION                  1..107
                        note = Synthetic
source                  1..107
                        mol_type = protein
                        organism = synthetic construct
SEQUENCE: 586
DIQLTQSPSF LSASVGDRVT ITCWASQGIS SYLAWYQKKP GKAPNLLIYD ASTLQSGVPS   60
RFSGSGSGTE FTLTLSSLQP EDFATYYCQQ LNIYPFTFGP GTKVDIK               107

SEQ ID NO: 587          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 587
cagggcatta gcagttat                                         18

SEQ ID NO: 588          moltype = AA  length = 6
FEATURE                 Location/Qualifiers
REGION                  1..6
                        note = Synthetic
source                  1..6
                        mol_type = protein
                        organism = synthetic construct
SEQUENCE: 588
QGISSY                                                      6

SEQ ID NO: 589          moltype =   length =
SEQUENCE: 589
000

SEQ ID NO: 590          moltype =   length =
SEQUENCE: 590
000

SEQ ID NO: 591          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 591
caacagctta atatttaccc attcact                               27
```

```
SEQ ID NO: 592           moltype = AA   length = 9
FEATURE                  Location/Qualifiers
REGION                   1..9
                         note = Synthetic
source                   1..9
                         mol_type = protein
                         organism = synthetic construct
SEQUENCE: 592
QQLNIYPFT                                                                 9

SEQ ID NO: 593           moltype = DNA  length = 363
FEATURE                  Location/Qualifiers
misc_feature             1..363
                         note = Synthetic
source                   1..363
                         mol_type = other DNA
                         organism = synthetic construct
SEQUENCE: 593
gaagtgcagc tggtggagtc tgggggaggc ttggtacagc ctgcaggtc cctgagactc           60
tcctgtgcag cctctggatt cacctttgat gattatgcca tgcactgggt ccggcaagct         120
ccagggaagg gcctgagtg gtctcaggt attaattgga acagtggtag cataggctat           180
gcggactctg tgaagggccg attcaccatc tccagagaca cgccaagca ctccctgtat          240
ctgcaaatga acagtctgag acctgaggac acggccttgt attactgtgt aaaagaggtg         300
actacgggat actactacgg tatggacgtc tggggccaag ggaccacggt caccgtctcc         360
tca                                                                      363

SEQ ID NO: 594           moltype = AA   length = 121
FEATURE                  Location/Qualifiers
REGION                   1..121
                         note = Synthetic
source                   1..121
                         mol_type = protein
                         organism = synthetic construct
SEQUENCE: 594
EVQLVESGGG LVQPGRSLRL SCAASGFTFD DYAMHWVRQA PGKGLEWVSG INWNSGSIGY          60
ADSVKGRFTI SRDNAKHSLY LQMNSLRPED TALYYCVKEV TTGYYYGMDV WGQGTTVTVS        120
S                                                                        121

SEQ ID NO: 595           moltype = DNA  length = 321
FEATURE                  Location/Qualifiers
misc_feature             1..321
                         note = Synthetic
source                   1..321
                         mol_type = other DNA
                         organism = synthetic construct
SEQUENCE: 595
gacatccagt tgacccagtc tccatccttc ctgtctgcat ctgtaggaga cagagtcacc          60
atcacttgct gggccagtca gggcattagc agttatttag cctggtatca gaaaaaacca        120
gggaaagccc ctaacctcct gatctatgat gcatccactt tgcaaagtgg ggtcccatca        180
aggttcagcg gcagtggatc tgggacagaa ttcactctca cactcagcag cctgcagcct        240
gaagattttg caacttatta ctgtcaacag cttaatattt acccattcac tttcggccct        300
gggaccaaag tggatatcaa a                                                  321

SEQ ID NO: 596           moltype = AA   length = 107
FEATURE                  Location/Qualifiers
REGION                   1..107
                         note = Synthetic
source                   1..107
                         mol_type = protein
                         organism = synthetic construct
SEQUENCE: 596
DIQLTQSPSF LSASVGDRVT ITCWASQGIS SYLAWYQKKP GKAPNLLIYD ASTLQSGVPS          60
RFSGSGSGTE FTLTLSSLQP EDFATYYCQQ LNIYPFTFGP GTKVDIK                      107

SEQ ID NO: 597           moltype = DNA  length = 363
FEATURE                  Location/Qualifiers
misc_feature             1..363
                         note = Synthetic
source                   1..363
                         mol_type = other DNA
                         organism = synthetic construct
SEQUENCE: 597
gaagtgcagc tggtggagtc tgggggaggc ttggtacagc ctgcaggtc cctgagactc           60
tcctgtgcag cctctggatt cacctttgat gattatgcca tgcactgggt ccggcaagct         120
ccagggaagg gcctgagtg gtctcaggt attaattgga acagtggtag cataggctat           180
gcggactctg tgaagggccg attcaccatc tccagagaca cgccaagaa ctccctgtat          240
ctgcaaatga acagtctgag agctgaggac acggccttgt attactgtgt aaaagaggtg         300
actacgggat actactacgg tatggacgtc tggggcaag ggaccacggt caccgtctcc          360
```

```
                                                        -continued
tca                                                              363

SEQ ID NO: 598          moltype = AA    length = 121
FEATURE                 Location/Qualifiers
REGION                  1..121
                        note = Synthetic
source                  1..121
                        mol_type = protein
                        organism = synthetic construct
SEQUENCE: 598
EVQLVESGGG LVQPGRSLRL SCAASGFTFD DYAMHWVRQA PGKGLEWVSG INWNSGSIGY    60
ADSVKGRFTI SRDNAKNSLY LQMNSLRAED TALYYCVKEV TTGYYYGMDV WGQGTTVTVS   120
S                                                                  121

SEQ ID NO: 599          moltype = DNA   length = 321
FEATURE                 Location/Qualifiers
misc_feature            1..321
                        note = Synthetic
source                  1..321
                        mol_type = other DNA
                        organism = synthetic construct
SEQUENCE: 599
gacatccagt tgacccagtc tccatccttc ctgtctgcat ctgtaggaga cagagtcacc    60
atcacttgcc gggccagtca gggcattagc agttatttag cctggtatca gcaaaaacca   120
gggaaagccc ctaagctcct gatctatgat gcatccactt tgcaaagtgg ggtcccatca   180
aggttcagcg gcagtggatc tgggacagaa ttcactctca caatcagcag cctgcagcct   240
gaagattttg caacttatta ctgtcaacag cttaatattt acccattcac tttcggccct   300
gggaccaaag tggatatcaa a                                             321

SEQ ID NO: 600          moltype = AA    length = 107
FEATURE                 Location/Qualifiers
REGION                  1..107
                        note = Synthetic
source                  1..107
                        mol_type = protein
                        organism = synthetic construct
SEQUENCE: 600
DIQLTQSPSF LSASVGDRVT ITCRASQGIS SYLAWYQQKP GKAPKLLIYD ASTLQSGVPS    60
RFSGSGSGTE FTLTISSLQP EDFATYYCQQ LNIYPFTFGP GTKVDIK                 107

SEQ ID NO: 601          moltype = DNA   length = 366
FEATURE                 Location/Qualifiers
misc_feature            1..366
                        note = Synthetic
source                  1..366
                        mol_type = other DNA
                        organism = synthetic construct
SEQUENCE: 601
gaggtgcagt tgttggagtc tgggggaggc ttggtacagc ctgggggtc cctgagactc     60
tcctgtgcag cctctggatt cacgtttagt agctatgcca tgaactgggt ccgccaggct   120
ccagggaagg ggctggattg ggtctcaggt atcagtggta tggtggtag caccta         180
gcagactccg tgaagggccg gttcaccatc tccagagaca tttccaagaa cacgctgtat   240
gtgcaaatgc acagcctgag agtcgaggac acggccgttt actactgtgc gaaagcccgt   300
tattacgatt tttggggggg gaatttcgat ctctggggcc gtggcaccca ggtcactgtc   360
tcctca                                                             366

SEQ ID NO: 602          moltype = AA    length = 122
FEATURE                 Location/Qualifiers
REGION                  1..122
                        note = Synthetic
source                  1..122
                        mol_type = protein
                        organism = synthetic construct
SEQUENCE: 602
EVQLLESGGG LVQPGGSLRL SCAASGFTFS SYAMNWVRQA PGKGLDWVSG ISGNGGSTYY    60
ADSVKGRFTI SRDISKNTLY VQMHSLRVED TAVYYCAKAR YYDFWGGNFD LWGRGTQVTV   120
SS                                                                 122

SEQ ID NO: 603          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 603
ggattcacgt ttagtagcta tgcc                                           24

SEQ ID NO: 604          moltype = AA    length = 8
```

```
FEATURE                 Location/Qualifiers
REGION                  1..8
                        note = Synthetic
source                  1..8
                        mol_type = protein
                        organism = synthetic construct
SEQUENCE: 604
GFTFSSYA                                                                      8

SEQ ID NO: 605          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 605
atcagtggta atggtggtag cacc                                                   24

SEQ ID NO: 606          moltype = AA  length = 8
FEATURE                 Location/Qualifiers
REGION                  1..8
                        note = Synthetic
source                  1..8
                        mol_type = protein
                        organism = synthetic construct
SEQUENCE: 606
ISGNGGST                                                                      8

SEQ ID NO: 607          moltype = DNA  length = 45
FEATURE                 Location/Qualifiers
misc_feature            1..45
                        note = Synthetic
source                  1..45
                        mol_type = other DNA
                        organism = synthetic construct
SEQUENCE: 607
gcgaaagccc gttattacga tttttggggg gggaatttcg atctc                            45

SEQ ID NO: 608          moltype = AA  length = 15
FEATURE                 Location/Qualifiers
REGION                  1..15
                        note = Synthetic
source                  1..15
                        mol_type = protein
                        organism = synthetic construct
SEQUENCE: 608
AKARYYDFWG GNFDL                                                             15

SEQ ID NO: 609          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 609
gaaattgtgt tgacgcagtc tccaggcacc ctgtctttgt ctccagggga aagagccacc            60
ctctcctgca gggccagtca gagtgttagc atcaggtact tagcctggta tcagcagaaa           120
cctggccagg ctcccaggct cctcatctat ggtgcatcca gcagggccac tggcatccca           180
gacaggttca gtgtcagtgt gtctgggaca gacttcactc tcaccatcac tagactggag           240
cctgaagatt ttgcagtcta ttactgtcag caatatggta gttcaccgct cacttttcggc          300
ggagggacca aggtggagat caaa                                                  324

SEQ ID NO: 610          moltype = AA  length = 108
FEATURE                 Location/Qualifiers
REGION                  1..108
                        note = Synthetic
source                  1..108
                        mol_type = protein
                        organism = synthetic construct
SEQUENCE: 610
EIVLTQSPGT LSLSPGERAT LSCRASQSVS IRYLAWYQQK PGQAPRLLIY GASSRATGIP            60
DRFSVSVSGT DFTLTITRLE PEDFAVYYCQ QYGSSPLTFG GGTKVEIK                        108

SEQ ID NO: 611          moltype = DNA  length = 21
FEATURE                 Location/Qualifiers
misc_feature            1..21
                        note = Synthetic
```

```
source                  1..21
                        mol_type = other DNA
                        organism = synthetic construct
SEQUENCE: 611
cagagtgtta gcatcaggta c                                              21

SEQ ID NO: 612          moltype = AA  length = 7
FEATURE                 Location/Qualifiers
REGION                  1..7
                        note = Synthetic
source                  1..7
                        mol_type = protein
                        organism = synthetic construct
SEQUENCE: 612
QSVSIRY                                                              7

SEQ ID NO: 613          moltype =   length =
SEQUENCE: 613
000

SEQ ID NO: 614          moltype =   length =
SEQUENCE: 614
000

SEQ ID NO: 615          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 615
cagcaatatg gtagttcacc gctcact                                        27

SEQ ID NO: 616          moltype = AA  length = 9
FEATURE                 Location/Qualifiers
REGION                  1..9
                        note = Synthetic
source                  1..9
                        mol_type = protein
                        organism = synthetic construct
SEQUENCE: 616
QQYGSSPLT                                                            9

SEQ ID NO: 617          moltype = DNA  length = 366
FEATURE                 Location/Qualifiers
misc_feature            1..366
                        note = Synthetic
source                  1..366
                        mol_type = other DNA
                        organism = synthetic construct
SEQUENCE: 617
gaggtgcagt tgttggagtc tggggggaggc ttggtacagc ctgggggggtc cctgagactc   60
tcctgtgcag cctctggatt cacgtttagt agctatgcca tgaactgggt ccgccaggct  120
ccaggggaagg ggctggattg ggtctcaggt atcagtggta atggtggtag cacctactac  180
gcagactccg tgaagggccg gttcaccatc tccagagaca tttccaagaa cacgctgtat  240
gtgcaaatgc acagcctgag agtcgaggac acggccgttt actactgtgc gaaagcccgt  300
tattacgatt tttggggggg gaatttcgat ctctggggcc gtggcaccct ggtcactgtc  360
tcctca                                                             366

SEQ ID NO: 618          moltype = AA  length = 122
FEATURE                 Location/Qualifiers
REGION                  1..122
                        note = Synthetic
source                  1..122
                        mol_type = protein
                        organism = synthetic construct
SEQUENCE: 618
EVQLLESGGG LVQPGGSLRL SCAASGFTFS SYAMNWVRQA PGKGLDWVSG ISGNGGSTYY    60
ADSVKGRFTI SRDISKNTLY VQMHSLRVED TAVYYCAKAR YYDFWGGNFD LWGRGTLVTV   120
SS                                                                 122

SEQ ID NO: 619          moltype = DNA  length = 324
FEATURE                 Location/Qualifiers
misc_feature            1..324
                        note = Synthetic
source                  1..324
                        mol_type = other DNA
                        organism = synthetic construct
```

```
SEQUENCE: 619
gaaattgtgt tgacgcagtc tccaggcacc ctgtctttgt ctccagggga aagagccacc    60
ctctcctgca gggccagtca gagtgttagc atcaggtact tagcctggta tcagcagaaa   120
cctggccagg ctcccaggct cctcatctat ggtgcatcca gcagggccac tggcatccca   180
gacaggttca gtgtcagtgt gtctgggaca gacttcactc tcaccatcac tagactggag   240
cctgaagatt ttgcagtcta ttactgtcag caatatggta gttcaccgct cactttcggc   300
ggagggacca aggtggagat caaa                                          324

SEQ ID NO: 620              moltype = AA   length = 108
FEATURE                     Location/Qualifiers
REGION                      1..108
                            note = Synthetic
source                      1..108
                            mol_type = protein
                            organism = synthetic construct
SEQUENCE: 620
EIVLTQSPGT LSLSPGERAT LSCRASQSVS IRYLAWYQQK PGQAPRLLIY GASSRATGIP    60
DRFSVSVSGT DFTLTITRLE PEDFAVYYCQ QYGSSPLTFG GGTKVEIK                108

SEQ ID NO: 621              moltype = DNA   length = 366
FEATURE                     Location/Qualifiers
misc_feature                1..366
                            note = Synthetic
source                      1..366
                            mol_type = other DNA
                            organism = synthetic construct
SEQUENCE: 621
gaggtgcagc tgttggagtc tgggggaggc ttggtacagc ctggggggtc cctgagactc    60
tcctgtgcag cctctggatt cacgtttagt agctatgcca tgagctgggt ccgccaggct   120
ccagggaagg ggctggagtg ggtctcagct atcagtggta gtggtggtag cacctactac   180
gcagactccg tgaagggccg gttcaccatc tccagagaca attccaagaa cacgctgtat   240
ctgcaaatga acagcctgag agccgaggac acggccgtat attactgtgc gaaagccgt    300
tattacgatt ttgggggggg gaatttcgat ctctggggcc gtggcaccct ggtcactgtc   360
tcctca                                                              366

SEQ ID NO: 622              moltype = AA   length = 122
FEATURE                     Location/Qualifiers
REGION                      1..122
                            note = Synthetic
source                      1..122
                            mol_type = protein
                            organism = synthetic construct
SEQUENCE: 622
EVQLLESGGG LVQPGGSLRL SCAASGFTFS SYAMSWVRQA PGKGLEWVSA ISGNGGSTYY    60
ADSVKGRFTI SRDNSKNTLY LQMNSLRAED TAVYYCAKAR YYDFWGGNFD LWGRGTLVTV   120
SS                                                                  122

SEQ ID NO: 623              moltype = DNA   length = 324
FEATURE                     Location/Qualifiers
misc_feature                1..324
                            note = Synthetic
source                      1..324
                            mol_type = other DNA
                            organism = synthetic construct
SEQUENCE: 623
gaaattgtgt tgacgcagtc tccaggcacc ctgtctttgt ctccagggga aagagccacc    60
ctctcctgca gggccagtca gagtgttagc atcaggtact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag caatatggta gttcaccgct cactttcggc   300
ggagggacca aggtggagat caaa                                          324

SEQ ID NO: 624              moltype = AA   length = 108
FEATURE                     Location/Qualifiers
REGION                      1..108
                            note = Synthetic
source                      1..108
                            mol_type = protein
                            organism = synthetic construct
SEQUENCE: 624
EIVLTQSPGT LSLSPGERAT LSCRASQSVS IRYLAWYQQK PGQAPRLLIY GASSRATGIP    60
DRFSGSGSGT DFTLTISRLE PEDFAVYYCQ QYGSSPLTFG GGTKVEIK                108

SEQ ID NO: 625              moltype = DNA   length = 381
FEATURE                     Location/Qualifiers
misc_feature                1..381
                            note = Synthetic
source                      1..381
                            mol_type = other DNA
```

```
                        organism = synthetic construct
SEQUENCE: 625
caggttcagc tggtgcagtc tggacctgag gtgaagaacc ctggggcctc agtgaaggtc   60
tcctgcaagg cttctggtta cacctttacc acctatggta tcagttgggt acgacaggcc  120
cctggacaag ggcttgagtg gatgggatgg atcagcggtt acaatggtaa aacaaacgat  180
gcacagaagt tccaggacag agtcgccatg accacagaca catccacgag cacagcctac  240
atggagctga ggagcctgag atctgacgac acggccattt attactgttc gagagatcgt  300
ttagtagtac cacctgccct ttattattcc tactacgtta tggacgtctg gggccaaggg  360
accacggtca ccgtctcctc a                                             381

SEQ ID NO: 626          moltype = AA  length = 127
FEATURE                 Location/Qualifiers
REGION                  1..127
                        note = Synthetic
source                  1..127
                        mol_type = protein
                        organism = synthetic construct
SEQUENCE: 626
QVQLVQSGPE VKNPGASVKV SCKASGYTFT TYGISWVRQA PGQGLEWMGW ISGYNGKTND   60
AQKFQDRVAM TTDTSTSTAY MELRSLRSDD TAIYYCSRDR LVVPPALYYS YYVMDVWGQG  120
TTVTVSS                                                             127

SEQ ID NO: 627          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 627
ggttacacct ttaccaccta tggt                                           24

SEQ ID NO: 628          moltype = AA  length = 8
FEATURE                 Location/Qualifiers
REGION                  1..8
                        note = Synthetic
source                  1..8
                        mol_type = protein
                        organism = synthetic construct
SEQUENCE: 628
GYTFTTYG                                                              8

SEQ ID NO: 629          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 629
atcagcggtt acaatggtaa aaca                                           24

SEQ ID NO: 630          moltype = AA  length = 8
FEATURE                 Location/Qualifiers
REGION                  1..8
                        note = Synthetic
source                  1..8
                        mol_type = protein
                        organism = synthetic construct
SEQUENCE: 630
ISGYNGKT                                                              8

SEQ ID NO: 631          moltype = DNA  length = 60
FEATURE                 Location/Qualifiers
misc_feature            1..60
                        note = Synthetic
source                  1..60
                        mol_type = other DNA
                        organism = synthetic construct
SEQUENCE: 631
tcgagagatc gtttagtagt accacctgcc ctttattatt cctactacgt tatggacgtc   60

SEQ ID NO: 632          moltype = AA  length = 20
FEATURE                 Location/Qualifiers
REGION                  1..20
                        note = Synthetic
source                  1..20
                        mol_type = protein
                        organism = synthetic construct
```

```
SEQUENCE: 632
SRDRLVVPPA LYYSYYVMDV                                                  20

SEQ ID NO: 633           moltype = DNA  length = 336
FEATURE                  Location/Qualifiers
misc_feature             1..336
                         note = Synthetic
source                   1..336
                         mol_type = other DNA
                         organism = synthetic construct
SEQUENCE: 633
gatgttgtga tgactcagtc tccactctcc ctgcccgtca cccttggaca gccggcctcc      60
atctcctgca ggtctagtca aagcctcgta tacagtgatg gaaacaccta cttgaattgg    120
tttcagcaga ggccaggtca atctccaagg cgcctaattt ataaggtttc taaccgggac    180
tctggggtcc cagacagatt cagcggcagt gggtcaggca ctgatttcac actgaaaatc    240
agcagggtgg aggctgagga tgttggggtt tattactgca tgcaaggtac acactggccg    300
tacacttttg gccaggggac caagctggag atcaaa                              336

SEQ ID NO: 634           moltype = AA  length = 112
FEATURE                  Location/Qualifiers
REGION                   1..112
                         note = Synthetic
source                   1..112
                         mol_type = protein
                         organism = synthetic construct
SEQUENCE: 634
DVVMTQSPLS LPVTLGQPAS ISCRSSQSLV YSDGNTYLNW FQQRPGQSPR RLIYKVSNRD      60
SGVPDRFSGS GSGTDFTLKI SRVEAEDVGV YYCMQGTHWP YTFGQGTKLE IK             112

SEQ ID NO: 635           moltype = DNA  length = 33
FEATURE                  Location/Qualifiers
misc_feature             1..33
                         note = Synthetic
source                   1..33
                         mol_type = other DNA
                         organism = synthetic construct
SEQUENCE: 635
caaagcctcg tatacagtga tggaaacacc tac                                   33

SEQ ID NO: 636           moltype = AA  length = 11
FEATURE                  Location/Qualifiers
REGION                   1..11
                         note = Synthetic
source                   1..11
                         mol_type = protein
                         organism = synthetic construct
SEQUENCE: 636
QSLVYSDGNT Y                                                           11

SEQ ID NO: 637           moltype =     length =
SEQUENCE: 637
000

SEQ ID NO: 638           moltype =     length =
SEQUENCE: 638
000

SEQ ID NO: 639           moltype = DNA  length = 27
FEATURE                  Location/Qualifiers
misc_feature             1..27
                         note = Synthetic
source                   1..27
                         mol_type = other DNA
                         organism = synthetic construct
SEQUENCE: 639
atgcaaggta cacactggcc gtacact                                          27

SEQ ID NO: 640           moltype = AA  length = 9
FEATURE                  Location/Qualifiers
REGION                   1..9
                         note = Synthetic
source                   1..9
                         mol_type = protein
                         organism = synthetic construct
SEQUENCE: 640
MQGTHWPYT                                                               9

SEQ ID NO: 641           moltype = DNA  length = 381
FEATURE                  Location/Qualifiers
```

```
misc_feature          1..381
                      note = Synthetic
source                1..381
                      mol_type = other DNA
                      organism = synthetic construct
SEQUENCE: 641
caggttcagc tggtgcagtc tggacctgag gtgaagaacc ctggggcctc agtgaaggtc    60
tcctgcaagg cttctggtta cacctttacc acctatggta tcagttgggt acgacaggcc   120
cctggacaag ggcttgagtg gatgggatgg atcagcggtt acaatggtaa aacaaacgat   180
gcacagaagt tccaggacag agtcgccatg accacagaca catccacgag cacagcctac   240
atggagctga ggagcctgag atctgacgac acggccattt attactgttc gagagatcgt   300
ttagtagtac cacctgccct ttattattcc tactacgtta tggacgtctg gggccaaggg   360
accacggtca ccgtctcctc a                                             381

SEQ ID NO: 642        moltype = AA   length = 127
FEATURE               Location/Qualifiers
REGION                1..127
                      note = Synthetic
source                1..127
                      mol_type = protein
                      organism = synthetic construct
SEQUENCE: 642
QVQLVQSGPE VKNPGASVKV SCKASGYTFT TYGISWVRQA PGQGLEWMGW ISGYNGKTND    60
AQKFQDRVAM TTDTSTSTAY MELRSLRSDD TAIYYCSRDR LVVPPALYYS YYVMDVWGQG   120
TTVTVSS                                                             127

SEQ ID NO: 643        moltype = DNA   length = 336
FEATURE               Location/Qualifiers
misc_feature          1..336
                      note = Synthetic
source                1..336
                      mol_type = other DNA
                      organism = synthetic construct
SEQUENCE: 643
gatgttgtga tgactcagtc tccactctcc ctgcccgtca cccttggaca gccggcctcc    60
atctcctgca ggtctagtca aagcctcgta tacagtgatg gaaacaccta cttgaattgg   120
tttcagcaga ggccaggtca aatcccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggccg   300
tacacttttg gccaggggac caagctggag atcaaa                             336

SEQ ID NO: 644        moltype = AA   length = 112
FEATURE               Location/Qualifiers
REGION                1..112
                      note = Synthetic
source                1..112
                      mol_type = protein
                      organism = synthetic construct
SEQUENCE: 644
DVVMTQSPLS LPVTLGQPAS ISCRSSQSLV YSDGNTYLNW FQQRPGQSPR RLIYKVSNRD    60
SGVPDRFSGS GSGTDFTLKI SRVEAEDVGV YYCMQGTHWP YTFGQGTKLE IK           112

SEQ ID NO: 645        moltype = DNA   length = 381
FEATURE               Location/Qualifiers
misc_feature          1..381
                      note = Synthetic
source                1..381
                      mol_type = other DNA
                      organism = synthetic construct
SEQUENCE: 645
caggttcagc tggtgcagtc tggagctgag gtgaagaagc ctggggcctc agtgaaggtc    60
tcctgcaagg cttctggtta cacctttacc acctatggta tcagctgggt gcgacaggcc   120
cctggacaag ggcttgagtg gatgggatgg atcagcggtt acaatggtaa aacaaactat   180
gcacagaagc tccagggcag agtcaccatg accacagaca catccacgag cacagcctac   240
atggagctga ggagcctgag atctgacgac acggccgtgt attactgttc gagagatcgt   300
ttagtagtac cacctgccct ttattattcc tactacgtta tggacgtctg ggggcaaggg   360
accacggtca ccgtctcctc a                                             381

SEQ ID NO: 646        moltype = AA   length = 127
FEATURE               Location/Qualifiers
REGION                1..127
                      note = Synthetic
source                1..127
                      mol_type = protein
                      organism = synthetic construct
SEQUENCE: 646
QVQLVQSGAE VKKPGASVKV SCKASGYTFT TYGISWVRQA PGQGLEWMGW ISGYNGKTNY    60
AQKLQGRVTM TTDTSTSTAY MELRSLRSDD TAVYYCSRDR LVVPPALYYS YYVMDVWGQG   120
TTVTVSS                                                             127
```

```
SEQ ID NO: 647          moltype = DNA   length = 336
FEATURE                 Location/Qualifiers
misc_feature            1..336
                        note = Synthetic
source                  1..336
                        mol_type = other DNA
                        organism = synthetic construct
SEQUENCE: 647
gatgttgtga tgactcagtc tccactctcc ctgcccgtca cccttggaca gccggcctcc    60
atctcctgca ggtctagtca aagcctcgta tacagtgatg gaaacaccta cttgaattgg   120
tttcagcaga ggccaggcca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggccg   300
tacactttg gccaggggac caagctggag atcaaa                              336

SEQ ID NO: 648          moltype = AA   length = 112
FEATURE                 Location/Qualifiers
REGION                  1..112
                        note = Synthetic
source                  1..112
                        mol_type = protein
                        organism = synthetic construct
SEQUENCE: 648
DVVMTQSPLS LPVTLGQPAS ISCRSSQSLV YSDGNTYLNW FQQRPGQSPR RLIYKVSNRD    60
SGVPDRFSGS GSGTDFTLKI SRVEAEDVGV YYCMQGTHWP YTFGQGTKLE IK           112

SEQ ID NO: 649          moltype = DNA   length = 381
FEATURE                 Location/Qualifiers
misc_feature            1..381
                        note = Synthetic
source                  1..381
                        mol_type = other DNA
                        organism = synthetic construct
SEQUENCE: 649
caggttcagc tggtgcagtc tggacctgag gtgaagaacc ctggggcctc agtgaaggtc    60
tcctgcaagg cttctggtta caccttacc acctatggta tcagttgggt acgacaggcc   120
cctgacaag ggcttgagtg gatgggatgg atcagcggtt acaatggtaa acaaacgat    180
gcacagaagt tccaggacag agtcgccatg accacagaca catccacgag cacagcctac   240
atggagctga ggagcctgag atctgacgac acggccattt attactgttc gagagatcgt   300
ttagtagtac cacctgccct taattattac tactacgtta tggacgtctg gggccaaggg   360
accacggtca ccgtctcctc a                                             381

SEQ ID NO: 650          moltype = AA   length = 127
FEATURE                 Location/Qualifiers
REGION                  1..127
                        note = Synthetic
source                  1..127
                        mol_type = protein
                        organism = synthetic construct
SEQUENCE: 650
QVQLVQSGPE VKNPGASVKV SCKASGYTFT TYGISWVRQA PGQGLEWMGW ISGYNGKTND    60
AQKFQDRVAM TTDTSTSTAY MELRSLRSDD TAIYYCSRDR LVVPPALNYY YYVMDVWGQG   120
TTVTVSS                                                             127

SEQ ID NO: 651          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 651
ggttacacct ttaccaccta tggt                                           24

SEQ ID NO: 652          moltype = AA   length = 8
FEATURE                 Location/Qualifiers
REGION                  1..8
                        note = Synthetic
source                  1..8
                        mol_type = protein
                        organism = synthetic construct
SEQUENCE: 652
GYTFTTYG                                                              8

SEQ ID NO: 653          moltype = DNA   length = 24
FEATURE                 Location/Qualifiers
misc_feature            1..24
                        note = Synthetic
```

```
source                  1..24
                        mol_type = other DNA
                        organism = synthetic construct
SEQUENCE: 653
atcagcggtt acaatggtaa aaca                                              24

SEQ ID NO: 654          moltype = AA   length = 8
FEATURE                 Location/Qualifiers
REGION                  1..8
                        note = Synthetic
source                  1..8
                        mol_type = protein
                        organism = synthetic construct
SEQUENCE: 654
ISGYNGKT                                                                8

SEQ ID NO: 655          moltype = DNA   length = 60
FEATURE                 Location/Qualifiers
misc_feature            1..60
                        note = Synthetic
source                  1..60
                        mol_type = other DNA
                        organism = synthetic construct
SEQUENCE: 655
tcgagagatc gtttagtagt accacctgcc cttaattatt actactacgt tatggacgtc       60

SEQ ID NO: 656          moltype = AA   length = 20
FEATURE                 Location/Qualifiers
REGION                  1..20
                        note = Synthetic
source                  1..20
                        mol_type = protein
                        organism = synthetic construct
SEQUENCE: 656
SRDRLVVPPA LNYYYYVMDV                                                   20

SEQ ID NO: 657          moltype = DNA   length = 336
FEATURE                 Location/Qualifiers
misc_feature            1..336
                        note = Synthetic
source                  1..336
                        mol_type = other DNA
                        organism = synthetic construct
SEQUENCE: 657
gatgttgtga tgactcagtc tccactctcc ctgcccgtca cccttggaca gccggcctcc       60
atctcctgca ggtctagtca aagcctcgta tacagtgatg gaaacaccta cttgaattgg      120
tttcagcaga ggccaggtca atctccaagg cgcctaattt ataaggtttc taaccgggac      180
tctggggtcc cagacagatt cagcggcagt gggtcaggca ctgatttcac actgaaaatc      240
agcagggtgg aggctgagga tgttggggtt tattactgca tgcaaggtac acactggccg      300
tacactttg gccaggggac caagctggag atcaaa                                 336

SEQ ID NO: 658          moltype = AA   length = 112
FEATURE                 Location/Qualifiers
REGION                  1..112
                        note = Synthetic
source                  1..112
                        mol_type = protein
                        organism = synthetic construct
SEQUENCE: 658
DVVMTQSPLS LPVTLGQPAS ISCRSSQSLV YSDGNTYLNW FQQRPGQSPR RLIYKVSNRD       60
SGVPDRFSGS GSGTDFTLKI SRVEAEDVGV YYCMQGTHWP YTFGQGTKLE IK              112

SEQ ID NO: 659          moltype = DNA   length = 33
FEATURE                 Location/Qualifiers
misc_feature            1..33
                        note = Synthetic
source                  1..33
                        mol_type = other DNA
                        organism = synthetic construct
SEQUENCE: 659
caaagcctcg tatacagtga tggaaacacc tac                                    33

SEQ ID NO: 660          moltype = AA   length = 11
FEATURE                 Location/Qualifiers
REGION                  1..11
                        note = Synthetic
source                  1..11
                        mol_type = protein
                        organism = synthetic construct
```

```
SEQUENCE: 660
QSLVYSDGNT Y                                                              11

SEQ ID NO: 661         moltype =    length =
SEQUENCE: 661
000

SEQ ID NO: 662         moltype =    length =
SEQUENCE: 662
000

SEQ ID NO: 663         moltype = DNA   length = 27
FEATURE                Location/Qualifiers
misc_feature           1..27
                       note = Synthetic
source                 1..27
                       mol_type = other DNA
                       organism = synthetic construct
SEQUENCE: 663
atgcaaggta cacactggcc gtacact                                             27

SEQ ID NO: 664         moltype = AA   length = 9
FEATURE                Location/Qualifiers
REGION                 1..9
                       note = Synthetic
source                 1..9
                       mol_type = protein
                       organism = synthetic construct
SEQUENCE: 664
MQGTHWPYT                                                                  9

SEQ ID NO: 665         moltype = DNA   length = 381
FEATURE                Location/Qualifiers
misc_feature           1..381
                       note = Synthetic
source                 1..381
                       mol_type = other DNA
                       organism = synthetic construct
SEQUENCE: 665
caggttcagc tggtgcagtc tggacctgag gtgaagaacc ctggggcctc agtgaaggtc          60
tcctgcaagg cttctggtta cacctttacc acctatggta tcagttgggt acgacaggcc        120
cctggacaag gccttgagtg gatgggatgg atcagcggtt acaatggtaa aacaaacgat        180
gcacagaagt tccaggacag agtcgccatg accacagaca catccacgag cacagcctac        240
atggagctga ggagcctgag atctgacgac acggccattt attactgttc gagagatcgt        300
ttagtagtac cacctgccct taattattac tactacgtta tggacgtctg gggccaaggg        360
accacggtca ccgtctcctc a                                                  381

SEQ ID NO: 666         moltype = AA   length = 127
FEATURE                Location/Qualifiers
REGION                 1..127
                       note = Synthetic
source                 1..127
                       mol_type = protein
                       organism = synthetic construct
SEQUENCE: 666
QVQLVQSGPE VKNPGASVKV SCKASGYTFT TYGISWVRQA PGQGLEWMGW ISGYNGKTND          60
AQKFQDRVAM TTDTSTSTAY MELRSLRSDD TAIYYCSRDR LVVPPALNYY YYVMDVWGQG         120
TTVTVSS                                                                  127

SEQ ID NO: 667         moltype = DNA   length = 336
FEATURE                Location/Qualifiers
misc_feature           1..336
                       note = Synthetic
source                 1..336
                       mol_type = other DNA
                       organism = synthetic construct
SEQUENCE: 667
gatgttgtga tgactcagtc tccactctcc ctgcccgtca cccttggaca gccggcctcc          60
atctcctgca ggtctagtca aagcctcgta tacagtgatg aaacacccta cttgaattgg        120
tttcagcaga ggccaggtca atctccaagg cgcctaattt ataaggtttc taaccgggac        180
tctggggtcc cagacagatt cagcggcagt gggtcaggca ctgatttcac actgaaaatc        240
agcagggtgg aggctgagga tgttggggtt tattactgca tgcaaggtac acactggccg        300
tacacttttg gccaggggac caagctggag atcaaa                                  336

SEQ ID NO: 668         moltype = AA   length = 112
FEATURE                Location/Qualifiers
REGION                 1..112
                       note = Synthetic
source                 1..112
```

```
                       mol_type = protein
                       organism = synthetic construct
SEQUENCE: 668
DVVMTQSPLS LPVTLGQPAS ISCRSSQSLV YSDGNTYLNW FQQRPGQSPR RLIYKVSNRD     60
SGVPDRFSGS GSGTDFTLKI SRVEAEDVGV YYCMQGTHWP YTFGQGTKLE IK            112

SEQ ID NO: 669         moltype = DNA   length = 381
FEATURE                Location/Qualifiers
misc_feature           1..381
                       note = Synthetic
source                 1..381
                       mol_type = other DNA
                       organism = synthetic construct
SEQUENCE: 669
caggttcagc tggtgcagtc tggagctgag gtgaagaagc ctggggcctc agtgaaggtc     60
tcctgcaagg cttctggtta cacctttacc acctatggta tcagctgggt gcgacaggcc    120
cctggacaag ggcttgagtg gatgggatgg atcagcggtt acaatggtaa acaaactat    180
gcacagaaag tccagggcag agtcaccatg accacagaca tccacgag acagcctac      240
atggagctga ggagcctgag atctgacgac acggccgtgt attactgttc gagagatcgt    300
ttagtagtac cacctgccct taattattac tactacgtta tggacgtctg ggggcaaggg    360
accacggtca ccgtctcctc a                                              381

SEQ ID NO: 670         moltype = AA   length = 127
FEATURE                Location/Qualifiers
REGION                 1..127
                       note = Synthetic
source                 1..127
                       mol_type = protein
                       organism = synthetic construct
SEQUENCE: 670
QVQLVQSGAE VKKPGASVKV SCKASGYTFT TYGISWVRQA PGQGLEWMGW ISGYNGKTNY     60
AQKLQGRVTM TTDTSTSTAY MELRSLRSDD TAVYYCSRDR LVVPPALNYY YYVMDVWGQG    120
TTVTVSS                                                              127

SEQ ID NO: 671         moltype = DNA   length = 336
FEATURE                Location/Qualifiers
misc_feature           1..336
                       note = Synthetic
source                 1..336
                       mol_type = other DNA
                       organism = synthetic construct
SEQUENCE: 671
gatgttgtga tgactcagtc tccactctcc ctgcccgtca cccttggaca gccggcctcc     60
atctcctgca ggtctagtca aagcctcgta tacagtgatg gaaacaccta cttgaattgg    120
tttcagcaga ggccaggcca atctccaagg cgcctaattt ataaggtttc taaccgggac    180
tctggggtcc cagacagatt cagcggcagt gggtcaggca ctgatttcac actgaaaatc    240
agcagggtgg aggctgagga tgttggggtt tattactgca tgcaaggtac acactggccg    300
tacacttttg gccaggggac caagctggag atcaaa                              336

SEQ ID NO: 672         moltype = AA   length = 112
FEATURE                Location/Qualifiers
REGION                 1..112
                       note = Synthetic
source                 1..112
                       mol_type = protein
                       organism = synthetic construct
SEQUENCE: 672
DVVMTQSPLS LPVTLGQPAS ISCRSSQSLV YSDGNTYLNW FQQRPGQSPR RLIYKVSNRD     60
SGVPDRFSGS GSGTDFTLKI SRVEAEDVGV YYCMQGTHWP YTFGQGTKLE IK            112

SEQ ID NO: 673         moltype = DNA   length = 381
FEATURE                Location/Qualifiers
misc_feature           1..381
                       note = Synthetic
source                 1..381
                       mol_type = other DNA
                       organism = synthetic construct
SEQUENCE: 673
caggttcagc tggtgcagtc tggacctgag gtgaagaacc ctggggcctc agtgaaggtc     60
tcctgcaagg cttctggtta cacctttacc acctatggta tcagttgggt acgacaggcc    120
cctggacaag ggcttgagtg gatgggatgg atcagcggtt acaatggtaa acaaaacgat    180
gcacagaagt tccaggacag agtcgccatg accacagaca tccacgag cacagcctac      240
atggagctga ggagcctgag atctgacgac acggccattt attactgttc gagagatcgt    300
ttagtagtac cacctgccct ttattattac tactacgtta tggacgtctg ggggccaaggg   360
accacggtca ccgtctcctc a                                              381

SEQ ID NO: 674         moltype = AA   length = 127
FEATURE                Location/Qualifiers
REGION                 1..127
```

-continued

```
                        note = Synthetic
source                  1..127
                        mol_type = protein
                        organism = synthetic construct
SEQUENCE: 674
QVQLVQSGPE VKNPGASVKV SCKASGYTFT TYGISWVRQA PGQGLEWMGW ISGYNGKTND    60
AQKFQDRVAM TTDTSTSTAY MELRSLRSDD TAIYYCSRDR LVVPPALYYY YYVMDVWGQG   120
TTVTVSS                                                             127

SEQ ID NO: 675          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 675
ggttacacct ttaccaccta tggt                                           24

SEQ ID NO: 676          moltype = AA  length = 8
FEATURE                 Location/Qualifiers
REGION                  1..8
                        note = Synthetic
source                  1..8
                        mol_type = protein
                        organism = synthetic construct
SEQUENCE: 676
GYTFTTYG                                                              8

SEQ ID NO: 677          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 677
atcagcggtt acaatggtaa aaca                                           24

SEQ ID NO: 678          moltype = AA  length = 8
FEATURE                 Location/Qualifiers
REGION                  1..8
                        note = Synthetic
source                  1..8
                        mol_type = protein
                        organism = synthetic construct
SEQUENCE: 678
ISGYNGKT                                                              8

SEQ ID NO: 679          moltype = DNA  length = 60
FEATURE                 Location/Qualifiers
misc_feature            1..60
                        note = Synthetic
source                  1..60
                        mol_type = other DNA
                        organism = synthetic construct
SEQUENCE: 679
tcgagagatc gtttagtagt accacctgcc cttattatt actactacgt tatggacgtc    60

SEQ ID NO: 680          moltype = AA  length = 20
FEATURE                 Location/Qualifiers
REGION                  1..20
                        note = Synthetic
source                  1..20
                        mol_type = protein
                        organism = synthetic construct
SEQUENCE: 680
SRDRLVVPPA LYYYYYVMDV                                                20

SEQ ID NO: 681          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 681
gatgttgtga tgactcagtc tccactctcc ctgcccgtca cccttggaca gccggcctcc    60
atctcctgca ggtctagtca aagcctcgta tacagtgatg gaaacaccta cttgaattgg   120
```

```
tttcagcaga ggccaggtca atctccaagg cgcctaattt ataaggtttc taaccgggac    180
tctggggtcc cagacagatt cagcggcagt gggtcaggca ctgatttcac actgaaaatc    240
agcagggtgg aggctgagga tgttgggggtt tattactgca tgcaaggtac acactggccg   300
tacactttttg gccaggggac caagctggag atcaaa                              336
```

SEQ ID NO: 682   moltype = AA   length = 112
FEATURE          Location/Qualifiers
REGION           1..112
                 note = Synthetic
source           1..112
                 mol_type = protein
                 organism = synthetic construct
SEQUENCE: 682
DVVMTQSPLS LPVTLGQPAS ISCRSSQSLV YSDGNTYLNW FQQRPGQSPR RLIYKVSNRD    60
SGVPDRFSGS GSGTDFTLKI SRVEAEDVGV YYCMQGTHWP YTFGQGTKLE IK           112

SEQ ID NO: 683   moltype = DNA   length = 33
FEATURE          Location/Qualifiers
misc_feature     1..33
                 note = Synthetic
source           1..33
                 mol_type = other DNA
                 organism = synthetic construct
SEQUENCE: 683
caaagcctcg tatacagtga tggaaacacc tac                                  33

SEQ ID NO: 684   moltype = AA   length = 11
FEATURE          Location/Qualifiers
REGION           1..11
                 note = Synthetic
source           1..11
                 mol_type = protein
                 organism = synthetic construct
SEQUENCE: 684
QSLVYSDGNT Y                                                          11

SEQ ID NO: 685   moltype =    length =
SEQUENCE: 685
000

SEQ ID NO: 686   moltype =    length =
SEQUENCE: 686
000

SEQ ID NO: 687   moltype = DNA   length = 27
FEATURE          Location/Qualifiers
misc_feature     1..27
                 note = Synthetic
source           1..27
                 mol_type = other DNA
                 organism = synthetic construct
SEQUENCE: 687
atgcaaggta cacactggcc gtacact                                         27

SEQ ID NO: 688   moltype = AA   length = 9
FEATURE          Location/Qualifiers
REGION           1..9
                 note = Synthetic
source           1..9
                 mol_type = protein
                 organism = synthetic construct
SEQUENCE: 688
MQGTHWPYT                                                              9

SEQ ID NO: 689   moltype = DNA   length = 381
FEATURE          Location/Qualifiers
misc_feature     1..381
                 note = Synthetic
source           1..381
                 mol_type = other DNA
                 organism = synthetic construct
SEQUENCE: 689
```
caggttcagc tggtgcagtc tggacctgag gtgaagaacc ctggggcctc agtgaaggtc    60
tcctgcaagg cttctggtta caccttttacc acctatggta tcagttgggt acgacaggcc   120
cctggacaag gcttgagtg gatgggatgg atcagcggtt acaatggtaa aacaaacgat    180
gcacagaagt tccaggacag agtcgccatg accacagaca catccacgag cacagcctac    240
atggagctga ggagcctgag atctgacgac acggccattt attactgttc gagagatcgt    300
ttagtagtac cacctgccct ttattattac tactacgtta tggacgtctg ggggccaaggg   360
accacggtca ccgtctcctc a                                              381
```

```
SEQ ID NO: 690            moltype = AA  length = 127
FEATURE                   Location/Qualifiers
REGION                    1..127
                          note = Synthetic
source                    1..127
                          mol_type = protein
                          organism = synthetic construct
SEQUENCE: 690
QVQLVQSGPE VKNPGASVKV SCKASGYTFT TYGISWVRQA PGQGLEWMGW ISGYNGKTND    60
AQKFQDRVAM TTDTSTSTAY MELRSLRSDD TAIYYCSRDR LVVPPALYYY YYVMDVWGQG   120
TTVTVSS                                                             127

SEQ ID NO: 691            moltype = DNA  length = 336
FEATURE                   Location/Qualifiers
misc_feature              1..336
                          note = Synthetic
source                    1..336
                          mol_type = other DNA
                          organism = synthetic construct
SEQUENCE: 691
gatgttgtga tgactcagtc tccactctcc ctgcccgtca cccttggaca gccggcctcc    60
atctcctgca ggtctagtca aagcctcgta tacagtgatg aaacaccta cttgaattgg   120
tttcagcaga ggccaggtca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggccg   300
tacacttttg gccaggggac caagctggag atcaaa                             336

SEQ ID NO: 692            moltype = AA  length = 112
FEATURE                   Location/Qualifiers
REGION                    1..112
                          note = Synthetic
source                    1..112
                          mol_type = protein
                          organism = synthetic construct
SEQUENCE: 692
DVVMTQSPLS LPVTLGQPAS ISCRSSQSLV YSDGNTYLNW FQQRPGQSPR RLIYKVSNRD    60
SGVPDRFSGS GSGTDFTLKI SRVEAEDVGV YYCMQGTHWP YTFGQGTKLE IK           112

SEQ ID NO: 693            moltype = DNA  length = 381
FEATURE                   Location/Qualifiers
misc_feature              1..381
                          note = Synthetic
source                    1..381
                          mol_type = other DNA
                          organism = synthetic construct
SEQUENCE: 693
caggttcagc tggtgcagtc tggagctgag gtgaagaagc ctggggcctc agtgaaggtc    60
tcctgcaagg cttctggtta cacctttacc acctatggta tcagctgggt gcgacaggcc   120
cctggacaag gccttgagtg gatgggatgg atcagcggtt acaatggtaa aacaaactat   180
gcacagaagc tccagggcag agtcaccatg accacagaca catccacgag cacagcctac   240
atggagctga ggagcctgag atctgacgac acggccgtgt attactgttc gagagatcgt   300
ttagtagtac cacctgccct ttattattac tactacgtta tggacgtctg ggggcaaggg   360
accacggtca ccgtctcctc a                                             381

SEQ ID NO: 694            moltype = AA  length = 127
FEATURE                   Location/Qualifiers
REGION                    1..127
                          note = Synthetic
source                    1..127
                          mol_type = protein
                          organism = synthetic construct
SEQUENCE: 694
QVQLVQSGAE VKKPGASVKV SCKASGYTFT TYGISWVRQA PGQGLEWMGW ISGYNGKTNY    60
AQKLQGRVTM TTDTSTSTAY MELRSLRSDD TAVYYCSRDR LVVPPALYYY YYVMDVWGQG   120
TTVTVSS                                                             127

SEQ ID NO: 695            moltype = DNA  length = 336
FEATURE                   Location/Qualifiers
misc_feature              1..336
                          note = Synthetic
source                    1..336
                          mol_type = other DNA
                          organism = synthetic construct
SEQUENCE: 695
gatgttgtga tgactcagtc tccactctcc ctgcccgtca cccttggaca gccggcctcc    60
atctcctgca ggtctagtca aagcctcgta tacagtgatg aaacaccta cttgaattgg   120
tttcagcaga ggccaggcca atctccaagg cgcctaattt ataaggtttc taaccgggac   180
tctggggtcc cagacagatt cagcggcagt gggtcaggca ctgatttcac actgaaaatc   240
```

```
agcagggtgg aggctgagga tgttggggtt tattactgca tgcaaggtac acactggccg   300
tacactttg gccaggggac caagctggag atcaaa                              336
```

SEQ ID NO: 696          moltype = AA  length = 112
FEATURE                 Location/Qualifiers
REGION                  1..112
                        note = Synthetic
source                  1..112
                        mol_type = protein
                        organism = synthetic construct
SEQUENCE: 696
```
DVVMTQSPLS LPVTLGQPAS ISCRSSQSLV YSDGNTYLNW FQQRPGQSPR RLIYKVSNRD   60
SGVPDRFSGS GSGTDFTLKI SRVEAEDVGV YYCMQGTHWP YTFGQGTKLE IK          112
```

SEQ ID NO: 697          moltype = DNA  length = 384
FEATURE                 Location/Qualifiers
misc_feature            1..384
                        note = Synthetic
source                  1..384
                        mol_type = other DNA
                        organism = synthetic construct
SEQUENCE: 697
```
caggtgcacc tggtggagtc tgggggaggc ttggtcaagc ctggagggtc cctgagactc   60
tcctgtgcag cctctggatt caccttcagt gaccactaca tgagctggat ccgccaggct  120
ccagggaagg ggctggagtg gatttcatac attagtaatg atggtggtac caaatactat  180
gtggactctg tggagggccg attcatcatt tccagggaca acgccaagaa ctcattgtat  240
ctacatatga acagcctcag agccgacgac acggccgtgt attactgtgc gagagatcag  300
ggatatattg gctacgactc gtattattac tattcctacg gtatggacgt ctggggccaa  360
gggaccacgg tcaccgtcgc ctca                                         384
```

SEQ ID NO: 698          moltype = AA  length = 128
FEATURE                 Location/Qualifiers
REGION                  1..128
                        note = Synthetic
source                  1..128
                        mol_type = protein
                        organism = synthetic construct
SEQUENCE: 698
```
QVHLVESGGG LVKPGGSLRL SCAASGFTFS DHYMSWIRQA PGKGLEWISY ISNDGGTKYY   60
VDSVEGRFII SRDNAKNSLY LHMNSLRADD TAVYYCARDQ GYIGYDSYYY YSYGMDVWGQ  120
GTTVTVAS                                                           128
```

SEQ ID NO: 699          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 699
```
ggattcacct tcagtgacca ctac                                          24
```

SEQ ID NO: 700          moltype = AA  length = 8
FEATURE                 Location/Qualifiers
REGION                  1..8
                        note = Synthetic
source                  1..8
                        mol_type = protein
                        organism = synthetic construct
SEQUENCE: 700
```
GFTFSDHY                                                             8
```

SEQ ID NO: 701          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 701
```
attagtaatg atggtggtac caaa                                          24
```

SEQ ID NO: 702          moltype = AA  length = 8
FEATURE                 Location/Qualifiers
REGION                  1..8
                        note = Synthetic
source                  1..8
                        mol_type = protein
                        organism = synthetic construct

```
SEQUENCE: 702
ISNDGGTK                                                            8

SEQ ID NO: 703          moltype = DNA  length = 63
FEATURE                 Location/Qualifiers
misc_feature            1..63
                        note = Synthetic
source                  1..63
                        mol_type = other DNA
                        organism = synthetic construct
SEQUENCE: 703
gcgagagatc agggatatat tggctacgac tcgtattatt actattccta cggtatggac   60
gtc                                                                 63

SEQ ID NO: 704          moltype = AA   length = 21
FEATURE                 Location/Qualifiers
REGION                  1..21
                        note = Synthetic
source                  1..21
                        mol_type = protein
                        organism = synthetic construct
SEQUENCE: 704
ARDQGYIGYD SYYYYSYGMD V                                             21

SEQ ID NO: 705          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 705
aaaattgtgt tgacgcagtc tccaggcacc ctgcctttgt ttccagggga agagccacc    60
ctctcctgta gggccagtca gagtgttaac aacaaattct tagcctggta ccagcagaaa  120
tctggccagg ctcccaggct cctcatctat ggtgcatcca gcagggccac tggcatccca  180
gacaggttca gtggcagtgg gtctgggacc gacttcactc tcaccatcag cggactggag  240
cctgaagatt ttgaagtgta ttattgtcaa gtatatggta actcactcac tttcggcgga  300
gggaccaagg tggagatcaa g                                            321

SEQ ID NO: 706          moltype = AA   length = 107
FEATURE                 Location/Qualifiers
REGION                  1..107
                        note = Synthetic
source                  1..107
                        mol_type = protein
                        organism = synthetic construct
SEQUENCE: 706
KIVLTQSPGT LPLFPGERAT LSCRASQSVN NKFLAWYQQK SGQAPRLLIY GASSRATGIP   60
DRFSGSGSGT DFTLTISGLE PEDFEVYYCQ VYGNSLTFGG GTKVEIK                107

SEQ ID NO: 707          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 707
cagagtgtta acaacaaatt c                                             21

SEQ ID NO: 708          moltype = AA   length = 7
FEATURE                 Location/Qualifiers
REGION                  1..7
                        note = Synthetic
source                  1..7
                        mol_type = protein
                        organism = synthetic construct
SEQUENCE: 708
QSVNNKF                                                             7

SEQ ID NO: 709          moltype =   length =
SEQUENCE: 709
000

SEQ ID NO: 710          moltype =   length =
SEQUENCE: 710
000

SEQ ID NO: 711          moltype = DNA  length = 24
```

| FEATURE | Location/Qualifiers |
|---|---|
| misc_feature | 1..24 |
| | note = Synthetic |
| source | 1..24 |
| | mol_type = other DNA |
| | organism = synthetic construct |

SEQUENCE: 711
```
caagtatatg gtaactcact cact                                            24
```

| SEQ ID NO: 712 | moltype = AA   length = 8 |
|---|---|
| FEATURE | Location/Qualifiers |
| REGION | 1..8 |
| | note = Synthetic |
| source | 1..8 |
| | mol_type = protein |
| | organism = synthetic construct |

SEQUENCE: 712
```
QVYGNSLT                                                              8
```

| SEQ ID NO: 713 | moltype = DNA   length = 384 |
|---|---|
| FEATURE | Location/Qualifiers |
| misc_feature | 1..384 |
| | note = Synthetic |
| source | 1..384 |
| | mol_type = other DNA |
| | organism = synthetic construct |

SEQUENCE: 713
```
caggtgcagc tggtggagtc tgggggaggc ttggtcaagc ctggagggtc cctgagactc     60
tcctgtgcag cctctggatt caccttcagt gaccactaca tgagctggat ccgccaggct    120
ccagggaagg ggctggagtg gatttcatac attagtaatg atggtggtac caaatactat    180
gtggactctg tggagggccg attcatcatt tccagggaca cgccaagaa ctcattgtat     240
ctacatatga acagcctcag agccgacgac acggccgtgt attactgtgc gagagatcag    300
ggatatattg gctacgactc gtattattac tattcctacg gtatggacgt ctggggccaa    360
gggaccacgg tcaccgtctc ctca                                           384
```

| SEQ ID NO: 714 | moltype = AA   length = 128 |
|---|---|
| FEATURE | Location/Qualifiers |
| REGION | 1..128 |
| | note = Synthetic |
| source | 1..128 |
| | mol_type = protein |
| | organism = synthetic construct |

SEQUENCE: 714
```
QVQLVESGGG LVKPGGSLRL SCAASGFTFS DHYMSWIRQA PGKGLEWISY ISNDGGTKYY     60
VDSVEGRFII SRDNAKNSLY LHMNSLRADD TAVYYCARDQ GYIGYDSYYY YSYGMDVWGQ    120
GTTVTVSS                                                             128
```

| SEQ ID NO: 715 | moltype = DNA   length = 321 |
|---|---|
| FEATURE | Location/Qualifiers |
| misc_feature | 1..321 |
| | note = Synthetic |
| source | 1..321 |
| | mol_type = other DNA |
| | organism = synthetic construct |

SEQUENCE: 715
```
gaaattgtgt tgacgcagtc tccaggcacc ctgcctttgt tcccagggga aagagccacc     60
ctctcctgta gggccagtca gagtgttaac aacaaattct tagcctggta ccagcagaaa    120
tctggccagg ctcccaggct cctcatctat ggtgcatcca gcagggccac tggcatccca    180
gacaggttca gtggcagtgg gtctgggacc gacttcactc tcaccatcag cggactgag     240
cctgaagatt ttgaagtgta ttattgtcaa gtatatggta actcactcac tttcggcgga    300
gggaccaagg tggagatcaa a                                              321
```

| SEQ ID NO: 716 | moltype = AA   length = 107 |
|---|---|
| FEATURE | Location/Qualifiers |
| REGION | 1..107 |
| | note = Synthetic |
| source | 1..107 |
| | mol_type = protein |
| | organism = synthetic construct |

SEQUENCE: 716
```
EIVLTQSPGT LPLFPGERAT LSCRASQSVN NKFLAWYQQK SGQAPRLLIY GASSRATGIP     60
DRFSGSGSGT DFTLTISGLE PEDFEVYYCQ VYGNSLTFGG GTKVEIK                  107
```

| SEQ ID NO: 717 | moltype = DNA   length = 384 |
|---|---|
| FEATURE | Location/Qualifiers |
| misc_feature | 1..384 |
| | note = Synthetic |
| source | 1..384 |
| | mol_type = other DNA |

```
                        organism = synthetic construct
SEQUENCE: 717
caggtgcagc tggtggagtc tgggggaggc ttggtcaagc ctggagggtc cctgagactc    60
tcctgtgcag cctctggatt caccttcagt gaccactaca tgagctggat ccgccaggct   120
ccagggaagg ggctggagtg ggtttcatac attagtaatg atggtggtac caaatactac   180
gcagactctg tgaagggccg attcaccatc tccagggaca cgccaagaa ctcactgtat    240
ctgcaaatga acagcctgag agccgaggac acggccgtgt attactgtgc gagagatcag   300
ggatatattg gctacgactc gtattattac tattcctacg gtatggacgt ctgggggcaa   360
gggaccacgg tcaccgtctc ctca                                          384

SEQ ID NO: 718           moltype = AA  length = 128
FEATURE                  Location/Qualifiers
REGION                   1..128
                         note = Synthetic
source                   1..128
                         mol_type = protein
                         organism = synthetic construct
SEQUENCE: 718
QVQLVESGGG LVKPGGSLRL SCAASGFTFS DHYMSWIRQA PGKGLEWVSY ISNDGGTKYY    60
ADSVKGRFTI SRDNAKNSLY LQMNSLRAED TAVYYCARDQ GYIGYDSYYY YSYGMDVWGQ   120
GTTVTVSS                                                            128

SEQ ID NO: 719           moltype = DNA  length = 321
FEATURE                  Location/Qualifiers
misc_feature             1..321
                         note = Synthetic
source                   1..321
                         mol_type = other DNA
                         organism = synthetic construct
SEQUENCE: 719
gaaattgtgt tgacgcagtc tccaggcacc ctgtctttgt ctccagggga aagagccacc    60
ctctcctgca gggccagtca gagtgttaac aacaaattct tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcaa gtatatggta actcactcac tttcggcgga   300
gggaccaagg tggagatcaa a                                             321

SEQ ID NO: 720           moltype = AA  length = 107
FEATURE                  Location/Qualifiers
REGION                   1..107
                         note = Synthetic
source                   1..107
                         mol_type = protein
                         organism = synthetic construct
SEQUENCE: 720
EIVLTQSPGT LSLSPGERAT LSCRASQSVN NKFLAWYQQK PGQAPRLLIY GASSRATGIP    60
DRFSGSGSGT DFTLTISRLE PEDFAVYYCQ VYGNSLTFGG GTKVEIK                 107

SEQ ID NO: 721           moltype = DNA  length = 378
FEATURE                  Location/Qualifiers
misc_feature             1..378
                         note = Synthetic
source                   1..378
                         mol_type = other DNA
                         organism = synthetic construct
SEQUENCE: 721
caaattctgc tggtgcaatc tggacctgag gtgaaggagc ctggggcctc agtgaaggtc    60
tcctgcaagg cttctggtta cacctttacc aactacgcta tcagctgggt gcgacaggtc   120
cctggacaag ggcttgagtg gatgggatgg gtcagcgctt acaatggtca cacaaactat   180
gcacatgaag tccagggcag agtcaccatg accacagaca catccacgac cacagcctac   240
atggagctga ggagcctgag atctgacgac acggccatgt attactgtgc gagaggggt    300
gtagtcgtgc cagttgctcc ccacttctac aacggtatgg acgtctgggg ccaagggacc   360
acggtcaccg tctcctca                                                 378

SEQ ID NO: 722           moltype = AA  length = 126
FEATURE                  Location/Qualifiers
REGION                   1..126
                         note = Synthetic
source                   1..126
                         mol_type = protein
                         organism = synthetic construct
SEQUENCE: 722
QILLVQSGPE VKEPGASVKV SCKASGYTFT NYAISWVRQV PGQGLEWMGW VSAYNGHTNY    60
AHEVQGRVTM TTDTSTTTAY MELRSLRSDD TAMYYCARGG VVVPVAPHFY NGMDVWGQGT   120
TVTVSS                                                              126

SEQ ID NO: 723           moltype = DNA  length = 24
FEATURE                  Location/Qualifiers
misc_feature             1..24
```

```
                            note = Synthetic
source                      1..24
                            mol_type = other DNA
                            organism = synthetic construct
SEQUENCE: 723
ggttacacct ttaccaacta cgct                                                24

SEQ ID NO: 724              moltype = AA  length = 8
FEATURE                     Location/Qualifiers
REGION                      1..8
                            note = Synthetic
source                      1..8
                            mol_type = protein
                            organism = synthetic construct
SEQUENCE: 724
GYTFTNYA                                                                   8

SEQ ID NO: 725              moltype = DNA  length = 24
FEATURE                     Location/Qualifiers
misc_feature                1..24
                            note = Synthetic
source                      1..24
                            mol_type = other DNA
                            organism = synthetic construct
SEQUENCE: 725
gtcagcgctt acaatggtca caca                                                24

SEQ ID NO: 726              moltype = AA  length = 8
FEATURE                     Location/Qualifiers
REGION                      1..8
                            note = Synthetic
source                      1..8
                            mol_type = protein
                            organism = synthetic construct
SEQUENCE: 726
VSAYNGHT                                                                   8

SEQ ID NO: 727              moltype = DNA  length = 57
FEATURE                     Location/Qualifiers
misc_feature                1..57
                            note = Synthetic
source                      1..57
                            mol_type = other DNA
                            organism = synthetic construct
SEQUENCE: 727
gcgagagggg gtgtagtcgt gccagttgct ccccacttct acaacggtat ggacgtc            57

SEQ ID NO: 728              moltype = AA  length = 19
FEATURE                     Location/Qualifiers
REGION                      1..19
                            note = Synthetic
source                      1..19
                            mol_type = protein
                            organism = synthetic construct
SEQUENCE: 728
ARGGVVVPVA PHFYNGMDV                                                      19

SEQ ID NO: 729              moltype = DNA  length = 336
FEATURE                     Location/Qualifiers
misc_feature                1..336
                            note = Synthetic
source                      1..336
                            mol_type = other DNA
                            organism = synthetic construct
SEQUENCE: 729
gatattgtga tgactcagtt tccactctcc ctgcccgtca ccctggaga  gccggcctcc         60
atctcctgca ggtctagtca gagcctcctg catattaatg aatacaacta tttggattgg        120
tacctaaaga agccagggca gtctccacag ctcctgatct atttgggttt taatcgggcc        180
tccgggggtcc ctgacaggtt cagtggcagt ggatcaggca cagattttac actgaaaatc       240
agcagagtgg aggctgagga tgttggggtc tattactgca tgcaagctct tcaaactccg        300
tggacgttcg gccaagggac caaggtggaa atcaaa                                  336

SEQ ID NO: 730              moltype = AA  length = 112
FEATURE                     Location/Qualifiers
REGION                      1..112
                            note = Synthetic
source                      1..112
                            mol_type = protein
                            organism = synthetic construct
```

-continued

```
SEQUENCE: 730
DIVMTQFPLS LPVTPGEPAS ISCRSSQSLL HINEYNYLDW YLKKPGQSPQ LLIYLGFNRA   60
SGVPDRFSGS GSGTDFTLKI SRVEAEDVGV YYCMQALQTP WTFGQGTKVE IK          112

SEQ ID NO: 731           moltype = DNA  length = 33
FEATURE                  Location/Qualifiers
misc_feature             1..33
                         note = Synthetic
source                   1..33
                         mol_type = other DNA
                         organism = synthetic construct
SEQUENCE: 731
cagagcctcc tgcatattaa tgaatacaac tat                                33

SEQ ID NO: 732           moltype = AA   length = 11
FEATURE                  Location/Qualifiers
REGION                   1..11
                         note = Synthetic
source                   1..11
                         mol_type = protein
                         organism = synthetic construct
SEQUENCE: 732
QSLLHINEYN Y                                                        11

SEQ ID NO: 733           moltype =     length =
SEQUENCE: 733
000

SEQ ID NO: 734           moltype =     length =
SEQUENCE: 734
000

SEQ ID NO: 735           moltype = DNA  length = 27
FEATURE                  Location/Qualifiers
misc_feature             1..27
                         note = Synthetic
source                   1..27
                         mol_type = other DNA
                         organism = synthetic construct
SEQUENCE: 735
atgcaagctc ttcaaactcc gtggacg                                       27

SEQ ID NO: 736           moltype = AA   length = 9
FEATURE                  Location/Qualifiers
REGION                   1..9
                         note = Synthetic
source                   1..9
                         mol_type = protein
                         organism = synthetic construct
SEQUENCE: 736
MQALQTPWT                                                           9

SEQ ID NO: 737           moltype = DNA  length = 378
FEATURE                  Location/Qualifiers
misc_feature             1..378
                         note = Synthetic
source                   1..378
                         mol_type = other DNA
                         organism = synthetic construct
SEQUENCE: 737
caggttcagc tggtgcagtc tggacctgag gtgaaggagc ctggggcctc agtgaaggtc   60
tcctgcaagg cttctggtta cacctttacc aactacgcta tcagctgggt gcgacaggtc  120
cctggacaag ggcttgagtg gatgggatgg gtcagcgctt acaatggtca cacaaactat  180
gcacatgaag tccagggcag agtcaccatg accacagaca catccacgac cacagcctac  240
atggagctga ggagcctgag atctgacgac acggccatgt attactgtgc gagagggggt  300
gtagtcgtgc cagttgctcc ccacttctac aacggtatgg acgtctgggg ccaagggacc  360
acggtcaccg tctcctca                                                378

SEQ ID NO: 738           moltype = AA   length = 126
FEATURE                  Location/Qualifiers
REGION                   1..126
                         note = Synthetic
source                   1..126
                         mol_type = protein
                         organism = synthetic construct
SEQUENCE: 738
QVQLVQSGPE VKEPGASVKV SCKASGYTFT NYAISWVRQV PGQGLEWMGW VSAYNGHTNY   60
AHEVQGRVTM TTDTSTTTAY MELRSLRSDD TAMYYCARGG VVVPAPHFY NGMDVWGQGT   120
TVTVSS                                                             126
```

```
SEQ ID NO: 739            moltype = DNA  length = 336
FEATURE                   Location/Qualifiers
misc_feature              1..336
                          note = Synthetic
source                    1..336
                          mol_type = other DNA
                          organism = synthetic construct
SEQUENCE: 739
gatattgtga tgactcagtc tccactctcc ctgcccgtca ccctggaga gccggcctcc     60
atctcctgca ggtctagtca gagcctcctg catattaatg aatacaacta tttggattgg  120
tacctaaaga agccagggca gtctccacag ctcctgatct atttgggttt taatcgggcc  180
tccgggtcc ctgacaggtt cagtggcagt ggatcaggca cagattttac actgaaaatc   240
agcagagtgg aggctgagga tgttggggtc tattactgca tgcaagctct tcaaactccg  300
tggacgttcg gccaagggac caaggtggaa atcaaa                            336

SEQ ID NO: 740            moltype = AA  length = 112
FEATURE                   Location/Qualifiers
REGION                    1..112
                          note = Synthetic
source                    1..112
                          mol_type = protein
                          organism = synthetic construct
SEQUENCE: 740
DIVMTQSPLS LPVTPGEPAS ISCRSSQSLL HINEYNYLDW YLKKPGQSPQ LLIYLGFNRA   60
SGVPDRFSGS GSGTDFTLKI SRVEAEDVGV YYCMQALQTP WTFGQGTKVE IK          112

SEQ ID NO: 741            moltype = DNA  length = 378
FEATURE                   Location/Qualifiers
misc_feature              1..378
                          note = Synthetic
source                    1..378
                          mol_type = other DNA
                          organism = synthetic construct
SEQUENCE: 741
caggttcagc tggtgcagtc tggagctgag gtgaagaagc ctggggcctc agtgaaggtc   60
tcctgcaagg cttctggtta cacctttacc aactacgcta tcagctgggt gcgacaggcc  120
cctggacaag gcttgagtg gatgggatgg gtcagcgctt acaatggtca cacaaactat   180
gcacagaagc tccagggcag agtcaccatg accacagaca catccacgag cacagcctac  240
atggagctga ggagcctgag atctgacgac acggccgtgt attactgtgc gagaggggggt  300
gtagtcgtgc cagttgctcc ccacttctac aacggtatgg acgtctgggg caagggacc   360
acggtcaccg tctcctca                                                378

SEQ ID NO: 742            moltype = AA  length = 126
FEATURE                   Location/Qualifiers
REGION                    1..126
                          note = Synthetic
source                    1..126
                          mol_type = protein
                          organism = synthetic construct
SEQUENCE: 742
QVQLVQSGAE VKKPGASVKV SCKASGYTFT NYAISWVRQA PGQGLEWMGW VSAYNGHTNY   60
AQKLQGRVTM TTDTSTSTAY MELRSLRSDD TAVYYCARGG VVVPVAPHFY NGMDVWGQGT  120
TVTVSS                                                             126

SEQ ID NO: 743            moltype = DNA  length = 336
FEATURE                   Location/Qualifiers
misc_feature              1..336
                          note = Synthetic
source                    1..336
                          mol_type = other DNA
                          organism = synthetic construct
SEQUENCE: 743
gatattgtga tgactcagtc tccactctcc ctgcccgtca ccctggaga gccggcctcc     60
atctcctgca ggtctagtca gagcctcctg catattaatg aatacaacta tttggattgg  120
tacctgcaga agccagggca gtctccacag ctcctgatct atttgggttc taatcgggcc  180
tccgggtcc ctgacaggtt cagtggcagt ggatcaggca cagattttac actgaaaatc   240
agcagagtgg aggctgagga tgttggggtt tattactgca tgcaagctct tcaaactccg  300
tggacgttcg gccaagggac caaggtggaa atcaaa                            336

SEQ ID NO: 744            moltype = AA  length = 112
FEATURE                   Location/Qualifiers
REGION                    1..112
                          note = Synthetic
source                    1..112
                          mol_type = protein
                          organism = synthetic construct
SEQUENCE: 744
DIVMTQSPLS LPVTPGEPAS ISCRSSQSLL HINEYNYLDW YLQKPGQSPQ LLIYLGSNRA   60
```

SGVPDRFSGS GSGTDFTLKI SRVEAEDVGV YYCMQALQTP WTFGQGTKVE IK    112

SEQ ID NO: 745          moltype =    length =
SEQUENCE: 745
000

SEQ ID NO: 746          moltype =    length =
SEQUENCE: 746
000

SEQ ID NO: 747          moltype =    length =
SEQUENCE: 747
000

SEQ ID NO: 748          moltype =    length =
SEQUENCE: 748
000

SEQ ID NO: 749          moltype =    length =
SEQUENCE: 749
000

SEQ ID NO: 750          moltype =    length =
SEQUENCE: 750
000

SEQ ID NO: 751          moltype = AA   length = 330
FEATURE                 Location/Qualifiers
REGION                  1..330
                        note = Synthetic
source                  1..330
                        mol_type = protein
                        organism = synthetic construct
SEQUENCE: 751
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 752          moltype = AA   length = 327
FEATURE                 Location/Qualifiers
REGION                  1..327
                        note = Synthetic
source                  1..327
                        mol_type = protein
                        organism = synthetic construct
SEQUENCE: 752
ASTKGPSVFP LAPCSRSTSE STAALGCLVK DYFPEPVTVS WNSGALTSGV HTFPAVLQSS    60
GLYSLSSVVT VPSSSLGTPEVT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 753          moltype = AA   length = 327
FEATURE                 Location/Qualifiers
REGION                  1..327
                        note = Synthetic
source                  1..327
                        mol_type = protein
                        organism = synthetic construct
SEQUENCE: 753
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 754          moltype = DNA   length = 2076
FEATURE                 Location/Qualifiers
source                  1..2076
                        mol_type = genomic DNA
                        organism = Homo sapiens
SEQUENCE: 754
atgggcaccg tcagctccag gcggtcctgg tggccgctgc cactgctgct gctgctgctg    60
ctgctcctgg gtcccgcggg cgcccgtgcg caggaggacg aggacggcga ctacgaggag   120

```
ctggtgctag ccttgcgttc cgaggaggac ggcctggccg aagcacccga gcacggaacc    180
acagccacct tccaccgctg cgccaaggat ccgtggaggt tgcctggcac ctacgtggtg    240
gtgctgaagg aggagaccca cctctcgcag tcagagcgca ctgcccgccg cctgcaggcc    300
caggctgccc gccggggata cctcaccaag atcctgcatg tcttccatgg ccttcttcct    360
ggcttcctgg tgaagatgag tggcgacctg ctggagctgg ccttgaagtt gcccatgtc    420
gactacatcg aggaggactc ctctgtcttt gcccagagca tcccgtggaa cctggagcgg    480
attacccctc cacggtaccg ggcggatgaa taccagcccc ccgacggagg cagcctggtg    540
gaggtgtatc tcctagacac cagcatacag agtgaccacc gggaaatcga gggcagggtc    600
atggtcaccg acttcgagaa tgtgcccgag gaggacggga cccgcttcca cagacaggcc    660
agcaagtgtg acagtcatgg cacccacctg gcaggggtgg tcagcggccg ggatgccggc    720
gtggccaagg gtgccagcat gcgcagcctg cgcgtgctca actgccaagg gaagggcacg    780
gttagcggca ccctcatagg cctggagttt attcggaaaa gccagctggt ccagcctgtg    840
gggccactgg tggtgctgct gcccctggcg ggtgggtaca gccgcgtcct caacgccgcc    900
tgccagaggc tggcgagggc tggggtcgtg ctggtcaccg ctgccggcaa cttccgggac    960
gatgcctgcc tctactcccc agcctcagct cccgaggtca tcacagttgg ggccaccaat   1020
gcccaggacc agccggtgac cctggggact tggggacca actttggccg ctgtgtggac   1080
ctctttgccc caggggagga catcattggt gcctccagcg actgcagcac ctgctttgtg   1140
tcacagagtg gacatcaca ggctgctgcc cacgtgggta gcattgcagc catgatgctg   1200
tctgccgagc cggagctcac cctggccgag ttgaggcaga gactgatcca cttctctgcc   1260
aaagatgtca tcaatgaggc ctggttccct gaggaccagc gggtactgac ccccaacctg   1320
gtggccgccc tgcccccag cacccatggg gcaggttggc agctgttttg caggactgtg   1380
tggtcagcac actcgggggc c tacacggatg gccacagaca tcgcccgcaq tgccccagat   1440
gaggagctgc tgagctgctc cagtttctcc aggagtggga gcggcgggg cgagcgcatg   1500
gaggcccaag ggggcaagct ggtctgccgg gcccacaacg cttttggggg tgagggtgtc   1560
tacgccattg ccaggtgctg cctgctaccc caggccaact gcagcgtcca cacagctcca   1620
ccagctgggg ccagcatggg gacccgtgtc cactgccaca acagggcca cgtcctcaca   1680
ggctgcagct cccactggga ggtggaggac cttggcaccc acaagccgcc tgtgctgagg   1740
ccacgaggtc agcccaacca gtgcgtgggc cacagggagg ccagcatcca cgcttcctgc   1800
tgccatgccc caggtctgga atgcaaagtc aaggagcatg gaatcccggc ccctcaggag   1860
caggtgaccg tggcctgcga ggagggctgg accctgactg gctgcagtgc cctccctggg   1920
acctcccacg tcctggggc ctacgccgta gacaacacgt gtgtagtcag gagccgggac   1980
gtcagcacta caggcagcac cagcgaagag gccgtgacag ccgttgccat ctgctgccgg   2040
agccggcacc tggcgcaggc ctcccaggag ctccag                             2076

SEQ ID NO: 755        moltype = AA   length = 692
FEATURE               Location/Qualifiers
source                1..692
                      mol_type = protein
                      organism = Homo sapiens
SEQUENCE: 755
MGTVSSRRSW WPLPLLLLLL LLLGPAGARA QEDEDGDYEE LVLALRSEED GLAEAPEHGT    60
TATFHRCAKD PWRLPGTYVV VLKEETHLSQ SERTARRLQA QAARRGYLTK ILHVFHGLLP   120
GFLVKMSGDL LELALKLPHV DYIEEDSSVF AQSIPWNLER ITPPRYRADE YQPPDGGSLV   180
EVYLLDTSIQ SDHREIEGRV MVTDFENVPE EDGTRFHRQA SKCDSHGTHL AGVVSGRDAG   240
VAKGASMRSL RVLNCQGKGT VSGTLIGLEF IRKSQLVQPV GPLVVLLPLA GGYSRVLNAA   300
CQRLARAGVV LVTAAGNFRD DACLYSPASA PEVITVGATN AQDQPVTLGT LGTNFGRCVD   360
LFAPGEDIIG ASSDCSTCFV SQSGTSQAAA HVAGIAAMML SAEPELTLAE LRQRLIHFSA   420
KDVINEAWFP EDQRVLTPNL VAALPPSTHG AGWQLFCRTV WSAHSGPTRM ATAIARCAPD   480
EELLSCSSFS RSGKRRGERM EAQGGKLVCR AHNAFGGEGV YAIARCCLLP QANCSVHTAP   540
PAEASMGTRV HCHQQGHVLT GCSSHWEVED LGTHKPPVLR PRGQPNQCVG HREASIHASC   600
CHAPGLECKV KEHGIPAPQE QVTVACEEGW TLTGCSALPG TSHVLGAYAV DNTCVVRSRD   660
VSTTGSTSEE AVTAVAICCR SRHLAQASQE LQ                                 692

SEQ ID NO: 756        moltype = AA   length = 692
FEATURE               Location/Qualifiers
source                1..692
                      mol_type = protein
                      organism = Macaca mulatta
SEQUENCE: 756
MGTVSSRRSW WPLPLPLLLL LLLGPAGARA QEDEDGDYEE LVLALRSEED GLADAPEHGA    60
TATFHRCAKD PWRLPGTYVV VLKEETHRSQ SERTARRLQA QAARRGYLTK ILHVFHHLLP   120
GFLVKMSGDL LELALKLPHV DYIEEDSSVF AQSIPWNLER ITPARYRADE YQPPKGGSLV   180
EVYLLDTSIQ SDHREIEGRV MVTDFESVPE EDGTRFHRQA SKCDSHGTHL AGVVSGRDAG   240
VAKGAGLRSL RVLNCQGKGT VSGTLIGLEF IRKSQLVQPV GPLVVLLPLA GGYSRVFNAA   300
CQRLARAGVV LVTAAGNFRD DACLYSPASA PEVITVGATN AQDQPVTLGT LGTNFGRCVD   360
LFAPGEDIIG ASSDCSTCFV SRSGTSQAAA HVAGIAAMML SAEPELTLAE LRQRLIHFSA   420
KDVINEAWFP EDQRVLTPNL VAALPPSTHR AGWQLFCRTV WSAHSGPTRM ATAVARCAQD   480
EELLSCSSFS RSGKRRGERI EAQGGKRVCR AHNAFGGEGV YAIARCCLLP QVNCSVHTAP   540
PAGASMGTRV HCHQQGHVLT GCSSHWEVED LGTHKPPVLR PRGQPNQCVG HREASIHASC   600
CHAPGLECKV KEHGIPAPQE QVIVACEDGW TLTGCSPLPG TSHVLGAYAV DNTCVVRSRD   660
VSTTGSTSKE AVAAVAICCR SRHLVQASQE LQ                                 692

SEQ ID NO: 757        moltype = AA   length = 694
FEATURE               Location/Qualifiers
source                1..694
                      mol_type = protein
                      organism = Mus musculus
SEQUENCE: 757
MGTHCSAWLR WPLLPLLPPL LLLLLLLCPT GAGAQDEDGD YEELMLALPS QEDGLADEAA    60
```

```
HVATATATFRRC SKEAWRLPGT YIVVLMEETQ RLQIEQTAHR LQTRAARRGY VIKVLHIFYD    120
LFPGFLVKMS SDLLGLALKL PHVEYIEEDS FVFAQSIPWN LERIIPAWHQ TEEDRSPDGS    180
SQVEVYLLDT SIQGAHREIE GRVTITDFNS VPEEDGTRFH RQASKCDSHG THLAGVVSGR    240
DAGVAKGTSL HSLRVLNCQG KGTVSGTLIG LEFIRKSQLI QPSGPLVVLL PLAGGYSRIL    300
NAACRHLART GVVLVAAAGN FRDDACLYSP ASAPEVITVG ATNAQDQPVT LGTLGTNFGR    360
CVDLFAPGKD IIGASSDCST CFMSQSGTSQ AAAHVAGIVA RMLSREPTLT LAELRQRLIH    420
FSTKDVINMA WFPEDQQVLT PNLVATLPPS THETGGQLLC RTVWSAHSGP TRTATATARC    480
APEEELLSCS SFSRSGRRRG DWIEAIGGQQ VCKALNAFGG EGVYAVARCC LVPRANCSIH    540
NTPAARAGLE THVHCHQKDH VLTGCSFHWE VEDLSVRRQP ALRSRRQPGQ CVGHQAASVY    600
ASCCHAPGLE CKIKEHGISG PSEQVTVACE AGWTLTGCNV LPGASLTLGA YSVDNLCVAR    660
VHDTARADRT SGEATVAAAI CCRSRPSAKA SWVQ                               694

SEQ ID NO: 758          moltype = AA   length = 653
FEATURE                 Location/Qualifiers
source                  1..653
                        mol_type = protein
                        organism = Homo sapiens
SEQUENCE: 758
EFRCHDGKCI SRQFVCDSDR DCLDGSDEAS CPVLTCGPAS FQCNSSTCIP QLWACDNDPD     60
CEDGSDEWPQ RCRGLYVFQG DSSPCSAFEF HCLSGECIHS SWRCDGGPDC KDKSDEENCA    120
VATCRPDEFQ CSDGNCIHGS RQCDREYDCK DMSDEVGCVN VTLCEGPNKF KCHSGECITL    180
DKVCNMARDC RDWSDEPIKE CGTNECLDNN GGCSHVCNDL KIGYECLCPD GFQLVAQRRC    240
EDIDECQDPD TCSQLCVNLE GGYKCQCEEG FQLDPHTKAC KAVGSIAYLF FTNRHEVRKM    300
TLDRSEYTSL IPNLRNVVAL DTEVASNRIY WSDLSQRMIC STQLDRAHGV SSYDTVISRD    360
IQAPDGLAVD WIHSNIYWTD SVLGTVSVAD TKGVKRKTLF RENGSKPRAI VVDPVHGFMY    420
WTDWGTPAKI KKGGLNGVDI YSLVTENIQW PNGITLDLLS GRLYWVDSKL HSISSIDVNG    480
GNRKTILEDE KRLAHPFSLA VFEDKVFWTD IINEAIFSAN RLTGSDVNLL AENLLSPEDM    540
VLFHNLTQPR GVNWCERTTL SNGGCQYLCL PAPQINPHSP KFTCACPDGM LLARDMRSCL    600
TEAEAAVATQ ETSTVRLKVS STAVRTQHTT TRPVPDTSRL PGATPGLTTV EIV           653

SEQ ID NO: 759          moltype = AA   length = 753
FEATURE                 Location/Qualifiers
source                  1..753
                        mol_type = protein
                        organism = Homo sapiens
SEQUENCE: 759
MERRAWSLQC TAFVLFCAWC ALNSAKAKRQ FVNEWAAEIP GGPEAASAIA EELGYDLLGQ     60
IGSLENHYLF KHKNHPRRSR RSAPHITKRL SDDDRVIWAE QQYEKERSKR SALRDSALNL    120
FNDPMWNQQW YLQDTRMTAA LPKLDLHVIP VWQKGITGKG VVITVLDDGL EWNHTDIYAN    180
YDPEASYDFN DNDHDPFPRY DPTNENKHGT RCAGEIAMQA NNHKCGVGVA YNSKVGGIRM    240
LDGIVTDAIE ASSIGFNPGH VDIYSASWGP NDDGKTVEGP GRLAQKAFEY GVKQGRQGKG    300
SIFVWASGNG GRQGDNCDCD GYTDSIYTIS ISSASQQGLS PWYAEKCSST LATSYSSGDY    360
TDQRITSADL HNDCTETHTG TSASAPLAAG IFALALEANP NLTWRDMQHL VVWTSEYDPL    420
ANNPGWKKNG AGLMVNSRFG FGLLNAKALV DLADPRTWRS VPEKKECVVK DNDFEPRALK    480
ANGEVIIEIP TRACEGQENA IKSLEHVQFE ATIEYSRRGD LHVTLTSAAG TSTVLLAERE    540
RDTSPNGFKN WDFMSVHTWG ENPIGTWTLR ITDMSGRIQN EGRIVNWKLI LHGTSSQPEH    600
MKQPRVYTSY NTVQNDRRGV EKMVDPGEEQ PTQENPKENT LVSKSPSSSS VGGRRDELEE    660
GAPSQAMLRL LQSAFSKNSP PKQSPKKSPS AKLNIPYENF YEALEKLNKP SQLKDSEDSL    720
YNDYVDVFYN TKPYKHRDDR LLQALVDILN EEN                                753

SEQ ID NO: 760          moltype = AA   length = 785
FEATURE                 Location/Qualifiers
source                  1..785
                        mol_type = protein
                        organism = Homo sapiens
SEQUENCE: 760
MPKGRQKVPH LDAPLGLPTC LWLELAGLFL LVPWVMGLAG TGGPDGQGTG GPSWAVHLES     60
LEGDGEEETL EQQADALAQA AGLVNAGRIG ELQGHYLFVQ PAGHRPALEV EAIRQQVEAV    120
LAGHEAVRWH SEQRLLRRAK RSVHFNDPKY PQQWHLNNRR SPGRDINVTG VWERNVTGRG    180
VTVVVVDDGV EHTIQDIAPN YSPEGSYDLN SNDPDPMPHP DVENGNHHGT RCAGEIAAVP    240
NNSFCAVGVA YGSRIAGIRV LDGPLTDSME AVAFNKHYQI NDIYSCSWGP DDDGKTVDGP    300
HQLGKAALQH GVIAGRQGFG SIFVVASGNG GQHNDNCNYD GYANSIYTVT IGAVDEEGRM    360
PPYAEECASM LAVTFSGGDK MLRSIVTTDW DLQKGTGCTE GHTGTSAAAP LAAGMIALML    420
QVRPCLTWRD VQHIIVFTAT RYEDRRAEWV TNEAGFSHSH QHGFGLLNAW RLVNAAKIWT    480
SVPYLASYVS PVLKENKAIP QSPRSLEVLW NVSRMDLEMS GLKTLEHVAV TVSITHPRRG    540
SLELKLFCPS GMMSLIGAPR SMDSDPNGFN DWTFSTVRCW GERARGTYRL VIRDVGDESF    600
QVGILRQWQL TLYGSVWSAV DIRDRQRLLE SAMSGKYLHD DFALPCPPGL KIPEEDGYTI    660
TPNTLKTLVL VGCFTVFWTV YYMLEVYLSQ RNVASNQVCR SGPCHWPHRS RKAKEEGTEL    720
ESVPLCSSKD PDEVETESRG PPTTSDLLAP DLLEQGDWSL SQNKSALDCP HQHLDVPHGK    780
EEQIC                                                               785

SEQ ID NO: 761          moltype = AA   length = 692
FEATURE                 Location/Qualifiers
source                  1..692
                        mol_type = protein
                        organism = Macaca fascicularis
SEQUENCE: 761
MGTVSSRRSW WPLPLPLLLL LLLGPAGARA QEDEDGDYEE LVLALRSEED GLADAPEHGA     60
TATFHRCAKD PWRLPGTYVV VLKEETHRSQ SERTARRLQA QAARRGYLTK ILHVFHHLLP    120
```

```
GFLVKMSGDL LELALKLPHV DYIEEDSSVF AQSIPWNLER ITPARYRADE YQPPKGGSLV  180
EVYLLDTSIQ SDHREIEGRV MVTDFESVPE EDGTRFHRQA SKCDSHGTHL AGVVSGRDAG  240
VAKGAGLRSL RVLNCQGKGT VSGTLIGLEF IRKSQLVQPV GPLVVLLPLA GGYSRVFNAA  300
CQRLARAGVV LVTAAGNFRD DACLYSPASA PEVITVGATN AQDQPVTLGT LGTNFGRCVD  360
LFAPGEDIIG ASSDCSTCFV SRSGTSQAAA HVAGIAAMML SAEPELTLAE LRQRLIHFSA  420
KDVINEAWFP EDQRVLTPNL VAALPPSTHR AGWQLFCRTV WSAHSGPTRM ATAVARCAQD  480
EELLSCSSFS RSGKRRGERI EAQGGKRVCR AHNAFGGEGV YAIARCCLLP QVNCSVHTAP  540
PAGASMGTRV HCHQQGHVLT GCSSHWEVED LGTHKPPVLR PRGQPNQCVG HREASIHASC  600
CHAPGLECKV KEHGIPAPQE QVIVACEDGW TLTGCSALPG TSHVLGAYAV DNTCVVRSRD  660
VSTTGSTSEE AVAAVAICCR SRHLVQASQE LQ                               692

SEQ ID NO: 762          moltype = AA  length = 698
FEATURE                 Location/Qualifiers
source                  1..698
                        mol_type = protein
                        organism = Mesocricetus auratus
SEQUENCE: 762
MGTSCSARPR WLLSPLLLLL LLLRYMGASA QDEDAEYEEL MLTLQSQDDG LADETDEAPQ   60
GATAAFHRCP EEAWRVPGTY IVMLAEEAQW VHIEQTMHRL QTQAARRGYV IKIQHIFYDF  120
LPAFVVKMSS DLLDLALKLP HVKYIEEDSL VFAQSIPWNL DRIIPAGRQA QEYSSSRKVP  180
SGSGQVEVYL LDTSIQSDHR EIEGRVTVTD FNSVPEEDGT RFHRQASKCD SHGTHLAGVV  240
SGRDAGVAKG TILHGLRVLN CQGKGIVSGI LTGLEFIWKS QLMQPSGPQV VLLPLAGRYS  300
RVLNTACQHL ARTGVVLVAA AGNFRDDACL YSPASAPEVI TVGATDVQDQ PVTLGTLGTN  360
FGRCVDLFAP GKDIIGASSD CSACFMSQSG TSQAAAHVAG IVAMMLTLEP ELTLTELRQR  420
LIHFSTKDAI NMAWFPEDQR VLTPNLVATL PPSTHGTGGQ LLCRTVWSAH SGPTRAATAT  480
ARCAPGEELL SCSSFSRSGR RRGDRIEAAG TQQVCKALNA FGGEGVYAVA RCCLLPRANC  540
SIHTTPAART SLETHAHCHQ KDHVLTGCSL HWEVEGIGVQ PLAVLRSRHQ PGQCTGHREA  600
SVHASCCHAP GLECKIKEHG ISGPAEQVTV ACEAGWTLTG CNVLPGAFIT LGAYAVDNTC  660
VARSRVTDTA GRTGEEATVA AAICCRNRPS AKASWVHQ                         698

SEQ ID NO: 763          moltype = AA  length = 691
FEATURE                 Location/Qualifiers
source                  1..691
                        mol_type = protein
                        organism = Rattus norvegicus
SEQUENCE: 763
MGIRCSTWLR WPLSPQLLLL LLLCPTGSRA QDEDGDYEEL MLALPSQEDS LVDEASHVAT   60
ATFRRCSKEA WRLPGTYVVV LMEETQRLQV EQTAHRLQTW AARRGYVIKV LHVFYDLFPG  120
FLVKMSSDLL GLALKLPHVE YIEEDSLVFA QSIPWNLERI IPAWQQTEED SSPDGSSQVE  180
VYLLDTSIQS GHREIEGRVT ITDFNSVPEE DGTRFHRQAS KCDSHGTHLA GVVSGRDAGV  240
AKGTSLHSLR VLNCQGKGTV SGTLIGLEFI RKSQLIQPSG PLVVLLPLAG GYSRILNTAC  300
QRLARTGVVL VAAAGNFRDD ACLYSPASAP EVITVGATNA QDQPVTLGTL GTNFGRCVDL  360
FAPGKDIIGA SSDCSTCYMS QSGTSQAAAH VAGIVAMMLN RDPALTLAEL RQRLILFSTK  420
DVINMAWFPE DQRVLTPNRV ATLPPSTQET GGQLLCRTVW SAHSGPTRTA TATARCAPEE  480
ELLSCSSFSR SGRRRGDRIE AIGGQQVCKA LNAFGGEGVY AVARCCLLPR VNCSIHNTPA  540
ARAGPQTPVH CHQKDHVLTG CSFHWEVENL RAQQQPLLRS RHQPGQCVGH QEASVHASCC  600
HAPGLECKIK EHGIAGPAEQ VTVACEAGWT LTGCNVLPGA SLPLGAYSVD NVCVARIRDA  660
GRADRTSEEA TVAAAICCRS RPSAKASWVH Q                                691
```

ANTI-PCSK9 ANTIBODIES

CROSS-REFERENCE TO RELATED APPLICATIONS

This application is a continuation of U.S. patent application Ser. No. 17/160,634, filed Jan. 28, 2021, which is a continuation of U.S. patent application Ser. No. 15/996,773, filed Jun. 4, 2018, now U.S. Pat. No. 10,941,210, which is a continuation of U.S. patent application Ser. No. 15/377,364, filed Dec. 13, 2016, now U.S. Pat. No. 10,023,654, which is a continuation of U.S. patent application Ser. No. 14/737,488, filed Jun. 12, 2015, now U.S. Pat. No. 9,550,837, which is a continuation of U.S. patent application Ser. No. 13/690,585, filed Nov. 30, 2012, which is a continuation of U.S. patent application Ser. No. 12/949,846, filed Nov. 19, 2010, now U.S. Pat. No. 8,501,184, which is a division of U.S. patent application Ser. No. 12/637,942, filed Dec. 15, 2009, now U.S. Pat. No. 8,062,640, which claims priority to U.S. Provisional Patent Application Serial Nos. 61/261,776, filed Nov. 17, 2009, 61/249,135, filed Oct. 6, 2009, 61/218,136, filed Jun. 18, 2009, 61/168,753, filed Apr. 13, 2009, 61/210,566, filed Mar. 18, 2009, and 61/122,482, filed Dec. 15, 2008, the entire disclosures of which are hereby incorporated herein by reference.

SEQUENCE LISTING

The instant application contains a Sequence Listing which has been submitted electronically in XML format and is hereby incorporated by reference in its entirety. Said XML file, created on Mar. 30, 2023, is named 741055_5 A9-151DIVCON6_ST26.xml and is 969,645 bytes in size.

FIELD OF THE INVENTION

The present invention is related to human antibodies and antigen-binding fragments of human antibodies that specifically bind human proprotein convertase subtilisin/kexin type 9 (PCSK9), and therapeutic methods of using those antibodies.

STATEMENT OF RELATED ART

Proprotein convertase subtilisin/kexin type 9 (PCSK9) is a proprotein convertase belonging to the proteinase K subfamily of the secretory subtilase family. The encoded protein is synthesized as a soluble zymogen that undergoes autocatalytic intramolecular processing in the endoplasmic reticulum. Evidence suggest that PCSK9 increases plasma LDL cholesterol by promoting degradation of the LDL receptor, which mediates LDL endocytosis in the liver, the major route of LDL clearance from circulation. The structure of PCSK9 protein shows that it has a signal sequence, followed by a prodomain, a catalytic domain that contains a conserved triad of residues (D186, H226 and S386), and a C-terminal domain. It is synthesized as a soluble 74-kDa precursor that undergoes autocatalytic cleavage in the ER, generating a 14-kDa prodomain and 60-kDa catalytic fragment. The autocatalytic activity has been shown to be required for secretion. After cleavage, the prodomain remains tightly associated with the catalytic domain.

Antibodies to PCSK9 are described in, for example, WO 2008/057457, WO 2008/057458, WO 2008/057459, WO 2008/063382, WO 2008/125623, and US 2008/0008697.

BRIEF SUMMARY OF THE INVENTION

In a first aspect, the invention provides fully human monoclonal antibodies (mAbs) and antigen-binding fragments thereof that specifically bind and neutralize human PCSK9 (hPCSK9) activity.

In one embodiment, the invention comprises an antibody or antigen-binding fragment of an antibody that specifically binds hPCSK9 and is characterized by at least one of:
  (i) capable of reducing serum total cholesterol at least about 25-35% and sustaining the reduction over at least a 24 day period relative to a predose level, preferably the reduction in serum total cholesterol is at least about 30-40%;
  (ii) capable of reducing serum LDL cholesterol at least about 65-80% and sustaining the reduction over at least a 24-day period relative to a predose level;
  (iii) capable of reducing serum triglyceride at least about 25-40% relative to predose level;
  (iv) does not reduce serum HDL cholesterol or reduces serum HDL cholesterol no more than 5% relative to predose level.

In one embodiment, the invention comprises an antibody or antigen-binding fragment of an antibody that specifically binds hPCSK9 and is characterized by at least one of:
  (i) capable of reducing serum LDL cholesterol at least about 40-70% and sustaining the reduction over at least a 60 or 90 day period relative to a predose level;
  (ii) capable of reducing serum triglyceride at least about 25-40% relative to predose level;
  (iii) does not reduce serum HDL cholesterol or reduces serum HDL cholesterol no more than 5% relative to predose level.

In one embodiment, the antibody or antigen-binding fragment is characterized as binding an epitope comprising amino acid residue 238 of hPCSK9 (SEQ ID NO:755). In a more specific embodiment, the antibody or antigen-binding fragment binds an epitope comprising one or more of amino acid residue 238, 153, 159 and 343 of hPCSK9 (SEQ ID NO:755).). In a more specific embodiment, the antibody or fragment thereof is characterized as binding an epitope that does not comprise an amino acid residue at position 192, 194, 197 and/or 237 of SEQ ID NO:755.

In one embodiment, the antibody or antigen-binding fragment is characterized as binding an epitope comprising amino acid residue 366 of hPCSK9 (SEQ ID NO:755). In a more specific embodiment, the antibody or antigen-binding fragment binds an epitope comprising one or more of amino acid residue at position 147, 366 and 380 of SEQ ID NO:755. In a more specific embodiment, the antibody or antigen-binding fragment of an antibody is characterized as binding an epitope that does not comprise an amino acid residue at position 215 or 238 of SEQ ID NO:755.

In one embodiment, the antibody or antigen-binding fragment is characterized as exhibiting an enhanced binding affinity ($K_D$) for hPCSK9 at pH 5.5 relative to the $K_D$ at pH 7.4, as measured by plasmon surface resonance. In a specific embodiment, the antibody or fragment thereof exhibits at least a 20-fold, at least a 40-fold or at least a 50-fold enhanced affinity for PCSK9 at an acidic pH relative to a neutral pH, as measured by surface plasmon resonance.

In one embodiment, the antibody or antigen-binding fragment is characterized as not exhibiting an enhanced binding affinity for PCSK9 at an acidic pH relative to a neutral pH, as measured by surface plasmon resonance. In a specific embodiment, the antibody or fragment thereof exhibits a decreased binding affinity at an acidic pH.

In another embodiment, the antibody or antigen-binding fragment binds human, human GOF mutation D374Y, cynomolgus monkey, rhesus monkey, mouse, rat and hamster PCSK9.

In one embodiment, the antibody or antigen-binding fragment binds human and monkey PCSK9, but does not bind mouse, rat or hamster PCSK9.

The mAbs can be full-length (e.g., an IgG1 or IgG4 antibody) or may comprise only an antigen-binding portion (e.g., a Fab, F(ab')$_2$ or scFv fragment), and may be modified to affect functionality, e.g., to eliminate residual effector functions (Reddy et al. (2000) J. Immunol. 164:1925-1933).

In one embodiment, the invention comprises an antibody or antigen-binding fragment of an antibody comprising a heavy chain variable region (HCVR) selected from the group consisting of SEQ ID NO:2, 18, 22, 26, 42, 46, 50, 66, 70, 74, 90, 94, 98, 114, 118, 122, 138, 142, 146, 162, 166, 170, 186, 190, 194, 210, 214, 218, 234, 238, 242, 258, 262, 266, 282, 286, 290, 306, 310, 314, 330, 334, 338, 354, 358, 362, 378, 382, 386, 402, 406, 410, 426, 430, 434, 450, 454, 458, 474, 478, 482, 498, 502, 506, 522, 526, 530, 546, 550, 554, 570, 574, 578, 594, 598, 602, 618, 622, 626, 642, 646, 650, 666, 670, 674, 690, 694, 698, 714, 718, 722, 738 and 742, or a substantially similar sequence thereof having at least 90%, at least 95%, at least 98% or at least 99% sequence identity. In one embodiment, the HCVR comprises an amino acid sequence selected from the group consisting of SEQ ID NO:50, 66, 70, 74, 90, 94, 122, 138, 142, 218, 234, 238, 242, 258, 262, 314, 330 and 334. In a more specific embodiment, the HCVR comprises SEQ ID NO:90 or 218.

In one embodiment, the antibody or fragment thereof further comprises a light chain variable region (LCVR) selected from the group consisting of SEQ ID NO:10, 20, 24, 34, 44, 48, 58, 68, 72, 82, 92, 96, 106, 116, 120, 130, 140, 144, 154, 164, 168, 178, 188, 192, 202, 212, 216, 226, 236, 240, 250, 260, 264, 274, 284, 288, 298, 308, 312, 322, 332, 336, 346, 356, 360, 370, 380, 384, 394, 404, 408, 418, 428, 432, 442, 452, 456, 466, 476, 480, 490, 500, 504, 514, 524, 528, 538, 548, 552, 562, 572, 576, 586, 596, 600, 610, 620, 624, 634, 644, 648, 658, 668, 672, 682, 692, 696, 706, 716, 720, 730, 740 and 744, or a substantially similar sequence thereof having at least 90%, at least 95%, at least 98% or at least 99% sequence identity. In one embodiment, the LCVR comprises an amino acid sequence selected from the group consisting of SEQ ID NO: 58, 68, 72, 82, 92, 96, 130, 140, 144, 226, 236, 240, 250, 260, 264, 322, 332 and 336. In a more specific embodiment, the LCVR comprises SEQ ID NO:92 or 226.

In specific embodiments, the antibody or fragment thereof comprises a HCVR and LCVR (HCVR/LCVR) sequence pair selected from the group consisting of SEQ ID NO: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, 502/504, 506/514, 522/524, 526/528, 530/538, 546/548, 550/552, 554/562, 570/572, 574/576, 578/586, 594/596, 598/600, 602/610, 618/620, 622/624, 626/634, 642/644, 646/648, 650/658, 666/668, 670/672, 674/682, 690/692, 694/696, 698/706, 714/716, 718/720, 722/730, 738/740 and 742/744. In one embodiment, the HCVR and LCVR sequence pair comprises one of SEQ ID NO: 50/58, 66/68, 70/72, 74/82, 90/92, 94/96, 122/130, 138/140, 142/144, 218/226, 234/236, 238/240, 242/250, 258/260, 262/264, 314/322, 330/332 and 334/336. In a more specific embodiment, the HCVR/LCVR pair comprises SEQ ID NO:90/92 or 218/226.

In a second aspect, the invention features an antibody or antigen-binding fragment of an antibody comprising a heavy chain CDR3 (HCDR3) domain selected from the group consisting of SEQ ID NO:8, 32, 56, 80, 104, 128, 152, 176, 200, 224, 248, 272, 296, 320, 344, 368, 392, 416, 440, 464, 488, 512, 536, 560, 584, 608, 632, 656, 680, 704 and 728, or a substantially similar sequence thereof having at least 90%, at least 95%, at least 98% or at least 99% sequence identity; and a light chain CDR3 (LCDR3) domain selected from the group consisting of SEQ ID NO:16, 40, 64, 88, 112, 136, 160, 184, 208, 232, 256, 280, 304, 328, 352, 376, 400, 424, 448, 472, 496, 520, 544, 568, 592, 616, 640, 664, 688, 712 and 736, or substantially similar sequences thereof having at least 90%, at least 95%, at least 98% or at least 99% sequence identity. In one embodiment, the HCDR3/LCDR3 sequence pair is selected from the group consisting of SEQ ID NO:56/64, 80/88, 128/136, 224/232, 248/256 and 320/328. In a more specific embodiment, the HCDR3/LCDR3 sequence pair comprises SEQ ID NO:80/88 or 224/232.

In a further embodiment, the invention comprising an antibody or fragment thereof further comprising a heavy chain CDR1 (HCDR1) domain selected from the group consisting of SEQ ID NO:4, 28, 52, 76, 100, 124, 148, 172, 196, 220, 244, 268, 292, 316, 340, 364, 388, 412, 436, 460, 484, 508, 532, 556, 580, 604, 628, 652, 676, 700 and 724, or a substantially similar sequence thereof having at least 90%, at least 95%, at least 98% or at least 99% sequence identity; a heavy chain CDR2 (HCDR2) domain selected from the group consisting of SEQ ID NO: 6, 30, 54, 78, 102, 126, 150, 174, 198, 222, 246, 270, 294, 318, 342, 366, 390, 414, 438, 462, 486, 510, 534, 558, 582, 606, 630, 654, 678, 702 and 726, or a substantially similar sequence thereof having at least 90%, at least 95%, at least 98% or at least 99% sequence identity; a light chain CDR1 (LCDR1) domain selected from the group consisting of SEQ ID NO: 12, 36, 60, 84, 108, 132, 156, 180, 204, 228, 252, 276, 300, 324, 348, 372, 396, 420, 444, 468, 492, 516, 540, 564, 588, 612, 636, 660, 684, 708 and 732, or a substantially similar sequence thereof having at least 90%, at least 95%, at least 98% or at least 99% sequence identity; and a light chain CDR2 (LCDR2) domain selected from the group consisting of SEQ ID NO:14, 38, 62, 86, 110, 134, 158, 182, 206, 254, 278, 302, 326, 350, 374, 398, 422, 446, 470, 494, 518, 542, 566, 590, 614, 638, 662, 686, 710, 734, and amino acid sequence LGS or a substantially similar sequence thereof having at least 90%, at least 95%, at least 98% or at least 99% sequence identity. In one embodiment, the heavy and light chain CDR sequences SEQ ID NO:52, 54, 56, 60, 62, 64; 76, 78, 80, 84, 86, 88; 124, 126, 128, 132, 134, 136; 220, 222, 224, 228, 232; 244, 246, 248, 252, 254, 256; and 316, 318, 320, 324, 326, 328 and amino acid sequence LGS. In more specific embodiments, the heavy and light chain CDR sequences SEQ ID NO: 76, 78, 80, 84, 86, 88; or 220, 222, 224, 228, 232 or amino acid sequence LGS.

In a related embodiment, the invention comprises an antibody or antigen-binding fragment of an antibody which specifically binds hPCSK9, wherein the antibody or fragment comprises heavy and light chain CDR domains contained within heavy and light chain sequence pairs selected from the group consisting of SEQ ID NO: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, 502/504, 506/514, 522/524, 526/528, 530/538, 546/548, 550/552, 554/562, 570/572, 574/576, 578/586, 594/596, 598/600, 602/610, 618/620, 622/624, 626/634, 642/644, 646/648, 650/658, 666/668, 670/672, 674/682, 690/692, 694/696, 698/706, 714/716, 718/720, 722/730, 738/740 and 742/744. In one embodiment, the CDR sequences are contained within HCVR and LCVR selected from the amino acid sequence pairs of SEQ ID NO: 50/58, 66/68, 70/72, 74/82, 90/92, 94/96, 122/130, 138/140, 142/144, 218/226, 234/236, 238/240, 242/250, 258/260, 262/264, 314/322, 330/332 and 334/336. In more specific embodiments, the CDR sequences are comprised within HCVR/LCVR sequences selected from SEQ ID NO: 90/92 or 218/226.

In one embodiment, the invention provides fully human monoclonal antibody or antigen-binding fragment thereof that specifically bind hPCSK9 and neutralize PCSK9 activity, wherein the antibody or fragment thereof exhibits one or more of the following characteristics: (i) capable of reducing serum total cholesterol at least about 25-35% and sustaining the reduction over at least a 24 day period relative to a predose level, preferably the reduction in serum total cholesterol is at least about 30-40%; (ii) capable of reducing serum LDL cholesterol at least about 65-80% and sustaining the reduction over at least a 24 day period relative to a predose level; (iii) capable of reducing serum triglyceride at least about 25-40% relative to predose level; (iv) does not reduce serum HDL cholesterol or reduces serum HDL cholesterol no more than 5% relative to predose level; (v) binds an epitope comprising amino acid residue 238 of hPCSK9 (SEQ ID NO:755); (vi) exhibits an enhanced binding affinity ($K_D$) for hPCSK9 at pH 5.5 relative to the $K_D$ at pH 7.4, as measured by plasmon surface resonance, wherein the enhanced affinity is at least about a 20- to 50-fold increase in affinity; (vii) binds human, human GOF mutation D374Y, cynomolgus monkey, rhesus monkey, mouse, rat and hamster PCSK9; (viii) comprises heavy and light chain CDR3 sequences comprising SEQ ID NO:80 and 88; and (ix) comprises CDR sequences from SEQ ID NO:90 and 92.

In one embodiment, the invention provides fully human monoclonal antibody or antigen-binding fragment thereof that specifically bind human PCSK9 (hPCSK9) and neutralize PCSK9 activity, wherein the antibody or fragment thereof exhibits one or more of the following characteristics: (i) capable of reducing serum LDL cholesterol at least about 40-70% and sustaining the reduction over at least a 60 or 90 day period relative to a predose level; (ii) capable of reducing serum triglyceride at least about 25-40% relative to predose level; (iii) does not reduce serum HDL cholesterol or reduces serum HDL cholesterol no more than 5% relative to predose level; (iv) binds an epitope comprising amino acid residue 366 of hPCSK9 (SEQ ID NO:755); (v) does not exhibit an enhanced binding affinity for PCSK9 at an acidic pH relative to a neutral pH, as measured by surface plasmon resonance; (vi) binds human and monkey PCSK9, but does not bind mouse, rat or hamster PCSK9; (vii) comprises heavy and light chain CDR3 sequences comprising SEQ ID NO:224 and 232; and (viii) comprises CDR sequences from SEQ ID NO:218 and 226.

In a third aspect, the invention provides nucleic acid molecules encoding anti-PCSK9 antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 21, 25, 41, 45, 49, 65, 69, 73, 89, 93, 97, 113, 117, 121, 137, 141, 145, 161, 165, 169, 185, 189, 193, 209, 213, 217, 233, 237, 241, 257, 261, 265, 281, 285, 289, 305, 309, 313, 329, 333, 337, 353, 357, 361, 377, 381, 385, 401, 405, 409, 425, 429, 433, 449, 453, 457, 473, 477, 481, 497, 501, 505, 521, 525, 529, 545, 549, 553, 569, 573, 577, 593, 597, 601, 617, 621, 625, 641, 645, 649, 665, 669, 673, 689, 693, 697, 713, 717, 721, 737 and 741, or a substantially identical sequence having at least 90%, at least 95%, at least 98%, or at least 99% homology thereof. In one embodiment, the HCVR is encoded by a nucleic acid sequence selected from the group consisting of SEQ ID NO: 49, 65, 69, 73, 89, 93, 121, 137, 141, 217, 233, 237, 241, 257, 261, 313, 329 and 333. In more specific embodiments, the HCVR is encoded by a nucleic acid sequence selected from the group consisting of SEQ ID NO: 89 and 217.

In one embodiment, the antibody or fragment thereof further comprises a LCVR encoded by a nucleic acid sequence selected from the group consisting of SEQ ID NO: 9, 19, 23, 33, 43, 47, 57, 67, 71, 81, 91, 95, 105, 115, 119, 129, 139, 143, 153, 163, 167, 177, 187, 191, 201, 211, 215, 225, 235, 239, 249, 259, 263, 273, 283, 287, 297, 307, 311, 321, 331, 335, 345, 355, 359, 369, 379, 383, 393, 403, 407, 417, 427, 431, 441, 451, 455, 465, 475, 479, 489, 499, 503, 513, 523, 527, 537, 547, 551, 561, 571, 575, 585, 595, 599, 609, 619, 623, 633, 643, 647, 657, 667, 671, 681, 691, 695, 705, 715, 719, 729, 739 and 743, or a substantially identical sequence having at least 90%, at least 95%, at least 98%, or at least 99% homology thereof. In one embodiment, the LCVR is encoded by a nucleic acid sequence selected from the group consisting of SEQ ID NO: 57, 67, 71, 81, 91, 95, 129, 139, 143, 225, 235, 239, 249, 259, 263, 321, 331 and 335. In more specific embodiments, the LCVR is encoded by a nucleic acid sequence selected from the group consisting of SEQ ID NO: 91 and 225.

In one embodiment, the invention features an antibody or antigen-binding fragment of an antibody comprising a HCDR3 domain encoded by a nucleotide sequence selected from the group consisting of SEQ ID NO:7, 31, 55, 79, 103, 127, 151, 175, 199, 223, 247, 271, 295, 319, 343, 367, 391, 415, 439, 463, 487, 511, 535, 559, 583, 607, 631, 655, 679, 703 and 727, or a substantially identical sequence having at least 90%, at least 95%, at least 98%, or at least 99% homology thereof; and a LCDR3 domain encoded by a nucleotide sequence selected from the group consisting of SEQ ID NO: 15, 39, 63, 87, 111, 135, 159, 183, 207, 231, 255, 279, 303, 327, 351, 375, 399, 423, 447, 471, 495, 519, 543, 567, 591, 615, 639, 663, 687, 711 and 735, or a substantially identical sequence having at least 90%, at least 95%, at least 98%, or at least 99% homology thereof. In one embodiment, the HCDR3 and LCDR3 comprise a sequence pair encoded by the nucleic acid sequence of SEQ ID NO:

55/63, 79/87, 127/135, 223/231, 247/255 and 319/327, respectively. In more specific embodiments, the HCDR3 and LCDR3 comprise a sequence pair encoded by the nucleic acid sequence of SEQ ID NO: 79/87 and 223/231.

In a further embodiment, the antibody or fragment thereof further comprises, a HCDR1 domain encoded by a nucleotide sequence selected from the group consisting of SEQ ID NO: 3, 27, 51, 75, 99, 123, 147, 171, 195, 219, 243, 267, 291, 315, 339, 363, 387, 411, 435, 459, 483, 507, 531, 555, 579, 603, 627, 651, 675, 699 and 723, or a substantially identical sequence having at least 90%, at least 95%, at least 98%, or at least 99% homology thereof; a HCDR2 domain encoded by a nucleotide sequence selected from the group consisting of SEQ ID NO:5, 29, 53, 77, 101, 125, 149, 173, 197, 221, 245, 269, 293, 317, 341, 365, 389, 413, 437, 461, 485, 509, 533, 557, 581, 605, 629, 653, 677, 701 and 725, or a substantially identical sequence having at least 90%, at least 95%, at least 98%, or at least 99% homology thereof; a LCDR1 domain encoded by a nucleotide sequence selected from the group consisting of SEQ ID NO: 11, 35, 59, 83, 107, 131, 155, 179, 203, 227, 251, 275, 299, 323, 347, 371, 395, 419, 443, 467, 491, 515, 539, 563, 587, 611, 635, 659, 683, 707 and 731, or a substantially identical sequence having at least 90%, at least 95%, at least 98%, or at least 99% homology thereof; and a LCDR2 domain encoded by a nucleotide sequence selected from the group consisting of SEQ ID NO: 13, 37, 61, 85, 109, 133, 157, 181, 205, 229, 253, 277, 301, 325, 349, 373, 397, 421, 445, 469, 493, 517, 541, 565, 589, 613, 637, 661, 685, 709 and 733, or a substantially identical sequence having at least 90%, at least 95%, at least 98%, or at least 99% homology thereof. In one embodiment, the heavy and light chain CDR sequences are encoded by the nucleic acid sequences of SEQ ID NO: 51, 53, 55, 59, 61, 63; 75, 77, 79, 83, 85, 87; 123, 125, 127, 131, 133, 135; 219, 221, 223, 227, 229, 231; 243, 245, 247, 251, 253, 255; and 315, 317, 319, 323, 325, 327. In more specific embodiments, the heavy and light chain CDR sequences are encoded by the nucleic acid sequences of SEQ ID NO: 75, 77, 79, 83, 85, 87; and 219, 221, 223, 227, 229, 231.

In a fourth aspect, the invention features an isolated antibody or antigen-binding fragment thereof that specifically binds hPCSK9, comprising a HCDR3 and a LCDR3, wherein HCDR3 comprises an amino acid sequence of the formula $X^1$—$X^2$—$X^3$—$X^4$—$X^5$—$X^6$—$X^7$—$X^8$—$X^9$—$X^{10}$—$X^{11}$—$X^{12}$—$X^{13}$—$X^{14}$—$X^{15}$—$X^{16}$—$X^{17}$—$X^{18}$—$X^{19}$—$X^{20}$ (SEQ ID NO:747), wherein $X^1$ is Ala, $X^2$ is Arg or Lys, $X^3$ is Asp, $X^4$ is Ser or Ile, $X^5$ is Asn or Val, $X^6$ is Leu or Trp, $X^7$ is Gly or Met, $X^8$ is Asn or Val, $X^9$ is Phe or Tyr, $X^{10}$ is Asp, $X^{11}$ is Leu or Met, $X^{12}$ is Asp or absent, $X^{13}$ is Tyr or absent, $X^{14}$ is Tyr or absent, $X^{15}$ is Tyr or absent, $X^{16}$ is Tyr or absent, $X^{17}$ is Gly or absent, $X^{18}$ is Met or absent, $X^{19}$ is Asp or absent, and $X^{20}$ is Val or absent; and LCDR3 comprises an amino acid sequence of the formula $X^1$—$X^2$—$X^3$—$X^4$—$X^5$—$X^6$—$X^7$—$X^8$—$X^9$ (SEQ ID NO:750), wherein $X^1$ is Gln or Met, $X^2$ is Gln, $X^3$ is Tyr or Thr, $X^4$ is Tyr or Leu, $X^5$ is Thr or Gln, $X^6$ is Thr, $X^7$ is Pro, $X^8$ is Tyr or Leu, and $X^9$ is Thr.

In a further embodiment, the antibody or fragment thereof further comprise a HCDR1 sequence of the formula $X^1$—$X^2$—$X^3$—$X^4$—$X^5$—$X^6$—$X^7$—$X^8$ (SEQ ID NO:745), wherein $X^1$ is Gly, $X^2$ is Phe, $X^3$ is Thr, $X^4$ is Phe, $X^5$ is Ser or Asn, $X^6$ is Ser or Asn, $X^7$ is Tyr or His, and $X^8$ is Ala or Trp; a HCDR2 sequence of the formula $X^1$—$X^2$—$X^3$—$X^4$—$X^5$—$X^6$—$X^7$—$X^8$ (SEQ ID NO:746), wherein $X^1$ is Ile, $X^2$ is Ser or Asn, $X^3$ is Gly or Gln, $X^4$ is Asp or Ser, $X^5$ is Gly, $X^6$ is Ser or Gly, $X^7$ is Thr or Glu, and $X^8$ is Thr or Lys; a LCDR1 sequence of the formula $X^1$—$X^2$—$X^3$—$X^4$—$X^5$—$X^6$—$X^7$—$X^8$—$X^9$—$X^{10}$—$X^{11}$-$x^{12}$ (SEQ ID NO:748) wherein $X^1$ is Gln, $X^2$ is Ser, $X^3$ is Val or Leu, $X^4$ is Leu, $X^5$ is His or Tyr, $X^6$ is Arg or Ser, $X^7$ is Ser or Asn, $X^8$ is Asn or Gly, $X^9$ is Asn, $X^{10}$ is Arg or Asn, $X^{11}$ is Asn or Tyr, and $X^{12}$ is Phe or absent; a LCDR2 sequence of the formula $X^1$—$X^2$—$X^3$ (SEQ ID NO:749) wherein $X^1$ is Trp or Leu, $X^2$ is Ala or Gly, and $X^3$ is Ser. FIG. 1 shows the sequence alignment of heavy and light chain variable regions for 316P and 300N mAbs.

In a fifth aspect, the invention features a human anti-PCSK9 antibody or antigen-binding fragment of an antibody comprising a heavy chain variable region (HCVR) encoded by nucleotide sequence segments derived from $V_H$, $D_H$ and $J_H$ germline sequences, and a light chain variable region (LCVR) encoded by nucleotide sequence segments derived from $V_K$ and $J_K$ germline sequences, wherein the germline sequences are (a) $V_H$ gene segment 3-23, $D_H$ gene segment 7-27, $J_H$ gene segment 2, $V_K$ gene segment 4-1 and $J_K$ gene segment 2; or (b) $V_H$ gene segment 3-7, $D_H$ gene segment 2-8, $J_H$ gene segment 6, $V_K$ gene segment 2-28 and $J_K$ gene segment 4.

In a sixth aspect, the invention features an antibody or antigen-binding fragment thereof that binds to a PCSK9 protein of SEQ ID NO:755, wherein the binding of the antibody or fragment thereof to a variant PCSK9 protein is less than 50% of the binding between the antibody or fragment thereof and the PCSK9 protein of SEQ ID NO:755. In specific embodiment, the antibody or fragment thereof binds to the variant PCSK9 protein with a binding affinity ($K_D$) which is less than about 50%, less than about 60%, less than about 70%, less than about 80%, less than about 90% or less than about 95% compared to the binding to PCSK9 (SEQ ID NO:755).

In one embodiment, the variant PCSK9 protein comprises at least one mutation at position 238 of SEQ ID NO:755. In a more specific embodiment, the mutation is D238R. In one embodiment, the antibody or antibody fragment binding affinity for the variant PCSK9 protein is at least 90% less relative to the wildtype protein of SEQ ID NO:755, wherein the variant protein comprises a mutation at residue 238. In one embodiment, the antibody or antibody fragment binding affinity for the variant PCSK9 protein is at least 80% less relative to the wildtype protein of SEQ ID NO:755, wherein the variant protein comprises a mutation at one or more of residue 153, 159, 238 and 343. In a more specific embodiment, the mutation is one of S153R, E159R, D238R and D343R.

In one embodiment, the variant PCSK9 protein comprises at least one mutation at position 366 of SEQ ID NO:755. In a more specific embodiment, the mutation is E366K. In one embodiment, the antibody or antibody fragment binding affinity for the variant PCSK9 protein is at least 95% less relative to the wildtype protein of SEQ ID NO:755, wherein the variant protein comprises a mutation at residue 366. In one embodiment, the antibody or antibody fragment binding affinity for the variant PCSK9 protein is at least 90% less relative to the wildtype protein of SEQ ID NO:755, wherein the variant protein comprises a mutation at one or more of residue 147, 366 and 380. In a more specific embodiment, the mutation is one of S147F, E366K and V380M. In one embodiment, the antibody or antibody fragment binding affinity for the variant PCSK9 protein is at least 80% less relative to the wildtype protein of SEQ ID NO:755, wherein the variant protein comprises a mutation at one or more of residue 147, 366 and 380. In a more specific embodiment, the mutation is one of S147F, E366K and V380M.

The invention encompasses anti-PCSK9 antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, modification of galactosylation can be made in order to modify complement dependent cytotoxicity (CDC).

In a seventh aspect, the invention features a pharmaceutical composition comprising a recombinant human antibody or fragment thereof that specifically binds hPCSK9 and a pharmaceutically acceptable carrier. In one embodiment, the invention features a composition that is a combination of an antibody or antigen-binding fragment of an antibody of the invention, and a second therapeutic agent. The second therapeutic agent may be any agent that is advantageously combined with the antibody or fragment thereof of the invention, for example, an agent capable of inducing a cellular depletion of cholesterol synthesis by inhibiting 3-hydroxy-3-methylglutaryl (HMG)-coenzyme A (CoA) reductase, such as, for example, cerovastatin, atorvastatin, simvastatin, pitavastin, rosuvastatin, fluvastatin, lovastatin, pravastatin, etc.; capable of inhibiting cholesterol uptake and or bile acid re-absorption; capable of increasing lipoprotein catabolism (such as niacin); and/or activators of the LXR transcription factor that plays a role in cholesterol elimination such as 22-hydroxycholesterol.

In an eighth aspect, the invention features methods for inhibiting hPCSK9 activity using the anti-PCSK9 antibody or antigen-binding portion of the antibody of the invention, wherein the therapeutic methods comprise administering a therapeutically effective amount of a pharmaceutical composition comprising an antibody or antigen-binding fragment of an antibody of the invention. The disorder treated is any disease or condition that is improved, ameliorated, inhibited or prevented by removal, inhibition or reduction of PCSK9 activity. Specific populations treatable by the therapeutic methods of the invention include subjects indicated for LDL apheresis, subjects with PCSK9-activating mutations (gain of function mutations, "GOF"), subjects with heterozygous Familial Hypercholesterolemia (heFH); subjects with primary hypercholesterolemia who are statin intolerant or statin uncontrolled; and subjects at risk for developing hypercholesterolemia who may be preventably treated. Other indications include dyslipidemia associated with secondary causes such as Type 2 diabetes mellitus, cholestatic liver diseases (primary biliary cirrhosis), nephrotic syndrome, hypothyroidism, obesity; and the prevention and treatment of atherosclerosis and cardiovascular diseases.

In specific embodiments of the method of the invention, the anti-hPCSK9 antibody or antibody fragment of the invention is useful to reduce elevated total cholesterol, non-HDL cholesterol, LDL cholesterol, and/or apolipoprotein B (apolipoprotein B100).

The antibody or antigen-binding fragment of the invention may be used alone or in combination with a second agent, for example, an HMG-CoA reductase inhibitor and/or other lipid lowering drugs.

Other embodiments will become apparent from a review of the ensuing detailed description.

BRIEF DESCRIPTION OF THE FIGURES

FIG. 1. Sequence comparison tables of heavy chain (A) and light chain (B) variable regions and CDRs of antibodies H1H316P and H1M300N.

DETAILED DESCRIPTION

Figure 2:
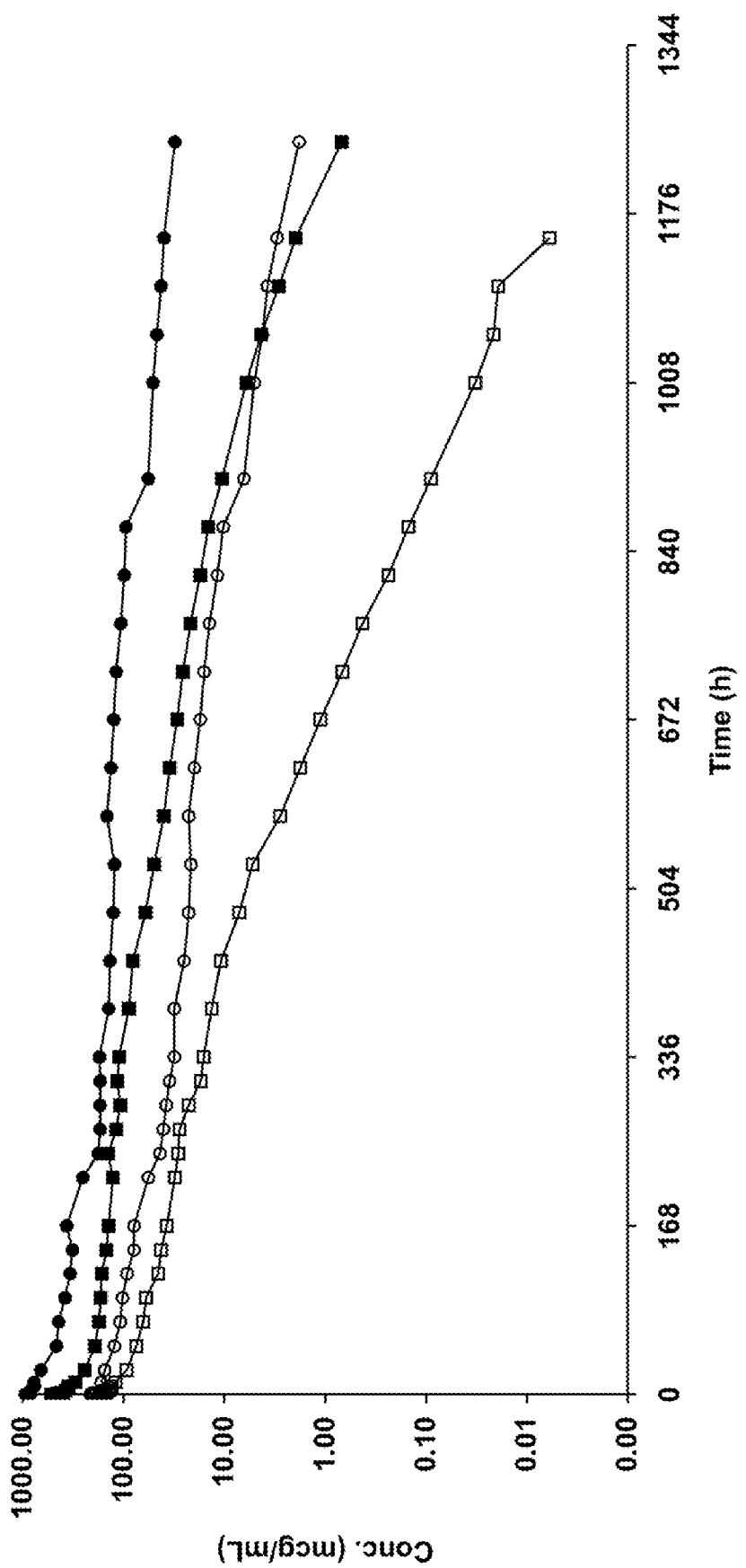
FIG. 2. Antibody concentrations in serum over time. 316P 5 mg/kg (□); 300N 5 mg/kg (○); 316P 15 mg/kg (■); 300N 15 mg/kg (●).
Figure 3:
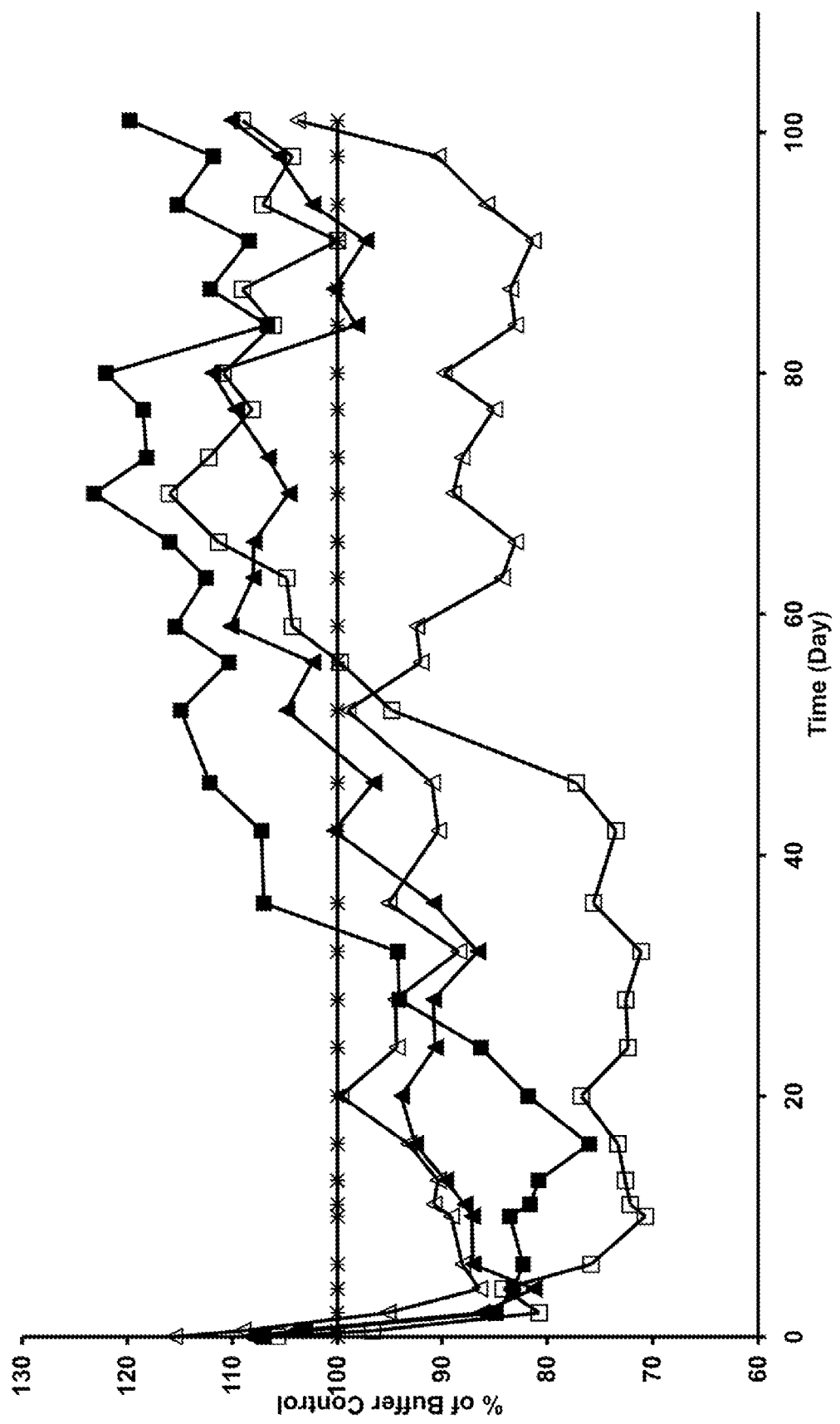
FIG. 3. Serum total cholesterol level as a percentage of change over buffer control. Buffer control (✱) 316P 5 mg/kg (■); 300N 5 mg/kg (▲); 316P 15 mg/kg (□); 300N 15 mg/kg (△).
Figure 4:
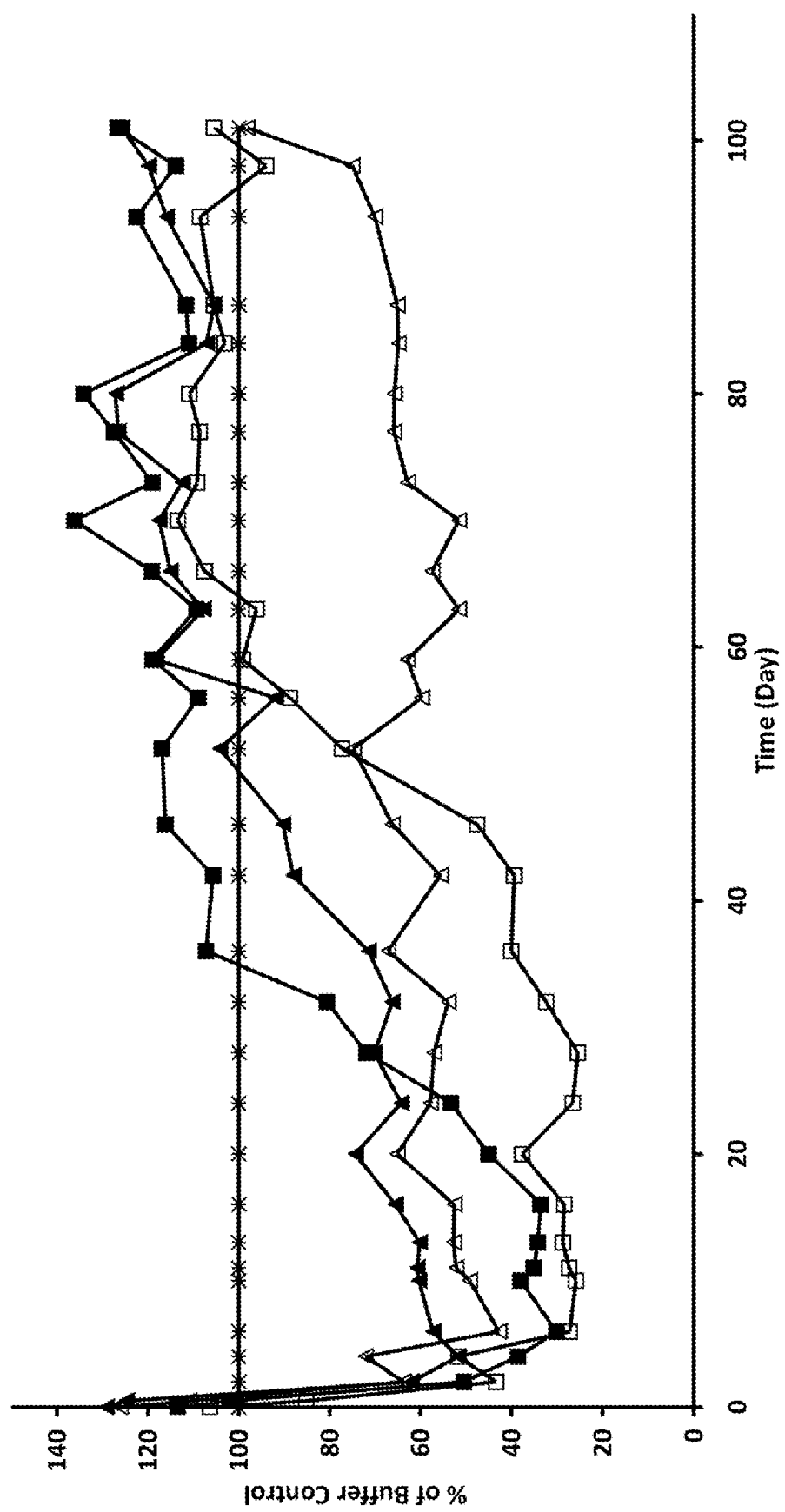
FIG. 4. Serum LDL cholesterol level as a percentage of change over buffer control: Buffer Control (✱); 316P 5 mg/kg (■); 300N 5 mg/kg (▲); 316P 15 mg/kg (□); 300N 15 mg/kg (△).
Figure 5:
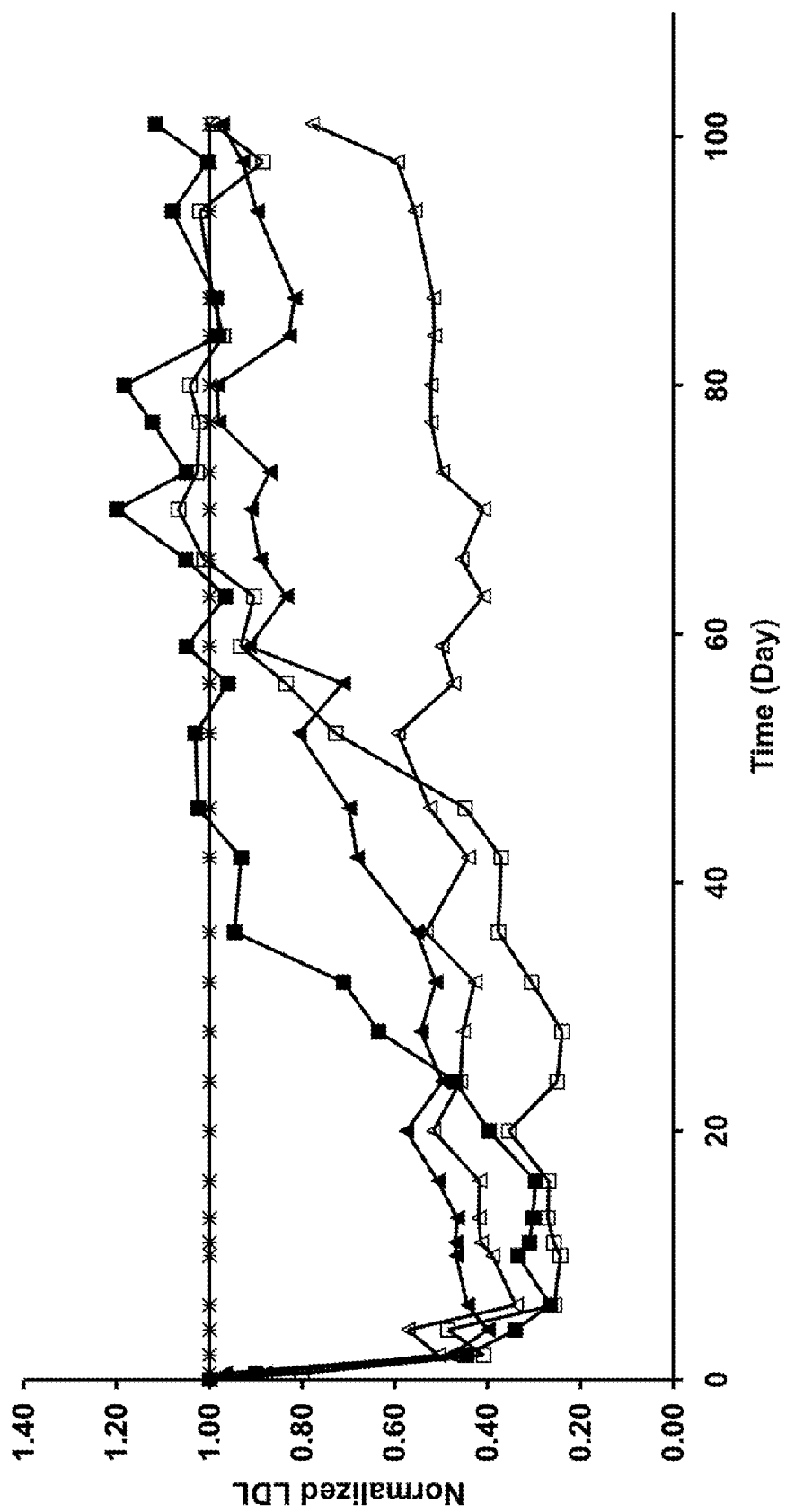
FIG. 5. Serum LDL cholesterol level normalized to buffer control. Buffer control (✱); 316P 5 mg/kg (■); 300N 5 mg/kg (▲); 316P 15 mg/kg (□); 300N 15 mg/kg (△).

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The term "human proprotein convertase subtilisin/kexin type 9" or "hPCSK9", as used herein, refers to hPCSK9 having the nucleic acid sequence shown in SEQ ID NO:754 and the amino acid sequence of SEQ ID NO:755, or a biologically active fragment thereof.

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region ("HCVR" or "VH") and a heavy chain constant region (comprised of domains CH1, CH2 and CH3). Each light chain is comprised of a light chain variable region ("LCVR or "VL") and a light chain constant region (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The term "specifically binds," or the like, means that an antibody or antigen-binding fragment thereof forms a complex with an antigen that is relatively stable under physiologic conditions. Specific binding can be characterized by an equilibrium dissociation constant of at least about $1\times10^{-6}$ M or less (e.g., a smaller $K_D$ denotes a tighter binding). Methods for determining whether two molecules specifically bind are well known in the art and include, for example, equilibrium dialysis, surface plasmon resonance, and the like. An isolated antibody that specifically binds hPCSK9 may, however, exhibit cross-reactivity to other antigens such as PCSK9 molecules from other species. Moreover, multi-specific antibodies (e.g., bispecifics) that bind to hPCSK9 and one or more additional antigens are nonetheless considered antibodies that "specifically bind" hPCSK9, as used herein.

The term "high affinity" antibody refers to those mAbs having a binding affinity to hPCSK9 of at least $10^{-10}$ M; preferably $10^{-11}$M; even more preferably $10^{-12}$ M, as measured by surface plasmon resonance, e.g., BIACORE™ or solution-affinity ELISA.

By the term "slow off rate", "Koff" or "kd" is meant an antibody that dissociates from hPCSK9 with a rate constant of $1\times10^{-3}$ $s^{-1}$ or less, preferably $1\times10^{-4}$ $s^{-1}$ or less, as determined by surface plasmon resonance, e.g., BIACORE™.

The term "antigen-binding portion" of an antibody (or simply "antibody fragment"), as used herein, refers to one or more fragments of an antibody that retain the ability to specifically bind to hPCSK9. An antibody fragment may include a Fab fragment, a F(ab')$_2$ fragment, a Fv fragment, a dAb fragment, a fragment containing a CDR, or an isolated CDR.

The specific embodiments, antibody or antibody fragments of the invention may be conjugated to a therapeutic moiety ("immunoconjugate"), such as a cytotoxin, a chemotherapeutic drug, an immunosuppressant or a radioisotope.

An "isolated antibody", as used herein, is intended to refer to an antibody that is substantially free of other mAbs having different antigenic specificities (e.g., an isolated antibody that specifically binds hPCSK9 is substantially free of mAbs that specifically bind antigens other than hPCSK9). An isolated antibody that specifically binds hPCSK9 may, however, have cross-reactivity to other antigens, such as PCSK9 molecules from other species.

A "neutralizing antibody", as used herein (or an "antibody that neutralizes PCSK9 activity"), is intended to refer to an antibody whose binding to hPCSK9 results in inhibition of at least one biological activity of PCSK9. This inhibition of the biological activity of PCSK9 can be assessed by measuring one or more indicators of PCSK9 biological activity by one or more of several standard in vitro or in vivo assays known in the art (see examples below).

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions that are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT, which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra).

Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403 410 and (1997) Nucleic Acids Res. 25:3389 402, each of which is herein incorporated by reference.

In specific embodiments, the antibody or antibody fragment for use in the method of the invention may be monospecific, bispecific, or multispecific. Multispecific antibodies may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise an Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 mAbs; N44S, K52N, and V82I (IMGT; N384S, K392N, and V422I by EU) in the case of IgG2 mAbs; and Q15R, N44S, K52N, V57M, R69K, E79Q, and V82I (by IMGT; Q355R, N384S, K392N, V397M, R409K, E419Q, and V422I by EU) in the case of IgG4 mAbs. Variations on the bi-specific antibody format described above are contemplated within the scope of the present invention.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

Preparation of Human Antibodies

Methods for generating human antibodies in transgenic mice are known (see for example, U.S. Pat. No. 6,596,541, Regeneron Pharmaceuticals, VELOCIMMUNE™). The VELOCIMMUNE™ technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody. In specific embodiment, the cell is a CHO cell.

Antibodies may be therapeutically useful in blocking a ligand-receptor interaction or inhibiting receptor component interaction, rather than by killing cells through fixation of complement and participation in complement-dependent cytotoxicity (CDC), or killing cells through antibody-dependent cell-mediated cytotoxicity (ADCC). The constant region of an antibody is thus important in the ability of an antibody to fix complement and mediate cell-dependent cytotoxicity. Thus, the isotype of an antibody may be selected on the basis of whether it is desirable for the antibody to mediate cytotoxicity.

Human antibodies can exist in two forms that are associated with hinge heterogeneity. In one form, an antibody molecule comprises a stable four-chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, CH2, or CH3 region, which may be desirable, for example, in production, to improve the yield of the desired antibody form.

Generally, a VELOCIMMUNE™ mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As described below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4 (for example, SEQ ID NO:751, 752, 753). While the constant region selected may vary according to specific use, high affinity antigen binding and target specificity characteristics reside in the variable region.

Epitope Mapping and Related Technologies

To screen for antibodies that bind to a particular epitope (e.g., those which block binding of IgE to its high affinity receptor), a routine cross-blocking assay such as that described Antibodies, Harlow and Lane (Cold Spring Harbor Press, Cold Spring Harb., NY) can be performed. Other methods include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9: 487-496) (herein specifically incorporated by reference in its entirety).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920, herein specifically incorporated by reference in its entirety). Each category may reflect a unique epitope either distinctly different from or partially overlapping with epitope represented by another category. This technology allows rapid filtering of genetically identical mAbs, such that characterization can be focused on genetically distinct mAbs. When applied to hybridoma screening, MAP may facilitate identification of rare hybridoma clones that produce mAbs having the desired characteristics. MAP may be used to sort the anti-PCSK9 mAbs of the invention into groups of mAbs binding different epitopes.

In various embodiments, the anti-hPCSK9 antibody or antigen-binding fragment of an antibody binds an epitope within the catalytic domain, which is about 153 to 425 of SEQ ID NO:755); more specifically, an epitope from about 153 to about 250 or from about 250 to about 425; more specifically, the antibody or antibody fragment of the invention binds an epitope within the fragment from about 153 to about 208, from about 200 to about 260, from about 250 to about 300, from about 275 to about 325, from about 300 to about 360, from about 350 to about 400, and/or from about 375 to about 425.

In various embodiments, the anti-hPCSK9 antibody or antigen-binding fragment of an antibody binds an epitope within the propeptide domain (residues 31 to 152 of SEQ ID NO:755); more specifically, an epitope from about residue 31 to about residue 90 or from about residue 90 to about residue 152; more specifically, the antibody or antibody fragment of the invention binds an epitope within the fragment from about residue 31 to about residue 60, from about residue 60 to about residue 90, from about residue 85 to about residue 110, from about residue 100 to about residue 130, from about residue 125 to about residue 150, from about residue 135 to about residue 152, and/or from about residue 140 to about residue 152.

In some embodiments, the anti-hPCSK9 antibody or antigen-binding fragment of an antibody binds an epitope within the C-terminal domain, (residues 426 to 692 of SEQ ID NO:755); more specifically, an epitope from about residue 426 to about residue 570 or from about residue 570 to about residue 692; more specifically, the antibody or antibody fragment of the invention binds an epitope within the fragment from about residue 450 to about residue 500, from about residue 500 to about residue 550, from about residue 550 to about residue 600, and/or from about residue 600 to about residue 692.

In some embodiments, the antibody or antibody fragment binds an epitope which includes more than one of the enumerated epitopes within the catalytic, propeptide or C-terminal domain, and/or within two or three different domains (for example, epitopes within the catalytic and C-terminal domains, or within the propeptide and catalytic domains, or within the propeptide, catalytic and C-terminal domains.

In some embodiments, the antibody or antigen-binding fragment binds an epitope on hPCSK9 comprising amino acid residue 238 of hPCSK9 (SEQ ID NO:755). Experimental results (Table 27) show that when D238 was mutated, the $K_D$ of mAb 316P exhibited >400-fold reduction in binding affinity (~$1\times10^{-9}$ M to ~$410\times10^{-9}$ M) and $T_{1/2}$ decreased >30-fold (from ~37 to ~1 min). In a specific embodiment, the mutation was D238R. In specific embodiments, the antibody or antigen-binding fragment of the invention binds an epitope of hPCSK9 comprising two or more of amino acid residues at positions 153, 159, 238 and 343.

As shown below, a mutation in amino acid residue 153, 159 or 343 resulted in about a 5- to 10-fold decrease in affinity or similar shortening in $T_{1/2}$. In specific embodiments, the mutation was S153R, E159R and/or D343R.

In some embodiments, the antibody or antigen-binding fragment binds an epitope on hPCSK9 comprising amino acid residue 366 of hPCSK9 (SEQ ID NO:755). Experimental results (Table 27) show that when E366 was mutated, the affinity of mAb 300N exhibited about 50-fold decrease (~$0.7\times10^{-9}$ M to ~$36\times10^{-9}$ M) and a similar shortening in $T_{1/2}$ (from ~120 to ~2 min). In a specific embodiment, the mutation is E366K.

The present invention includes anti-PCSK9 antibodies that bind to the same epitope as any of the specific exemplary antibodies described herein. Likewise, the present invention also includes anti-PCSK9 antibodies that compete for binding to PCSK9 or a PCSK9 fragment with any of the specific exemplary antibodies described herein.

One can easily determine whether an antibody binds to the same epitope as, or competes for binding with, a reference anti-PCSK9 antibody by using routine methods known in the art. For example, to determine if a test antibody binds to the same epitope as a reference anti-PCSK9 antibody of the invention, the reference antibody is allowed to bind to a PCSK9 protein or peptide under saturating conditions. Next, the ability of a test antibody to bind to the PCSK9 molecule is assessed. If the test antibody is able to bind to PCSK9 following saturation binding with the reference anti-PCSK9 antibody, it can be concluded that the test antibody binds to a different epitope than the reference anti-PCSK9 antibody. On the other hand, if the test antibody is not able to bind to the PCSK9 molecule following saturation binding with the reference anti-PCSK9 antibody, then the test antibody may bind to the same epitope as the epitope bound by the reference anti-PCSK9 antibody of the invention.

To determine if an antibody competes for binding with a reference anti-PCSK9 antibody, the above-described binding methodology is performed in two orientations: In a first orientation, the reference antibody is allowed to bind to a PCSK9 molecule under saturating conditions followed by assessment of binding of the test antibody to the PCSK9 molecule. In a second orientation, the test antibody is allowed to bind to a PCSK9 molecule under saturating conditions followed by assessment of binding of the reference antibody to the PCSK9 molecule. If, in both orientations, only the first (saturating) antibody is capable of binding to the PCSK9 molecule, then it is concluded that the test antibody and the reference antibody compete for binding to PCSK9. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

In a specific embodiment, the invention comprises an anti-PCSK9 antibody or antigen binding fragment of an antibody that binds an PCSK9 protein of SEQ ID NO:755, wherein the binding between the antibody or fragment thereof to PCSK9 and a variant PCSK9 protein is less than 50% of the binding between the antibody or fragment and the PCSK9 protein of SEQ ID NO:755. In one specific embodiment, the variant PCSK9 protein comprises at least one mutation of a residue at a position selected from the group consisting of 153, 159, 238 and 343. In a more specific embodiment, the at least one mutation is S153R, E159R, D238R, and/or D343R. In another specific embodiment, the variant PCSK9 protein comprises at least one mutation of a residue at a position selected from the group consisting of 366. In one specific embodiment, the variant PCSK9 protein comprises at least one mutation of a residue at a position selected from the group consisting of 147, 366 and 380. In a more specific embodiment, the mutation is S147F, E366K and V380M.

Immunoconjugates

The invention encompasses a human anti-PCSK9 monoclonal antibody conjugated to a therapeutic moiety ("immunoconjugate"), such as a cytotoxin, a chemotherapeutic drug, an immunosuppressant or a radioisotope. Cytotoxin agents include any agent that is detrimental to cells. Examples of suitable cytotoxin agents and chemotherapeutic agents for forming immunoconjugates are known in the art, see for example, WO 05/103081.

Bispecifics

The antibodies of the present invention may be monospecific, bispecific, or multispecific. Multispecific mAbs may be specific for different epitopes of one target polypeptide or may contain antigen-binding domains specific for more than one target polypeptide. See, e.g., Tutt et al. (1991) J. Immunol. 147:60-69. The human anti-PCSK9 mAbs can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity.

An exemplary bi-specific antibody format that can be used in the context of the present invention involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise a Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Bioequivalents

The anti-PCSK9 antibodies and antibody fragments of the present invention encompass proteins having amino acid sequences that vary from those of the described mAbs, but that retain the ability to bind human PCSK9. Such variant mAbs and antibody fragments comprise one or more additions, deletions, or substitutions of amino acids when compared to parent sequence, but exhibit biological activity that is essentially equivalent to that of the described mAbs. Likewise, the anti-PCSK9 antibody-encoding DNA sequences of the present invention encompass sequences that comprise one or more additions, deletions, or substitutions of nucleotides when compared to the disclosed sequence, but that encode an anti-PCSK9 antibody or antibody fragment that is essentially bioequivalent to an anti-PCSK9 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied. In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-PCSK9 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation.

Treatment Population

The invention provides therapeutic methods for treating a human patient in need of a composition of the invention. While modifications in lifestyle and conventional drug treatment are often successful in reducing cholesterol levels, not all patients are able to achieve the recommended target cholesterol levels with such approaches. Various conditions, such as familial hypercholesterolemia (FH), appear to be resistant to lowering of LDL-C levels in spite of aggressive use of conventional therapy. Homozygous and heterozygous familial hypercholesterolemia (hoFH, heFH) is a condition associated with premature atherosclerotic vascular disease. However, patients diagnosed with hoFH are largely unresponsive to conventional drug therapy and have limited treatment options. Specifically, treatment with statins, which reduce LDL-C by inhibiting cholesterol synthesis and upregulating the hepatic LDL receptor, may have little effect in patients whose LDL receptors are non-existent or defective. A mean LDL-C reduction of only less than about 20% has been recently reported in patients with genotype-confirmed hoFH treated with the maximal dose of statins. The addition of ezetimibe 10 mg/day to this regimen resulted in a total reduction of LDL-C levels of 27%, which is still far from optimal. Likewise, many patients are statin non-responsive, poorly controlled with statin therapy, or cannot tolerate statin therapy; in general, these patients are unable to achieve cholesterol control with alternative treatments. There is a large unmet medical need for new treatments that can address the shortcomings of current treatment options.

Specific populations treatable by the therapeutic methods of the invention include patients indicated for LDL apheresis, subjects with PCSK9-activating (GOF) mutations, heterozygous Familial Hypercholesterolemia (heFH); subjects with primary hypercholesterolemia who are statin intolerant or statin uncontrolled; and subjects at risk for developing hypercholesterolemia who may be preventably treated.

Therapeutic Administration and Formulations

The invention provides therapeutic compositions comprising the anti-PCSK9 antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the size of a subject to be administered, target disease, conditions, route of administration, and the like. When the antibody of the present invention is used for treating various conditions and diseases associated with PCSK9, including hypercholesterolemia, disorders associated with LDL and apolipoprotein B, and lipid metabolism disorders, and the like, in an adult patient, it is advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), CRC Pres., Boca Raton, Florida (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25 TM pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

The invention provides therapeutic methods in which the antibody or antibody fragment of the invention is useful to treat hypercholesterolemia associated with a variety of conditions involving hPCSK9. The anti-PCSK9 antibodies or antibody fragments of the invention are particularly useful for the treatment of hypercholesterolemia and the like. Combination therapies may include the anti-PCSK9 antibody of the invention with, for example, one or more of any agent that (1) induces a cellular depletion of cholesterol synthesis by inhibiting 3-hydroxy-3-methylglutaryl (HMG)-coenzyme A (CoA) reductase, such as cerivastatin, atorvastatin, simvastatin, pitavastatin, rosuvastatin, fluvastatin, lovastatin, pravastatin; (2) inhibits cholesterol uptake and or bile acid re-absorption; (3) increase lipoprotein catabolism (such as niacin); and activators of the LXR transcription factor that plays a role in cholesterol elimination such as 22-hydroxycholesterol or fixed combinations such as ezetimibe plus simvastatin; a statin with a bile resin (e.g., cholestyramine, colestipol, colesevelam), a fixed combination of niacin plus a statin (e.g., niacin with lovastatin); or with other lipid lowering agents such as omega-3-fatty acid ethyl esters (for example, omacor).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used but some experimental errors and deviations should be accounted for. Unless indicated otherwise, molecular weight is average molecular weight, temperature is in degrees Centigrade, and pressure is at or near atmospheric.

Example 1: Generation of Human Antibodies to Human PCSK9

VELOCIMMUNE™ mice were immunized with human PCSK9, and the antibody immune response monitored by antigen-specific immunoassay using serum obtained from these mice. Anti-hPCSK9 expressing B cells were harvested from the spleens of immunized mice shown to have elevated anti-hPCSK9 antibody titers were fused with mouse myeloma cells to form hybridomas. The hybridomas were screened and selected to identify cell lines expressing hPCSK9-specific antibodies using assays as described below. The assays identified several cell lines that produced chimeric anti-hPCSK9 antibodies designated as H1M300, H1M504, H1M505, H1M500, H1M497, H1M498, H1M494, H1M309, H1M312, H1M499, H1M493, H1M496, H1M503, H1M502, H1M508, H1M495 and H1M492.

Human PCSK9-specific antibodies were also isolated directly from antigen-immunized B cells without fusion to myeloma cells, as described in U.S. 2007/0280945A1, hereby incorporated by reference in its entirety. Heavy and light chain variable regions were cloned to generate fully human anti-hPCSK9 antibodies designated as H1H313, H1H314, H1H315, H1H316, H1H317, H1H318, H1H320, H1H321 and H1H334. Stable recombinant antibody-expressing CHO cell lines expressing these antibodies were established.

Example 2. Gene Utilization Analysis

To analyze the structure of the mAbs produced, the nucleic acids encoding antibody variable regions were cloned and sequenced. The predicted amino acid sequences of the variable regions were confirmed by N-terminal amino acid sequencing. From the nucleic acid sequence and predicted amino acid sequence of the mAbs, gene usage was identified for each antibody chain.

TABLE 1

| Antibody | Heavy Chain Variable Region | | | Light Chain Variable Region | |
|---|---|---|---|---|---|
| | VH | D | JH | VK | JK |
| H1H313 | 3-13 | 1-26 | 4 | 3-15 | 3 |
| H1H314 | 3-33 | 3-3 | 4 | 1-5 | 2 |
| H1H315 | 3-33 | 3-3 | 4 | 4-1 | 1 |
| H1H316 | 3-23 | 7-27 | 2 | 4-1 | 2 |
| H1H317 | 3-13 | 1-26 | 4 | 1-6 | 1 |
| H1H318 | 4-59 | 3-10 | 6 | 1-9 | 1 |
| H1H320 | 1-18 | 2-2 | 6 | 2-30 | 1 |
| H1H321 | 2-5 | 1-7 | 6 | 2-28 | 4 |
| H1H334 | 2-5 | 6-6 | 6 | 2-28 | 4 |
| H1M300 | 3-7 | 2-8 | 6 | 2-28 | 4 |
| H1M504 | 3-30 | 2-8 | 6 | 2-28 | 4 |
| H1M505 | 3-30 | 2-8 | 6 | 2-28 | 4 |
| H1M500 | 2-5 | 5-5 | 6 | 2-28 | 4 |
| H1M497 | 1-18 | 2-2 | 6 | 2-30 | 2 |
| H1M498 | 3-21 | 2-2 | 4 | 1-5 | 2 |
| H1M494 | 3-11 | 5-12 | 6 | 3-20 | 4 |
| H1M309 | 3-21 | 6-13 | 4 | 1-5 | 1 |
| H1M312 | 3-21 | 6-13 | 4 | 1-5 | 1 |
| H1M499 | 3-21 | 6-13 | 4 | 1-5 | 1 |
| H1M493 | 3-21 | 6-13 | 4 | 1-5 | 1 |
| H1M496 | 3-13 | 6-19 | 4 | 3-15 | 3 |
| H1M503 | 1-18 | 2-2 | 6 | 2-28 | 1 |
| H1M502 | 3-13 | 6-13 | 4 | 3-15 | 3 |
| H1M508 | 3-13 | 6-13 | 4 | 3-15 | 3 |
| H1M495 | 3-9 | 4-17 | 6 | 1-9 | 3 |
| H1M492 | 3-23 | 3-3 | 2 | 3-20 | 4 |

Example 3. Antigen Binding Affinity Determination

Equilibrium dissociation constants ($K_D$) for hPCSK9 binding to mAbs generated by hybridoma cell lines described above were determined by surface kinetics in a real-time biosensor surface plasmon resonance assay (BIACORE™ T100). Each antibody was captured at a flow rate of 4 µl/min for 90 sec on a goat anti-mouse IgG polyclonal antibody surface created through direct chemical coupling to a BIACORE™ chip to form a captured antibody surface. Human PCSK9-myc-myc-his (hPCSK9-mmh) at a concentration of 50 nM or 12.5 nM was injected over the captured antibody surfaces at a flowrate of 50 µl/min for 300 sec, and antigen-antibody dissociation was monitored for 15 min at either 25° C. or 37° C. ($K_D$=pM; $T_{1/2}$=min).

TABLE 2

| Antibody | 25° C. | | 37° C. | |
|---|---|---|---|---|
| | $K_D$ | $T_{1/2}$ | $K_D$ | $T_{1/2}$ |
| H1M300 | 399 | 170 | 1510 | 32 |
| H1M309 | 29.9 | 7461 | 537 | 326 |
| H1M312 | 0.225 | 15568 | 432 | 392 |
| H1M493 | 46.5 | 4921 | 522 | 341 |
| H1M494 | 870 | 114 | 2350 | 30 |
| H1M495 | 440 | 222 | 7500 | 19 |
| H1M496 | 254 | 257 | 421 | 118 |
| H1M497 | 20.1 | 5801 | 480 | 290 |
| H1M498 | 6400 | 30 | 7500 | 14 |
| H1M499 | 106 | 2253 | 582 | 316 |
| H1M500 | 1400 | 91 | 6010 | 15 |
| H1M502 | 78.3 | 958 | 411 | 151 |
| H1M503 | 510 | 118 | 1880 | 30 |
| H1M504 | 3470 | 35 | 11200 | 6 |

TABLE 2-continued

| | 25° C. | | 37° C. | |
|---|---|---|---|---|
| Antibody | $K_D$ | $T_{1/2}$ | $K_D$ | $T_{1/2}$ |
| H1M505 | 2740 | 42 | 9200 | 6 |
| H1M508 | 138 | 572 | 442 | 139 |
| H1M510 | 1070 | 68 | 3960 | 10 |

Equilibrium dissociation constants ($K_D$) for hPCSK9 binding to mAbs generated via direct isolation of splenocytes were determined by surface kinetics in a real-time biosensor surface plasmon resonance assay (BIACORE™ T100). Each selected antibody was captured at a flowrate of 2 µl/min for 6 min on a goat anti-human IgG polyclonal antibody surface created through direct chemical coupling to a BIACORE™ chip to form a captured antibody surface. Human PCSK9-mmh at a concentration of 50 nM or 12.5 nM was injected over the captured antibody surface at a flowrate of 70 µl/min for 5 min, and antigen-antibody dissociation was monitored for 15 min at either 25° C. or 37° C. ($K_D$=pM; $T_{1/2}$=min).

TABLE 3

| | 25° C. | | 37° C. | |
|---|---|---|---|---|
| Antibody | $K_D$ | $T_{1/2}$ | $K_D$ | $T_{1/2}$ |
| H1H313P | 244 | 230 | 780 | 60 |
| H1H314P | 3990 | 65 | 3560 | 43 |
| H1H315P | 129 | 151 | 413 | 35 |
| H1H316P | 377 | 42 | 1080 | 11 |
| H1H317P | 30400 | 137 | 18600 | 70 |
| H1H318P | 972 | 59 | 1690 | 28 |
| H1H320P | 771 | 28 | 1930 | 8 |
| H1H321P | 865 | 106 | 3360 | 23 |
| H1H334P | 3750 | 46 | 15900 | 8 |

Dissociation rate (kd) of selected mAbs for tagged rhesus monkey (*Macaca mulata*) PCSK9 (mmPCSK9; SEQ ID NO:756) (mmPCSK9-mmh) at 25° C. was determined as described above.

TABLE 4

| Antibody | kd (1/s) | $T_{1/2}$ (min) |
|---|---|---|
| H1H313P | $2.92 \times 10^{-5}$ | 396 |
| H1H318P | $3.69 \times 10^{-3}$ | 3 |
| H1H334P | $8.06 \times 10^{-3}$ | 1 |
| H1H315P | $2.29 \times 10^{-4}$ | 51 |
| H1H316P | $2.29 \times 10^{-4}$ | 51 |
| H1H320P | $3.17 \times 10^{-4}$ | 36 |
| H1M300 | $1.52 \times 10^{-4}$ | 76 |
| H1M504 | $5.04 \times 10^{-4}$ | 23 |
| H1M497 | $6.60 \times 10^{-5}$ | 175 |
| H1M503 | $8.73 \times 10^{-5}$ | 132 |
| H1M496 | $4.45 \times 10^{-5}$ | 260 |

Example 4. Effect of pH on Antigen Binding Affinity

The effects of pH on antigen binding affinity for CHO cell-produced fully human anti-hPCSK9 mAbs was assessed as described above. The mAbs tested are fully human versions of H1H316P ("316P") (HCVR/LCVR SEQ ID NO: 90/92; CDR sequences SEQ ID NO: 76/78/80 and 84/86/88) and H1M300N ("300N") (HCVR/LCVR SEQ ID NO: 218/226; CDR sequences SEQ ID NO:220/222/224 and 228/232 and amino acid sequence LGS). hPCSK9-mmh was captured on an anti-myc mAb surface either at a high density (about 35 to 45 resonance units) (RU) or at a low density (about 5 to 14 RU). Each antibody, at 50 nM in HBST (pH 7.4 or pH 5.5) was injected over the captured hPCSK9 surface at a flow rate of 100 µl/ml for 1.5 min at 25° C. and antigen-antibody dissociation was monitored for 10 min. Control I: anti-hPCSK9 mAb SEQ ID NO:79/101 (WO 2008/063382) ($K_D$=pM; $T_{1/2}$=min).

TABLE 5

| | High hPCSK9 Density Surface | | | | Low hPCSK9 Density Surface | | | |
|---|---|---|---|---|---|---|---|---|
| | pH 7.4 | | pH 5.5 | | pH 7.4 | | pH 5.5 | |
| Antibody | $K_D$ | $T_{1/2}$ | $K_D$ | $T_{1/2}$ | $K_D$ | $T_{1/2}$ | $K_D$ | $T_{1/2}$ |
| 316P | 191 | 74 | 144 | 83 | 339 | 45 | 188 | 58 |
| 300N | 65 | 507 | 1180 | 26 | 310 | 119 | 1380 | 13 |
| Control I | 20000 | 29 | ND | ND | ND | ND | ND | ND |

The antigen binding properties of 316P and 300N at pH 7.4 or pH 5.5 were determined by a modified BIACORE™ assay as described above. Briefly, mAbs were immobilized onto BIACORE™ CM5 sensor chips via amine coupling. Varying concentrations of myc-myc-his tagged hPCSK9, mouse PCSK9 (mPCSK9, SEQ ID NO:757), hPCSK9 with a gain of function (GOF) point mutation of D374Y (hPCSK9 (D374Y), cynomolgus monkey (*Macaca fascicularis*) PCSK9 (mfPCSK9, SEQ ID NO:761) (mfPCSK9), rat (*Rattus norvegicus*) PCSK9 (rPCSK9, SEQ ID NO:763), and his-tagged Syrian golden hamster (*Mesocricetus auratus*) PCSK9 (maPCSK9, SEQ ID NO:762) (maPCSK9), ranging from 11 to 100 nM, were injected over the antibody surface at the flow rate of 100 µl/ml for 1.5 min and antigen-antibody dissociation was monitored in real time for 5 min at either 25° C. (Table 6) or 37° C. (Table 7). Control II: anti-hPCSK9 mAbs SEQ ID NO:67/12 (WO 2009/026558) (NB: no binding was observed under the experimental condition) ($K_D$=pM; $T_{1/2}$=min).

TABLE 6

| pH Effect at 25° C. | | | | |
|---|---|---|---|---|
| | pH 7.4 | | pH 5.5 | |
| Antigen | $K_D$ | $T_{1/2}$ | $K_D$ | $T_{1/2}$ |
| 316P | | | | |
| hPCSK9-mmh | 1260 | 36 | 22 | 39 |
| mPCSK9-mmh | 4460 | 10 | 63 | 11 |
| hPCSK9(D347Y)-mmh | 2490 | 15 | 166 | 13 |
| mfPCSK9-mmh | 1420 | 42 | 8 | 23 |
| maPCSK9-h | 8350 | 8 | 87 | 8 |
| rPCSK9-mmh | 24100 | 2 | 349 | 5 |
| 300N | | | | |
| hPCSK9-mmh | 1100 | 76 | 3100 | 5 |
| mPCSK9-mmh | NB | NB | NB | NB |
| hPCSK9(D347Y)-mmh | 1310 | 46 | 9030 | 3 |
| mfPCSK9-mmh | 2170 | 31 | 38500 | 0.4 |
| maPCSK9-h | NB | NB | NB | NB |
| rPCSK9-mmh | NB | NB | NB | NB |
| Control I | | | | |
| hPCSK9-mmh | 33100 | 14 | 1740 | 31 |
| mPCSK9-mmh | NB | NB | NB | NB |
| hPCSK9(D347Y)-mmh | 71000 | 11 | 7320 | 30 |

TABLE 6-continued pH Effect at 25° C.

| | pH 7.4 | | pH 5.5 | |
|---|---|---|---|---|
| Antigen | $K_D$ | $T_{1/2}$ | $K_D$ | $T_{1/2}$ |
| mfPCSK9-mmh | 362000 | 0.2 | 67200 | 3 |
| maPCSK9-h | NB | NB | NB | NB |
| rPCSK9-mmh | NB | NB | NB | NB |
| Control II | | | | |
| hPCSK9-mmh | 143 | 266 | 2 | 212 |
| mPCSK9-mmh | 3500 | 11 | 33 | 12 |
| hPCSK9(D347Y)-mmh | 191 | 155 | 49 | 56 |
| mfPCSK9-mmh | 102 | 262 | 12 | 63 |
| maPCSK9-h | 6500 | 3 | ND | ND |
| rPCSK9-mmh | 22400 | 2 | 106 | 5 |

TABLE 7 pH Effect at 37° C.

| | pH 7.4 | | pH 5.5 | |
|---|---|---|---|---|
| Antigen | $K_D$ | $T_{1/2}$ | $K_D$ | $T_{1/2}$ |
| 316P | | | | |
| hPCSK9-mmh | 4000 | 9 | 142 | 11 |
| mPCSK9-mmh | 12200 | 3 | 13600 | 3 |
| hPCSK9(D347Y)-mmh | 6660 | 4 | 1560 | 5 |
| mfPCSK9-mmh | 3770 | 11 | 44 | 5 |
| maPCSK9-h | 21700 | 2 | ND | ND |
| rPCSK9-mmh | 55100 | 2 | 399 | 1 |
| 300N | | | | |
| hPCSK9-mmh | 2470 | 20 | 11900 | 1 |
| mPCSK9-mmh | NB | NB | NB | NB |
| hPCSK9(D347Y)-mmh | 2610 | 14 | 28000 | 1 |
| mfPCSK9-mmh | 4810 | 8 | 65200 | 0.1 |
| maPCSK9-h | NB | NB | NB | NB |
| rPCSK9-mmh | NB | NB | NB | NB |
| Control I | | | | |
| hPCSK9-mmh | 45900 | 0.1 | 11300 | 3 |
| mPCSK9-mmh | NB | NB | NB | NB |
| hPCSK9(D347Y)-mmh | 169000 | 0.4 | 27000 | 3 |
| mfPCSK9-mmh | 500000 | 0.6 | 5360 | 0.3 |
| maPCSK9-h | NB | NB | NB | NB |
| rPCSK9 | NB | NB | NB | NB |
| Control II | | | | |
| hPCSK9-mmh | 284 | 87 | 20 | 44 |
| mPCSK9-mmh | 8680 | 3 | 89 | 3 |
| hPCSK9(D347Y)-mmh | 251 | 57 | 483 | 26 |
| mfPCSK9-mmh | 180 | 127 | 214 | 65 |
| maPCSK9-h | 8830 | 0.5 | ND | ND |
| rPCSK9p-mmh | 30200 | 1 | 233 | 1 |

Example 5. Anti-hPCSK9 mAbs Binding to hPCSK9 with Point Mutation D374Y

The binding affinity of selected anti-hPCSK9 mAbs to hPCSK9 with a gain of function (GOF) point mutation of D374Y (hPCSK9(D374Y)-mmh) was determined as described above. Each antibody was captured at a flowrate of 40 μl/min for 8-30 sec on a goat anti-human IgG polyclonal antibody surface created through direct chemical coupling to a BIACORE™ chip to form a captured antibody surface. hPCSK9(D374Y)-mmh at varying concentrations of 1.78 nM to 100 nM was injected over the captured antibody surface at a flowrate of 50 μl/min for 5 min, and the dissociation of hPCSK9(D374Y)-mmh and antibody was monitored for 15 min at 25° C. Control III: anti-hPCSK9 mAbs SEQ ID NO:49/23 (WO 2009/026558) ($K_D$=pM; $T_{1/2}$=min).

TABLE 8

| Antibody | $K_D$ | $T_{1/2}$ |
|---|---|---|
| 316P | 1780 | 14 |
| 300N | 1060 | 49 |
| Control I | 23600 | 25 |
| Control II | 66 | 216 |
| Control III | 1020 | 126 |

Example 6. Binding Specificity of Anti-hPCSK9 mAbs 316P, 300N, and Control I anti-hPCSK9 mAbs were captured on an amine-coupled anti-hFc CM5 chip on BIACORE™2000. Tagged (myc-myc-his) human PCSK9, human PCSK1 (hPCSK1) (SEQ ID NO:759), human PCSK7 (hPCSK7) (SEQ ID NO:760), or mouse PCSK9 were injected (100 nM) over the captured mAb surface and allowed to bind at 25° C. for 5 min. Changes in RU were recorded. Results: 300N and Control I bound only to hPCSK9, and 316P bound both hPCSK9 and mPCSK9.

The binding specificities of anti-hPCSK9 mAbs were determined by ELISA. Briefly, anti-hPCSK9 antibody was coated on a 96-well plate. Human PCSK9-mmh, mPCSK9-mmh, maPCSK9-h, hPCSK1-mmh, or hPCSK7-mmh, at 1.2 nM, were added to antibody-coated plates and incubated at RT for 1 hr. Plate-bound PCSK protein was then detected by HRP-conjugated anti-His antibody. Results show that 316P binds human, mouse, and hamster PCSK9, whereas 300N and Control I only bound hPCSK9. None of the anti-hPCSK9 mAbs exhibited significant binding to hPCSK1 or hPCSK7.

Example 7. Cross-Reactivity of Anti-h PCSK9 mAbs

Cross-reactivity of anti-hPCSK9 mAbs with mmPCSK9, mfPCSK9, mPCSK9, maPCSK9, or rPCSK9 was determined using BIACORE™3000. Briefly, anti-hPCSK9 mAbs were captured on an anti-hFc surface created through direct chemical coupling to a BIACORE™ chip. Purified tagged hPCSK9, hPCSK9(D374Y), mmPCSK9, mfPCSK9, mPCSK9, maPCSK9, or rPCSK9, each at 1.56 nM to 50 nM, was injected over the antibody surface at either 25° C. or 37° C. Binding between 316P, 300N, Control I, Control II, or Control III and the PCSK9 proteins was determined ($K_D$=pM; $T_{1/2}$=min) (ND=not determined).

TABLE 9

316P mAb

| | 37° C. | | 25° C. | |
|---|---|---|---|---|
| Antigen | $K_D$ | $T_{1/2}$ | $K_D$ | $T_{1/2}$ |
| hPCSK9-mmh | 1800 | 9 | 580 | 36 |
| hPCSK9(D374Y)-mmh | 4200 | 4 | 1690 | 15 |
| mmPCSK9-mmh | 1800 | 21 | 550 | 92 |
| mfPCSK9-mmh | 1800 | 11 | 520 | 60 |
| mPCSK9-mmh | 4700 | 3 | 2300 | 11 |
| maPCSK9-h | 19000 | 1 | 6810 | 5 |
| rPCSK9-mmh | 37500 | 1 | 14500 | 2 |

TABLE 10

300N mAb

| | 37° C. | | 25° C. | |
|---|---|---|---|---|
| Antigen | $K_D$ | $T_{1/2}$ | $K_D$ | $T_{1/2}$ |
| hPCSK9-mmh | 2400 | 22 | 740 | 110 |
| hPCSK9(D374Y)-mmh | 2200 | 14 | 900 | 65 |
| mmPCSK9-mmh | 1600 | 26 | 610 | 79 |
| mfPCSK9-mmh | 3800 | 11 | 1500 | 45 |
| mPCSK9-mmh | NB | NB | NB | NB |
| maPCSK9-h | NB | NB | NB | NB |
| rPCSK9-mmh | NB | NB | NB | NB |

TABLE 11

Control I mAb

| | 37° C. | | 25° C. | |
|---|---|---|---|---|
| Antigen | $K_D$ | $T_{1/2}$ | $K_D$ | $T_{1/2}$ |
| hPCSK9-mmh | 226000 | 2 | 27500 | 16 |
| hPCSK9(D374Y)-mmh | ND | ND | 23600 | 25 |
| mmPCSK9-mmh | 420000 | 3 | 291000 | 2 |
| mfPCSK9-mmh | 14300 | 10 | 24900 | 14 |
| mPCSK9-mmh | NB | NB | NB | NB |
| maPCSK9-h | NB | NB | NB | NB |
| rPCSK9-mmh | NB | NB | NB | NB |

TABLE 12

Control II mAb

| | 37° C. | | 25° C. | |
|---|---|---|---|---|
| Antigen | $K_D$ | $T_{1/2}$ | $K_D$ | $T_{1/2}$ |
| hPCSK9-mmh | 91 | 162 | 61 | 372 |
| hPCSK9(D374Y)-mmh | 93 | 90 | 66 | 216 |
| mfPCSK9-mmh | 33 | 252 | 26 | 546 |
| mPCSK9-mmh | 4700 | 3 | 2300 | 11 |
| maPCSK9-h | 60800 | 0.4 | 25000 | 2 |
| rPCSK9-mmh | 14100 | 1 | 6900 | 3 |

TABLE 13

Control III mAb

| | 37° C. | | 25° C. | |
|---|---|---|---|---|
| Antigen | $K_D$ | $T_{1/2}$ | $K_D$ | $T_{1/2}$ |
| hPCSK9-mmh | 380 | 378 | 490 | 450 |
| hPCSK9(D374Y)-mmh | 130 | 660 | 1000 | 126 |
| mfPCSK9-mmh | 110 | 750 | 340 | 396 |
| mPCSK9-mmh | 33500 | 1 | 10900 | 4 |
| maPCSK9-h | 780 | 107 | 2100 | 67 |
| rPCSK9-mmh | NB | NB | 33200 | 2 |

Example 8. Inhibition of Binding Between hPCSK9 and hLDLR Domains

The ability of selected anti-hPCSK9 mAbs to block hPCSK9 binding to human LDLR full-length extracellular domain (hLDLR-ecto SEQ ID NO:758), hLDLR EGF-A domain (amino acids 313-355 of SED ID NO:758), or hLDLR EGF-AB domains (amino acids of 314-393 of SEQ ID NO:758) (LDLR Genbank number NM_000527) was evaluated using BIACORE™ 3000. Briefly, hLDLR-ecto, EGF-A-hFc, or EGF-AB-hFc protein was amine-coupled on a CM5 chip to create a receptor or receptor fragment surface. Selected anti-hPCSK9 mAbs, at 62.5 nM (2.5 fold excess over antigen), were premixed with 25 nM of hPCSK9-mmh, followed by 40 min incubation at 25° C. to allow antibody-antigen binding to reach equilibrium to form equilibrated solutions. The equilibrated solutions were injected over the receptor or receptor fragment surfaces at 2 µl/min for 40 min at 25° C. Changes in RU due to the binding of the anti-hPCSK9 mAbs to hLDLR-ecto, EGF-A-hFc, or EGF-AB-hFc were determined. Results show that H1H316P and H1M300N blocked the binding of hPCSK9-mmh to hLDLR-ecto, hLDLR EGF-A domain, and hLDLR EGF-AB domains; H1H320P blocked the binding of hPCSK9-mmh to hLDLR-ecto and hLDLR EGF-A domain; and H1H321P blocked the binding of hPCSK9-mmh to hLDLR EGF-A domain.

The ability of the mAbs to block hPCSK9 binding to hLDLR-ecto, hLDLR EGF-A domain, or hLDLR EGF-AB domains was also evaluated with an ELISA-based immunoassay. Briefly, hLDLR-ecto, hLDLR EGF-A-hFc or hLDLR EGF-AB-hFc, each at 2 µg/ml, was coated on a 96-well plate in PBS buffer overnight at 4° C., and nonspecific binding sites blocked with BSA. This plate was used to measure free hPCSK9-mmh in a PCSK9-mmh solution pre-equilibrated with varying concentrations of anti-hPCSK9 mAbs. A constant amount of hPCSK9-mmh (500 pM) was pre-mixed with varied amounts of antibody, ranging from 0 to ~50 nM in serial dilutions, followed by 1 hr incubation at room temperature (RT) to allow antibody-antigen binding to reach equilibrium. The equilibrated sample solutions were transferred to receptor or receptor fragment coated plates. After 1 hour of binding, the plates were washed and bound hPCSK9-mmh detected using HRP conjugated anti-myc antibody. $IC_{50}$ values (in pM) were determined as the amount of antibody required to achieve 50% reduction of hPCSK9-mmh bound to the plate-coated receptor or receptor fragment. The results show that specific mAbs functionally block PCSK9 from binding the three receptors at both neutral pH (7.2) and acidic pH (5.5).

TABLE 14

| | pH 7.2 | | | pH 5.5 | | |
|---|---|---|---|---|---|---|
| | Plate Coating Surface | | | | | |
| Ab | hLDLR-ecto | EGF-A | EGF-AB | hLDLR-ecto | EGF-A | EGF-AB |
| 316P | <125 | <125 | <125 | <125 | <125 | <125 |
| 300N | 144 | 146 | <125 | 1492 | 538 | 447 |
| Control I | — | >100,000 | >100,000 | — | >100,000 | >100,000 |
| Control II | 288 | 510 | 274 | 411 | 528 | 508 |
| Control III | 303 | 635 | 391 | 742 | 787 | 1073 |

The ability of the mAbs to block hPCSK9 GOF mutant hPCSK9(D374Y)-mmh binding to hLDLR EGF-A domain or hLDLR EGF-AB domain ($IC_{50}$ values in pM) was also evaluated with the ELISA-based immunoassay described above using a constant amount of 0.05 nM hPCSK9 (D374Y)-mmh.

TABLE 15

| | pH 7.2 | | pH 5.5 | |
| --- | --- | --- | --- | --- |
| | Plate Coating Surface | | | |
| | EGF-A | EGF-AB | EGF-A | EGF-AB |
| 316P | 203 | 139 | 1123 | 1139 |
| 300N | 135 | 142 | 3463 | 3935 |
| Control I | >100,000 | >100,000 | >100,000 | >100,000 |
| Control II | 72 | 57 | 129 | 118 |
| Control III | 537 | 427 | 803 | 692 |

The ability of the mAbs to block either mmPCSK9 or mPCSK9 binding to hLDLR-ecto domain, hLDLR EGF-A domain, or hLDLR EGF-AB domain ($IC_{50}$ values in pM) was evaluated at neutral pH (7.2) with the ELISA-based immunoassay describe above using a constant amount of 1 nM of mmh-tagged mmPCSK9 or 1 nM of mPCSK9.

TABLE 16

| | 1 nM mmPCSK9-mmh | | | 1 nM mPCSK9-mmh | |
| --- | --- | --- | --- | --- | --- |
| | hLDLR-ecto | EGF-A | EGF-AB | EGF-A | EGF-AB |
| 316P | <250 | <250 | <250 | <250 | <250 |
| 300N | 255 | 256 | 290 | >33000 | >33000 |

The ability of the mAbs to block hPCSK9, mmPCSK9, rPCSK9, maPCSK9, mfPCSK9, or mPCSK9 binding to hLDLR EGF-A domain ($IC_{50}$ values in pM) was evaluated at neutral pH (7.2) (Table 17) acidic pH (5.5, Table 18) with the ELISA-based immunoassay described above using a constant amount of 0.5 nM of hPCSK9-mmh, 1 nM of mmPCSK9-mmh, 1 nM of rPCSK9-mmh, 1 nM of maPCSK9-h, 0.3 nM of mfPCSK9-mmh, or 1 nM of mPCSK9-mmh.

TABLE 17

| | hPCSK9 | mmPCSK9 | rPCSK9 | maPCSK9 | mfPCSK9 | mPCSK9 |
| --- | --- | --- | --- | --- | --- | --- |
| 316P | <125 | <250 | 2662 | 349 | 75 | 305 |
| 300N | 182 | 460 | >100000 | >100000 | 473 | >100000 |
| Control I | — | >100000 | >100000 | >100000 | >100000 | >100000 |
| Control II | 146 | 83 | 2572 | 2038 | 361 | 855 |
| Control III | 249 | 293 | >100000 | 245 | 572 | >100000 |

TABLE 18

| | hPCSK9 | mmPCSK9 | rPCSK9 | maPCSK9 | mPCSK9 |
| --- | --- | --- | --- | --- | --- |
| 316P | <125 | <250 | 42880 | 1299 | 991 |
| 300N | 223 | 3704 | >100000 | >100000 | >100000 |
| Control I | >10000 | >100000 | >100000 | >100000 | >100000 |
| Control II | 154 | <250 | 11640 | 8339 | 2826 |
| Control III | 390 | 376 | >100000 | 414 | >100000 |

The ability of 316P and Control I to block hPCSK9 binding to hLDLR was also determined. Briefly, either recombinant hLDLR or hLDLR-EGFA-mFc was immobilized onto BIACORE™ CM5 chips via amine coupling. An antigen-antibody mixture of 100 nM hPCSK9-mmh and 316P, Control I mAb, or a non-hPCSK9 specific mAb (each at 250 nM) was incubated at RT for 1 hr, and then injected over the hLDLR or hLDLR-EGFA surface at the flow rate of 10 µl/ml for 15 min at 25° C. Changes in RU due to the binding between the free hPCSK9-mmh in the mixture to either hLDLR or hLDLR-EGFA were recorded. The binding of hPCSK9 to either hLDLR or hLDLR-EGFA was completely blocked by 316P and 300N but not by Control I mAb.

Example 9. Epitope Mapping

In order to determine epitope-binding specificity, three chimeric PCSK9-mmh proteins were generated in which specific human PCSK9 domains were substituted with mouse PCSK9 domains. Chimeric protein #1 consists of a mouse PCSK9 pro-domain (amino acid residues 1-155 of SEQ ID NO:757) followed by a human PCSK9 catalytic domain (residues 153-425 of SEQ ID NO:755) and a mouse PCSK9 C-terminal domain (residues 429-694 SEQ ID NO:757) (mPro-hCat-mC-term-mmh). Chimeric protein #2 consists of a human PCSK9 pro-domain (residues 1-152 of SEQ ID NO:755) followed by a mouse PCSK9 catalytic domain (residues 156-428 of SEQ ID NO:757) and a mouse PCSK9 C-terminal (hPro-mCat-mC-term-mmh). Chimeric protein #3 consists of mouse PCSK9 pro-domain and a mouse PCSK9 catalytic domain followed by a human PCSK9 C-terminal domain (residues 426-692 of SEQ ID NO:755) (mPro-mCat-hC-term-mmh). In addition, hPCSK9 with a point mutation of D374Y (hPCSK9 (D374Y)-mmh) was generated.

Binding specificity of mAbs to test proteins hPCSK9-mmh, mouse PCSK9-mmh, chimeric proteins #1, #2, and #3, and hPCSK9 (D374Y)-mmh were tested as follows: the mAbs were coated on a 96-well plate overnight at 4° C., then each test protein (1.2 nM) was added to the plate. After 1 hr binding at RT, the plate was washed and bound test protein detected using HRP-conjugated anti-myc polyclonal antibody (++=OD>1.0; +=OD 0.4-1.0; −=OD<0.4).

TABLE 19

| | | | Chimeric Protein | | | |
| --- | --- | --- | --- | --- | --- | --- |
| Antibody | hPCSK9 | mPCSK9 | #1 | #2 | #3 | hPCSK9(D374Y) |
| H1M300 | ++ | − | ++ | + | − | ++ |
| H1M309 | ++ | − | − | − | ++ | ++ |
| H1M312 | ++ | − | − | − | ++ | ++ |
| H1M492 | ++ | − | − | − | − | + |
| H1M493 | ++ | − | − | − | ++ | ++ |
| H1M494 | ++ | − | − | + | ++ | ++ |
| H1M495 | ++ | − | − | − | ++ | ++ |
| H1M496 | ++ | − | − | − | ++ | ++ |
| H1M497 | ++ | − | − | ++ | + | ++ |
| H1M498 | ++ | − | − | − | + | ++ |
| H1M499 | ++ | − | − | − | ++ | ++ |
| H1M500 | ++ | − | ++ | − | − | ++ |
| H1M502 | ++ | − | − | − | ++ | ++ |
| H1M503 | ++ | − | − | ++ | − | ++ |
| H1M504 | ++ | − | − | − | − | + |
| H1M505 | ++ | − | ++ | + | − | ++ |
| H1M508 | ++ | − | − | − | ++ | ++ |
| H1H318P | ++ | − | ++ | − | − | ++ |
| H1H334P | ++ | − | ++ | − | − | ++ |
| H1H316P | ++ | ++ | ++ | ++ | ++ | ++ |
| H1H320P | ++ | − | − | ++ | − | ++ |
| Control I | ++ | − | − | − | ++ | ++ |

Binding specificity of 316P, 300N and control anti-hPCSK9 mAbs to hPCSK9-mmh, mPCSK9-mmh, mmPCSK9-mmh, mfPCSK9-mmh, rPCSK9-mmh, chimeric proteins #1, #2, and #3, and hPCSK9 (D374Y)-mmh were tested as described above except that the protein concentration is 1.7 nM (−=OD<0.7; +=OD 0.7-1.5; ++=OD>1.5).

TABLE 20

|  | 316P | 300N | Control I | Control II | Control III |
|---|---|---|---|---|---|
| hPCSK9-mmh | ++ | ++ | ++ | ++ | ++ |
| mPCSK9-mmh | ++ | − | − | ++ | ++ |
| mmPCSK9-mmh | ++ | ++ | ++ | ++ | ++ |
| mfPCSK9-mmh | ++ | ++ | ++ | ++ | ++ |
| rPCSK9-mmh | ++ | − | − | ++ | + |
| Chimeric Protein #1 | ++ | ++ | − | ++ | ++ |
| Chimeric Protein #2 | ++ | ++ | − | ++ | ++ |
| Chimeric Protein #3 | ++ | + | ++ | ++ | ++ |
| hPCSK9 (D374Y) | ++ | ++ | ++ | ++ | ++ |

Similar results for selected mAbs were obtained by BIA-CORE™ binding assay. Briefly, 316P, 300N, or Control I mAb was captured on an amine-coupled anti-hFc CM5 chip and 100 nM of each protein injected over the mAb-captured surface. Changes in RU due to the binding of each protein to the mAb surface was determined.

TABLE 21

| Antibody | hPCSK9 | mPCSK9 | Chimeric Protein #1 | Chimeric Protein #2 | Chimeric Protein #3 |
|---|---|---|---|---|---|
| 316P | 500 | 505 | 529 | 451 | 467 |
| 300N | 320 | 13 | 243 | 76 | 10 |
| Control I | 65 | 7 | 4 | 3 | 69 |

To further assess the binding specificity of 316P, which cross-reacts with mPCSK9-mmh, a cross-competition ELISA assay was developed to determine binding domain specificity. Briefly, mAbs specific for chimeric protein #1, #2, or #3, were first coated on a 96-well plate overnight at 1 µg/ml. Human PCSK9-mmh (2 µg/ml) was then added to each well followed by 1 hr incubation at RT. 316P (1 µg/ml) was added and incubated for another hour at RT. Plate-bound 316P was detected using HRP-conjugated anti-hFc polyclonal antibody. Although 316P binding to hPCSK9-mmh was not affected by the presence of mAbs specific for either chimeric protein #2 or chimeric protein #3, 316P binding to hPCSK9-mmh was greatly reduced by the presence of antibody specific for chimeric protein #1.

Example 10. BIACORE™-Based Antigen Binding Profile Assessment

Antibody binding profiles were also established for 316P, 300N, Control I, II, and III mAbs using BIACORE™1000. Briefly, hPCSK9-mmh was captured on an anti-myc surface. A first anti-hPCSK9 mAb (50 µg/ml) was injected over the PCSK9-bound surface for 10 min, at a flow rate of 10 µl/min at 25° C. A second anti-hPCSK9 mAb (50 µg/ml) was then injected over the first mAb-bound surface for 10 min, at a flow rate of 10 µl/min at 25° C. Ability of the first mAb to block binding of the second mAb was measured and is expressed as percent inhibition.

TABLE 22

| First mAb | Second mAb | | | | |
|---|---|---|---|---|---|
|  | 316P | 300N | Control I | Control II | Control III |
| 316P | 100 | 101 | 27 | 99 | 101 |
| 300N | 77 | 100 | 12 | 82 | −2 |
| Control I | 6 | 12 | 100 | 6 | 9 |
| Control II | 91 | 102 | −6 | 100 | 3 |
| Control III | 73 | 10 | −12 | 1 | 100 |

Example 11. Increase of LDL Uptake by Anti-hPCSK9 Antibodies

The ability of anti-hPCSK9 mAbs to increase LDL uptake in vitro was determined using a human hepatocellular liver carcinoma cell line (HepG2). HepG2 cells were seeded onto 96-well plates at $9 \times 10^4$ cells/well in DMEM complete media and incubated at 37° C., 5% CO2, for 6 hr to form HepG2 monolayers. Human PCSK9-mmh, at 50 nM in lipoprotein deficient medium (LPDS), and a test mAb was added in various concentrations from 500 nM to 0.98 nM in LPDS medium. Data are expressed as $IC_{50}$ values for each experiment ($IC_{50}$=antibody concentration at which increases LDL uptake by 50%). In addition, the experiment also showed that both 316P and 300N were able to completely reverse the inhibitory effect of hPCSK9 on LDL uptake, while Control I mAb or H1M508 anti-hPCSK9 mAb reversed the inhibitory effect by about 50%.

TABLE 23

| Antibody | $IC_{50}$ (nM) |
|---|---|
| 316P | 21.30 |
| 300N | 22.12 |
| Control I | >250 |
| H1M508 | >250 |

The ability of anti-hPCSK9 mAbs to reverse the inhibitory effect on LDL uptake by PCSK9 protein from different mammalian species was also tested in a HepG2 cell line as described above. Briefly, HepG2 cells were incubated overnight with serial dilutions of antibody in LPDS medium (beginning with 500 nM) and 50 nM of hPCSK9-mmh, mfPCSK9-mmh, mPCSK9-mmh, rPCSK9-mmh, or maPCSK9-h. HepG2 cells were also incubated overnight with serial dilutions of antibody in LPDS (beginning with 50 nM) and 1 nM hPCSK9(D374Y). As shown in Table 24, while 316P was able to completely reverse the inhibitory effect on LDL by all PCSK9 proteins tested, 300N was only able to reverse the inhibitory effect on LDL uptake by hPCSK9, hPCSK9 (D374Y), and mfPCSK9. Values are expressed as nM $IC_{50}$.

TABLE 24

|  | 316P | 300N | Control I | Control II | Control III |
|---|---|---|---|---|---|
| hPCSK9-mmh | 14.1 | 12.6 | >500 | 13.4 | 12.4 |
| hPCSK9(D374Y)-mmh | 2.1 | 1.1 | >50 | 0.7 | 0.6 |
| mfPCSK9-mmh | 14.7 | 13.4 | >500 | 14.2 | 13.6 |
| mPCSK9-mmh | 21.2 | >500 | >500 | 19 | >500 |
| rPCSK9-mmh | 27.7 | >500 | >500 | 21.9 | >500 |
| maPCSK9-h | 14.4 | >500 | >500 | 29.5 | 12.7 |

Example 12. Neutralization of Biological Effect of hPCSK9 In Vivo

To assess the biological effect of neutralizing PCSK9, hPCSK9 was over-expressed in C57BL/6 mice by hydrodynamic delivery (HDD) of DNA constructs encoding full-length hPCSK9-mmh. 4 mice (C57BL/6) were injected with empty vector/saline (control), and 16 mice were injected with a 50 µg hPCSK9-mmh-DNA/saline mixture in the tail vein equal to 10% of their body weight. At day 7 after HDD, delivery of hPCSK9 resulted in a 1.6-fold elevation of total cholesterol, 3.4-fold elevation in LDL-cholesterol (LDL-C) and a 1.9-fold elevation in non-HDL cholesterol (relative to control). Serum hPCSK9 levels on day 7 were all greater than 1 µg/ml, as assessed by quantitative ELISA.

Administration of H1M300N on day 6 after HDD to 3 experimental groups (1, 5 or 10 mg/kg) (n=4 per group) via intraperitoneal (i.p.) injection resulted in a significant attenuation of serum cholesterol levels. At 18 hours after administration, total cholesterol was reduced by 9.8%, 26.3% and 26.8%, LDL-C was reduced by 5.1%, 52.3% and 56.7%, and non-HDL cholesterol was reduced by 7.4%, 33.8% and 28.6% in the 1, 5 or 10 mg/kg H1M300N treated groups, respectively.

Example 13. Pharmacokinetic and Serum Chemistry Study in Monkeys

A pharmacokinetic (PK) study was conducted in naïve male cynomolgus monkeys (*Macaca fascicularis*) with a body weight range between 5-7 kg and aged between 3-5 years.

Group assignments. The monkeys were assigned into 5 treatment groups: Treatment Group 1 (n=3) received control buffer (10 mM sodium phosphate, pH 6, 1 ml/kg); Treatment Group 2 (n=3) received 1 ml/kg of 316P (5 mg/ml); Treatment Group 3 (n=3) received 1 ml/kg 300N (5 mg/ml); Treatment Group 4 (n=3) received 1 ml/kg 316P (15 mg/ml); and Treatment Group 5 (n=3) received 1 ml/kg 300N (15 mg/ml). All treatments were administered by IV bolus followed by a 1 ml saline flush. Total dose volume (ml) was calculated on the most recent body weight (each animal was weighed twice during acclimation and once weekly throughout the study). A single dose of test mAb or buffer control was administered on Day 1.

Animal care. Animals were housed in a temperature- and humidity-monitored environment. The targeted range of temperature and relative humidity was between 18-29° C. and 30-70%, respectively. An automatic lighting system provided a 12-hour diurnal cycle. The dark cycle could be interrupted for study- or facility-related activities. The animals were individually housed in cages that comply with the Animal Welfare Act and recommendations set forth in The Guide for the Care and Use of Laboratory Animals (National Research Council 1996).

Diet and Feeding. Animals were fed twice per day according to SNBL USA SOPs. Animals were fasted when required by specific procedures (e.g., prior to blood draws for serum chemistry, urine collection, or when procedures involving sedation are performed). The diet was routinely analyzed for contaminants and found to be within manufacturer's specifications. No contaminants were expected to be present at levels that would interfere with the outcome of the study.

Experimental Design. An appropriate number of animals were selected from SNBL USA stock. Animals were examined for health by veterinary staff, and had undergone serum chemistry, hematology, and coagulation screening. Sixteen males, confirmed healthy, were assigned to the study. Fifteen males were assigned to specific study groups and the remaining animal was available as a spare. A stratified randomization scheme incorporating serum cholesterol level (based on the average of two draws in acclimation) was used to assign animals to study groups.

Acclimation Period. Previously quarantined animals were acclimated to the study room for a minimum of 14 days prior to initiation of dosing. Acclimation phase data was collected from all animals, including the spare. All animals were assessed for behavioral abnormalities that could affect performance on study. The spare animal was returned to stock after day 1.

Blood collection. Blood was collected by venipuncture from a peripheral vein from restrained, conscious animals. Whenever possible, blood was collected via a single draw and then divided appropriately.

PK Study. Blood samples (1.5 ml) were collected at pre-dose, 2 min, 15, min, 30 min, 1 hr, 2 hr, 4 hr, 8 hr, 12 hr, 24 hr, and subsequently once every 24 hr in serum separator tubes (SST). Specimen storage serum is transferred to 2 vials and stored at −60° C. or below.

Serum samples were analyzed using an optimized ELISA (enzyme-linked immunosorbant assay) procedure. Briefly, a microtiter plate was first coated with hPCSK9-mmh. Test mAb 316P or 300N was then captured on the hPCSK9-mmh plate. The captured 316P or 300N was detected using a biotinylated mouse anti-hIgG4 followed by binding to NeutrAvidin-HRP. Varying concentrations of 316P or 300N, ranging from 100 to 1.56 ng/ml, were used as standards. One percent monkey serum (assay matrix) in the absence of 316P or 300N was used as the zero (0 ng/ml) standard. The results, shown in FIG. 2, indicate a dose-dependent increase in serum 316P and 300N levels. PK parameters were analyzed using WinNonlin software (Noncompartmental analysis, Model 201-IV bolus administration).

TABLE 25

| | 316P | | 300N | |
|---|---|---|---|---|
| PK Parameter | 5 mg/kg | 15 mg/kg | 5 mg/kg | 15 mg/kg |
| $T_{max}$ (h) | 0.428 | 0.105 | 4.02 | 0.428 |
| $C_{max}$ (µg/ml) | 184 | 527 | 226 | 1223 |
| $T_{1/2}$ (h) | 83 | 184 | 215 | 366 |

Serum Chemistry. Blood samples were collected at pre-dose, 12 hr, 48 hr, and subsequently once every 48 hr, for clinical chemistry analysis, in particular lipid profiles (i.e. cholesterol, LDL-C, HDL-C, triglycerides). With the exception of the 12 hr post-dose sample, all animals were subject to an overnight fast prior to sample collection. The sample volume was approximately 1 ml. Chemistry parameters were determined using an Olympus automated analyzer. Parameters measured (Xybion code): Albumin (ALB); Alkaline Phosphatase (ALP); Alanine Aminotransferase (ALT); Aspartate Transaminase (AST); Total Bilirubin (TBIL); Calcium (Ca); Total Cholesterol (TCho); Creatine Kinase (CK); Creatinine (CRN); Gamma Glutamyltransaminase (GGT); Glucose (GLU); Inorganic Phosphorus (IP); Total Protein (TP); Triglyceride (TRIG); Blood Urea Nitrogen (BUN); Globulin (GLOB); Albumin/Globulin Ratio (NG); Chloride (CI); Potassium (K); Sodium (Na); LDL and HDL cholesterol. Residual serum was stored at −20° C. or below and disposed of no sooner than one week after analysis.

Results from samples through Day 105 post-dose time point are shown in FIGS. 3-7. There was a reduction in total cholesterol and LDL-C in animals receiving 316P and 300N, regardless of dose, within 24 hours of the first dose. Serum total cholesterol reduced rapidly and robustly (~35%, FIG. 3). A robust decrease of ~80% was seen in LDL-C(FIGS.

Figure 6:
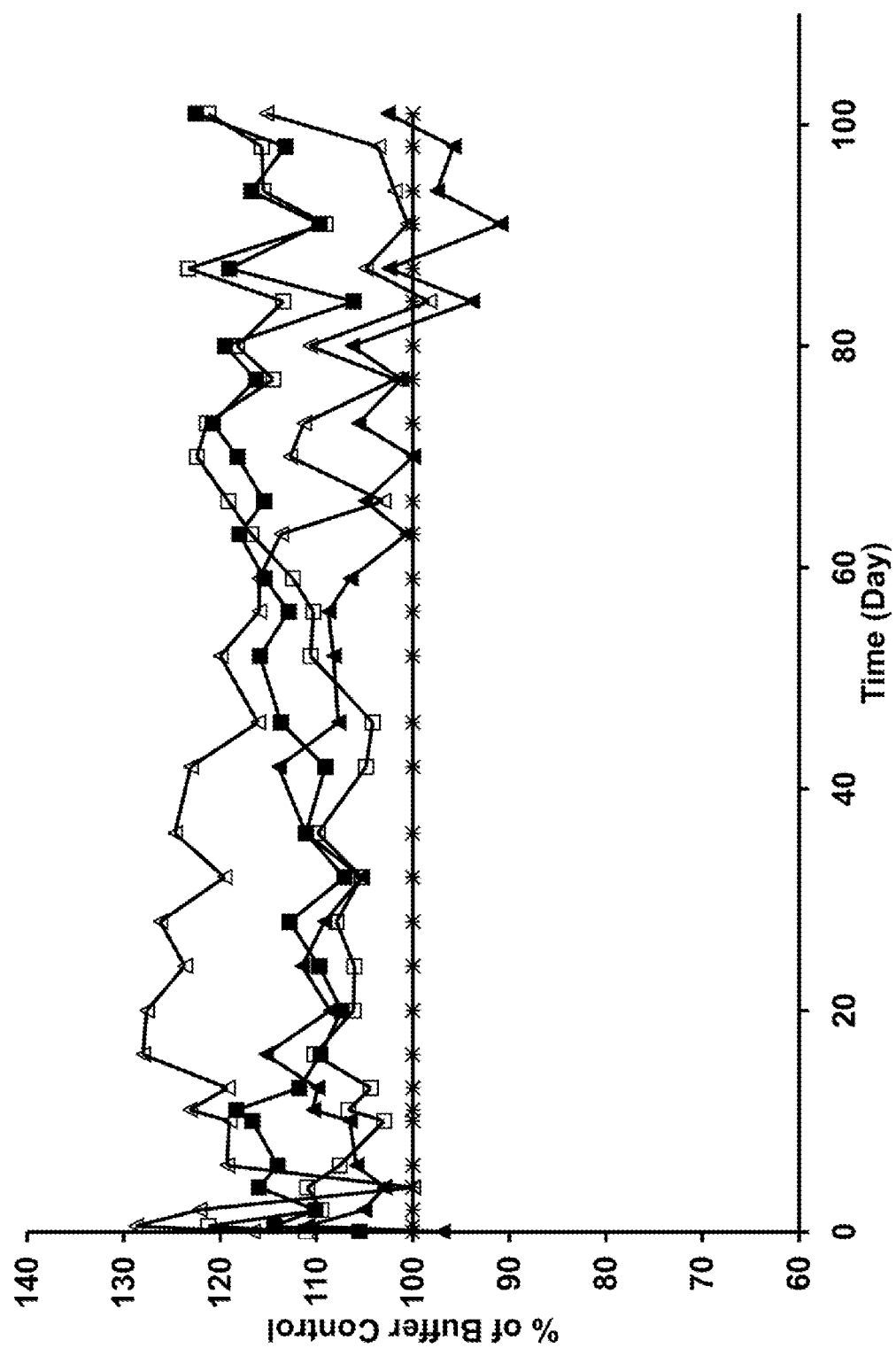
FIG. 6. Serum HDL cholesterol level as a percentage of change over buffer control. Buffer control (✱); 316P 5 mg/kg (■); 300N 5 mg/kg (▲); 316P 15 mg/kg (□); 300N 15 mg/kg (△).
Figure 7:
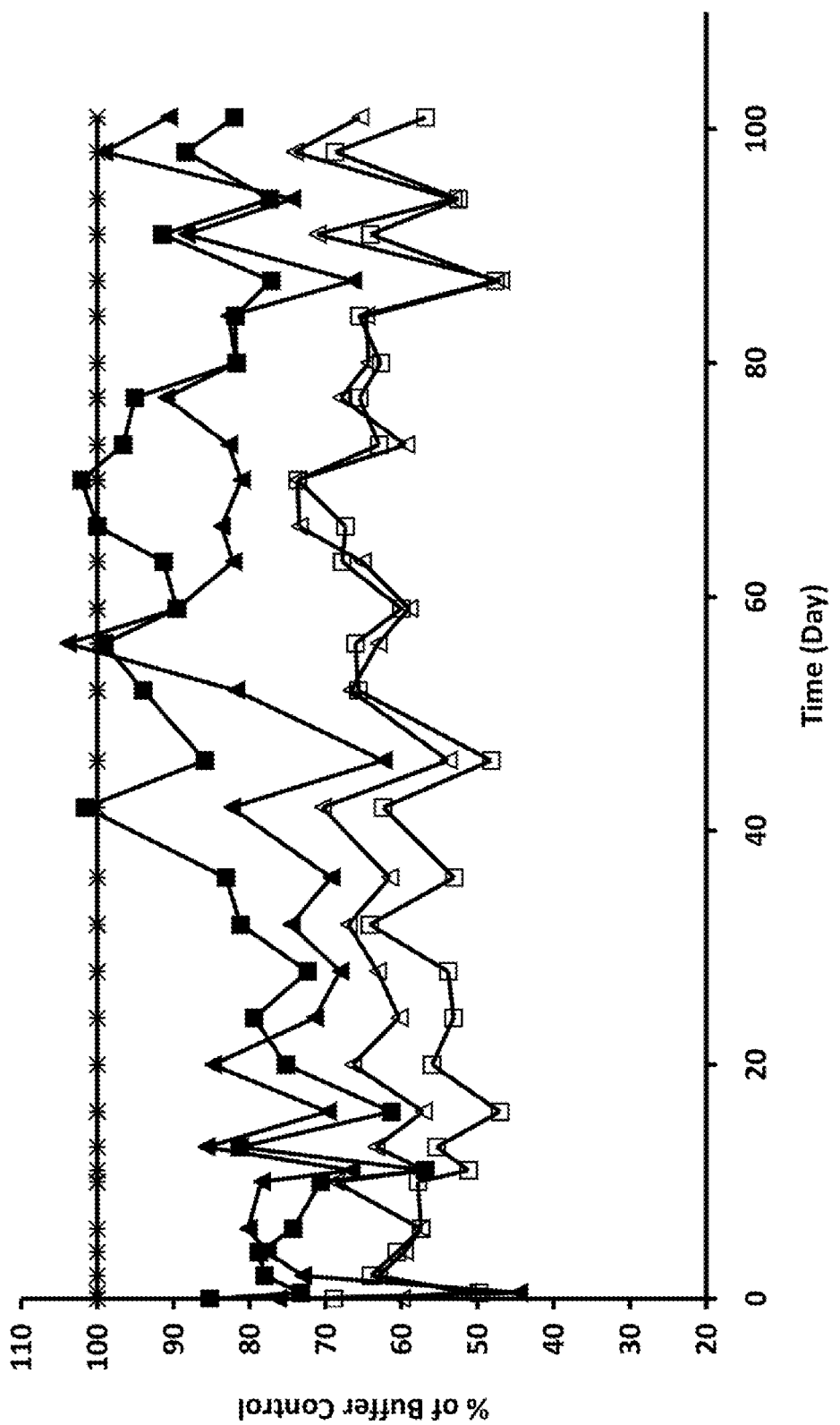
FIG. 7. Serum triglyceride level expressed as a percentage of change over buffer control. Buffer control (✱); 316P 5 mg/kg (■); 300N 5 mg/kg (▲); 316P 15 mg/kg (□); 300N 15 mg/kg (△).

4-5) by day 6. In animals that received a 15 mg/kg dose of 300N, the reduction in both total cholesterol (~10-15% reduction) and LDL-C (~40% reduction) continued to at least day 80 of the study. In addition, HDL-C was elevated in animals that received 316P at 15 mg/kg (FIG. 6). Animals that received a higher dose (15 mg/kg) of either 316P or 300N also showed a reduction in triglycerides during the course of study (FIG. 7). 316P exhibited maximal suppression of LDL-C levels of up to 80% relative to baseline. The length of this suppression was dose-dependent with at least 60% suppression (relative to baseline LDL-C levels) lasting approximately 18 days (5 mg/kg dose) and approximately 45 days (15 mg/kg dose). 300N exhibits a distinct pharmacodynamic profile from 316P. LDL-C suppression by 300N was sustained for a much longer period of time at comparable doses (50% LDL-C suppression for 28 days following a 5 mg/kg dose and 50% LDL-C suppression for approximately 90 days following a 15 mg/kg dose). There was little or no measurable change in liver function as determined by ALT and AST measurements. All animals receiving an anti-PCSK9 antibody in the study exhibited a rapid suppression If LDL-C and total cholesterol.

Figure 8:
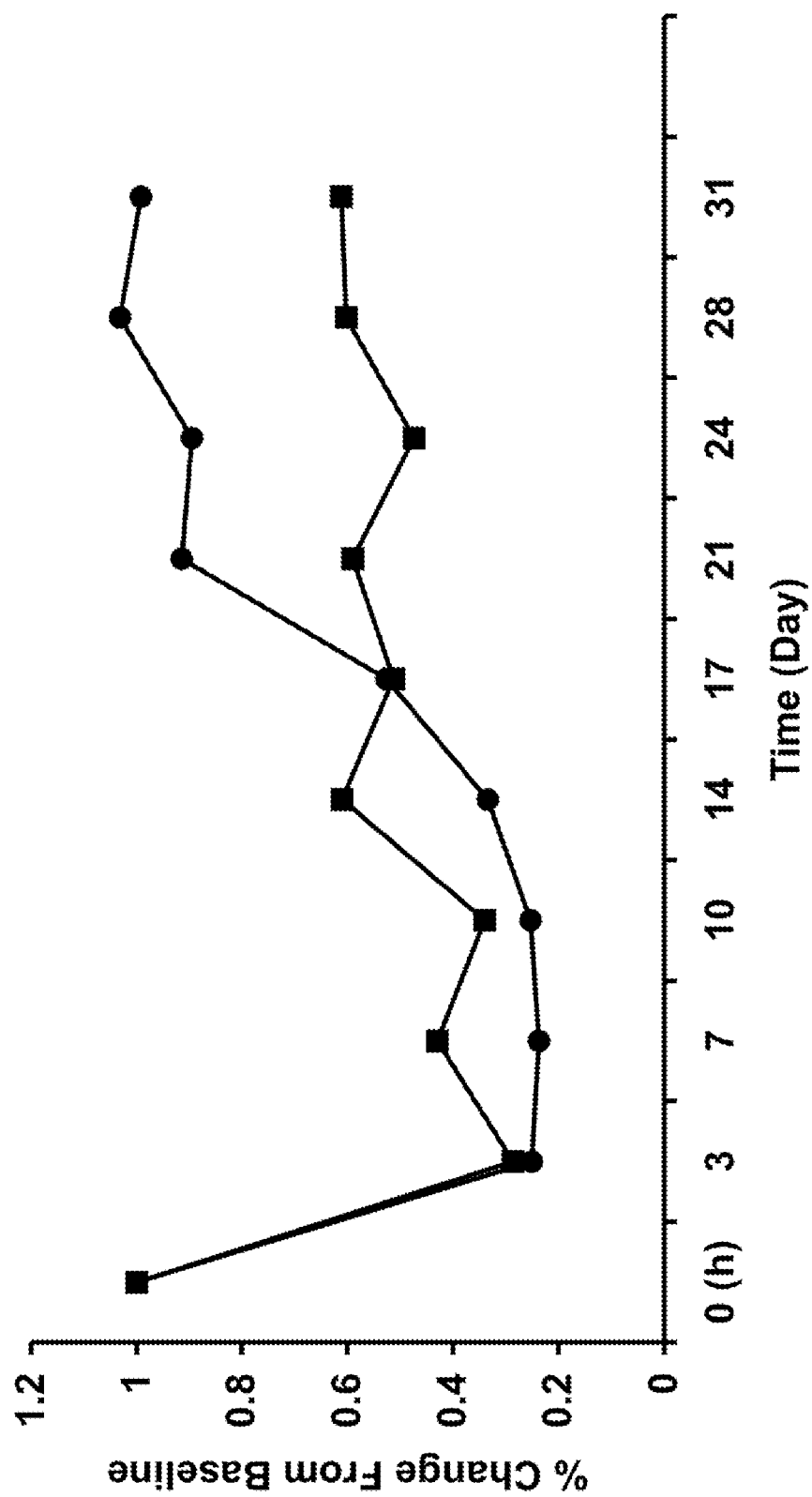
FIG. 8. Serum LDL cholesterol level expressed as a percentage of change over baseline following a single dose subcutaneous administration. 316P 5 mg/kg (■); 300N 5 mg/kg (●).
Figure 9:
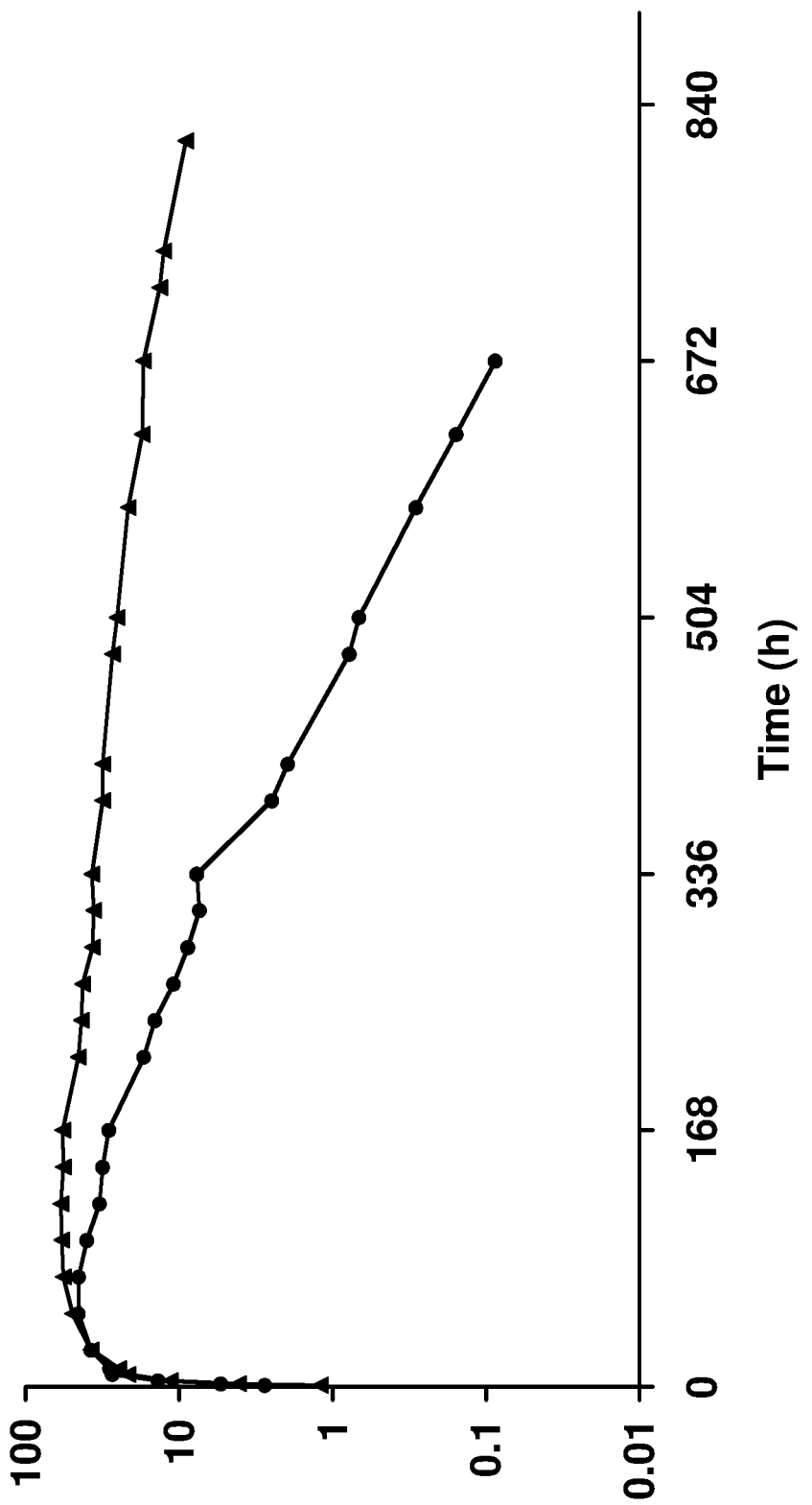
FIG. 9. Antibody concentrations in serum over time following a single dose subcutaneous administration. 316P 5 mg/kg (●); 300N 5 mg/kg (▲).

A similar LDL-C lowering effect of 316P and 300N was also observed in cynomolgus monkeys that received a single subcutaneous (SC) administration of either 5 mg/kg 316P or 5 mg/kg 300N (FIG. 8). Both 316P and 300N dramatically suppressed LDL-C levels and maintained an LDL-C lowering effect for approximately 15 and 30 days, respectively (FIG. 8). The pharmacodynamic effect (approximately 40% LDL-C suppression) approximately correlates with functional antibody levels in monkey serum (FIG. 9). As antibody levels decrease below 10 μg/ml, LDL-C suppression appeared to diminish as well. In addition, 300N demonstrated a substantially longer circulating half-life than 316P and hence a longer observed LDL-C suppression.

TABLE 26

| PK Parameter | 316P | 300N |
|---|---|---|
| $T_{max}$ (h) | 60 | 84 |
| $C_{max}$ (μg/ml) | 46 | 63 |
| $T_{1/2}$ (h) | 64 | 286 |

Example 14. Attenuation of LDL Receptor Degradation by Anti-hPCSK9 Antibodies

To assess the biological effect of PCSK9 on hepatic LDL receptor levels and subsequent effects on serum LDL-C levels, hPCSK9 was administered to mice expressing hPCSK9 but not mPCSK9 (PCSK9$^{hu/hu}$ mice) by intravenous injection. Specifically, PCSK9$^{hu/hu}$ mice were injected with PBS (control), or 1.2 mg/kg hPCSK9-mmh via the tail vein. Six hours after delivery of hPCSK9, a 1.4-fold elevation (relative to baseline level) in total cholesterol and a 2.3-fold elevation in LDL-C) in serum were observed. Analysis of hepatic LDL receptor levels in a separate cohort (n=3) of animals 4 hours after hPCSK9 administration revealed a significant reduction in detectable LDL receptor in liver homogenates.

Figure 10:
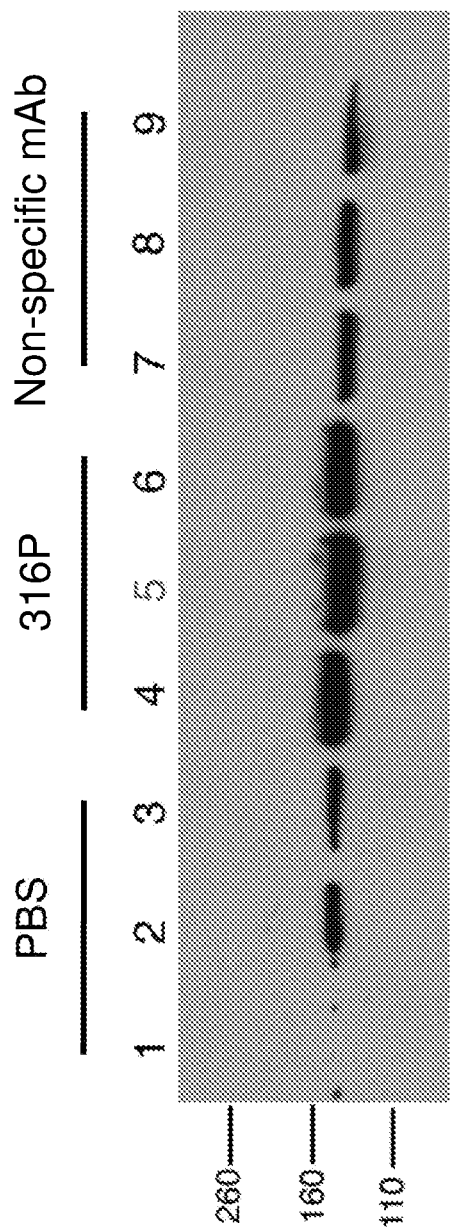
FIG. 10. Western blot for mouse LDL receptor of total liver homogenates. Samples were taken 24 hours after PBS (lanes 1-3), 5 mg/kg 316P (lanes 4-6), or 5 mg/kg of non-hPCSK9 specific mAb (lanes 7-8) administration and 4 hours after 1.2 mg/kg hPCSK9-mmh (all lanes).

To assess the biological effect of anti-hPCSK9 on hepatic LDL receptor levels and subsequent effects on serum LDL-C levels, 316P and a non-hPCSK9 specific mAb were administered to PCSK9$^{hu/hu}$ mice at equivalent dose (5 mg/kg i.p.) 20 hours prior to the hPCSK9-mmh protein injection described above. Four hours after the hPCSK9 administration, mice were sacrificed, a total of eight tissues (liver, brain, lung, kidney, heart, ileum, adrenal, and pancreas) were collected, and levels of LDL receptor were determined by Western blot. Changes in LDL receptor levels were only observed in liver. In comparison to PBS control dosing, administration of 316P significantly blocked the PCSK9-mediated increases in total cholesterol and LDL cholesterol (LDL-C=2.49 mg/dl at baseline and 3.1 mg/dl 6 hours after PCSK9; a 25% increase compared to 135% with vehicle). Prior administration of the non-hPCSK9 specific mAb blocked LDL-C increases by approximately 27% from PBS alone (LDL-C=4.1 mg/dl compared to PBS 5.6 mg/dl). Analysis of LDL receptor levels in a separate cohort of mice (n=3 per treatment group) revealed a significant reduction in LDL receptor levels with PCSK9 administration, which was blocked by 316P but not by the non-hPCSK9 specific mAb (FIG. 10).

Figure 11:
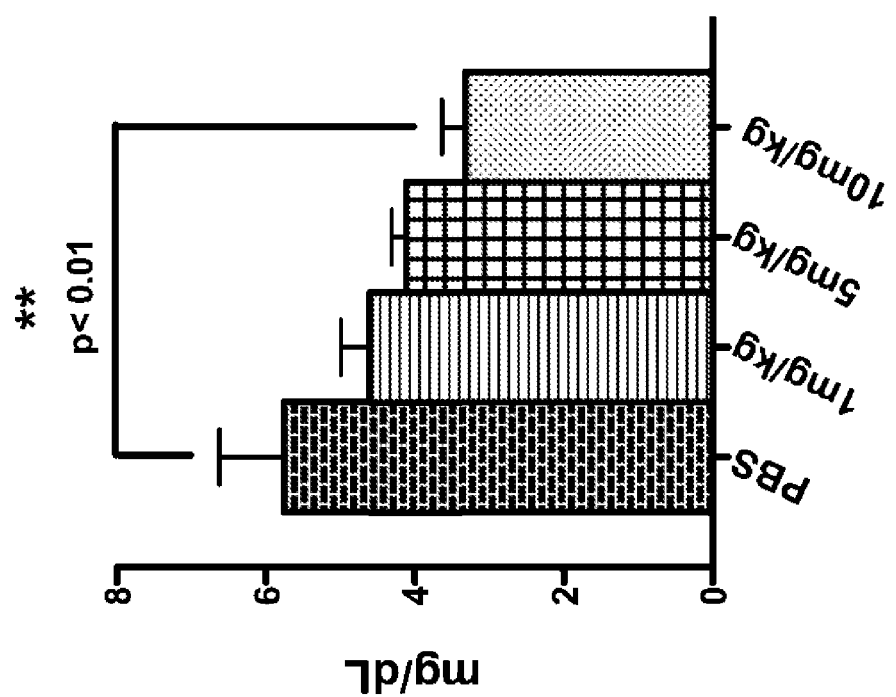
FIG. 11. Effects of 316P on serum LDL cholesterol level in PCSK9$^{hu/hu}$ mice. Buffer ▤ control 316P 1 mg/kg (▤); 316P 5 mg/kg (▤) 316P 10 mg/kg (▤).

Effect of different doses of 316P was also evaluated in PCSK9$^{hu/hu}$ mice with both elevated LDL-C and elevated hPCSK9 levels. PCSK9$^{hu/hu}$ mice were first placed on a high carbohydrate diet for 8 weeks, resulting in a ~2-fold elevation in both LDL-C and hPCSK9 levels. Either 316P or a non-hPCSK9 specific mAb, each at 1 mg/kg, 5 mg/kg, or 10 mg/kg, were administered to the mice. Sera were collected 24 hours later and LDL-C levels were analyzed. 316P was effective in decreasing LDL-C levels in a dose-dependent manner (FIG. 11). In addition, 316P administered at a dose of 10 mg/kg, rapidly reduced LDL-C levels back to original (pre-diet) values within 24 hours.

Example 15. Mouse PK Studies

Figure 12:
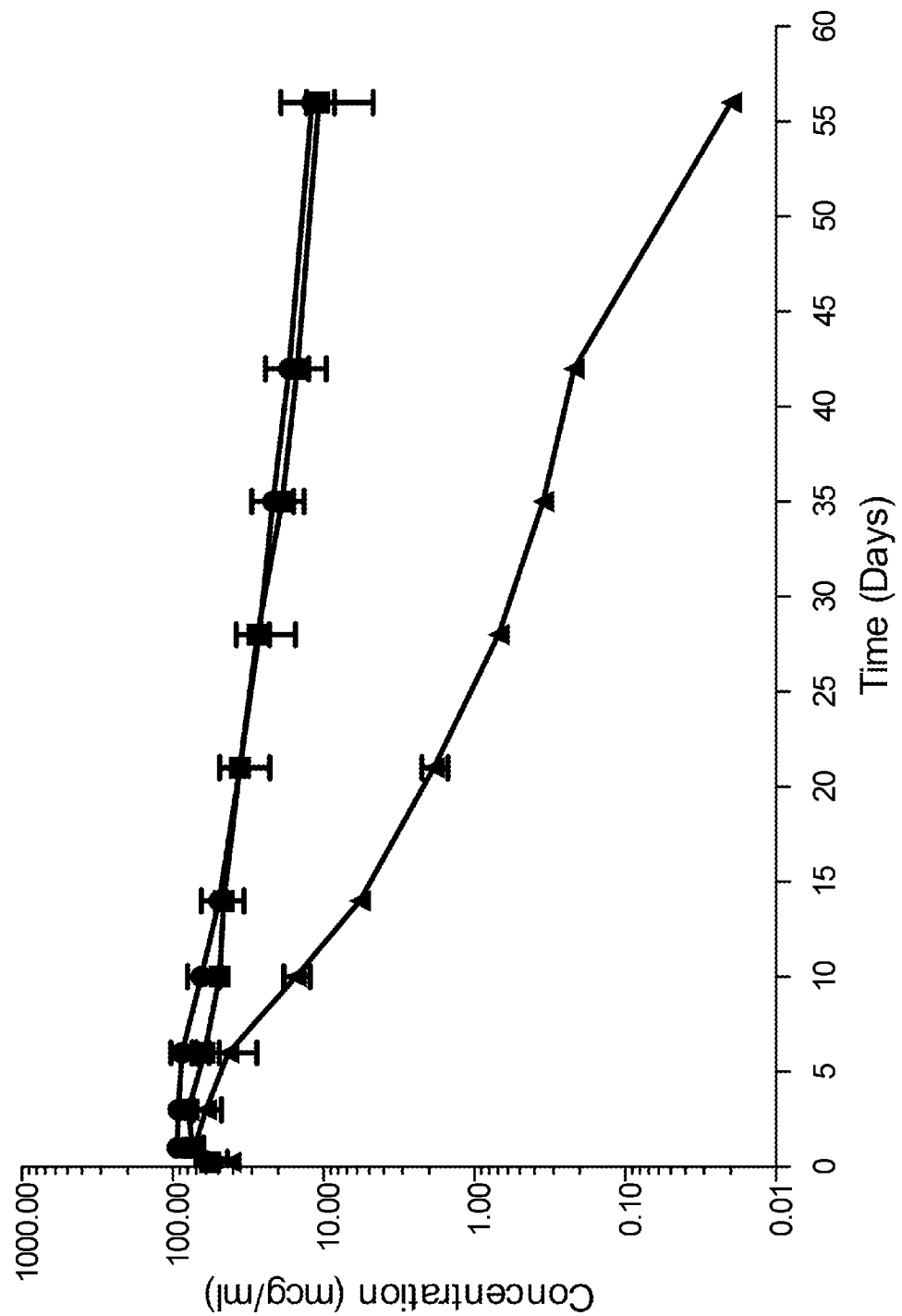
FIG. 12. Anti-hPCSK9 mAb serum pharmacokinetic profile in C57BL/6 mice. Single dose of Control I mAb (●) at 10 mg/kg; 316P (▲) at 10 mg/kg and 300N (■) at 10 mg/kg.
Figure 13:
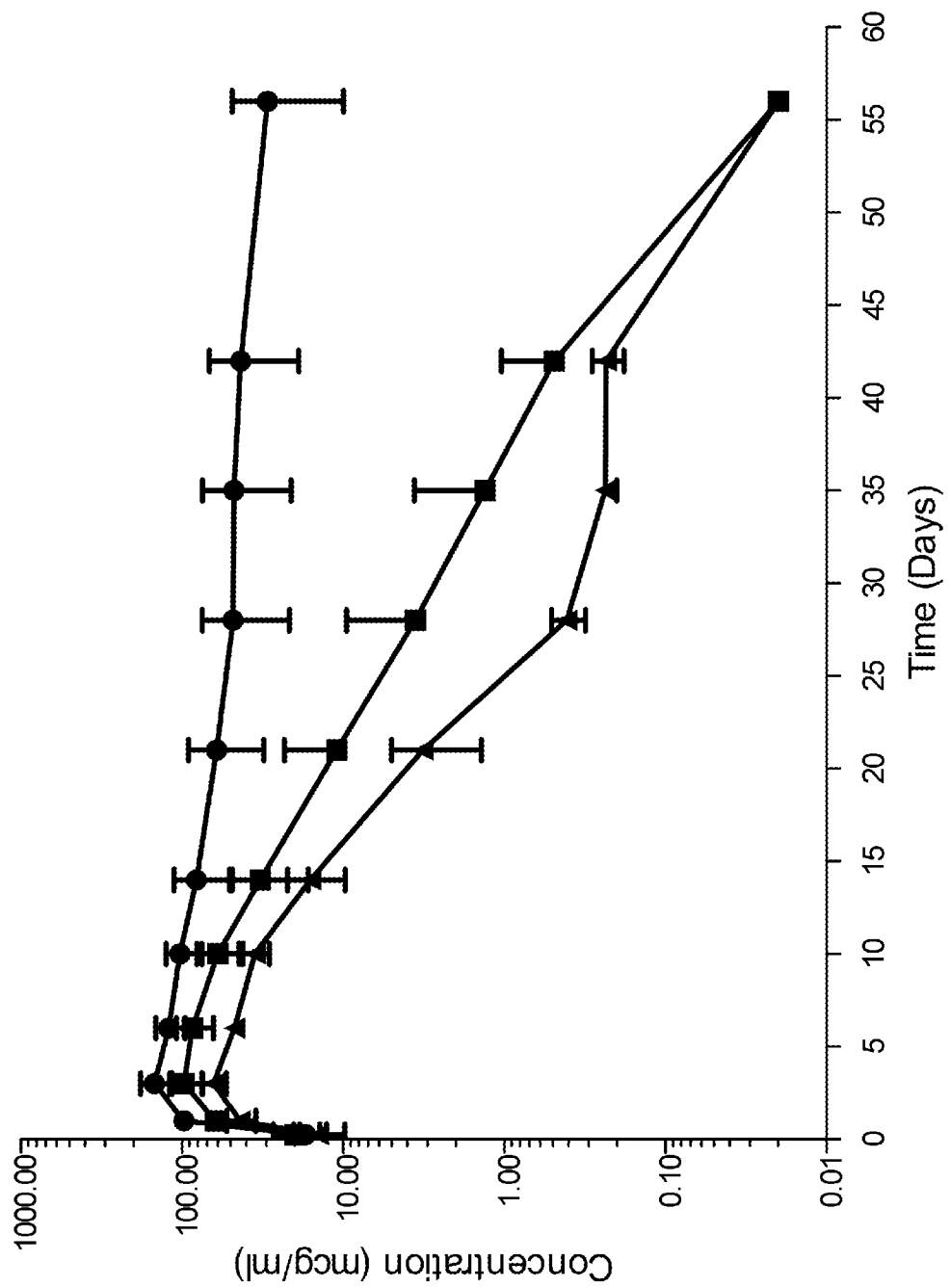
FIG. 13. Anti-hPCSK9 mAb serum pharmacokinetic profile in hPCSK9 heterozygous mice. Single dose of Control I mAb (●) at 10 mg/kg; 316P (▲) at 10 mg/kg and 300N (■) at 10 mg/kg.
Figure 14:
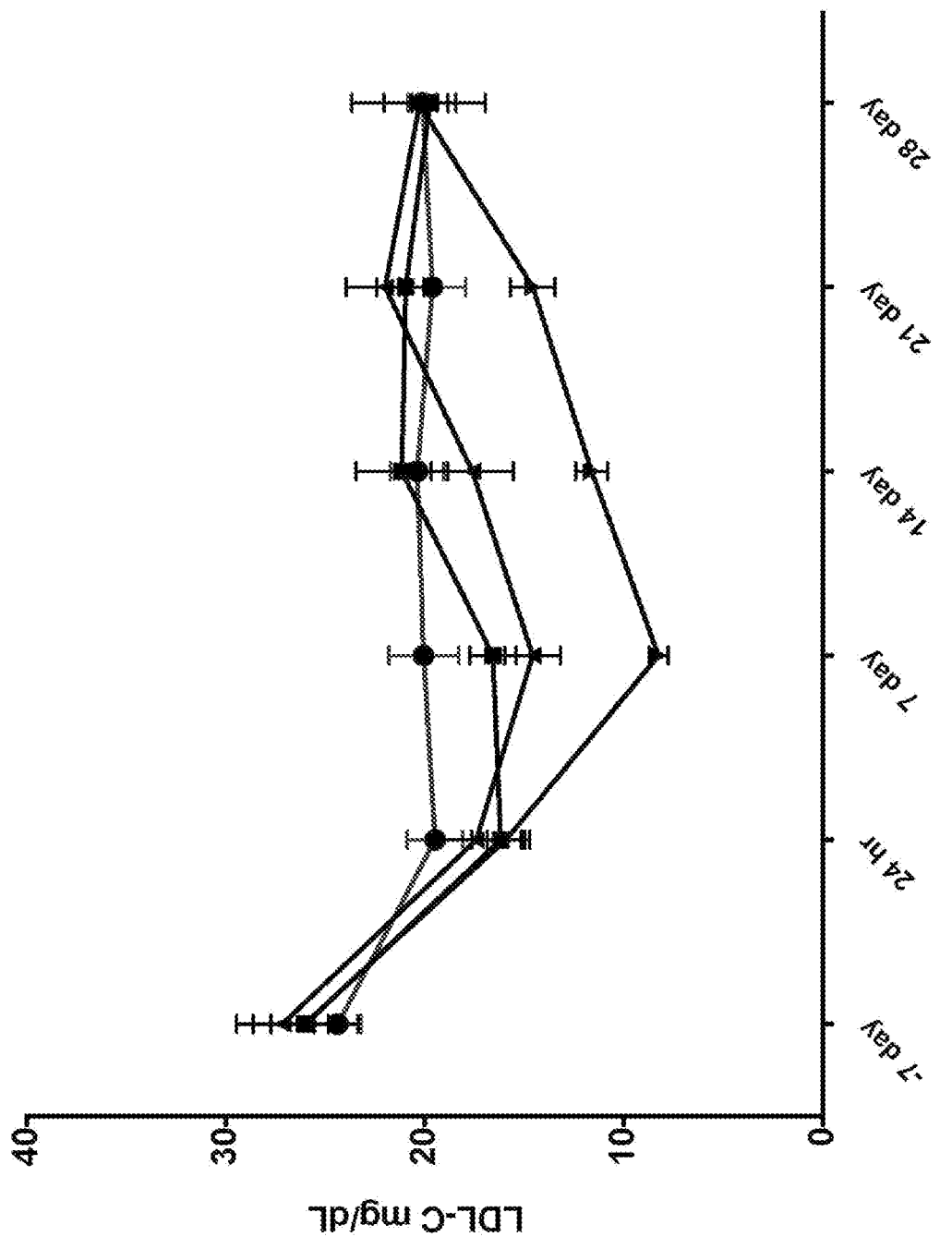
FIG. 14. Effect of 316P on serum LDL cholesterol levels in Syrian Hamster fed a normal diet. Buffer control (●); 316P 1 mg/kg (■); 316P 3 mg/kg (▲); 316P 5 mg/kg (▼).

A PK study was conducted in 6-week-old C57BL/6 mice and 11-15 week old hPCSK9 heterozygous mice. A single injection of Control I, 316P, or 300N, each at 10 mg/kg, was administered SC. Serum bleeds were measured for hIgG levels at 0 hr (pre-bleed), 6 hr, day 1, 3, 6, 10, 14, 21, 28, 35, 42 and 56, for a total of 12 time points, using an anti-hFc capture and anti-hFc detection sandwich ELISA (FIGS. 12 and 13). All mAbs achieved their $T_{max}$ at approximately 3 days with corresponding $C_{max}$ levels of approximately 47-115 μg/ml for C57BL/6 mice and 55-196 μg/ml for hPCSK9 heterozygous mice. At Day 56, Control I mAb levels were about 12 μg/ml and 300N levels were about 11 μg/ml whereas 316P levels were about less than 0.02 μg/ml in C57BL/6 mice. At Day 56 in hPCSK9 heterozygous mice, Control I mAb levels were about 29 μg/ml, while both 300N and 316P levels were below the quantifiable limit (BQL) of 0.02 μg/ml.

Example 16. Anti-hPCSK9 Antibody Binding to Mutant/Variant hPCSK9

To further assess binding between hPCSK9 and anti-hPCSK9 mAbs, 21 variant hPCSK9 proteins in which each variant contained a single point mutation and two variant hPCSK9 proteins each contained a double mutation were generated. Each selected antibody was captured on a F(ab')2 anti-hIgG surface created through direct chemical coupling to a BIACORE™ chip to form a captured antibody surface. Each mmh-tagged variant hPCSK9 at varying concentrations from 100 nM to 25 nM was then injected over the captured antibody surface at a flowrate of 60 μl/min for 240 sec, and the dissociation of variant hPCSK9 and antibody was monitored in real time for 20 min at 25° C. nb: no binding was observed under these experimental conditions ($K_D$=M×10$^{-9}$; $T_{1/2}$=min; WT=wildtype).

TABLE 27

|  | 316P | | 300N | | Control I | | Control II | | Control III | |
| --- | --- | --- | --- | --- | --- | --- | --- | --- | --- | --- |
|  | $K_D$ | $T_{1/2}$ | $K_D$ | $T_{1/2}$ | $K_D$ | $T_{1/2}$ | $K_D$ | $T_{1/2}$ | $K_D$ | $T_{1/2}$ |
| WT | 1.00 | 37 | 0.69 | 120 | 30.6 | 16 | 0.10 | 333 | 0.60 | 481 |
| P70A | 1.42 | 32 | 1.68 | 80 | 19.0 | 16 | 0.24 | 168 | 0.90 | 325 |
| S127R | 2.40 | 36 | 1.87 | 110 | 25.0 | 18 | 0.26 | 288 | 0.55 | 550 |
| D129G | 1.27 | 36 | 1.40 | 88 | 22.9 | 18 | 0.19 | 257 | 0.75 | 445 |
| S147F | 1.29 | 32 | 9.07 | 24 | 21.1 | 15 | 0.22 | 178 | 0.23 | 1468 |
| S153R | 5.64 | 4 | 0.56 | 141 | 36.6 | 17 | 0.09 | 322 | 3.33 | 60 |
| E159R | 6.96 | 5 | 0.82 | 94 | 31.7 | 16 | 0.08 | 350 | 2.97 | 68 |
| T162R | 0.98 | 43 | 0.58 | 140 | 29.0 | 17 | 0.09 | 322 | 0.48 | 362 |
| D192R | 1.35 | 28 | 0.75 | 119 | 30.2 | 15 | 0.09 | 326 | nb | nb |
| R194E | 0.38 | 71 | 0.65 | 129 | 31.4 | 16 | 0.07 | 389 | nb | nb |
| E197R | 1.42 | 27 | 0.67 | 115 | 30.2 | 17 | 0.09 | 339 | nb | nb |
| R215H | 0.86 | 41 | 1.03 | 98 | 37.8 | 17 | 0.65 | 49 | 0.74 | 272 |
| R215E | 0.90 | 43 | 1.81 | 77 | 44.0 | 16 | 4.48 | 12 | 0.78 | 276 |
| F216L | 1.83 | 32 | 0.99 | 121 | 21.2 | 15 | 1.35 | 39 | 0.33 | 880 |
| R237E | 2.48 | 15 | 1.03 | 109 | 29.6 | 15 | 0.07 | 481 | 5.89 | 43 |
| D238R | 410 | 1 | 0.78 | 123 | 25.9 | 19 | 0.24 | 144 | 0.14 | 1273 |
| A341R | 1.54 | 21 | 0.34 | 190 | 28.7 | 18 | 0.08 | 340 | 0.88 | 200 |
| D343R | 7.88 | 6 | 1.18 | 89 | 27.0 | 16 | 0.08 | 402 | 4.13 | 66 |
| R357H | 6.26 | 30 | 6.53 | 66 | 26.4 | 13 | 0.63 | 165 | 1.91 | 896 |
| E366K | 2.92 | 13 | 36.0 | 2 | 28.8 | 18 | 0.46 | 69 | 0.38 | 808 |
| D374Y | 2.04 | 15 | 0.66 | 83 | 25.0 | 17 | 0.08 | 285 | 1.02 | 161 |
| V380M | 0.48 | 63 | 2.82 | 28 | 25.9 | 17 | 0.15 | 177 | 0.35 | 711 |
| P70A, S147F | 1.18 | 34 | 7.87 | 24 | 23.5 | 18 | 0.23 | 164 | 0.79 | 348 |
| E366K, V380M | 3.33 | 12 | 78.3 | 1 | 25.5 | 18 | 0.59 | 60 | 0.52 | 551 |

The results show that when residue D238 was mutated, the binding affinity of 316P for hPCSK9 was reduced >400-fold, from a $K_D$ of 1×$10^{-9}$ M to 410×$10^{-9}$ M; and $T_{1/2}$ shortened about 30-fold, from 37 to 1 min, indicating that 316P binds an epitope on hPCSK9 comprising D238 of hPCSK9 (SEQ ID NO:755). Additionally, BIACORE™ assays show that 316P binding affinity and $T_{1/2}$ were reduced about 5- to 10-fold when a residue at 153, 159 or 343 was mutated. Specifically, $K_D$ was reduced from about 1×$10^{-9}$ M to between about 5-8×$10^{-9}$ M when any one of S153, E159 or D343 were mutated; while $T_{1/2}$ was decreased from about 37 min to between about 4-6 min.

300N binding to hPCSK9 was reduced about 50-fold when the residue at position 366 was mutated, resulting in a decreased $K_D$ of from about 0.7×$10^{-9}$ M to about 36×$10^{-9}$ M and a shorter $T_{1/2}$ from about 120 to 2 min. These results indicate that 300N binds an epitope on hPCSK9 comprising E366 of hPCSK9 (SEQ ID NO:755). Additionally, the BIACORE™ assays show that 300N binding affinity and $T_{1/2}$ were reduced between 2- to >10-fold when a residue at 147 or 380 was mutated. Specifically, $K_D$ was reduced from about 0.69×$10^{-9}$ M to between about 2-9×$10^{-9}$ M when any of S147 or V380 were mutated; while $T_{1/2}$ was shortened from about 120 min to between about 24-66 min. Compared to 316P, 300N binding to hPCSK9 was not reduced by a mutation at residue 238.

In contrast, Control I antibody did not exhibit an altered binding affinity or $T_{1/2}$ in response to any of the positional mutations tested; Control II antibody exhibited a 40-fold decreased affinity when residue 215 was mutated (R215E) (from ~0.1×$10^{-9}$ to ~4.5×$10^{-9}$), and $T_{1/2}$ was about 27-fold shorter (from ~333 to 12 min); while Control III antibody exhibited a decreased affinity when residue 237 was mutated ($K_D$ decreased from ~0.6×$10^{-9}$ to ~5.9×$10^{-9}$, and $T_{1/2}$ decreased from ~481 to ~43 min).

Binding specificity of 316P, 300N, and control anti-hPCSK9 mAbs to hPCSK9 variants was tested using an ELISA-based immunoassay. Anti-PCSK9 mAbs were coated on a 96-well plate overnight at 4° C. Each mmh-tagged variant hPCSK9 in CHO-k1 transient transfection lysate supernatants was added to the antibody-coated plate at various concentrations ranging from 0 to 5 nM. After 1 hr binding at RT, the plate was washed and bound variant hPCSK9 was detected using HRP-conjugated anti-myc polyclonal antibody (−=OD<0.7; +=OD 0.7-1.5; ++=OD>1.5).

TABLE 28

| hPCSK9 or Variant | 316P | 300N | Control I | Control II | Control III |
|---|---|---|---|---|---|
| hPCSK9(WT) | ++ | ++ | ++ | ++ | ++ |
| hPCSK9(S127R) | ++ | ++ | ++ | ++ | ++ |
| hPCSK9(D129G) | ++ | ++ | ++ | ++ | ++ |
| hPCSK9(S153R) | ++ | ++ | ++ | ++ | ++ |
| hPCSK9(R215H) | ++ | ++ | ++ | ++ | ++ |
| hPCSK9(F216L) | ++ | ++ | ++ | ++ | ++ |
| hPCSK9(R237E) | ++ | ++ | ++ | ++ | ++ |
| hPCSK9(D238R) | | ++ | ++ | ++ | ++ |
| hPCSK9(A341R) | ++ | ++ | ++ | ++ | ++ |
| hPCSK9(D343R) | ++ | ++ | ++ | ++ | ++ |
| hPCSK9(R357H) | ++ | ++ | ++ | ++ | ++ |
| hPCSK9(E159R) | ++ | ++ | ++ | ++ | ++ |
| hPCSK9(T162R) | ++ | ++ | ++ | ++ | ++ |
| HPCSK9(D192R) | ++ | ++ | ++ | ++ | – |
| hPCSK9(R194E) | ++ | ++ | ++ | ++ | – |
| hPCSK9(E197R) | ++ | ++ | ++ | ++ | – |
| hPCSK9(R215E) | ++ | ++ | ++ | ++ | ++ |
| hPCSK9(P70A) | ++ | ++ | ++ | ++ | ++ |
| hPCSK9(S147F) | ++ | ++ | ++ | ++ | ++ |
| hPCSK9(E366K) | ++ | + | ++ | ++ | ++ |
| hPCSK9(V380M) | ++ | ++ | ++ | ++ | ++ |
| hPCSK9(P70A, S147F) | ++ | ++ | ++ | ++ | ++ |
| hPCSK9(E366K, V380M) | ++ | + | ++ | ++ | ++ |

Example 17. Effect of 316P on Normolipemic and Hyperlipemic Hamster

The ability of anti-PCSK9 mAb 316P to reduce serum LDL-C was tested in normolipemic or hyperlipemic Gold Syrian hamsters (*Mesocricetus auratus*). Male Syrian Hamsters, age 6-8 weeks, weighing between 80-100 grams, were allowed to acclimate for a period of 7 days before entry into the study. All animals were placed on either a standard chow diet or a hyperlipemic diet of chow supplemented with 0.1% cholesterol and 10% coconut oil. The 316P mAb was delivered to hamsters by a single subcutaneous injection at doses of 1, 3, or 10 mg/kg for normolipemic hamsters and at doses of 3, 10, or 30 mg/kg for hyperlipemic hamsters. Serum samples were taken from all groups at 24 hr and 7, 14, and 22 days post injection, at which time serum lipid levels were assessed and compared to baseline levels taken 7 days prior to the administration of the mAbs. Circulating total cholesterol and LDL-C in normolipemic hamsters was significantly reduced in a dose-dependent manner compared to vehicle injection. As shown in FIG. 14, administration of 316P effectively reduced LDL-C levels by up to 60% seven days post injection at the highest dose (10 mg/kg) tested. Similar cholesterol reducing effect of 316P was not observed in hyperlipemic hamsters.

We claim:

1. A nucleic acid molecule encoding a heavy chain variable region (HCVR) and a light chain variable region (LCVR) of an anti-human proprotein convertase subtilisin/kexin type 9 (PCSK9) PCSK9 antibody or antigen-binding fragment thereof,
   wherein the HCVR comprises a heavy chain complementarity determining region (HCDR) 1 comprising the amino acid sequence of SEQ ID NO:220, an HCDR2 comprising the amino acid sequence of SEQ ID NO:222, and an HCDR3 comprising the amino acid sequence of SEQ ID NO:224; and
   wherein the LCVR comprises a light chain complementarity determining region (LCDR) 1 comprising the amino acid sequence of SEQ ID NO:228, an LCDR2 comprising the amino acid sequence LGS, and an LCDR3 comprising the amino acid sequence of SEQ ID NO: 232.

2. The nucleic acid molecule of claim 1 that encodes an HCVR comprising the amino acid sequence of SEQ ID NO:218.

3. The nucleic acid molecule of claim 1 that comprises a nucleotide sequence having at least 95% sequence identity to SEQ ID NO:217.

4. A recombinant expression vector comprising the nucleic acid molecule of claim 1.

5. The nucleic acid molecule of claim 1 that encodes an LCVR comprising the amino acid sequence of SEQ ID NO:226.

6. The nucleic acid molecule of claim 1 that comprises a nucleotide sequence having at least 95% sequence identity to SEQ ID NO:225.

7. A method of producing an anti-human PCSK9 antibody or antigen-binding fragment thereof, the method comprising:
   culturing a host cell under conditions permitting production of the antibody or antigen-binding fragment thereof,
   wherein the host cell comprises:
   (i) a first recombinant expression vector comprising a nucleic acid molecule encoding an HCVR of the anti-human PCSK9 antibody,
   wherein the HCVR comprises an HCDR1 having the amino acid sequence of SEQ ID NO:220, an HCDR2 having the amino acid sequence of SEQ ID NO:222 and an HCDR3 having the amino acid sequence of SEQ ID NO:224; and (ii) a second recombinant expression vector comprising a nucleic acid molecule encoding a LCVR of the anti-human PCSK9 antibody, wherein the LCVR comprises an LCDR1 having the amino acid sequence of SEQ ID NO:228, an LCDR2 having the amino acid sequence LGS, and an LCDR3 having the amino acid sequence of SEQ ID NO:232; and recovering the antibody or antigen-binding fragment produced.

8. The method of claim 7, wherein the first recombinant expression vector comprises a nucleic acid molecule encoding an HCVR comprising the amino acid sequence of SEQ ID NO:218.

9. The method of claim 7, wherein the first recombinant expression vector comprises a nucleic acid molecule comprising a nucleotide sequence having at least 95% sequence identity to SEQ ID NO:217.

10. The method of claim 7, wherein the second recombinant expression vector comprises a nucleic acid molecule encoding an LCVR comprising the amino acid sequence of SEQ ID NO:226.

11. The method of claim 7, wherein the second recombinant expression vector comprises a nucleic acid molecule comprising a nucleotide sequence having at least 95% sequence identity to SEQ ID NO:225.

12. The method of claim 7, wherein the host cell is a Chinese Hamster Ovary (CHO) cell.

* * * * *